(12) United States Patent
Furebring et al.

(10) Patent No.: US 8,173,774 B2
(45) Date of Patent: May 8, 2012

(54) POLYPEPTIDES AND USE THEREOF

(75) Inventors: Christina Furebring, Lund (SE);
Johannes A. G. Van Strijp, Odijk (NL);
Petrus J. A. Haas, Utrecht (NL); Anna Rosen, S. Sandby (SE); Karin Haraldsson, Lund (SE); Erika Gustafsson, Lund (SE); Lena Schultz, Bethesda, MD (US); Cornelis P. M. Van Kessel, Bunnik (NL)

(73) Assignee: Alligator Bioscience AB, Lund (SE)

( * ) Notice: Subject to any disclaimer, the term of this patent is extended or adjusted under 35 U.S.C. 154(b) by 370 days.

(21) Appl. No.: 12/297,860

(22) PCT Filed: Apr. 20, 2007

(86) PCT No.: PCT/GB2007/001443
§ 371 (c)(1),
(2), (4) Date: Oct. 20, 2008

(87) PCT Pub. No.: WO2007/122400
PCT Pub. Date: Nov. 1, 2007

(65) Prior Publication Data
US 2010/0298539 A1 Nov. 25, 2010

(30) Foreign Application Priority Data
Apr. 20, 2006 (GB) .................................. 0607798.6

(51) Int. Cl.
| C07K 1/00 | (2006.01) |
| C07K 16/00 | (2006.01) |
| C07K 17/00 | (2006.01) |
| C07K 14/00 | (2006.01) |
| C07K 5/00 | (2006.01) |
| C07K 7/00 | (2006.01) |
| A61K 38/00 | (2006.01) |
| A61K 39/00 | (2006.01) |
| A61K 39/38 | (2006.01) |
| A61K 39/085 | (2006.01) |
| A61K 39/09 | (2006.01) |
| A61K 39/02 | (2006.01) |

(52) U.S. Cl. ..................... 530/350; 530/300; 424/184.1; 424/185.1; 424/190.1; 424/234.1; 424/237.1; 424/243.1

(58) Field of Classification Search .................. None
See application file for complete search history.

(56) References Cited

U.S. PATENT DOCUMENTS

| 4,440,859 A | 4/1984 | Rutter et al. |
| 4,485,045 A | 11/1984 | Regen |
| 4,530,901 A | 7/1985 | Weissmann |
| 4,544,545 A | 10/1985 | Ryan et al. |
| 4,582,800 A | 4/1986 | Crowl |
| 4,677,063 A | 6/1987 | Mark et al. |
| 4,678,751 A | 7/1987 | Goeddel |
| 4,704,362 A | 11/1987 | Itakura et al. |
| 4,710,463 A | 12/1987 | Murray |
| 4,757,006 A | 7/1988 | Toole, Jr. et al. |
| 4,766,075 A | 8/1988 | Goeddel et al. |
| 4,810,648 A | 3/1989 | Stalker |
| 5,874,219 A | 2/1999 | Rava et al. |
| 6,027,726 A | 2/2000 | Ansell |
| 6,139,869 A | 10/2000 | Hosokawa et al. |
| 7,081,513 B2 * | 7/2006 | Van Strijp et al. ............. 530/300 |
| 7,388,078 B2 * | 6/2008 | Van Strijp et al. ............. 530/350 |
| 7,425,622 B2 * | 9/2008 | Rosen ........................ 530/388.2 |
| 7,608,276 B2 * | 10/2009 | Masignani et al. ......... 424/243.1 |
| 2006/0205655 A1 * | 9/2006 | Van Strijp et al. ............. 514/12 |
| 2008/0233137 A1 * | 9/2008 | Van Strijp et al. .......... 424/185.1 |
| 2009/0264359 A1 * | 10/2009 | Van Kessel et al. ............. 514/12 |
| 2010/0055130 A1 * | 3/2010 | Masignani et al. ......... 424/209.1 |
| 2010/0298539 A1 * | 11/2010 | Furebring et al. ............. 530/350 |

FOREIGN PATENT DOCUMENTS

| EP | 1 586 583 A2 | 10/2005 |
| EP | 1 586 583 A3 | 10/2005 |
| WO | WO-98/58080 A1 | 12/1998 |
| WO | WO-00/02913 A1 | 1/2000 |
| WO | WO-01/49711 A2 | 7/2001 |
| WO | WO-01/49711 A3 | 7/2001 |
| WO | WO-02/48351 A2 | 6/2002 |
| WO | WO-02/48351 A3 | 6/2002 |
| WO | WO 03/006048 A1 * | 1/2003 |
| WO | WO-03/097834 A2 | 11/2003 |
| WO | WO-03/097834 A3 | 11/2003 |
| WO | WO-2005/100385 A2 | 10/2005 |
| WO | WO-2005/100385 A3 | 10/2005 |
| WO | WO-2007/057682 A1 | 5/2007 |
| WO | WO-2007/122400 A2 | 11/2007 |
| WO | WO-2007/122400 A3 | 11/2007 |
| WO | WO 2010/079314 A2 * | 7/2010 |
| WO | WO 2010/090542 A2 * | 8/2010 |

OTHER PUBLICATIONS

Haas et al, Abstracts of Interscience Conference on Antimicrobial Agents Chemotherapy, 2003, vol. 43, pp. 63, abstract only.* Gustafsson et al, Protein Engineering Design and Selection, 2010, 23/2:91-101.*

(Continued)

Primary Examiner — Nita M Minnifield

(74) Attorney, Agent, or Firm — Morrison & Foerster LLP

(57) ABSTRACT

The present invention provides a polypeptide having a biological activity of the Chemotaxis Inhibitory Protein of Staphylococcus aureus ('CHIPS'), the polypeptide comprising a variant of the amino acid sequence of SEQ ID NO:1. Preferably, the polypeptide is a CHIPS variant wherein one or more of the following amino acids is modified: N31, S32, G33, L34, P35, K40, D42, R46, Y48, K50, G52, T53, K54, N55, S56, A57, Q58, K61, E67, K69, L76, N77, P79, D83, L90, K92, K100, K101, S104, K105, S107, Y108, N111 and G112. In a preferred embodiment, the polypeptide is less immunogenic hi humans than the wildtype CHIPS protein. The invention further provides methods of making and using such variant CHIPS polypeptides.

34 Claims, 70 Drawing Sheets

OTHER PUBLICATIONS

Figure 1:
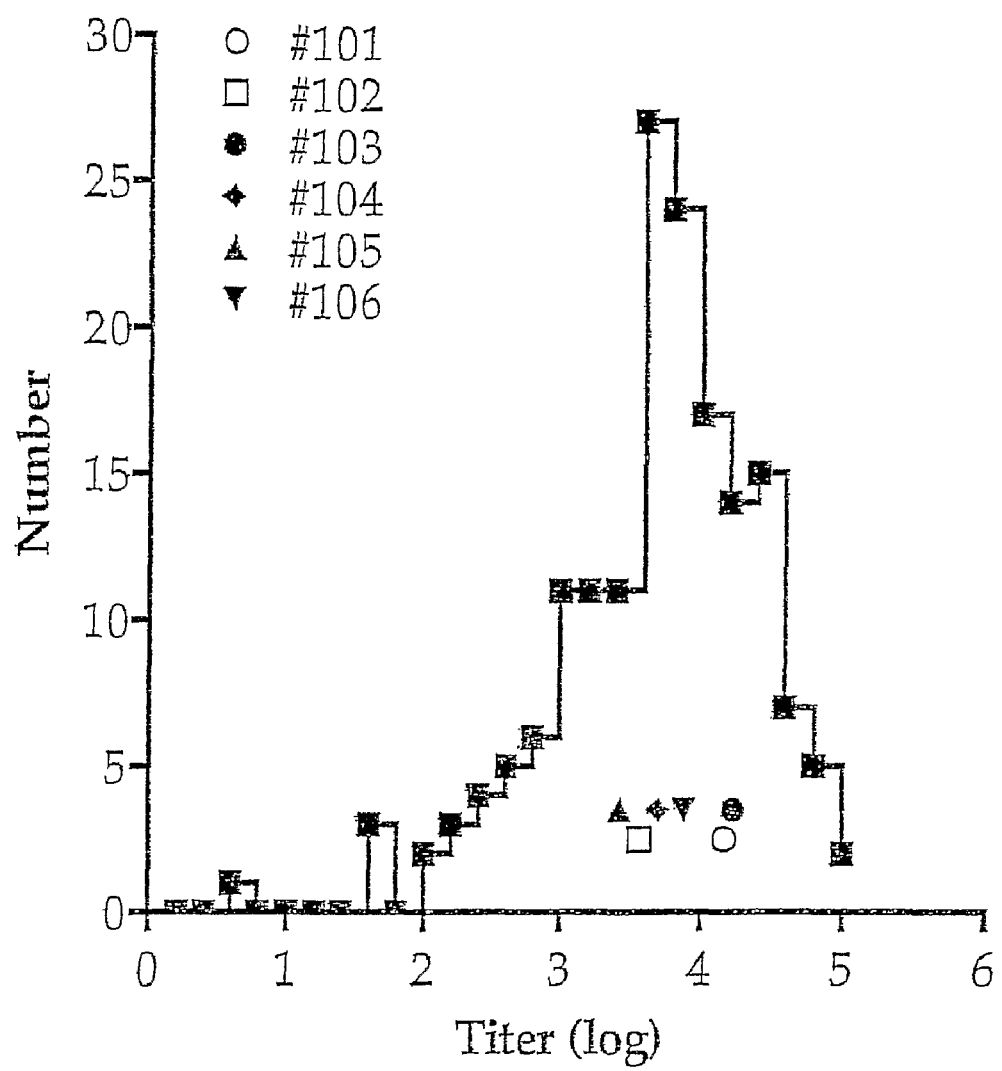

Gustafsson et al, BMC Immunology, 2009, vol. 10:13, 13 pages.*
Haas et al, J. Immunology, 2004, 173:5704-5711.*
Haas et al, J. Mol. Biol., 2005, 353:859-872.*
Diep et al, Lancet, 2006, 367/9512:731-739.*
Holden et al, PNAS, USA, 2004, 101:9786-9791.*
Bae et al, Mol. Microbiol., 2006, 62:1035-1047.*
Hui-hui et al, J. Int. Pharm. Res., Jun. 2010, 37/3:181-186.*
Greenspan et al, Nature Biotechnology 17:936-937, 1999.*
Aiyar, A. (2000). "The Use of Clustal W and Clustal X for Multiple Sequence Alignment," Chapter 11 in *Methods in Molecular Biology*, Humana Press Inc.: Totowa, NY 132:221-241.
Amitai, G. et al. (2004). "Network Analysis of Protein Structures Identifies Functional Residues," *J. Mol. Biol.* 344:1135-1146.
Becker, D.M. et al. (1991). "High-Efficiency Transformation of Yeast by Electroporation," *Methods Enzymolology*, vol. 194, Academic Press: New York, NY, pp. 182-187.
Beggs, J.D. (Sep. 14, 1978). "Transformation of Yeast by a Replicating Hybrid Plasmid," *Nature* 275:104-109.
Berent, S.L. et al. (May/Jun. 1985). "Comparison of Oligonucleotide and Long DNA Fragments as Probes in DNA and RNA Dot, Southern, Northern, Colony and Plaque Hybridizations," *Biotech.* 3:208-220.
Cohen, S.N. et al. (Aug. 1972). "Nonchromosomal Antibiotic Resistance in Bacteria: Genetic Transformation of *Escherichia coli* by R-Factor DNA," *Proc. Natl. Acad. Sci. USA* 69(8):2110-2114.
Cook, A.D. et al. (Sep. 1998). "Mimotopes Identified by Phage Display for the Monoclonal Antibody CII-C1 to Type II Collagen," *J. Autoimmun.* 11:205-211.
Crum, N.F. et al. (Sep. 2005). "Infections Associated With Tumor Necrosis Factor-α Antagonists," *Medicine* (Baltimore) 84(5):291-301.
Dahlén, E. et al. (2008). "Development of Interleukin-1 Receptor Antagonist Mutants with Enhanced Antagonistic Activity In Vitro and Improved Therapeutic Efficacy in Collagen-Induced Arthritis," *J. Immunotoxicol.* 5:189-199.
De Haas, C.J.C. et al. (Mar. 1, 2004). "Chemotaxis Inhibitory Protein of *Staphylococcus aureus*, a Bacterial Antiinflammatory Agent," *J. Exp. Med.* 199(5):687-695.
DeLano Scientific LLC. (2008). "PyMOL Molecular Viewer—SourceForge," located at <http://pymol.sourceforge.net >, last visited on Mar. 11, 2009, one page.
Engberg, J. et al. (1996). "Phage-Display Libraries of Murine and Human Antibody Fab Fragments," *Mol. Biotechnol.* 6:287-310.
Eppstein, D.A. et al. (Jun. 1985). "Biological Activity of Liposome-Encapsulated Murine Interferon γ is Mediated by a Cell Membrane Receptor," *Proc. Natl. Acad. Sci. USA* 82:3688-3692.
Falk, W. et al. (May 1982). "Only the Chemotactic Subpopulation of Human Blood Monocytes Expresses Receptors for the Chemotactic Peptide *N*-Formylmethionyl-Leucyl-Phenylalanine," *Infect. Immun.* 36(2):450-454.
Gunnarsson, L.C. et al. (2004; e-pub. Apr. 13, 2004). "A Carbohydrate Binding Module as a Diversity-Carrying Scaffold," *Protein Eng. Des. Sel.* 17(3):213-221.
Guo, R-F. et al. (Jan. 2004). "Role of C5a-C5aR Interaction in Sepsis," *Shock* 21(1):1-7.
Haas, P-J. et al. (2004). "N-Terminal Residues of the Chemotaxis Inhibitory Protein of *Staphylococcus aureus* Are Essential for Blocking Formylated Peptide Receptor but Not C5a Receptor," *J. Immunol.* 173:5704-5711.
Haas, P-J. et al. (2005; e-pub. Sep. 23, 2005). "The Structure of the C5a Receptor-blocking Domain of Chemotaxis Inhibitory Protein of *Staphylococcus aureus* is Related to a Group of Immune Evasive Molecules," *J. Mol. Bio.* 353(4):859-872.
Heller, T. et al. (1999). "Selection of a C5a Receptor Antagonist from Phage Libraries Attenuating the Inflammatory Response in Immune Complex Disease and Ischemic/Reperfusion Injury," *J. Immunol.* 163:985-994.
Ho, S.N. et al. (1989). "Site-Directed Mutagenesis by Overlap Extension Using the Polymerase Chain Reaction," *Gene* 77:51-59.
Huang, W. et al. (1991). "A Time-Efficient, Linear-Space Local Similarity Algorithm," *Adv. Appl. Math.* 12:337-357.

Hubbard, S.J. et al. (1991). "Molecular Recognition: Conformational Analysis of Limited Proteolytic Sites and Serine Proteinase Protein Inhibitors," *J. Mol. Biol.* 220:507-530.
Huber-Lang, M. et al. (2001). "Role of C5a in Multiorgan Failure During Sepsis," *J. Immunol.* 166:1193-1199.
Huey, R. et al. (Sep. 1985). "Characterization of a C5a Receptor on Human Polymorphonuclear Leukocytes (PMN)," *Immunol.* 135(3):2063-2068.
Hwang, K.J. et al. (Jul. 1980). "Hepatic Uptake and Degradation of Unilamellar Sphingomyelin/Cholesterol Liposomes: A Kinetic Study," *Proc. Natl. Acad. Sci. USA* 77(7):4030-4034.
International Conference on Harmonisation. (Jun. 10, 1996). "ICH Harmonised Tripartite Guideline: Guideline for Good Clinical Practice. E6(R1) Step 4 Version," *presented at the ICH Steering Committee Meeting of the International Conference on Harmonisation of Technical Requirements for Registration of Pharmaceuticals for Human Use* on May 1, 1996, pp. i-iii, 1-53.
International Search Report mailed on Feb. 7, 2008, for PCT Application No. PCT/GB2007/001443 filed on Apr. 20, 2007, six pages.
Jancar, S. et al. (Jan. 2005; e-pub. Nov. 24, 2004). "Immune Complex-Mediated Tissue Injury: A Multistep Paradigm," *Trends Immunol.* 26(1):48-55.
Johannes, T.W. et al. (2006; e-pub. Apr. 18, 2006). "Directed Evolution of Enzymes and Biosynthetic Pathways," *Curr. Opin. Microbiol.* 9:261-267.
Johansen, L.K. et al. (1995). "pFab60: A New, Efficient Vector for Expression of Antibody Fab Fragments Displayed on Phage," *Protein Engineering* 8(10):1063-1067.
Knecht, W. et al. (2006). "Limited Mutagenesis Increases the Stability of Human Carboxypeptidase U (TAFIa) and Demonstrates the Importance of CPU Stability Over proCPU Concentration in Down-Regulating Fibrinolysis," *FEBS J.* 273:778-792.
Le, Y. et al. (Nov. 2002; e-pub. Oct. 4, 2002). "Formyl-Peptide Receptors Revisited," *Trends Immunol.* 23(11):541-548.
Lee, B et al. (1971). "The Interpretation of Protein Structures: Estimation of Static Accessibility," *J. Mol. Biol.* 55:379-400.
Leung, D.W. et al. (Aug. 1989). "A Method for Random Mutagenesis of a Defined DNA Segment Using a Modified Polymerase Chain Reaction," *Technique* 1(1):11-15.
Listing, J. et al. (Nov. 2005). "Infections in Patients With Rheumatoid Arthritis Treated With Biologic Agents," *Arthritis Rheum.* 52(11):3403-3412.
Luchansky, J.B. et al. (1988). "Application of Electroporation for Transfer of Plasmid DNA to *Lactobacillus, Lactococcus, Leuconostoc, Listeria, Pediococcus, Bacillus, Staphylococcus, Enterococcus* and *Propionibacterium,*" *Mol. Microbiol.* 2(5):637-646.
Myers, M.A. et al. (2000). "Conformational Epitopes on the Diabetes Autoantigen GAD65 Identified by Peptide Phage Display and Molecular Modeling," *J. Immunol.* 165:3830-3838.
Payne, V. et al. (2004). "Mast Cell Tryptase: A Review of Its Physiology and Clinical Significance," *Anaesthesia* 59:695-703.
Pearson, W. (2009). "LALIGN—Find Multiple Matching Subsegments in Two Sequences," located at <http://www.ch.embnet.org/software/LALIGN_form.html>, lasted visited on Mar. 11, 2009, two pages.
Peters, E.A. et al. (Jul. 1994). "Membrane Insertion Defects Caused by Positive Charges in the Early Mature Region of Protein pIII of Filamentous Phage fd Can Be Corrected by *prlA* Suppressors," *J. Bacteriol.* 176(14):4296-4305.
Pike, M.C. et al. (Jul. 1, 1980). "Development of Specific Receptors for N-Formylated Chemotactic Peptides in a Human Monocyte Cell Line Stimulated with Lymphokines," *J. Exp. Med.* 152:31-40.
Plant, A.L. et al. (1995). "Phospholipid/Alkanethiol Bilayers for Cell-Surface Receptor Studies by Surface Plasmon Resonance," *Analyt. Biochem.* 226(2):342-348.
Postma, B. et al. (2004). "Chemotaxis Inhibitory Protein of *Staphylococcus aureus* Binds Specifically to the C5a and Formylated Peptide Receptor," *J. Immunol.* 172:6994-7001.
Ricklin, D. et al. (Nov. 2007; e-pub. Nov. 7, 2007). "Complement-Targeted Therapeutics," *Nat. Biotechnol.* 25(11):1265-1275.
Schluederberg, S.A. et al. (Feb. 21, 1980). "Recovery Frequency of Phages λ and M13 from Human and Animal Faeces," *Nature* 283:792-794.

Shaw, D.M. et al. (2002). "Glycosylation and Epitope Mapping of the 5T4 Glycoprotein Oncofoetal Antigen," *Biochem. J.* 363:137-145.

Smith, G.P. et al. (1997). "Phage Display," *Chem. Rev.* 97(2):391-410.

Southern, E.M. (1975). "Detection of Specific Sequences Among DNA Fragments Separated by Gel Electrophoresis," *J. Mol. Biol.* 98:503-517.

Stemmer, W.P.C. (Aug. 4, 1994). "Rapid Evolution of a Protein in Vitro by DNA Shuffling," *Nature* 370:389-391.

Stemmer, W.P.C. (Oct. 1994). "DNA Shuffling by Random Fragmentation and Reassembly: In Vitro Recombination for Molecular Evolution," *Proc. Natl. Acad. Sci. USA* 91:10747-10751.

Van Epps, D.E. et al. (Jan. 1, 1993). "Relationship of C5a Receptor Modulation to the Functional Responsiveness of Human Polymorphonuclear Leukocytes to C5a," *J. Immunol.* 150(1):246-252.

Veldkamp, K.E. et al. (1997). "*Staphylococcal* Culture Supernates Stimulate Human Phagocytes," *Inflammation* 21 (5):541-551.

Veldkamp, K.E. et al. (Oct. 2000). "Modulation of Neutrophil Chemokine Recpetors by *Staphylococcus aureus* Supernate," *Infect. Immun.* 68(10):5908-5913.

Wong, T.S. et al. (2007). "Steering Directed Protein Evolution: Strategies to Manage Combinatorial Complexity of Mutant Libraries," *Environ. Microbiol.* 9(11):2645-2659.

World Medical Organization. (Dec. 7, 1996). "Declaration of Helsinki (1964)," *Brit. Med. J.* 313(7070):1448-1449, located at <http://www.cirp.org/library/ethics/helsinki/>, lasted visited on Mar. 10, 2009, four pages.

Wu, X-C. et al. (Mar. 1998). "Engineering of Plasmin-Resistant Forms of Streptokinase and Their Production in *Bacillus subtilis*: Streptokinase with Longer Functional Half-Life," *Appl. Environ. Microbiol.* 64(3):824-829.

Yang, W-J. et al. (2005; e-pub. Jul. 1, 2005). "Epitope Mapping of *Mycoplasma hyopneumoniae* Using Phage Displayed Peptide Libraries and the Immune Responses of the Selected Phagotopes," *J. Immunol. Methods* 304:15-29.

Yuan, L. et al. (Sep. 2005). "Laboratory-Directed Protein Evolution," *Microbiol. Mol. Biol. Rev.* 69(3):373-392.

Zhao, H. et al. (Mar. 1998). "Molecular Evolution by Staggered Extension Process (StEP) In Vitro Recombination," *Nat. Biotechnol.* 16:258-261.

Zhao, H. (Oct. 1, 2007). "Directed Evolution of Novel Protein Functions," *Biotechnol. Bioeng.* 98(2):313-317.

\* cited by examiner

POLYPEPTIDES AND USE THEREOF

CROSS-REFERENCE TO RELATED APPLICATIONS

This application is a National Phase application under 35 U.S.C. §371 of International Application No. PCT/GB2007/001443 filed Apr. 20, 2007 and claims the benefit of Great Britain Application No. 0607798.6 filed Apr. 20, 2006, the disclosures of which are incorporated herein by reference in their entirety.

FIELD OF INVENTION

The present invention relates to novel polypeptides and their use in the treatment of conditions and diseases associated with activation of complement C5a receptors and/or formylated peptide receptors. In particular, the invention provides variant forms of the Chemotaxis Inhibitory Protein of *Staphylococcus aureus* ('CHIPS') and uses of the same in the treatment of acute and chronic inflammatory disorders.

INTRODUCTION

*Staphylococcus aureus* is a common human pathogen causing a variety of diseases. The mechanisms by which *S. aureus* causes disease are multi-factorial. With the exception of some staphylococcal diseases caused by specific toxins like Toxic Shock Syndrome Toxin (TSST-1), responsible for Toxic Shock syndrome, or enterotoxin, the pathogenicity of *S. aureus* infections does not depend on a single factor. *S. aureus* possesses a large variety of different 'tools' to cause disease. It is the whole complex of these different factors acting together in facilitating the colonisation, growth and spread within the host. Phagocytosis and killing of staphylococci by phagocytes is the most important host defence mechanism. Phagocytes are attracted to the site of infections by cytokines and chemokines released by the invader (like formylated peptides) and upon activation of inflammatory cascades like the complement system. The release of these chemoattractants creates a gradient by which the phagocytes are attracted to the site of inflammation.

The interaction of the supernate of growing *S. aureus* with phagocytes was studied by Veldkamp et al. They found that although staphylococcal supernate was able to stimulate phagocytes there also was a factor present that could specifically downregulate the expression of the complement C5a receptor (C5aR) and formylated peptide receptor (FPR) as detected by monoclonal antibodies (see Veldkamp et al., 2000, *Infect Immun* 68(10):5908-13; Veldkamp et al., 1997, *Inflammation* 21(5):541-51). From the supernate of *S. aureus* they isolated a 14.1 kDa protein responsible for this action; this protein was named CHIPS, CHemotaxis Inhibitory Protein of *Staphylococcus aureus*. CHIPS is able to inhibit neutrophil chemotaxis and activation with C5a and fMLP. Furthermore, CHIPS was found to be very selective, since it did not affect a broad selection of other receptors, including other chemoattractant receptors present on neutrophils, like the FPR-like 1, C3aR, IL-8RA and IL-8RB, LTB4 receptor, and PAF receptor. This indicates that CHIPS specifically inhibits two members of the G-protein coupled receptor family, the C5aR and the FPR. CHIPS is not toxic for the cells and also inhibits C5aR on other cells like monocytes and mast cells.

Postma et al. showed that CHIPS binds directly to both the C5aR and FPR in an energy independent way. Furthermore, CHIPS is not internalised upon binding to its receptors. CHIPS binds both receptors with apparent Kd values of 1.1 and 35.4 nM for the C5aR and FPR, respectively (see Postma et al., 2004, *J Immunol* 172(11):6994-7001). These Kd values are in the same range as those described for their natural ligands (see Van Epps et al., 1993, *J Immunol* 150(1):246-252; Falk et al., 1982, *Infect Immun* 36(2):450-454; Huey & Hugh, 1985, *Immunol.* 135(3):2063-8; Pike et al., 1980, *J Exp Med* 152(1):31-40). The active site in CHIPS for binding the formylated peptide receptor and C5a receptor are located within distinct regions of the CHIPS molecule. The N-terminal and C-terminal end and particularly the first and third amino acids are involved in the CHIPS activity towards the formylated peptide receptor (see Haas et al., 2004, *J Immunol* 173(9):5704-11). At least the first thirty N-terminal amino acids do not play a role in CHIPS binding and blocking the C5aR. Therefore, a CHIPS protein without the first 30 amino acids, $CHIPS_{31-121}$, shows a complete preservation of C5aR blocking activity but completely lost the activity towards the FPR (see Haas et al., 2005, *J Mol Biol* 353(4):859-872).

Over the last couple of years it has become clear that, next to host defence, chemokine receptors, like the FPR and C5aR, are also involved in a variety of other inflammatory processes. The recent identification of a variety of novel and host-derived agonists for the FPR has broadened the spectrum of functional significance of the FPR in disease processes (see Le et al., 2002, *Trends Immunol* 23(11):541-8). A lot of research has been done on the evident role of the C5aR in a wide range of different disease processes including; sepsis, ischemia-reperfusion injury, rheumatoid arthritis, asthma and immune complex disease. Various experimental studies with animal models demonstrated the beneficial effects of targeting the C5aR in these disease processes (see Guo et al., 2004, *Shock* 21(1):1-7; Huber-Lang et al., 2001, *J Immunol* 166(2):1193-1199; Heller et al., 1999, *J Immunol* 163(2):985-94). The unique properties of CHIPS to specifically inhibit the FPR and C5aR make this protein a promising candidate anti-inflammatory drug in those diseases in which FPR or C5aR stimulation play an important role.

Experiments with isolated human and mouse neutrophils show that the activity of CHIPS for the mouse C5aR is at least 30 times lower than for the human receptor. The human specificity of CHIPS as shown by this 30-fold difference in activity toward human cells as compared to mouse cells hampers testing of CHIPS in a mouse infection model or other animal models.

*S. aureus* is a normal commensal of the human skin and minor skin or wound infections caused by *S. aureus* are normally self-limiting. *S. aureus* can potentially infect any tissue of the body and occasionally spreads from the primary site of infection to cause life-threatening diseases like osteomyelitis, endocarditis, pneumonia, and septicaemia. The CHIPS gene is present in the majority of clinical *S. aureus* strains and strains from healthy carriers and CHIPS is produced in vivo as described by de Haas et al., using a mouse infection model (see Haas et al., 2004, *J Exp Med* 199(5):687-95). Since *S. aureus* is a very common bacterium, it is likely that most individuals encounter *S. aureus* and the CHIPS protein early in life, leading to the production of anti CHIPS antibodies.

The present invention seeks to provide medicaments based on novel variant forms of the CHIPS protein, which exhibit improved properties.

SUMMARY OF INVENTION

A first aspect of the invention provides a polypeptide having a biological activity of the Chemotaxis Inhibitory Protein of *Staphylococcus auras* ('CHIPS'), the polypeptide comprising a variant of the amino acid sequence of SEQ ID NO:1.

The amino acid sequence of the wildtype CHIPS protein is shown below:

```
                                              SEQ ID NO: 1
FTFEPFPTNEEIESNKKMLEKEKAYKESFKNSGLPTTLGKLDERLRNY

LKKGTKNSAQFEKMVILTENKGYYTVYLNTPLAEDRKNVELLGKMYKT

YFFKKGESKSSYVINGPGKTNEYAY
```

The amino acid sequence of the wildtype CHIPS protein is also disclosed in Database Accessions Nos. AAQ14339, CAG41022 and YP_041409.

By "variant" we mean that the polypeptide does not share 100% amino acid sequence identity with the wildtype CHIPS protein, i.e. the amino acids of the wildtype CHIPS protein must be modified. For example, the polypeptide may comprise an amino acid sequence with at least 60% identity to the amino acid sequence of SEQ ID NO: 1, more preferably at least 70% or 80% or 85% or 90% identity to said sequence, and most preferably at least 95%, 96%, 97%, 98% or 99% identity to said amino acid sequence.

Percent identity can be determined by methods well known in the art, for example using the LALIGN program (Huang and Miller, *Adv. Appl. Math.* (1991) 12:337-357) at the Expasy facility (www.ch.Embnet.org/software/LALIGN_form) using as parameters the global alignment option, scoring matrix BLOSUM62, opening gap penalty −14, extending gap penalty −4.

Alternatively, the percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally.

In one embodiment, the variant comprises a modification at one or more amino acids exposed at the polypeptide surface. Surface exposed amino acids may be determined using techniques well known in the art (see Example E). However, it will be appreciated that modification of a non-exposed amino acid may also result in a structural change at the surface of the variant polypeptide (relative to the wildtype CHIPS protein).

In a further embodiment, one or more of the following amino acids within the wildtype CHIPS protein is modified: N31, S32, G33, L34, P35, K40, D42, R46, Y48, K50, G52, T53, K54, N55, S56, A57, Q58, K61, E67, K69, L76, N77, P79, D83, L90, K92, K100, K101, S104, K105, S107, Y108, N111 and G112.

By "modified" we mean that the amino acid at the specified position is altered compared to the natural amino acid in the wildtype CHIPS protein. For example, the amino acid at the specified position may be non-natural, deleted, or substituted or may be the site of an insertion/addition of one or more amino acids.

The amino acid molecules may also be modified in other ways, for example by chemical modification Thus, the polypeptides of the present invention may be composed of amino acids joined to each other by peptide bonds or modified peptide bonds, e.g. peptide esters, and contain amino acids other than the 20 gene-encoded amino acids. For example, the polypeptides may contain L-amino acids and/or D-amino acids, as well as modified amino acids such as hydroxyproline, γ-carboxy glutamate, O-phosphoserine and O-phosphotyrosine. The polypeptides may be modified by natural processes, such as post-translational modification, or by chemical modification techniques well known in the art. Modifications can occur anywhere within the amino acid sequence of the variant CHIPS polypeptide, including the peptide backbone, the amino acid side chains and the amino- or carboxy-termini.

In one embodiment, however, the polypeptides of the present invention comprise or consist of natural L-amino acids.

Modified or variant forms of a known polypeptide can be produced using techniques well known in the art (see Sambrook & Russell, 2000, *Molecular Cloning, A Laboratory Manual*, Third Edition, Cold Spring Harbor, N.Y., which is incorporated herein by reference). For example, point mutations may be introduced at specific amino acid residues by site-directed mutagenesis (see Sambrook & Russell, supra, Chapter 13). Additional methods for generating variants of a parent polynucleotide are described below.

As used herein, "biological activity" refers to an effect of the wildtype CHIPS protein upon a living organism, tissue or cell. Included herein, but not limited to, is binding to its natural ligand(s), as well as down-stream events therefrom, causing direct or indirect effects on a living organism. Thus, by "a biological activity" of the CHIPS protein we include inhibition of the chemotaxis and/or activation of neutrophils induced by the complement component C5a and/or the N-formyl-peptide, fMLP. For example, the maintained activity may comprise antagonism of the C5a receptor (C5aR) and/or antagonism of the formylated peptide receptor (FPR).

In one embodiment, however, the variant CHIPS polypeptide of the present invention lacks the FPR binding site.

In a further embodiment, the polypeptide of the invention exhibits one or more biological activities of the CHIPS protein in vivo.

Assays for determining the biological activities and binding properties of the wildtype CHIPS protein and variants thereof are well known in the art (see Examples).

Of course, it will be appreciated by persons skilled in the art that the polypeptide of the first aspect of the invention may exhibit the biological activity at a level which is less than, the same as or greater than the level exhibited by the wildtype CHIPS protein. Preferably, the polypeptide of the invention exhibits the biological activity at a level of at least 10% of the level exhibited by the wildtype CHIPS protein, for example at least 20%, 30%, 40%, 50%, 60%, 70%, 80%, 90%, 100% or more. More preferably, the polypeptide of the invention exhibits the biological activity at the same level or more compared to the biological activity exhibited by the wildtype CHIPS protein. Most preferably, the polypeptide of the invention exhibits the biological activity at a greater level (i.e. is more active) than the wildtype CHIPS protein. For example, the polypeptide of the invention may exhibit the biological activity at a level of at least 110% of the level exhibited by the wildtype CHIPS protein, for example at least 120%, 130%, 140%, 150%, 160%, 170%, 180%, 190%, 200%, 250%, 300%, 500% or more.

In a further embodiment, the polypeptide of the invention has a specific binding activity for the C5aR and/or FPR which is equal to or greater than the corresponding activity exhibited by the wildtype CHIPS protein.

Thus, the polypeptide of the invention exhibits only biological activities of the CHIPS protein, i.e. the activity of the polypeptide is selective. For example, the polypeptide of the invention may inhibit the chemotaxis and/or activation of neutrophils induced by the complement component C5a and/or the by the N-formyl-peptide, fMLP selectively. By 'selective' we mean that the polypeptide inhibits said biological activity to a greater extent than it modulates the activity of other proteins in the cells. Thus, the polypeptide preferably inhibits only the biological activity of the wildtype CHIPS protein, although it will be appreciated that the expression and activity of other proteins within cells may change as a downstream consequence of a selective inhibition. Thus, we exclude agents which have a non-specific effect on cellular processes.

In a still further embodiment of the first aspect of the invention, the polypeptide is a variant of the wildtype CHIPS protein wherein one or more surface epitopes is modified. Such modifications can either be direct (i.e. modification of an amino acid within the epitope itself) or indirect (i.e. modification of an amino acid which is not in an epitope but, when modified, leads in the modification of an amino acid within the epitope or the structure of such an epitope).

By "surface epitope" we mean a conformation of exposed amino acid residues at the surface of the wildtype CHIPS protein which is recognised by anti-CHIPS antibodies produced in response to a challenge with the CHIPS antigen and/or by antibodies produced in response to a challenge with S. aureus.

For example, the surface epitope may be selected from the following group of epitopes:
Linear Surface Epitope:

|  | Epitope | | | | |
| --- | --- | --- | --- | --- | --- |
|  | N68 | K69 | G70 | Y71 | Y72 |
| Exemplary mutations | A, H | A, Q | — | A, S | — |

Conformational Surface Epitopes:

| Epitope | N55 | K100 | T53 | S107 | Y108 | |
| --- | --- | --- | --- | --- | --- | --- |
| Exemplary mutations | K | A, N | G | — | — | |
| Epitope | N111 | K95 | Y94 | Y97 | Y71 | |
| Exemplary mutations | K | A, S | H | K, S | A, S, K | |
| Epitope | N55 | K54 | T53 | Y108 | | |
| Exemplary mutations | K | E | G | — | | |
| Epitope | N55 | K100 | S107 | S108 | Y48 | G52 |
| Exemplary mutations | K | A, N | D, N | — | — | — |
| Epitope | N111 | K95 | Y94 | Y97 | Y71 | |
| Exemplary mutations | K | A, S | H | K, S | A, S, K | |
| Epitope | Q58 | K100 | S107 | Y108 | | |
| Exemplary mutations | K | A, N | D N | — | | |
| Epitope | K69 | L90 | P35 | K92 | E67 | |
| Exemplary mutations | A, Q | E, K | A | E | K | |
| Epitope | G39 | K40 | L34 | P35 | K92 | E67 |
| Exemplary mutations | — | E | S | A | E | K |
| Epitope | P79 | L76 | R46 | A57 | S56 | Q58 |
| Exemplary mutations | E K | — | — | D N | G | K |
| Epitope | G35 | L34 | K92 | G33 | S32 | N31 |
| Exemplary mutations | A | S | E | S | K | K |

For the avoidance of doubt, the above exemplary mutations are non-limiting.

It will be appreciated that the above list of epitopes is not necessarily exhaustive; other epitopes may exist on the surface of the wildtype CHIPS protein. For example, the following amino acid may form part of one or more additional surface epitopes:
N31, S32, G33, K50, K61, S104, N111 and G112;
N55, K100, S107, S108;
K69, L34, P35, K92 and E67; and
K69, L34, L90, P35, K92 and E67.

It will be further appreciated by skilled persons that the 'parental' CHIPS polypeptide, in which one or more of the above surface epitopes is mutated, may be the wildtype CHIPS sequence of SEQ ID NO: 1, or a fragment or variant thereof (for example, amino acids 1 to 112, amino acids 1 to 114 or amino acids 31 to 113 of SEQ ID NO: 1).

In another embodiment of the first aspect of the invention, the polypeptide comprises an amino acid substitution relative to SEQ ID NO: 1 at one or more of the following amino acids: N31, S32, G33, L34, P35, K40, D42, R46, Y48, K50, G52, T53, K54, N55, S56, A57, Q58, K61, E67, K69, L76, N77, P79, D83, L90, K92, K100, K101, S104, K105, S107, Y108, N111 and G112.

It will be appreciated by persons skilled in the art that the substitutions may be conservative or non-conservative. By "conservative substitutions" is intended combinations such as Gly, Ala; Val, Ile, Leu; Asp, Glu; Asn, Gln; Ser, Thr; Lys, Arg; and Phe, Tyr.

For example, the polypeptide may comprise one or more of the following amino acid mutations relative to the wildtype sequence:
N31A, S32A, G33A, L34A, P35A, Y48A, Y48H, K50N, G52A, T53A, N55A, S56A, K61A, K69A, P79A, L90A, L90P, K92R, K100R, S104Y, S107A, Y108, N111I, N111K and G112V.

In a particular embodiment of the first aspect of the invention, the polypeptide is less immunogenic in humans than the wildtype CHIPS protein.

By "immunogenic" we mean that the ability of the polypeptide to induce an immune response (i.e. production of anti-polypeptide antibodies) in the host organism. Preferably, the polypeptide is less immunogenic than the wildtype CHIPS protein in humans.

Immunogenicity may be determined by methods well known in the art. For example, rabbits or other animal species (such as mice, rats, guinea pigs, dogs, etc.) may be immunised with the polypeptide of the invention and the formation of immuno-complexes determined. Ideally, immune responses are studied in several different species, in order to exclude species-specific effects. One suitable method for assessing likely immunogenicity in humans involves purifying human anti-CHIPS IgG and determining the affinity of the variant polypeptide for such antibodies, e.g. using ELISA (see Examples below).

In a further embodiment, the polypeptide of the invention is capable of inhibiting C5a-induced activation of neutrophils and inhibiting fMLP-induced activation of neutrophils. Such inhibition may be partial or complete. Thus, the C5a-induced activation of neutrophils and/or fMLP-induced activation of neutrophils may be inhibited in response to the polypeptide of the invention by at least 10%, for example at least 20%, 30%, 40%, 50%, 60%, 70%, 80%, 90%, 95% and preferably by 100% compared to activation in the absence of the polypeptide.

The wildtype CHIPS protein contains 121 amino acids (following cleavage of a 28-amino acid signal peptide from the chb gene product). However, it will be appreciated by persons skilled in the art that the polypeptides of the invention may be of any length. For example, the polypeptides may comprise or consist of more or less than 121 amino acids, or may comprise or consist of 121 amino acids exactly. Preferably, the polypeptide is fewer than 500 amino acids in length, for example fewer than 400, 300, 200, 150, 140, 130, 125, 121, 120, 119, 118, 117, 116, 115, 114, 113, 112, 111, 110, 109, 108, 107, 106, 105, 104, 103, 102, 101, 100, 95, 90, 85, 80, 75, 70, 65, 60, 55, 50, 40, 30 or fewer amino acids in length.

For example, the polypeptide may be between 110 and 130 amino acids in length, for example between 110 and 120 amino acids in length, e.g. 111, 112, 113, 114, 115, 116, 117, 118 or 119 amino acids. In one embodiment, the polypeptide is 112 amino acids in length.

In a further embodiment of the first aspect of the invention, the polypeptide comprises or consists of a fragment of the amino acid sequence of SEQ ID NO:1, or variant thereof.

By "fragment" we include at least 10, 20, 30, 40, 50, 60, 70, 80, 90, 100, 105, 110, 111, 112, 113, 114, 115, 116, 117, 118, 119 or 120 contiguous amino acids of the amino acid sequence of SEQ ID NO:1. For example, the polypeptide may comprise or consist of a variant sequence of amino acids 1 to 114, amino acids 31 to 112, amino acids 31 to 113 or amino acids 31 to 121 of the amino acid sequence of SEQ ID NO:1.

In an exemplary embodiment of the first aspect of the invention, the polypeptide comprises or consists of amino acids 1 to 112 of SEQ ID NO:1 having the following modifications, or a combination of said modifications:
(a) K40E, K69A, N111K and G112V;
(b) G112V;
(c) K54R, K69R, K100R and K105R;
(d) K40N and K92R;
(e) S104Y and N111I;
(f) K69A and G112V;
(g) K69T;
(h) Y48H, D83G and L90P;
(i) K50N;
(j) K69A, K100R and K101R;
(k) K69A;
(l) N31A;
(m) S32A;
(n) G33A;
(o) L34A;
(p) P35A;
(q) Y48A;
(r) G52A;
(s) T53A;
(t) N55A;
(u) S56A;
(v) E67A;
(w) P79A;
(x) L90A;
(y) S107A; and
(z) Y108A.

In a further embodiment, the polypeptide comprises or consists of one or more additional amino acids, inserted at either the N- or C-termini or internally within the amino acid sequence of SEQ ID NO:1. For example, the polypeptide may comprises or consist of at least 2, 3, 4, 5, 6, 7, 8, 9, 10, 15 or 20 additional amino acids. Advantageously, the additional amino acids are located at the C-terminus of the amino acid sequence of SEQ ID NO:1.

One example of such an embodiment of the invention is a polypeptide comprising or consisting of amino acids 1 to 112 of SEQ ID NO:1 having the following modifications:
K40E, K69A, N111K and G112V In a further embodiment, the polypeptide of the invention comprises one or more of the following amino acid mutations relative to the wildtype sequence (i.e. SEQ ID NO: 1):
K40, D42, K50, K69, N77, D83, L90, K92, K100, K105, N111 and G112.

For example, the polypeptide may comprise or consist of one or more of the following amino acid mutations relative to the wildtype sequence:
K40E, K40N, D42V, K50N, K69R, N77Y, D83G, L90P, K92R, K100R, K105R, N111K, N111I and G112V.

Thus, the polypeptide may be selected from the group consisting of polypeptides consisting of amino acids 1 to 112 of SEQ ID NO:1 having the following modifications, and combinations thereof:
(a) K50N, K69R, N77Y, K92R, N111K and G112V;
(b) K40E, D42V, N77Y, K100R, K105R, N111K and G112V;
(c) K50N, N77Y, K92R, N111K and G112V;
(d) K40E, D42V, N77Y, N111K and G112V;
(e) K40E, D42V, N77Y, K92R, N111K and 0112V;
(f) K50N, N77Y, N111K and G112V;
(g) K40E, D42V, K50N, N77Y, K92R, N111K and 0112V;
(h) K40N, K50N, N77Y, K92R and N111I;
(i) K40N, N77Y, D83G, L90P, N111K and G112V; and
(j) K50N, N77Y, K92R, K100R and N111I.

In an alternative embodiment, the polypeptides defined in (a) to (j) above may comprise two additional amino acids at the C terminus, for example 'R' at amino acid position 113 and 'S' at amino acid position 114.

Polypeptides of the invention may be made by methods well known to persons skilled in the art (for example, see Sambrook & Russell, 2000, *Molecular Cloning, A Laboratory Manual*, Third Edition, Cold Spring Harbor, N.Y., which is incorporated herein by reference).

In brief, expression vectors may be constructed comprising a nucleic acid molecule which is capable, in an appropriate host, of expressing the polypeptide encoded by the nucleic acid molecule.

A variety of methods have been developed to operably link nucleic acid molecules, especially DNA, to vectors, for example, via complementary cohesive termini. For instance, complementary homopolymer tracts can be added to the DNA segment to be inserted into the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, e.g. generated by endonuclease restriction digestion, is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerising activities.

The combination of these activities therefore generates blunt-ended DNA segments. The blunt-ended segments are then incubated with a larger molar excess of linker molecules in the presence of an enzyme that is able to catalyse the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease site are commercially available from a number of sources including International Biotechnologies Inc., New Haven, Conn., USA.

A desirable way to modify the DNA encoding the polypeptide of the invention is to use PCR. This method may be used for introducing the DNA into a suitable vector, for example by engineering in suitable restriction sites, or it may be used to modify the DNA in other useful ways as is known in the art.

In this method the DNA to be enzymatically amplified is flanked by two specific primers which themselves become incorporated into the amplified DNA. The said specific primers may contain restriction endonuclease recognition sites which can be used for cloning into expression vectors using methods known in the art.

The DNA (or in the case of retroviral vectors, RNA) is then expressed in a suitable host to produce a polypeptide comprising the compound of the invention. Thus, the DNA encoding the polypeptide may be used in accordance with known techniques, appropriately modified in view of the teachings contained herein, to construct an expression vector, which is then used to transform an appropriate host cell for the expression and production of the compound of the invention. Such techniques include those disclosed in U.S. Pat. No. 4,440,859 issued 3 Apr. 1984 to Rutter et al, U.S. Pat. No. 4,530,901 issued 23 Jul. 1985 to Weissman, U.S. Pat. No. 4,582,800 issued 15 Apr. 1986 to Crowl, U.S. Pat. No. 4,677,063 issued 30 Jun. 1987 to Mark et al, U.S. Pat. No. 4,678,751 issued 7 Jul. 1987 to Goeddel, U.S. Pat. No. 4,704,362 issued 3 Nov. 1987 to Itakura et al, U.S. Pat. No. 4,710,463 issued 1 Dec. 1987 to Murray, U.S. Pat. No. 4,757,006 issued 12 Jul. 1988 to Toole, Jr. et al, U.S. Pat. No. 4,766,075 issued 23 Aug. 1988 to Goeddel et al and U.S. Pat. No. 4,810,648 issued 7 Mar. 1989 to Stalker (which is incorporated herein by reference).

The DNA (or in the case or retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the expression vector of the invention are then cultured for a sufficient time and under appropriate conditions known to those skilled in the art in view of the teachings disclosed herein to permit the expression of the polypeptide, which can then be recovered.

Many expression systems are known, including bacteria (for example, *E. coli* and *Bacillus subtilis*), yeasts (for example *Saccharomyces cerevisiae*), filamentous fungi (for example *Aspergillus*), plant cells, animal cells and insect cells.

The vectors typically include a prokaryotic replicon, such as the ColE1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA. Particularly preferred prokaryotic vector plasmids include pRSET and pHIP (Invitrogen, California, USA).

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps).

Other vectors and expression systems are well known in the art for use with a variety of host cells.

The host cell can be either prokaryotic or eukaryotic. Bacterial cells are preferred prokaryotic host cells and typically are a strain of *E. coli* such as, for example, the *E. coli* strains DH5 available from Bethesda Research Laboratories Inc., Bethesda, Md., USA, and RR1 available from the American Type Culture Collection (ATCC) of 10801 University Boulevard, Manassas, Va. 20110-2209 USA (No. ATCC 31343). Preferred eukaryotic host cells include yeast, insect and mammalian cells, preferably vertebrate cells such as those from a mouse, rat, monkey or human fibroblastic and kidney cell lines. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CRL 1658, 293 cells which are human embryonic kidney cells, and NS0 cells. Preferred insect cells are Sf9 cells which can be transfected with baculovirus expression vectors.

Transformation of appropriate cell hosts with a DNA construct of the present invention is accomplished by well known methods that typically depend on the type of vector used. With regard to transformation of prokaryotic host cells, see, for example, Cohen et al (1972) *Proc. Natl. Acad. Sci. USA* 69, 2110 and Sambrook et al (1989) *Molecular Cloning, A Laboratory Manual*, Cold Spring Harbor Laboratory, Cold Spring Harbor, N.Y. Transformation of yeast cells is described in Sherman et al (1986) *Methods In Yeast Genetics, A Laboratory Manual*, Cold Spring Harbor, N.Y. The method of Beggs (1978) *Nature* 275, 104-109 is also useful. With regard to vertebrate cells, reagents useful in transfecting such cells, for example calcium phosphate and DEAF-dextran or liposome formulations, are available from Stratagene Cloning Systems, or Life Technologies Inc., Gaithersburg, Md. 20877, USA.

Electroporation is also useful for transforming and/or transfecting cells and is well known in the art for transforming yeast cells, bacterial cells, insect cells and vertebrate cells.

For example, many bacterial species may be transformed by the methods described in Luchansky et al (1988) *Mol. Microbiol.* 2, 637-646 incorporated herein by reference. The greatest number of transformants is consistently recovered following electroporation of the DNA-cell mixture suspended in 2.5 PEB using 6250V per cm at 25 µFD.

Methods for transformation of yeast by electroporation are disclosed in Becker & Guarente (1990) *Methods Enzymol.* 194, 182.

Successfully transformed cells, i.e. cells that contain a DNA construct of the present invention, can be identified by well-known techniques. For example, cells resulting from the introduction of an expression construct of the present invention can be grown to produce the polypeptide of the invention. Cells can be harvested and lysed and their DNA content examined for the presence of the DNA using a method such as that described by Southern (1975) *J. Mol. Biol.* 98, 503 or Berent et al (1985) *Biotech.* 3, 208. Alternatively, the presence of the protein in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity.

Samples of cells suspected of being transformed are harvested and assayed for the protein using suitable antibodies.

The host cell may be a host cell within a non-human animal body. Thus, transgenic non-human animals which express a compound according to the first aspect of the invention (or a binding moiety thereof) by virtue of the presence of the transgene are included. Preferably, the transgenic non-human animal is a rodent such as a mouse. Transgenic non-human animals can be made using methods well known in the art.

Methods of cultivating host cells and isolating recombinant proteins are well known in the art. It will be appreciated that, depending on the host cell, the compounds of the invention (or binding moieties thereof) produced may differ. For example, certain host cells, such as yeast or bacterial cells, either do not have, or have different, post-translational modification systems which may result in the production of forms of compounds of the invention (or binding moieties thereof) which may be post-translationally modified in a different way.

It is preferred that compounds of the invention (or binding moieties thereof) are produced in a eukaryotic system, such as a mammalian cell.

According to a less preferred embodiment, the compounds of the invention (or binding moieties thereof) can be produced in vitro using a commercially available in vitro translation system, such as rabbit reticulocyte lysate or wheatgerm lysate (available from Promega). Preferably, the translation system is rabbit reticulocyte lysate. Conveniently, the translation system may be coupled to a transcription system, such as the TNT transcription-translation system (Promega). This system has the advantage of producing suitable mRNA transcript from an encoding DNA polynucleotide in the same reaction as the translation.

Thus, a second aspect of the invention provides a nucleic acid molecule encoding a polypeptide according to the first aspect of the invention. In one embodiment, the nucleic acid molecule is a DNA molecule. Advantageously, the nucleic acid molecule further comprises a signal peptide recognisable by the host cell in which the polypeptide of the invention is expressed.

A third aspect of the invention provides a vector comprising a nucleic acid molecule according to the second aspect of the invention. In one embodiment, the vector is an expression vector (such as pRSET and pHIP).

A fourth aspect of the invention provides a host cell comprising a nucleic acid molecule according to the second aspect of the invention or a vector according to the third aspect of the invention.

In one embodiment, the host cell is an *E. coli* cell.

A fifth aspect of the invention provides a method for producing a polypeptide according to the first aspect of the invention comprising culturing a population of host cells comprising a nucleic acid molecule according to the second aspect of the invention or a vector according to the third aspect of the invention under conditions in which the polypeptide is expressed, and isolating the polypeptide therefrom. By "isolating" the expressed polypeptide we include removing some or all impurities from the culture medium, such as cell debris. In one embodiment, the polypeptide is substantially pure.

It will be appreciated by persons skilled in the art that the polypeptides of the invention are preferably provided in the form of a pharmaceutical composition comprising the compound and a pharmaceutically acceptable carrier. Thus, a sixth aspect of the invention provides a pharmacological composition comprising a polypeptide according to the first aspect of the invention.

By "pharmaceutically acceptable" is included that the formulation is sterile and pyrogen free. Suitable pharmaceutical carriers are well known in the art of pharmacy. The carrier(s) must be "acceptable" in the sense of being compatible with the compound of the invention and not deleterious to the recipients thereof. Typically, the carriers will be water or saline which will be sterile and pyrogen free; however, other acceptable carriers may be used. Thus, "pharmaceutically acceptable carrier" and "pharmaceutically acceptable excipient" includes any compound(s) used in forming a part of the formulation that is intended to act merely as a carrier, i.e., not intended to have biological activity itself. The pharmaceutically acceptable carrier or excipient is generally safe, non-toxic, and neither biologically nor otherwise undesirable. A pharmaceutically acceptable carrier or excipient as used herein includes both one and more than one such carrier or excipient.

The polypeptides of the invention can be formulated at various concentrations, depending on the efficacy/toxicity of the compound being used. Preferably, the formulation comprises the agent of the invention at a concentration of between 0.1 µM and 1 mM, more preferably between 1 µM and 100 µM, between 5 µM and 50 µM, between 10 µM and 50 µM, between 20 µM and 40 µM and most preferably about 30 µM. For in vitro applications, formulations may comprise a lower concentration of a compound of the invention, for example between 0.0025 µM and 1 µM.

It will be appreciated by persons skilled in the art that the medicaments and agents (i.e. polypeptides) will generally be administered in admixture with a suitable pharmaceutical excipient diluent or carrier selected with regard to the intended route of administration and standard pharmaceutical practice (for example, see *Remington: The Science and Practice of Pharmacy,* 19$^{th}$ edition, 1995, Ed. Alfonso Gennaro, Mack Publishing Company, Pennsylvania, USA, which is incorporated herein by reference).

For example, the medicaments and agents can be administered orally, buccally or sublingually in the form of tablets, capsules, ovules, elixirs, solutions or suspensions, which may contain flavouring or colouring agents, for immediate-, delayed- or controlled-release applications. The medicaments and agents may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The medicaments and agents of the invention can also be administered parenterally, for example, intravenously, intra-articularly, intra-arterially, intraperitoneally, intra-thecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of the medicaments and agents will usually be from 1 to 1000 mg per adult (i.e. from about 0.015 to 15 mg/kg), administered in single or divided doses.

The medicaments and agents can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoro-methane, dichlorotetrafluoroethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or 'puff' contains at least 1 mg of a compound of the invention for delivery to the patient. It will be appreciated that the overall daily dose with an aerosol will vary from patient to patient, and may be administered in a single dose or, more usually, in divided doses throughout the day.

Alternatively, the medicaments and agents can be administered in the form of a suppository or pessary, or they may be applied topically in the form of a lotion, solution, cream, ointment or dusting powder. The compounds of the invention may also be transdermally administered, for example, by the use of a skin patch. They may also be administered by the ocular route.

For application topically to the skin, the medicaments and agents can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Where the medicament or agent is a polypeptide, it may be preferable to use a sustained-release drag delivery system, such as a microsphere. These are designed specifically to reduce the frequency of injections. An example of such a system is Nutropin Depot which encapsulates recombinant human growth hormone (rhGH) in biodegradable microspheres that, once injected, release rhGH slowly over a sustained period.

Sustained-release immunoglobulin compositions also include liposomally entrapped immunoglobulin. Liposomes containing the immunoglobulin are prepared by methods known per se. See, for example Epstein et al., *Proc. Natl. Acad. Sci. USA* 82: 3688-92 (1985); Hwang et al., *Proc. Natl. Acad. Sci. USA* 77: 4030-4 (1980); U.S. Pat. Nos. 4,485,045; 4,544,545; 6,139,869; and 6,027,726. Ordinarily, the liposomes are of the small (about 200 to about 800 Angstroms), unilamellar type in which the lipid content is greater than about 30 mole percent (mol. %) cholesterol; the selected proportion being adjusted for the optimal immunoglobulin therapy.

Alternatively, polypeptide medicaments and agents can be administered by a surgically implanted device that releases the drug directly to the required site.

Electroporation therapy (EPT) systems can also be employed for the administration of proteins and polypeptides. A device which delivers a pulsed electric field to cells increases the permeability of the cell membranes to the drug, resulting in a significant enhancement of intracellular drug delivery.

Proteins and polypeptides can also be delivered by electroincorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with drugs or genes or can simply act as "bullets" that generate pores in the skin through which the drugs can enter.

An alternative method of protein and polypeptide delivery is the thereto-sensitive ReGel injectable. Below body temperature, ReGel is an injectable liquid while at body temperature it immediately forms a gel reservoir that slowly erodes and dissolves into known, safe, biodegradable polymers. The active drug is delivered over time as the biopolymers dissolve.

Protein and polypeptide pharmaceuticals can also be delivered orally. One such system employs a natural process for oral uptake of vitamin B12 in the body to co-deliver proteins and polypeptides. By riding the vitamin B12 uptake system, the protein or polypeptide can move through the intestinal wall. Complexes are produced between vitamin B12 analogues and the drug that retain both significant affinity for intrinsic factor (IF) in the vitamin B12 portion of the complex and significant bioactivity of the drug portion of the complex.

Thus, one aspect of the invention provides a polypeptide according to the first aspect of the invention for use in medicine.

A further aspect of the invention provides the use of a polypeptide according to the first aspect of the invention in the preparation of a medicament for inhibiting a biological activity of complement 5a (C5a) and/or the N-formyl-peptide, fMLP.

The anaphylatoxin C5a mediates a wide array of inflammatory responses. Acting on the C5aR it plays an important role in the activation and recruitment of phagocytes and is crucial for an effective clearance of invading microorganisms. In recent years it has become clear that C5a also plays an important role in destructive inflammatory processes like tissue damage and severe inflammatory syndromes that lead to organ failure. Additionally, C5a has also been associated with several other biologic processes that affect normal organ development, early differentiation of various cell lineages, and protection of cells from apoptotic death (see Table 1).

TABLE 1

| C5a-associated biologic processes |
|---|
| Activation of MAPK |
| Angiogenesis |
| Apoptosis |
| Arachidonic acid metabolism |
| Astrocyte activation |
| Basophil activation |
| Blood coagulation |
| Bone remodeling |
| Bone resorption |
| Catecholamine biosynthesis |
| Cell adhesion |
| Cell cycle |
| Cell differentiation |
| Cell growth |
| Cell invasion |
| Cell migration |
| Cyclooxygenase pathway |
| Eicosanoid biosynthesis |
| Endocytosis |
| Endothelial cell activation |
| Eosinophil chemotaxis |
| Exocytosis |
| Fertilization |
| Fibrinolysis |
| Glucose metabolism |
| Glycolysis |
| Hexose transport |
| Hyperphosphorylation |
| Lipid metabolism |

TABLE 1-continued

| C5a-associated biologic processes |
|---|
| Lipoxygenase pathway |
| Lymphocyte activation |
| Lymphocyte chemotaxis |
| Lymphocyte proliferation |
| Macrophage activation |
| Macrophage chemotaxis |
| Macrophage differentiation |
| Mast cell activation |
| Microtubule polymerization |
| Monocyte activation |
| Myelination |
| Neutrophil activation |
| Neutrophil chemotaxis |
| Phospholipase C activation |
| Phospholipid metabolism |
| Platelet activation |
| Protein kinase C activation |
| Regulation of actin polymerization |
| Respiratory burst |
| Smooth muscle contraction |
| Spermatogenesis |
| Superoxide release |
| T-cell proliferation |
| Vasoconstriction |
| Vasodilation |
| Viral entry |
| Wound healing |

The human formyl-peptide-receptor (FPR) and its variants FPRL-1 (FPR-like 1) and FPRL-2 (FPR-like 2) belong to the seven transmembrane domain Gi-protein-coupled receptors. Both receptors are present in high levels on neutrophils and monocytes. The FPR is defined as the high affinity formyl-peptide receptor and FPRL-1 as the low affinity receptor based on its activation only by high concentrations of fMLP. Since the only source of formyl peptides in nature is bacterial and mitochondrial protein synthesis, it is thought that these receptors act as mediators for the recruitment of phagocytes towards a site of bacterial invasion or tissue damage. This is supported by the observation that FPR knockout mice are more susceptible to infection with *Listeria monocytogenes*. Also, dysfunctional FPR alleles are associated with localised juvenile periodontitis.

Over the last years a large number of non-formylated peptide ligands for these receptors have been identified (see Table 2) These ligands originate from different sources including random peptide libraries, endogenous sources and pathogens. Some of them are associated with human diseases including Alzheimer's disease, amyloidosis and prion disease. Therefore, formyl-peptide receptors are a target in the treatment of different inflammatory processes.

TABLE 2

| FPR and FPRL-1 agonists and antagonists | | | |
|---|---|---|---|
| | Origin | Receptor | $EC_{50}$ or $IC_{50}$ |
| Agonists | | | |
| Bacterial peptides | | | |
| fMLF and analogues | Bacteria and mitochondria | FPR | 0.1-1 nM |
| | | FPRL-1 | 1 μM |
| | | mFPR1 | 1 μM |
| | | mFPR2 | 10 μM |
| Hp(2-20) | *Helicobacter pylori* | FPRL1 | 0.3 μM |
| | | FPRL-2 | 10 μM |

TABLE 2-continued

FPR and FPRL-1 agonists and antagonists

| | Origin | Receptor | EC$_{50}$ or IC$_{50}$ |
|---|---|---|---|
| HIV-1 envelope peptides | | | |
| T20 (DP178) | HIV-1$_{LAV}$gp41 (aa643-678) | FPR | 0.5 µM |
| | | mFPR1 | 1 µM |
| | | mFPR-2 | 0.5 µM |
| T21 | HIV-1$_{LAV}$gp41 (aa558-595) | FPR | 0.1 µM |
| | | FPRL-1 | 50 nM |
| N36 | HIV-1$_{LAV}$gp41 (aa546-581) | FPRL-1 | 12.5 µM |
| F peptide | HIV-1$_{Bru}$gp120 (aa414-434) | FPRL1 | 10 µM |
| V3 peptide | HIV-1$_{MN}$gp120 (V3 loop) | FPRL-1 | 2 µM |
| Peptide library derived agonists | | | |
| W-peptide (WKYMVm) | Random peptide library | FPR | 1 nM |
| | | FPRL-1 | 1 pM |
| | | FPRL-2 | 5 nM |
| | | mFPR-1 | 50 nM |
| | | mFPR-2 | 1 nM |
| MMK-1 | Random peptide library | FPRL-1 | 0.5 nM |
| | | mFPR2 | 0.5 nM |
| WKYMVM | Random peptide | FPRL-1 | 2 nM |
| | | FPRL-2 | 80 nM |
| Host-derived agonists | | | |
| MHC binding peptide | NADH dehydrogenase subunit I | FPRL-1 | 0.5 nM |
| LL-37 | hCAP18$_{1-37}$ | FPRL-1 | 1.0 µM |
| Ac1-26 | Annexin(aa1-26) | FPR | 5 µM |
| Ac9-25 | Annexin(aa9-25) | FPR | 10 nM |
| D2D388-274 | uPAR(aa88-274) | FPRL1 | 5 pM |
| LXA4 | Lipid metabolite | FPRL1 | 1.0 nM |
| SAA | Acute phase protein | FPRL-1 | 0.1 µM |
| | | mFPR-2 | 1 µM |
| Aβ$_2$42 | APP(aa1-42) | FPRL-1 | 1 µM |
| | | mFPR-2 | 2 µM |
| PrP$_{106-1262}$ | Prion(aa106-126) | FPRL-1 | 25 µM |
| Antagonists | | | |
| Boc-FLFLF | Synthetic | FPR | 2 µM |
| Cylosporin H | Fungus | FPR | 0.5 µM |
| DCA | Bile acid | FPR | 100 µM |
| CDCA | Bile acid | FPR | 175 µM |
| | | FPRL-1 | 300 µM |
| Spinorphin | Cerebrospinal fluid | FPR | 50 µM |

Thus, the polypeptide is for use in the preparation of a medicament which acts as an antagonist at the C5aR and/or FPR. Conveniently, the polypeptide is capable of binding directly to one or both of these receptors.

In one embodiment, the medicament is for inhibiting, in whole or in part, the function of C5a receptors.

In an alternative embodiment, the medicament is for inhibiting, in whole or in part, the function of formylated peptide receptors.

In a further embodiment, the C5a receptors and/or formylated peptide receptors are located on neutrophils, monocytes and/or endothelial cells.

Thus, the medicament may be for inhibiting the activation of neutrophils induced by complement 5a (C5a) and/or the N-formyl-peptide, fMLP.

In one embodiment, the medicament is for treating inflammation, for example acute or chronic inflammatory reactions.

The terms "treating", and "treatment", and the like are used herein to generally mean obtaining a desired pharmacological and physiological effect. Further, it refers to any process, action, application, therapy, or the like, wherein a mammal, including a human being, is subject to medical aid with the object of improving the mammal's condition, directly or indirectly. Thus, treatment includes both therapeutic and prophylactic use.

In further embodiments, the medicament is for treating a disease or condition selected from the group consisting of acute reactive arthritis, acute transplant rejection, adult respiratory distress syndrome (ARDS), alcoholic hepatitis, allotransplantation, Alzheimer's disease, arteriosclerosis, arthus reaction, asthma, atherosclerosis, atopic dermatitis, bacterial meningitis, bronchogenic carcinoma, bullos pemphigoid, burns, cardiopulmonary bypass, cardiovascular diseases, chronic bronchitis, chronic lymph leukaemia, chronic obstructive pulmonary disease (COPD), contact dermatitis, Crohn's disease, cutaneous T-cell lymphoma, cystic fibrosis, dermatoses, diseases of the central nervous system, endometriosis, experimental allergic encephalomyelitis (EAE), experimental allergic neuritis (EAN), frost bite, gastric carcinoma, gastrointestinal diseases, genitourinary diseases, gout, *Heliobacter pylori* gastritis, haemodialysis, hereditary angioedema, hypersensitive pneumonia, idiopathic pulmonary fibrosis, immune-complex (IC)-induced vasculitis, ischaemic shock, ischaemic reperfusion episodes, ischaemic reperfusion injury, joint diseases, (large) vessel surgery, metal fume fever, multiple sclerosis, multiple system organ failure, myasthenia gravis, myocardial infarction, pancreatitis, peritonitis, pleural emphesema, post-cardiopulmonary bypass (CPB) inflammation, psoriasis, repetitive strain injury (RSI), respiratory diseases, rheumatoid arthritis, sepsis, septic shock, sinusitis, skin diseases, stroke, systemic lupus erythematosis (SLE), transplantation, (traumatic) brain injury, ulcerative colitis, urinary tract infection, vascular leak syndrome, vasculitis and xenotransplantation.

In one embodiment, the medicament is for treating reperfusion injury. For example, the reperfusion injury may be associated with acute myocardial infarction (AMI), a coronary artery bypass graft (CABG), stroke and/or organ transplantation.

In a further embodiment, the medicament is for treating acute respiratory distress syndrome (ARDS).

Thus, the invention further provides a method of treatment of a subject in need of treatment with an inhibitor of a biological activity of complement 5a (C5a) and/or the N-formyl-peptide, fMLP, the method comprising administering to the subject a polypeptide according to the first aspect of the invention or a pharmaceutical composition according to the sixth aspect of the invention.

Persons skilled in the art will appreciate that the subject is human.

The polypeptide or pharmaceutical composition of the invention is administered to the patient in an effective amount. A 'therapeutically effective amount', or 'effective amount', or 'therapeutically effective', as used herein, refers to that amount which provides inhibition of a biological activity of complement 5a (C5a) and/or the N-formyl-peptide, fMLP. This is a predetermined quantity of active material calculated to produce the desired therapeutic effect. Further, it is intended to mean an amount sufficient to reduce and most preferably prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is Well known in the art.

Thus, in one embodiment, the method comprises administering to the individual an amount of the compound sufficient to act as an antagonist at C5aR and/or FPR.

It will be appreciated by persons skilled in the art that such an effective amount of the compound or formulation thereof may be delivered as a single bolus dose (i.e. acute administration) or, more preferably, as a series of doses over time (i.e. chronic administration).

Variant CHIPS proteins according to the present invention may be produced by directed evolution technology, such as the Fragment-Induced Nucleotide Diversity ('FIND') methodology developed by Alligator Bioscience AB. The FIND methodology is described in detail in WO 98/58080, WO 02/48351 and WO 03/97834.

Thus, a further aspect of the invention provides a method for producing a polypeptide according to the first aspect of the invention, the method comprising the following steps:
(a) providing one or more parent polynucleotide molecules encoding the wildtype CHIPS protein or variant(s) thereof;
(b) digesting the one or more parent polynucleotide molecules with a nuclease (e.g. an exonuclease) to generate polynucleotide fragments;
(c) contacting said polynucleotide fragments generated in step (b) with each other; and
(d) amplifying the fragments that anneal to each other to generate at least one polynucleotide sequence encoding a variant CHIPS polypeptide having an altered amino acid sequence as compared to those encoded by the one or more parent polynucleotide molecules.

It will be appreciated by skilled persons that the parent polynucleotides provided in step (a) may be double-stranded or single-stranded. Preferably, however, parent polynucleotide molecules in step (a) are single-stranded.

In one embodiment, step (d) comprises adding oligonucleotides of predefined variability in order to control the degree of variability introduced into defined regions of the parent polynucleotides.

In a further embodiment, the method additionally comprises step (e) of expressing the at least one polynucleotide sequence produced in step (d) and screening the resultant polypeptide for a biological activity of the wildtype CHIPS protein, such as the ability to inhibit C5a-induced activation of neutrophils and/or fMLP-induced activation of neutrophils.

Step (e) may also comprise testing the resultant polypeptide for the ability to bind to C5aR and/or FPR. Such binding properties may be assessed using techniques well known in the art, for example affinity chromatography and phage display.

More preferably, the method further comprises step (f) of screening the resultant polypeptide for reduced immunogenicity relative to the wildtype CHIPS protein.

For example, step (e) may comprise one or more of the following screening procedures:
(i) Assay for ability of variant CHIPS polypeptides to bind to C5aR.
    For example, phage selection may be used to screen for binding of variant polypeptides to a peptide corresponding to the N-terminal part of the C5aR. After the first positive selection, eluted phages may be amplified and a subsequent positive selection performed. In the second positive selection, human anti-CHIPS antibodies may be added to absorb unwanted CHIPS molecules with retained binding to anti-CHIPS antibodies; this can increase the possibility of identifying clones which are less immunogenic.
    Directly after the second positive selection, the eluted phages may be incubated with human anti-CHIPS antibodies coated to magnetic beads. Pools of eluates are then collected, as follows; (1) phages that did not bind the antibodies, (2) phages eluted after washing steps, (3) phages eluted with low or (4) high concentration of CHIPS. Clones from pools (1) and (2) may be preferentially selected for further screening.
    The genes from the selected pool of mutants may be cloned into the pRSET vector and protein produced in HT format.
(ii) Assay for the concentration of each variant CHIPS polypeptide by expression ELISA.
(iii) Assay for the binding activity of the variant CHIPS polypeptides to anti-CHIPS antibodies, for example by inhibition ELISA and/or human anti-CHIPS antibody ELISA.
(iv) Selected variant CHIPS polypeptides may also be re-expressed and analysed in expression ELISA and peptide ELISA.

Further details of exemplary screening procedures are provided in the Examples (see below).

It will be appreciated that screening assays which are capable of high throughput operation will be particularly preferred. Examples may include cell-based assays and protein-protein binding assays. An SPA-based (Scintillation Proximity Assay; Amersham International) system may be used.

Other methods of detecting polypeptide/polypeptide interactions include ultrafiltration with ion spray mass spectroscopy/HPLC methods or other physical and analytical methods. Fluorescence Energy Resonance Transfer (FRET) methods, for example, well known to those skilled in the art, may be used, in which binding of two fluorescent labelled entities may be measured by measuring the interaction of the fluorescent labels when in close proximity to each other.

Alternative methods of detecting binding of a polypeptide to macromolecules, for example DNA, RNA, proteins and phospholipids, include a surface plasmon resonance assay, for example as described in Plant et al (1995) *Analyt Biochem* 226(2), 342-348 (which is incorporated herein by reference). Methods may make use of a polypeptide that is labelled, for example with a radioactive or fluorescent label.

A further method of identifying a polypeptide that is capable of binding to a target macromolecule (such as C5aR or FPR) is one where the target macromolecule is exposed to the polypeptide and any binding of the polypeptide to the said macromolecule is detected and/or measured. The binding constant for the binding of the polypeptide to the macromolecule may be determined. Suitable methods for detecting and/or measuring (quantifying) the binding of a polypeptide to a macromolecule are well known to those skilled in the art and may be performed, for example, using a method capable of high throughput operation, for example a chip-based method. New technology, called VLSIPS™, has enabled the production of extremely small chips that contain hundreds of thousands or more of different molecular probes. These biological chips or arrays have probes arranged in arrays; each probe assigned a specific location. Biological chips have been produced in which each location has a scale of, for example, ten microns. The chips can be used to determine whether target molecules interact with any of the probes on the chip. After exposing the array to target molecules under selected test conditions, scanning devices can examine each location in the array and determine whether a target molecule has interacted with the probe at that location.

Biological chips or arrays are useful in a variety of screening techniques for obtaining information about either the probes or the target molecules. For example, a library of peptides can be used as probes to screen for drugs. The peptides can be exposed to a receptor, and those probes that bind to the receptor can be identified. See U.S. Pat. No. 5,874,219 issued 23 Feb. 1999 to Rava et al.

It will be understood that it will be desirable to identify polypeptides that may block C5aR and/or FPR in vivo. Thus it will be understood that reagents and conditions used in the method may be chosen such that the interactions between the said and the interacting polypeptide are substantially the same as between a said naturally occurring polypeptide and a naturally occurring interacting polypeptide in vivo.

Exemplary embodiments of the invention are described in the following non-limiting examples, with reference to the following figures:

FIG. 1—Frequency distribution of IgG anti-CHIPS titres in healthy human donors (n=168). The titre was defined as the log dilution that gives an absorbance of 0.300 after subtraction of background value. The mean titre was 3.62 with an SD of 0.72. The insert depicts the anti-CHIPS titres of the 6 subjects before study entry (mean of 3 values corrected for human pooled serum as reference in every ELISA).

Figure 2:
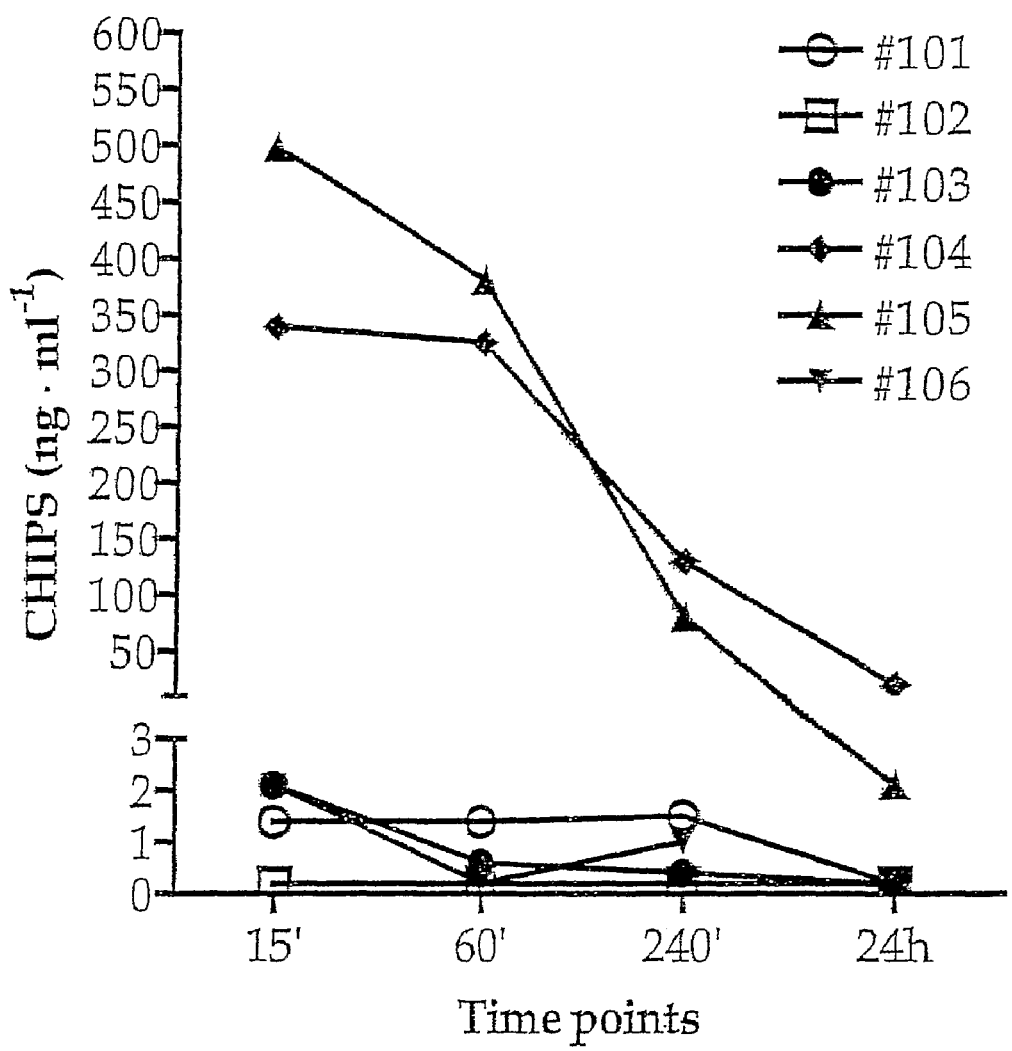

FIG. 2—Pharmaco dynamic of CHIPS detected in the sera of the volunteers. CHIPS was measured by a specific capture ELISA at the various time points after iv injection of CHIPS. Open symbols represent placebo and closed symbols CHIPS receiver.

Figure 3:
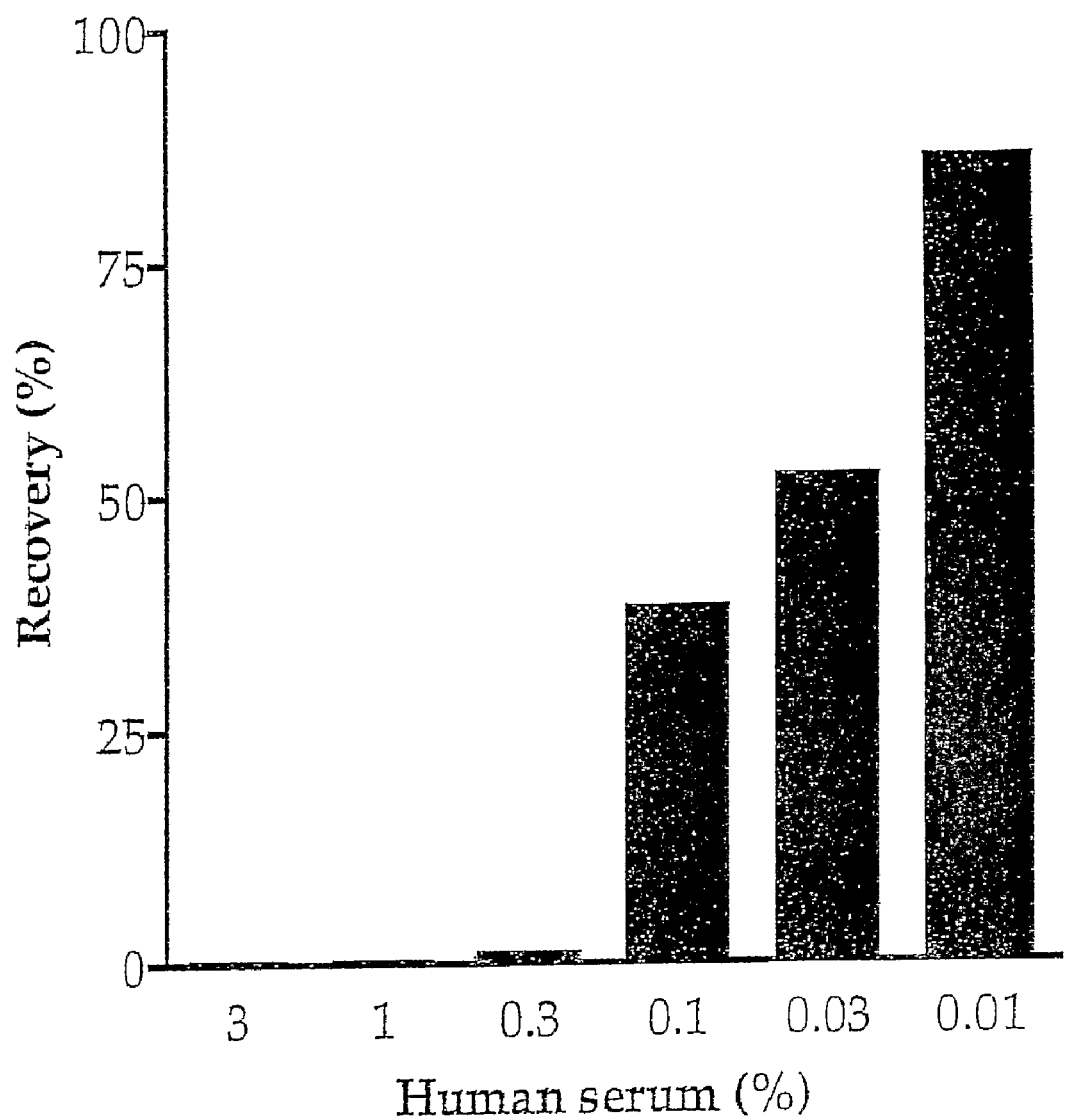

FIG. 3—Human anti-CHIPS IgG inhibits detection of CHIPS by capture ELISA. Recovery of 2.5 ng mL$^{-1}$ CHIPS spiked into various concentrations pooled human serum and measured by capture ELISA (a). Depletion of IgG from human serum by passage over Protein-G-Sepharose eliminates the inhibitory effect on the CHIPS capture ELISA (b). Various concentrations CHIPS were incubated with buffer (•), 1% human serum (from a single donor; ▲), or 1% serum after Protein-G-Sepharose passage (▼). Data show one representative experiment.

Figure 4:
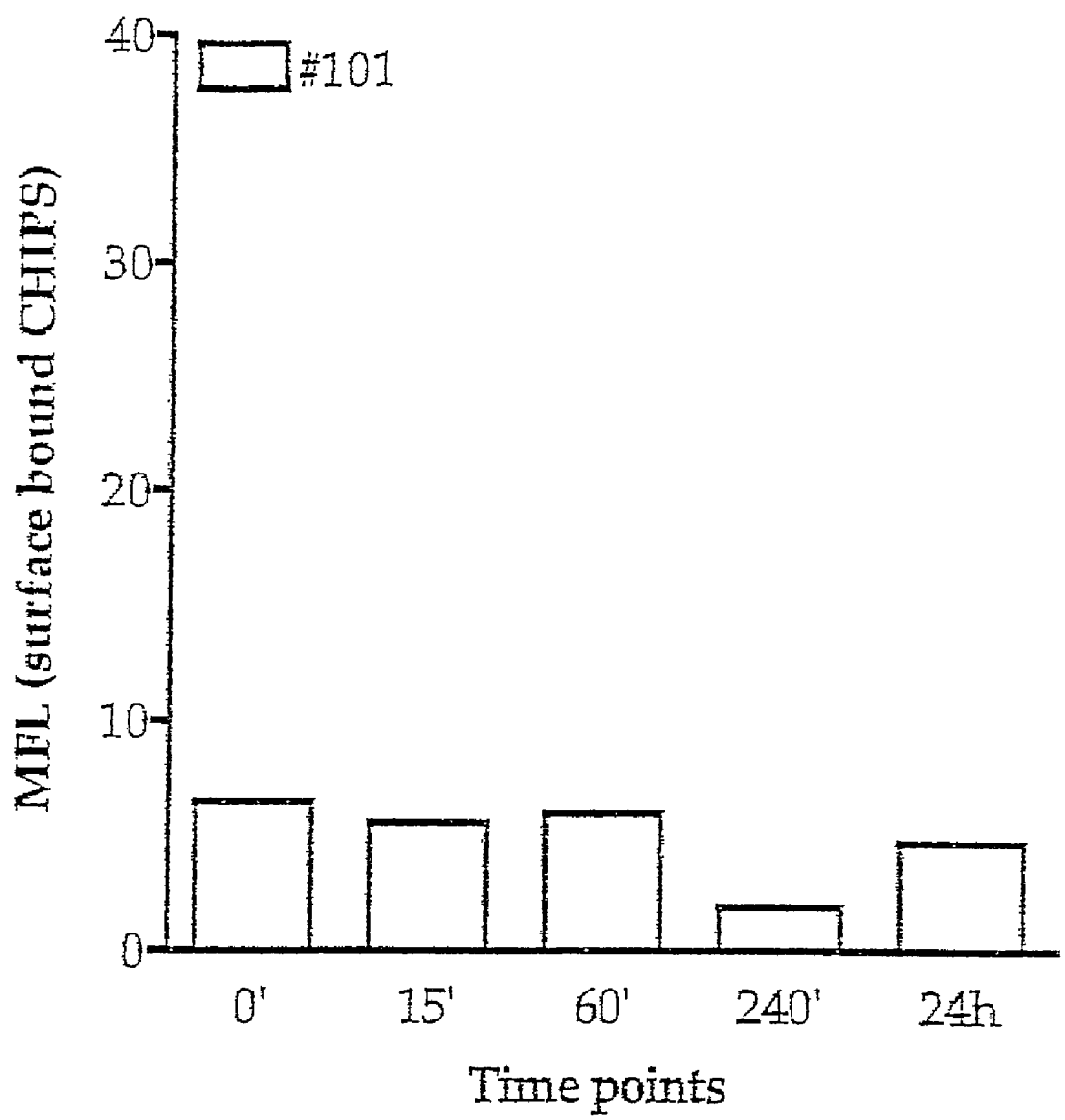
Figure 4:
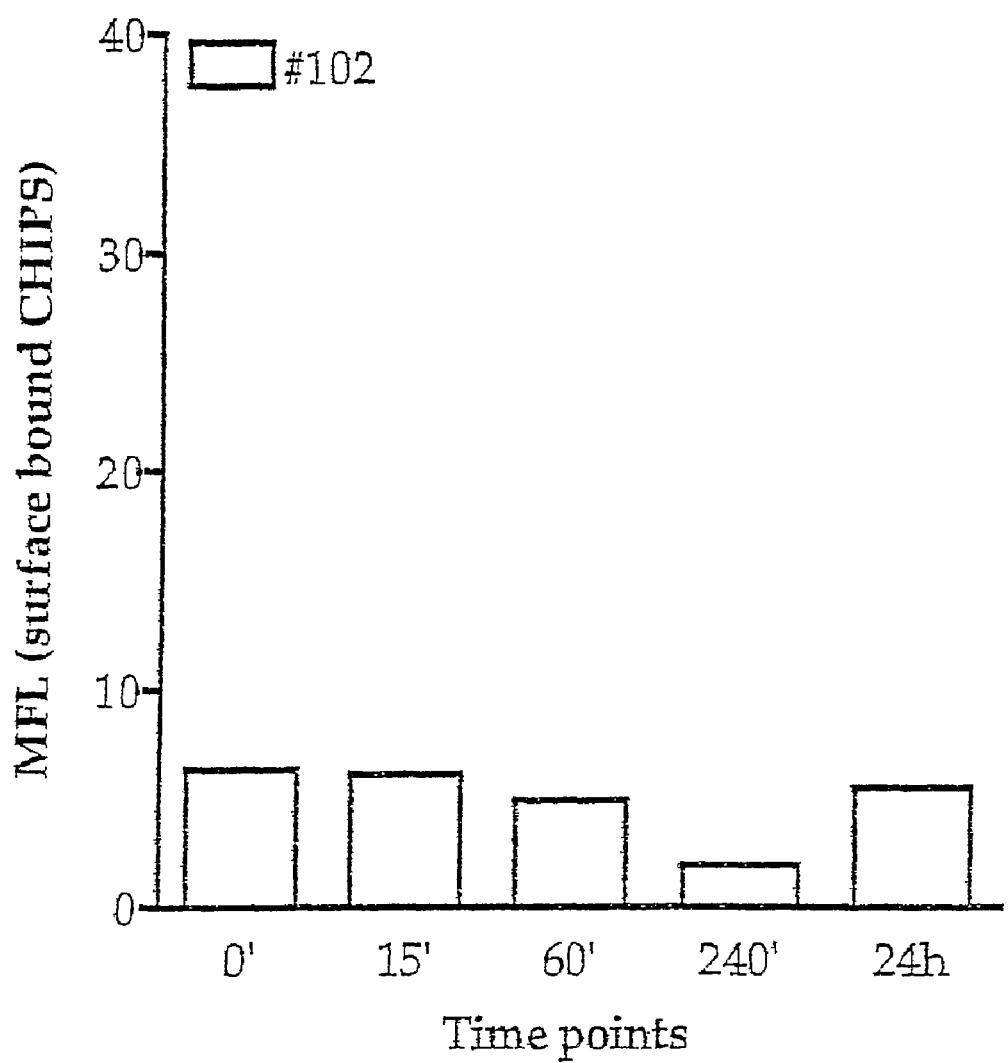
Figure 4:
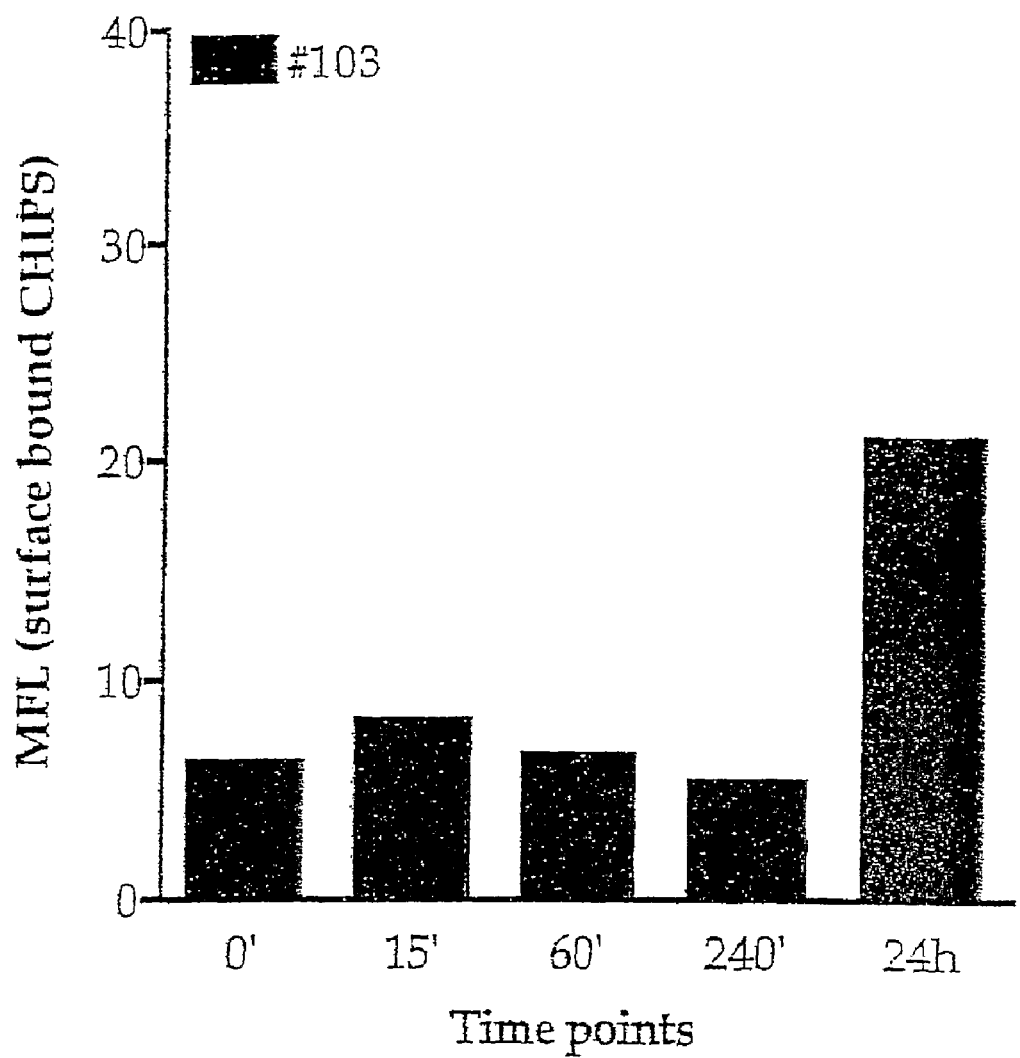
Figure 4:
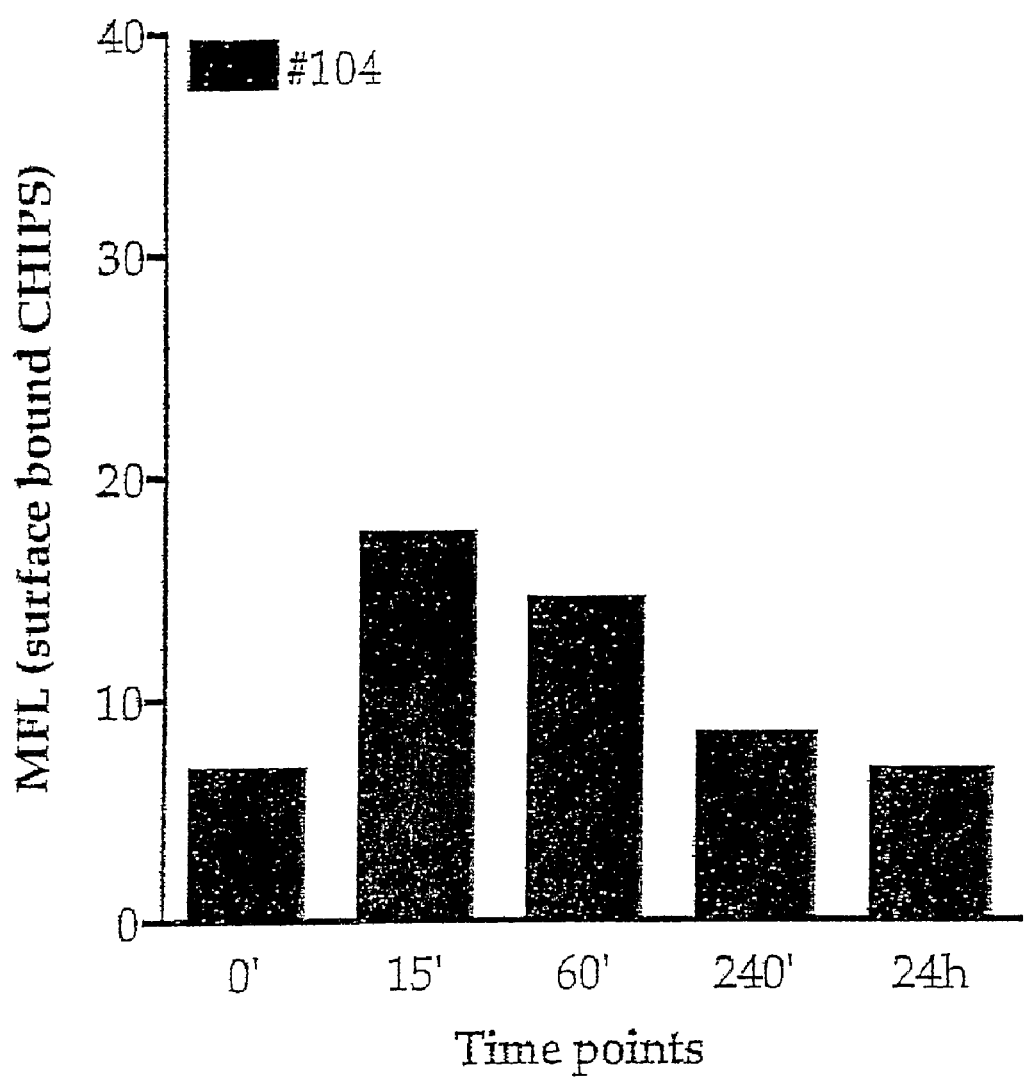
Figure 4:
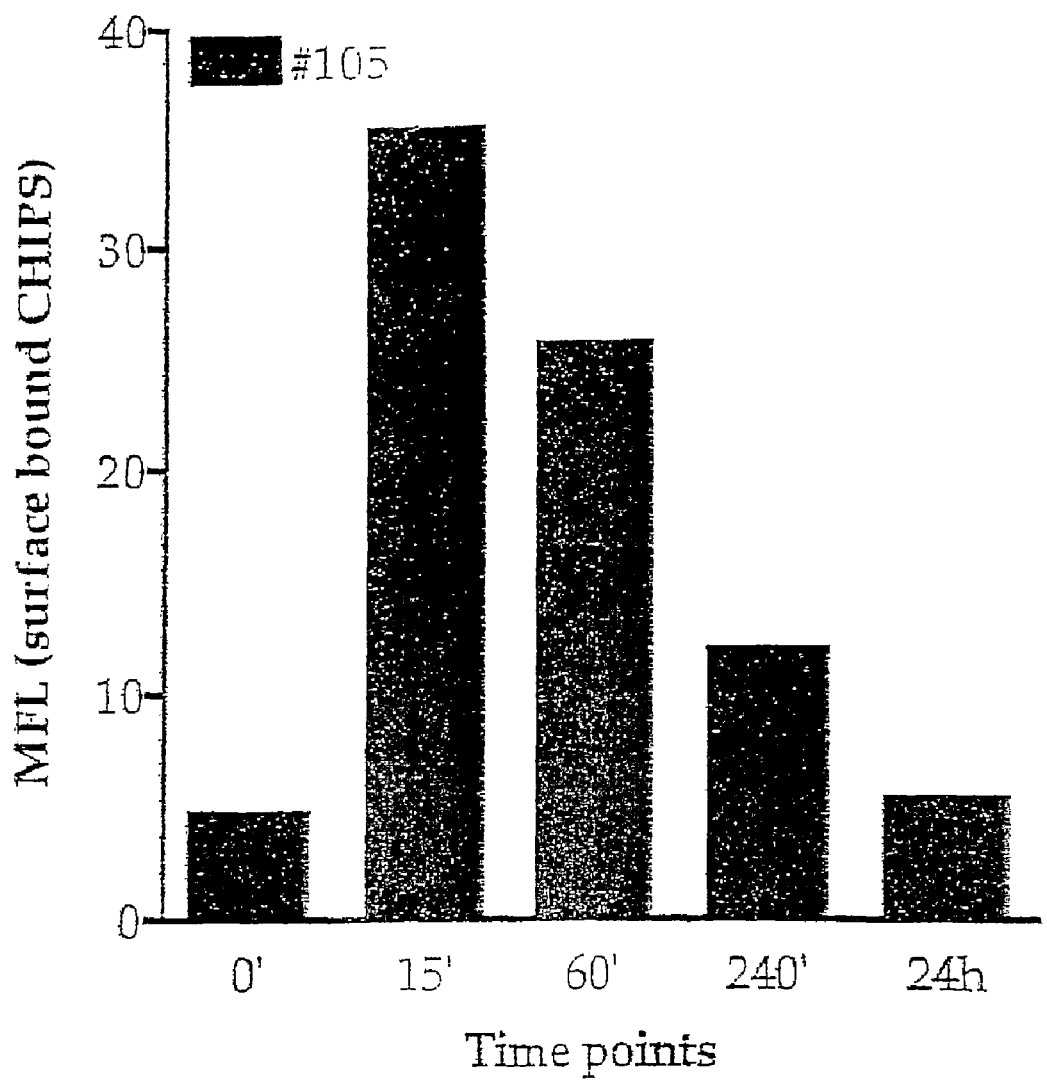
Figure 4:
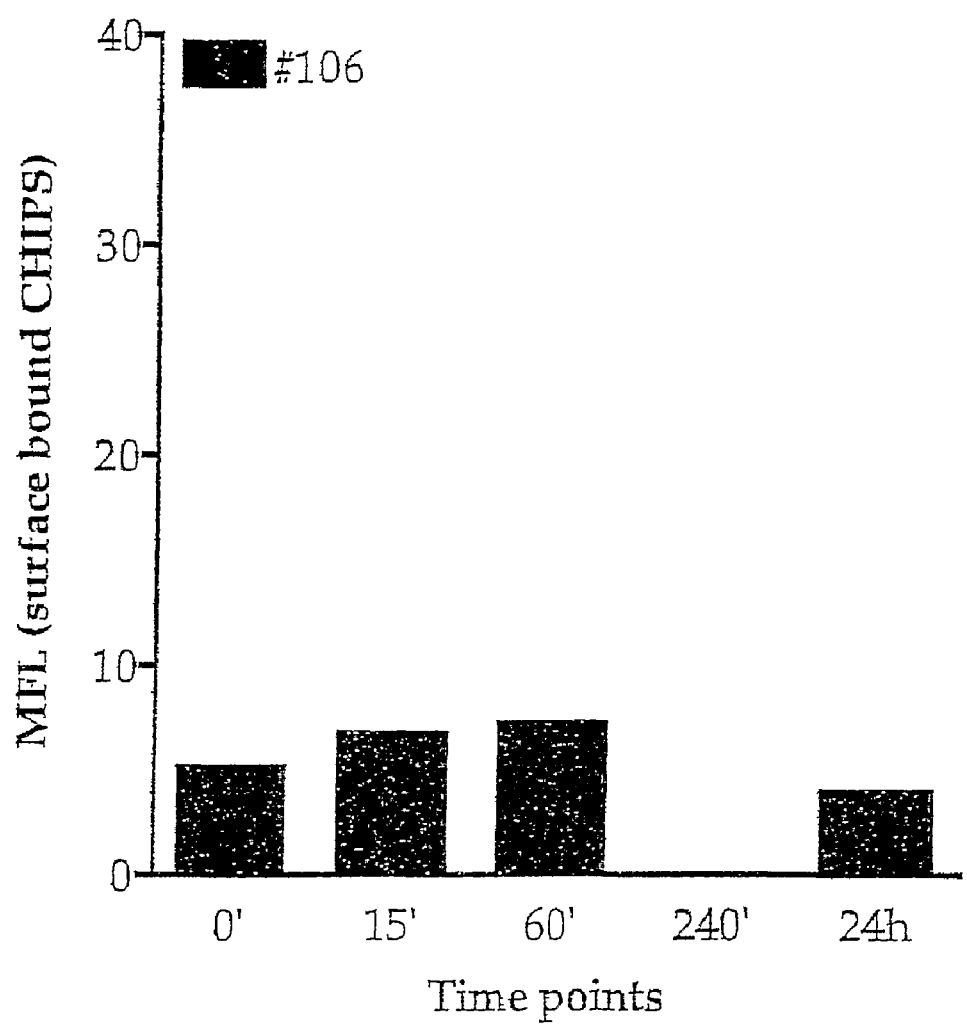
Figure 5A:
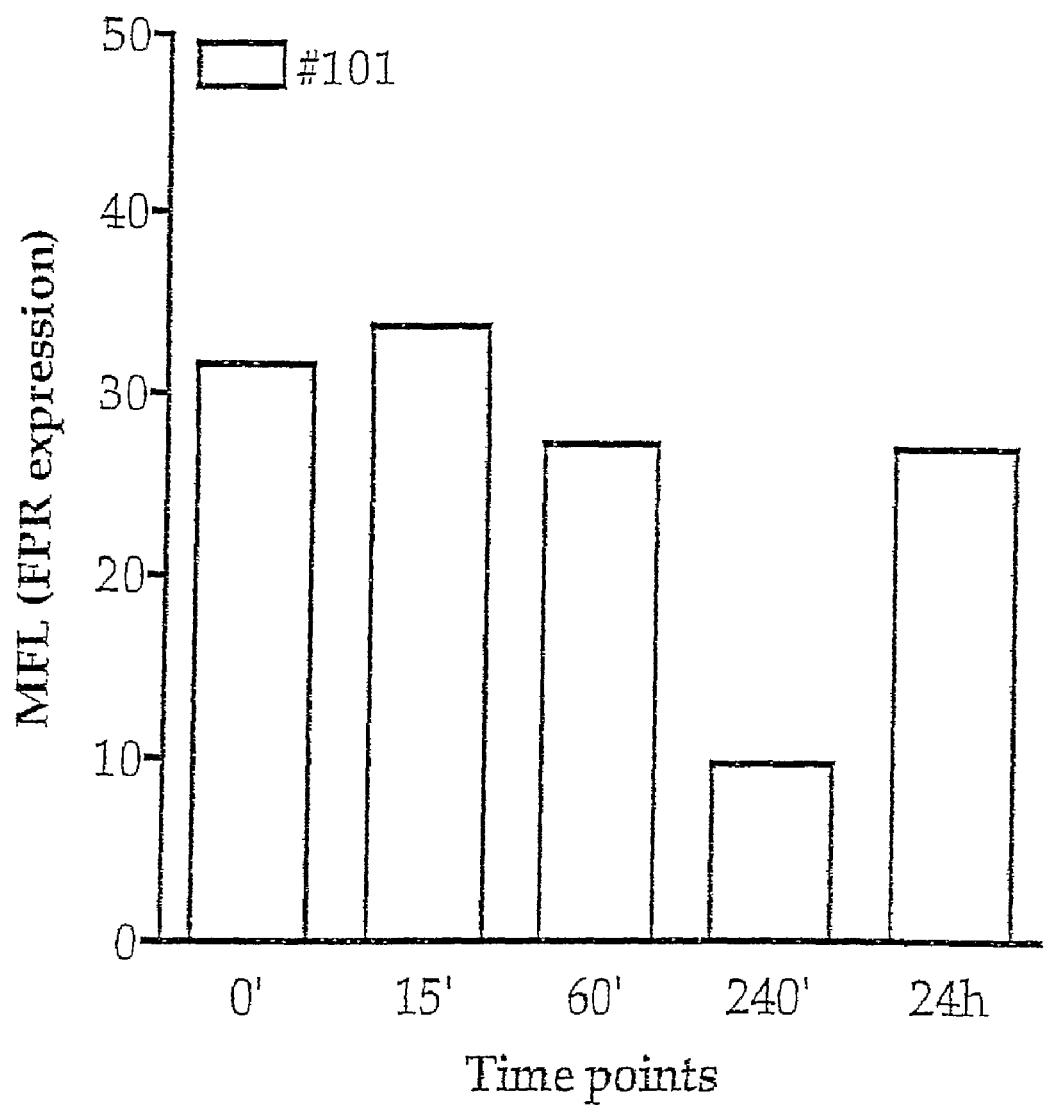
Figure 5A:
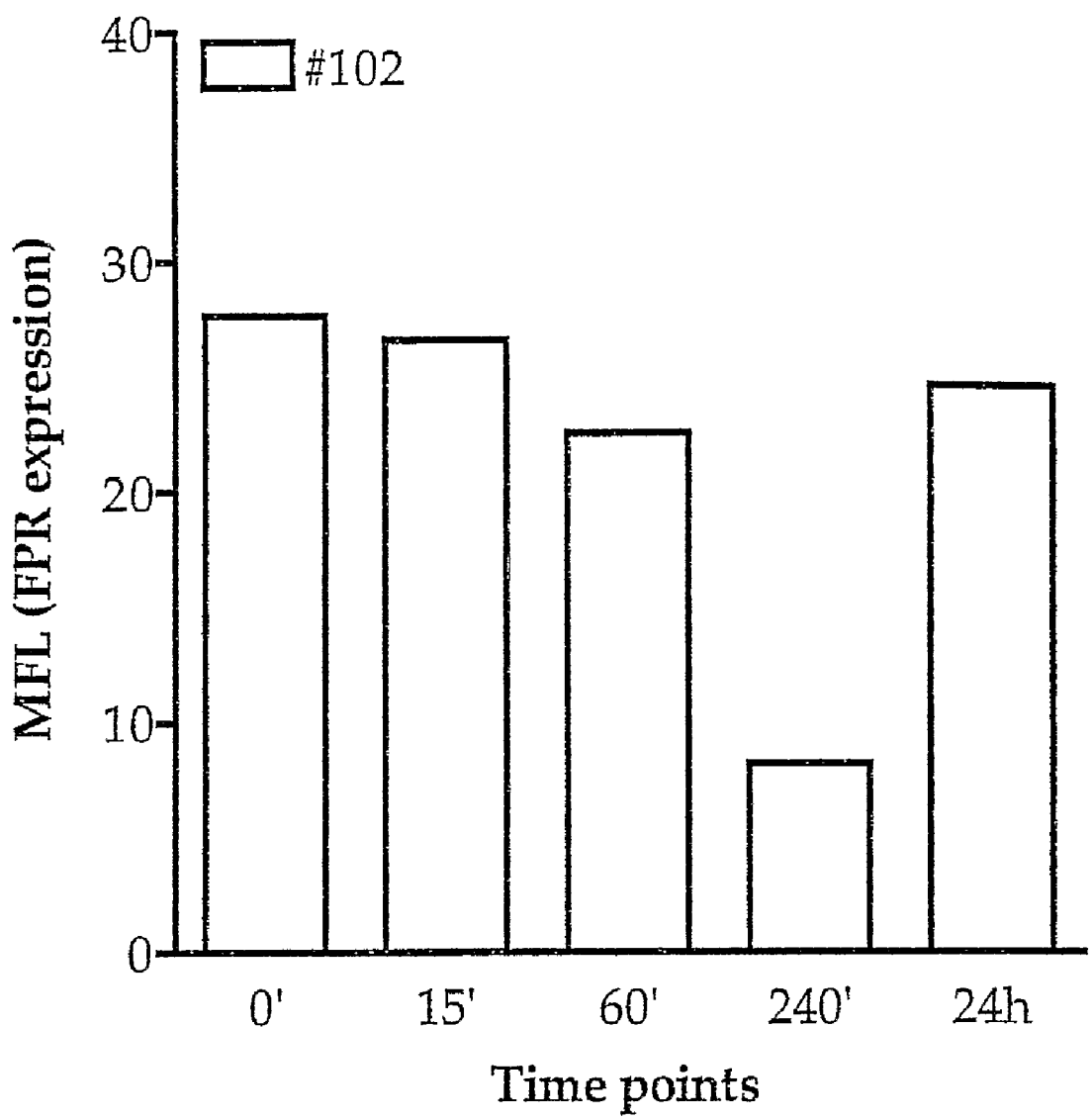
Figure 5A:
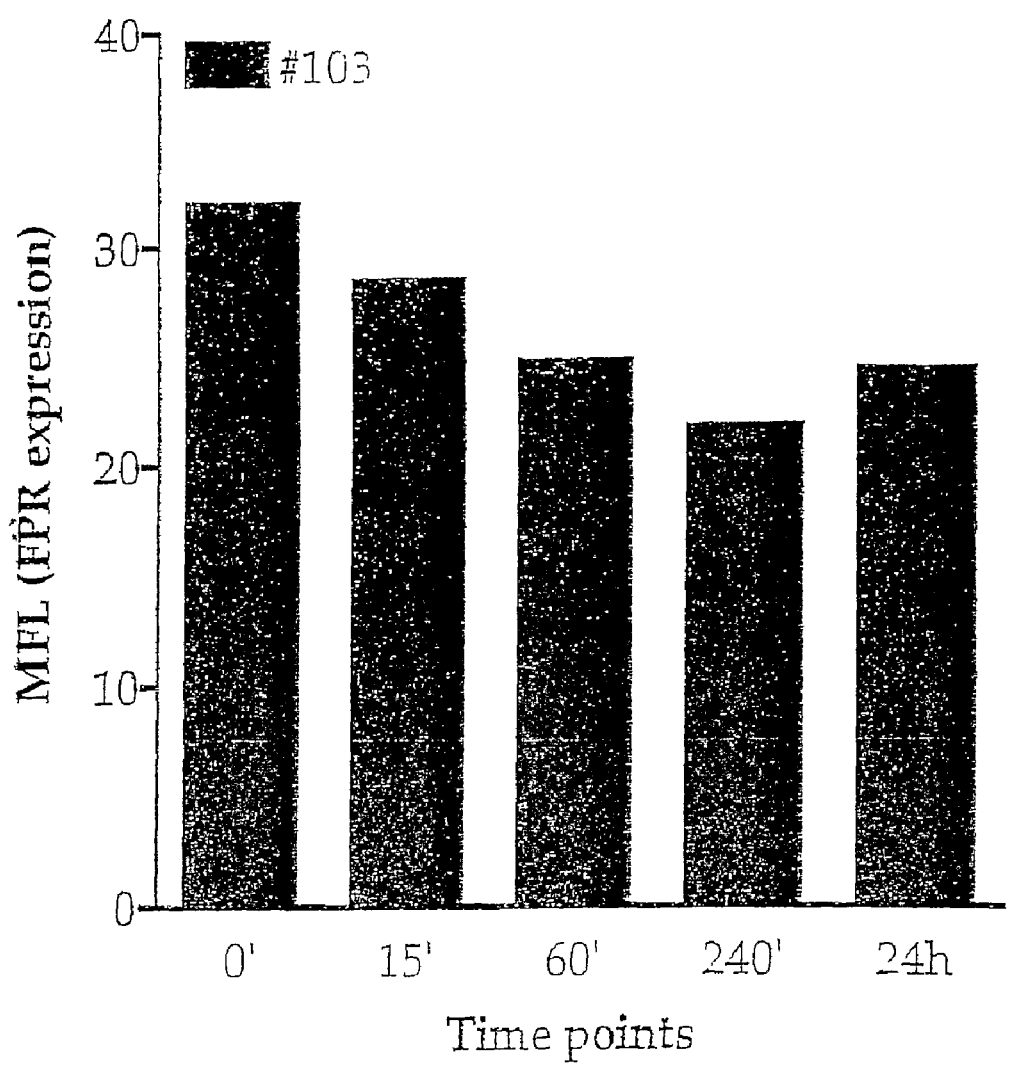
Figure 5A:
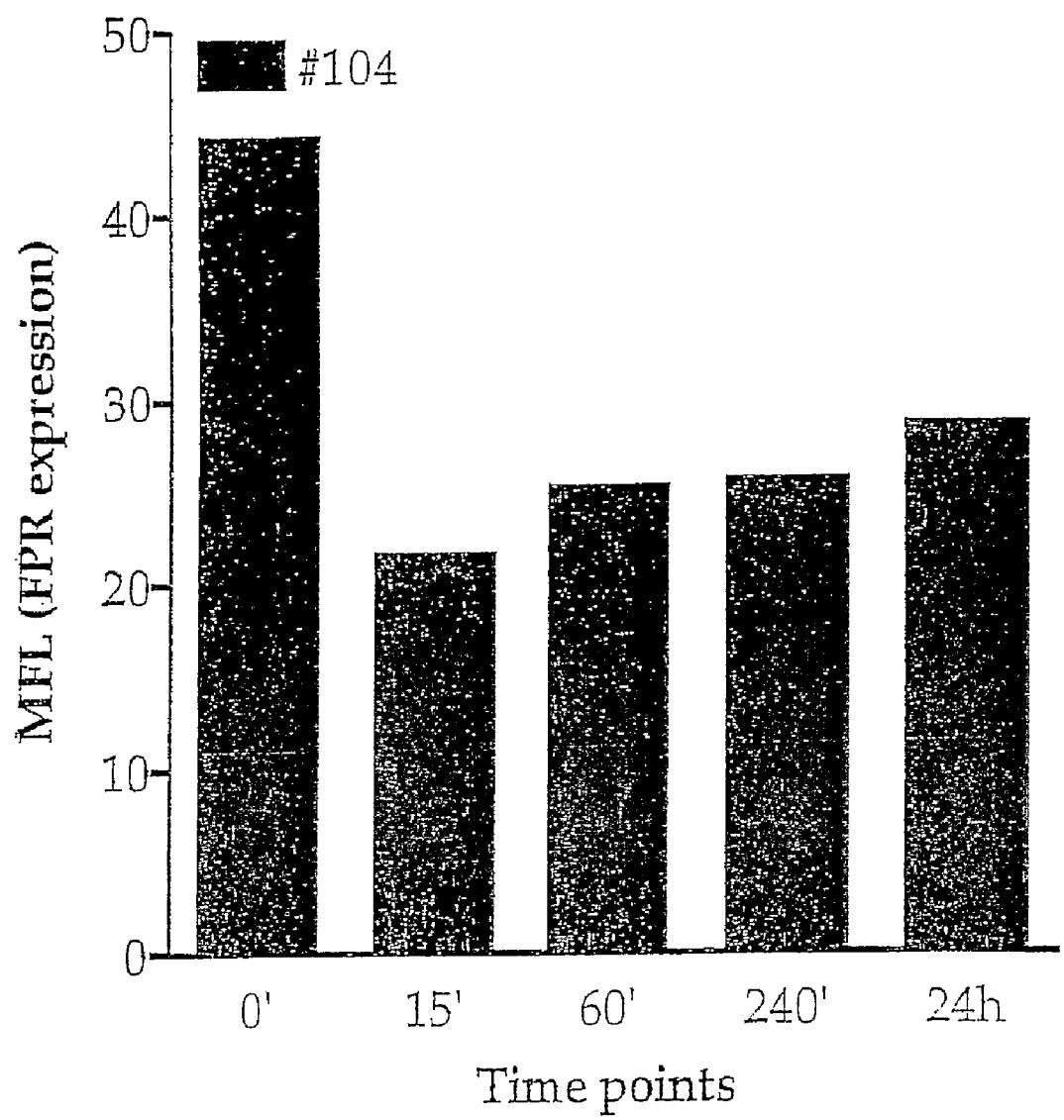
Figure 5A:
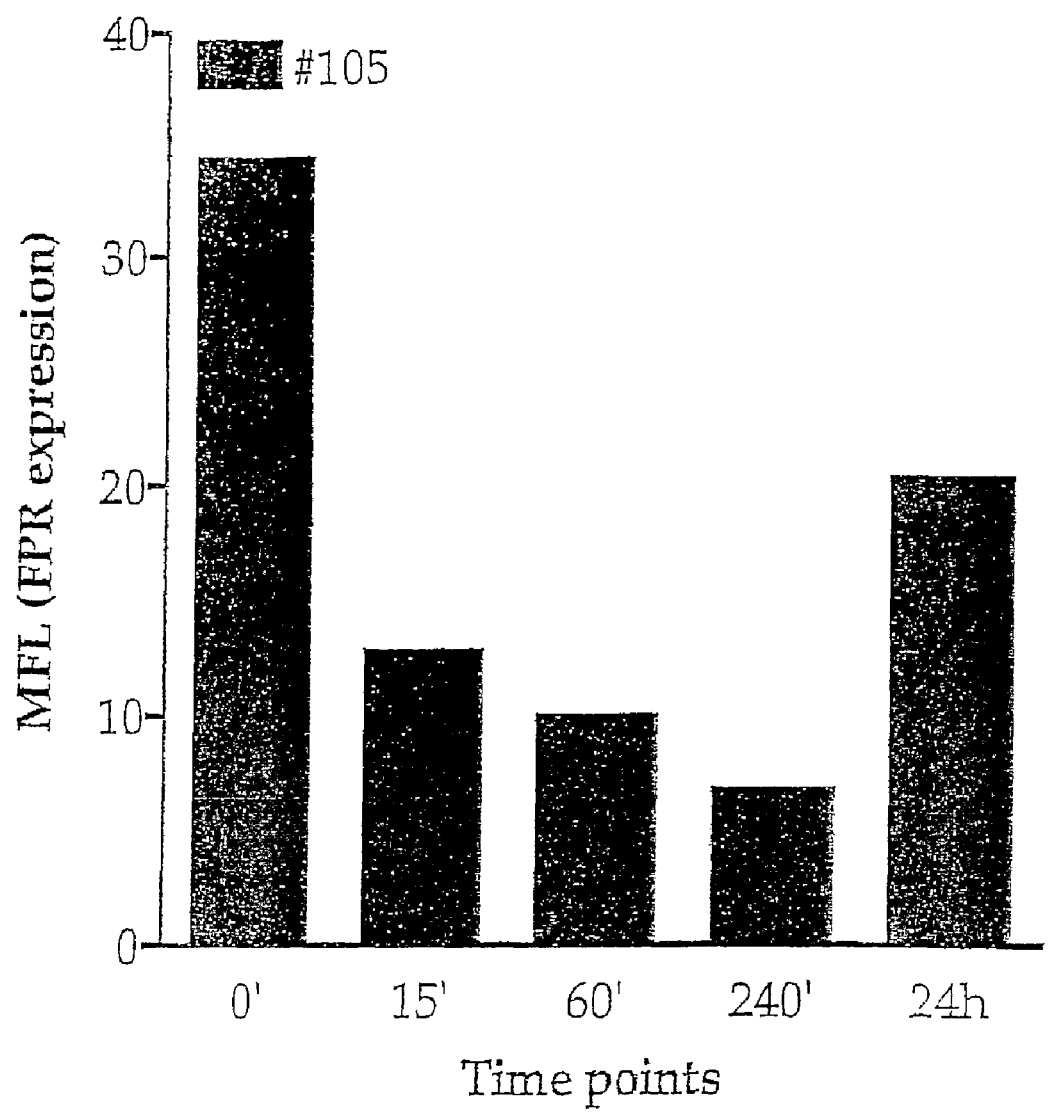
Figure 5A:
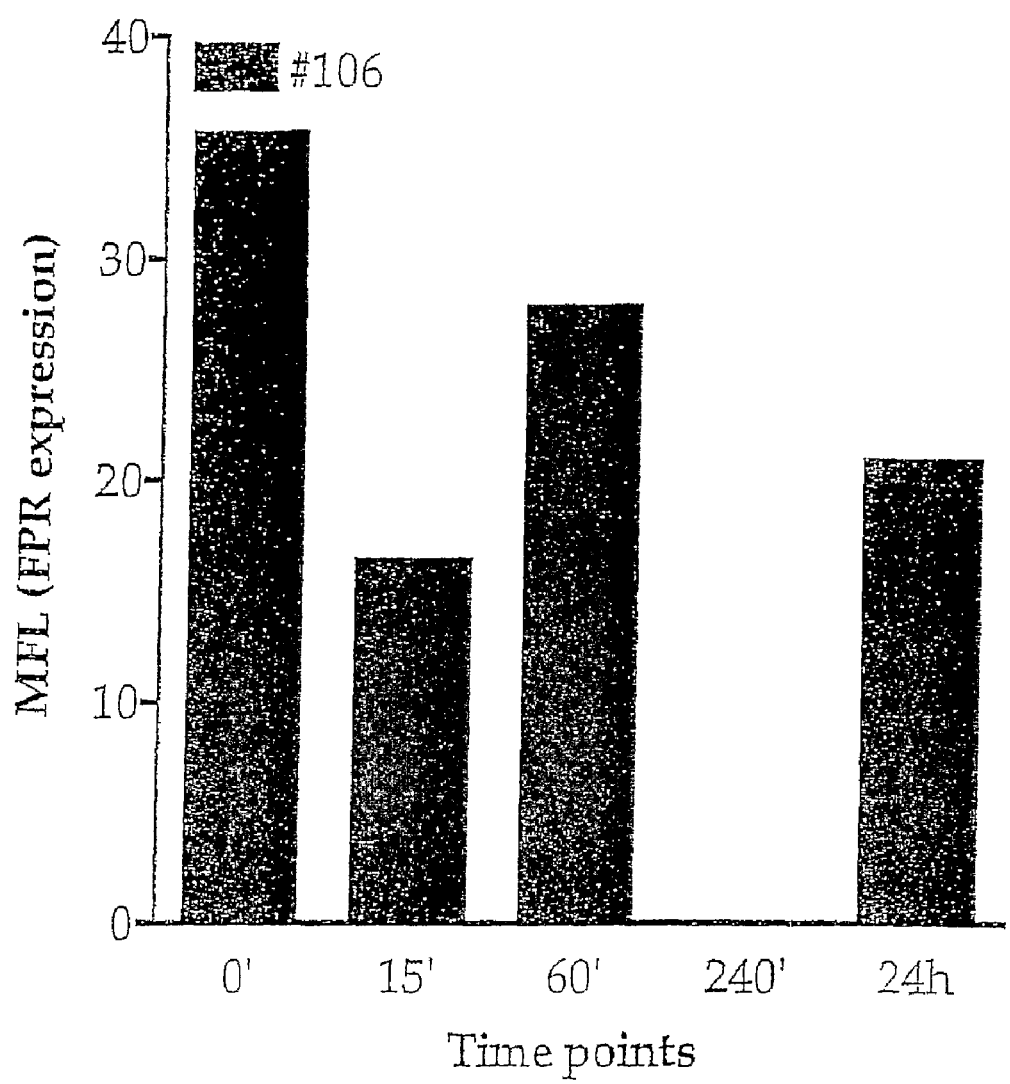
Figure 5B:
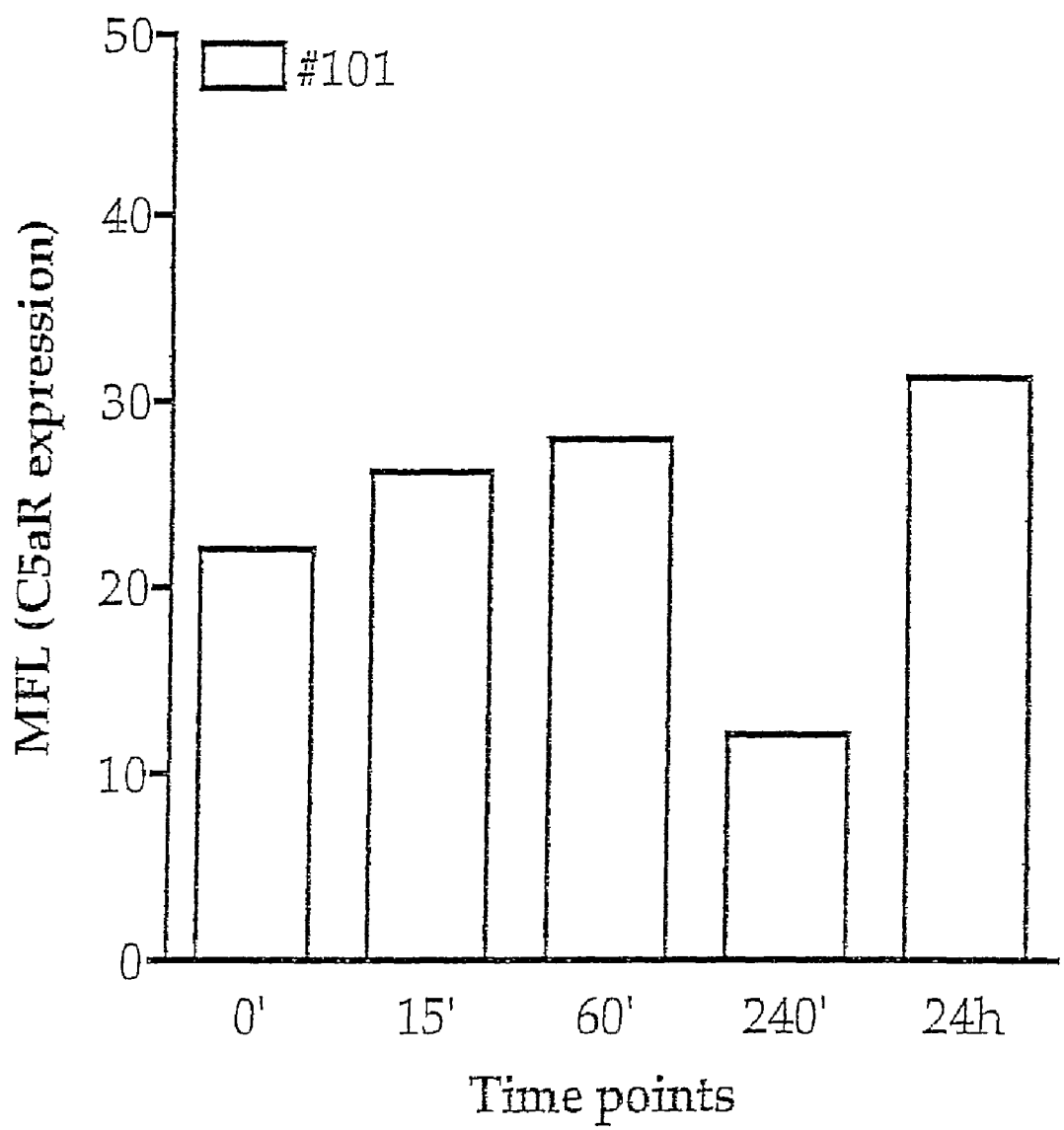
Figure 5B:
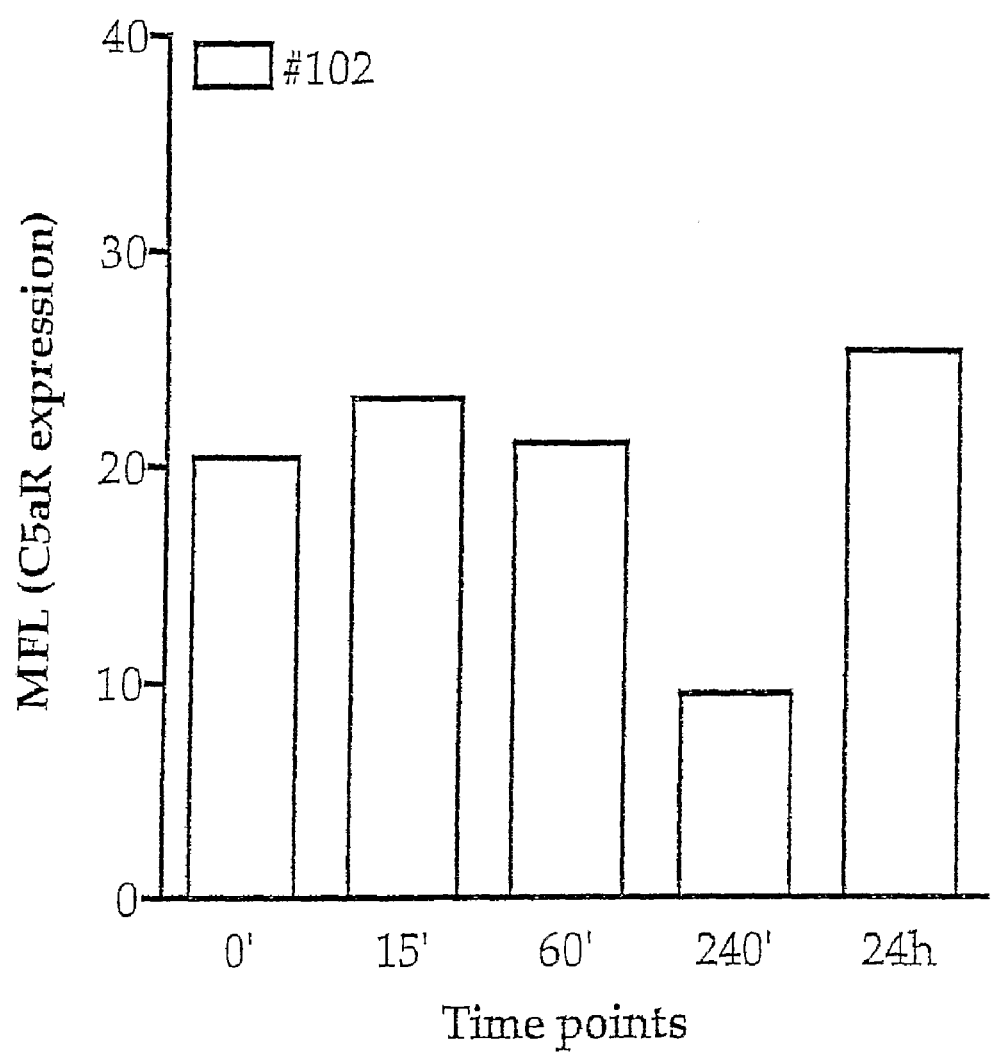
Figure 5B:
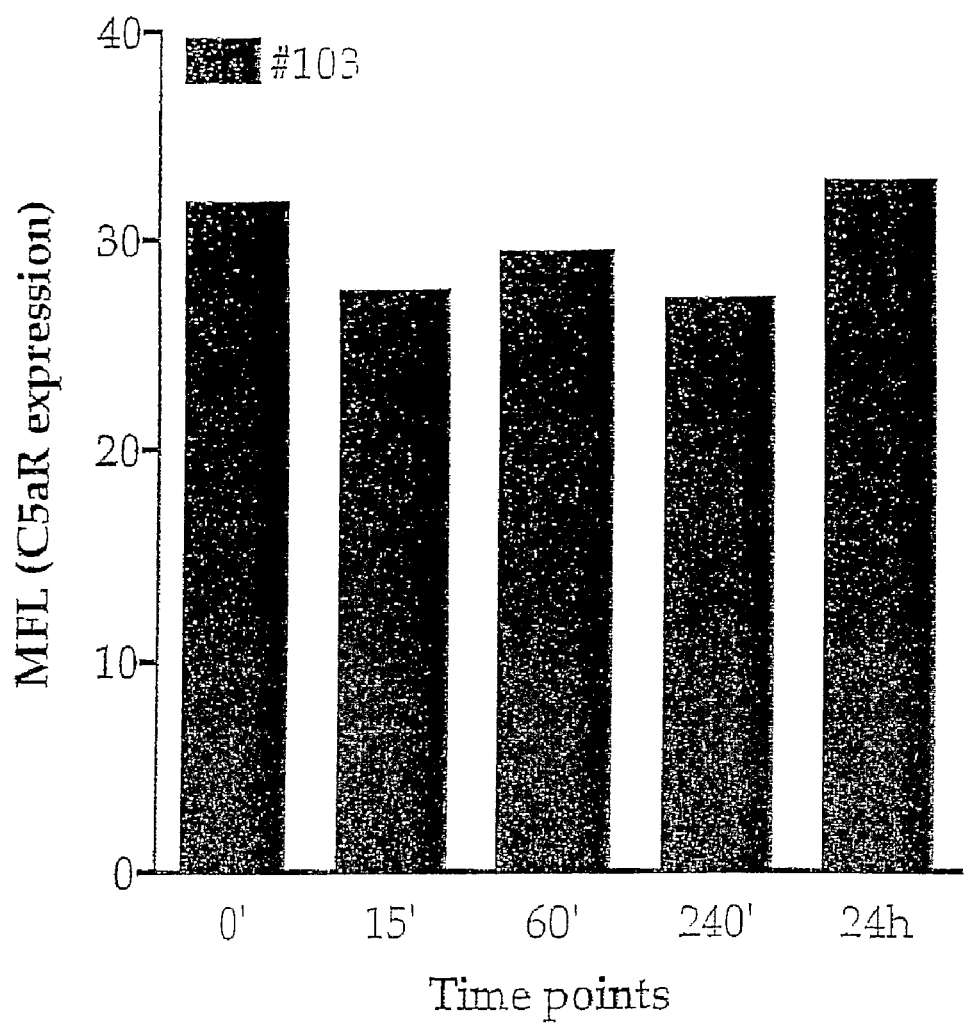
Figure 5B:
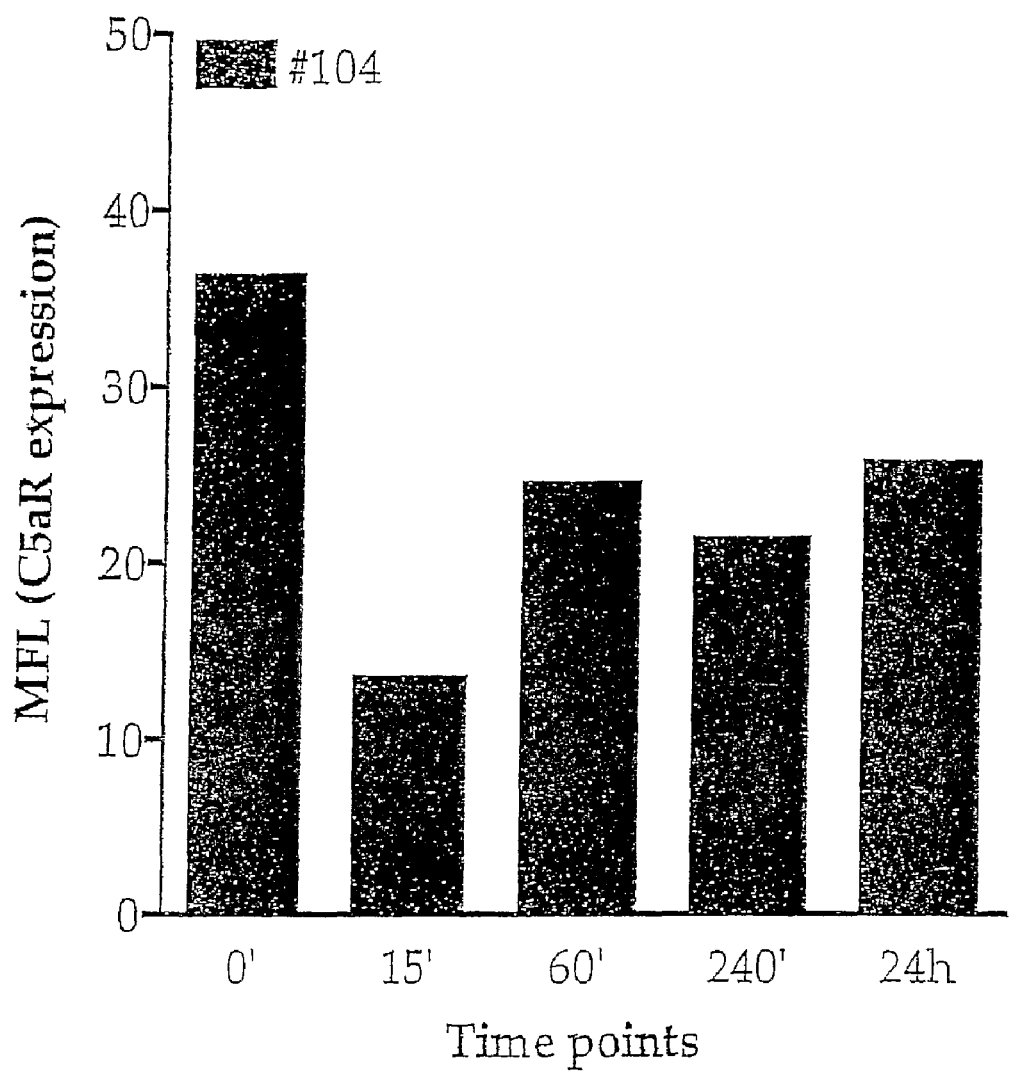
Figure 5B:
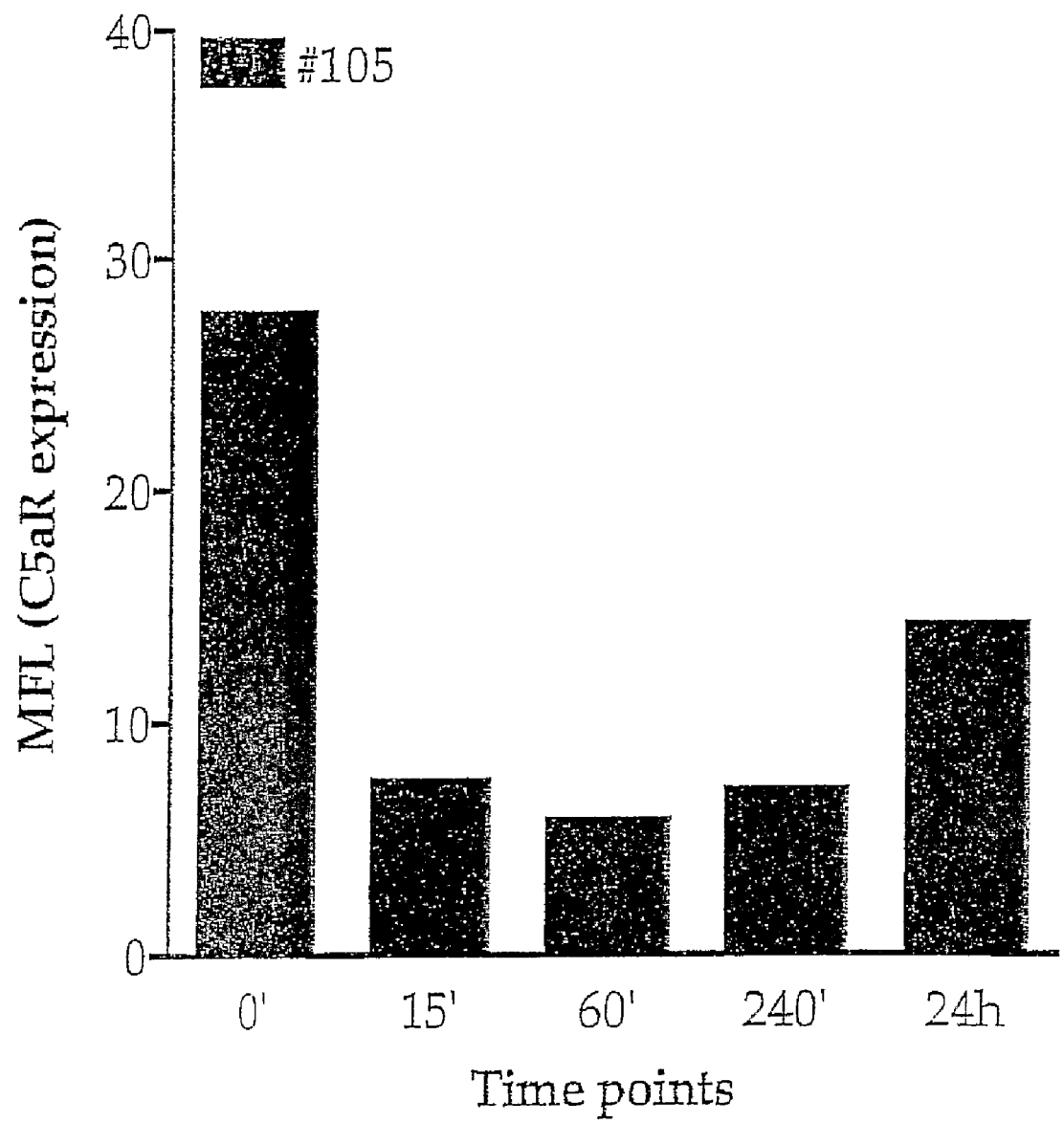
Figure 5B:
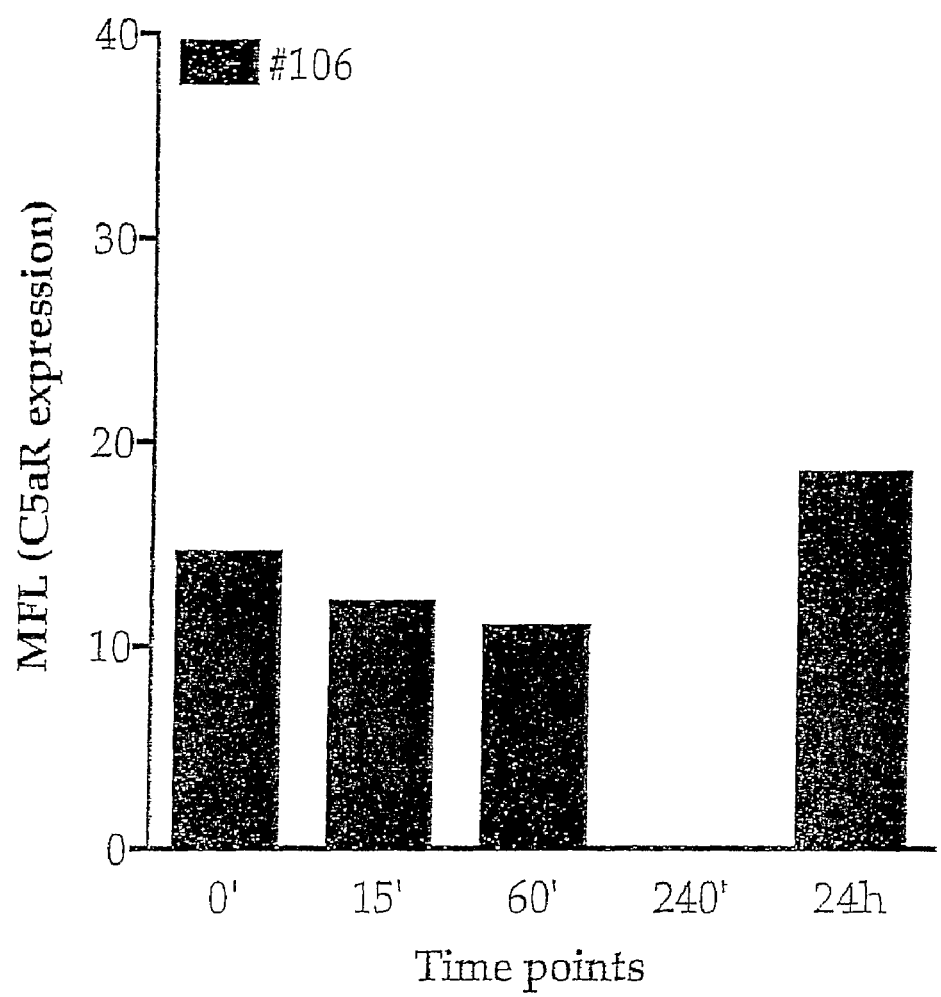

FIG. 4—CHIPS is recovered on the surface of peripheral blood neutrophils. At various time points after iv injection of CHIPS, the presence of CHIPS bound to the surface of neutrophils was detected with a rabbit-anti-CHIPS antibody. Individual subjects are shown; white bars represent placebo and black bars CHIPS receiver. Values are expressed as mean fluorescence (MFL) of gated neutrophils in EDTA whole blood samples at various time points (T=0, 15, 60, 240 min and after 24 hours). Background MFL value for the secondary FITC labelled conjugate was 6.

FIG. 5—Expression of FPR (a) and C5aR (b) on human peripheral blood neutrophils. At various time points after iv injection of CHIPS, the presence of FPR on the surface of neutrophils was detected with FITC-labelled fMLP and the presence of C5aR with a FITC labelled anti-CD88 mAb. White bars represent placebo and black bars CHIPS receiver. Values are expressed as mean fluorescence (MFL) of gated neutrophils.

Figure 6:
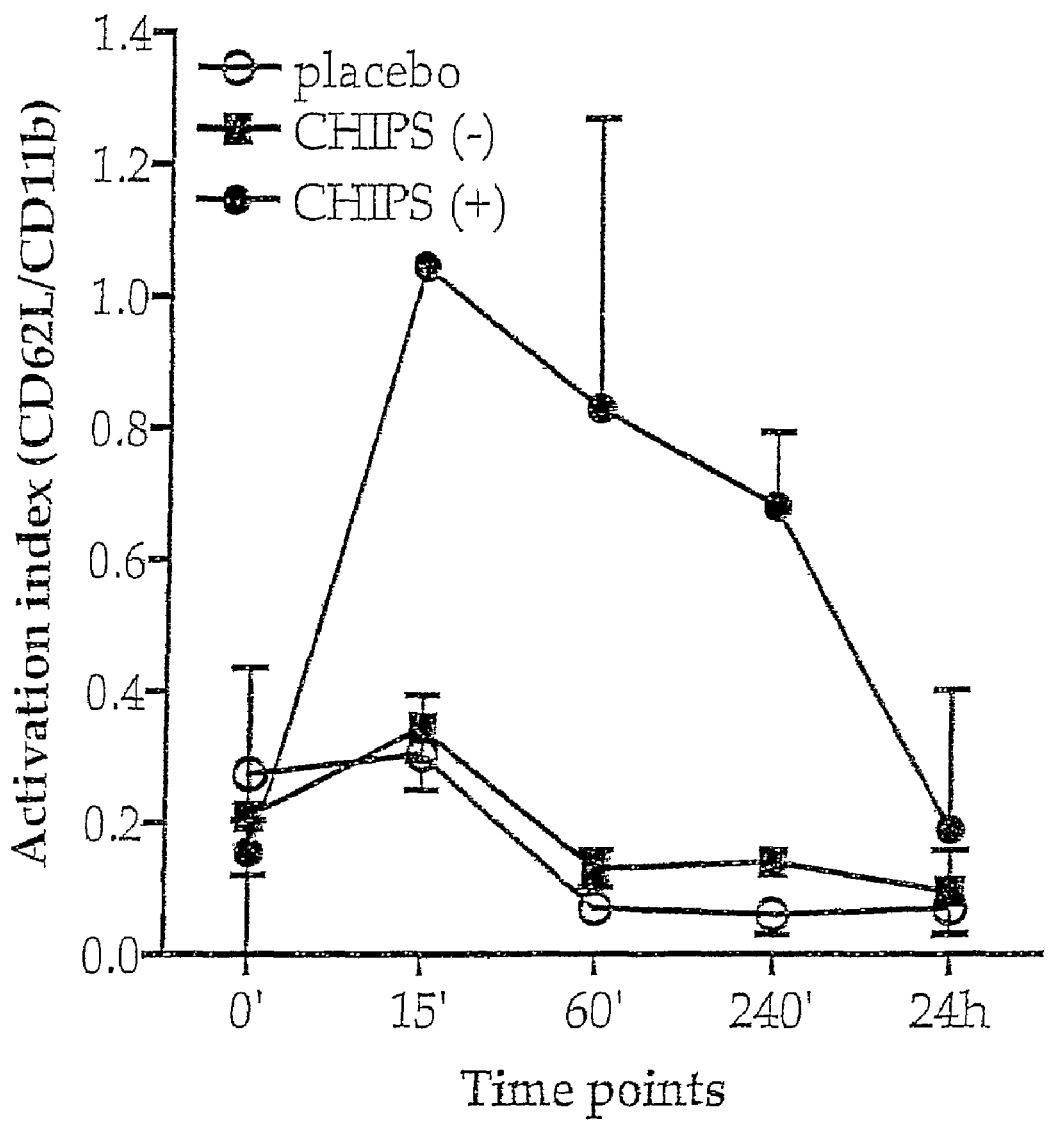

FIG. 6—Inhibition index of peripheral blood neutrophils after ex vivo whole blood fMLP stimulation. At various time points after iv injection of CHIPS, EDTA anticoagulated blood was incubated with buffer and fMLP for 30 min at 37° C. and analysed for the expression of both CD11b and CD62L. For every time point the expression of CD11b and CD62L was expressed relative to the buffer treated control sample (relative increase for CD11b and relative decrease for CD62L expression). These values were used to calculate the activation index for each subject at every time point (relative value for CD62L/relative value for CD11b). Data are expressed as the mean SSD of placebo (○), serum and neutrophil CHIPS negative (−) subjects (•) and CHIPS positive (+) subjects (■).

Figure 7:
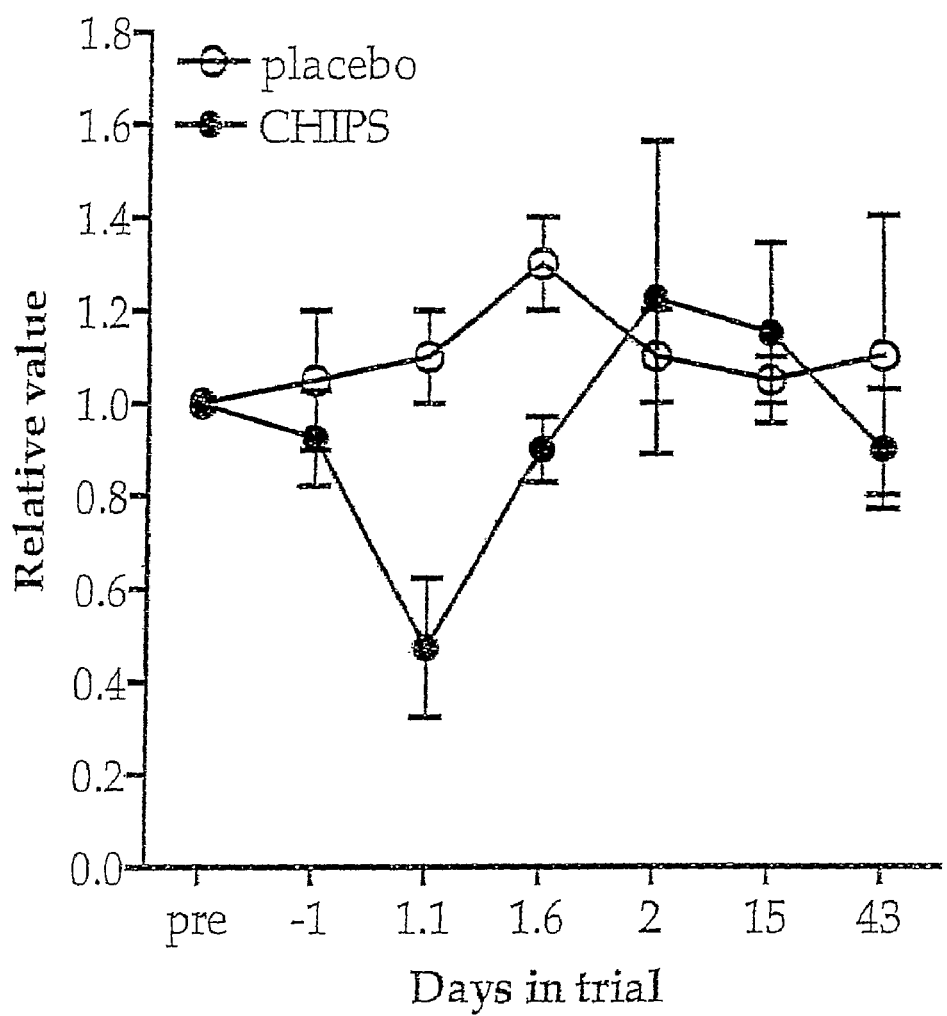
Figure 7:
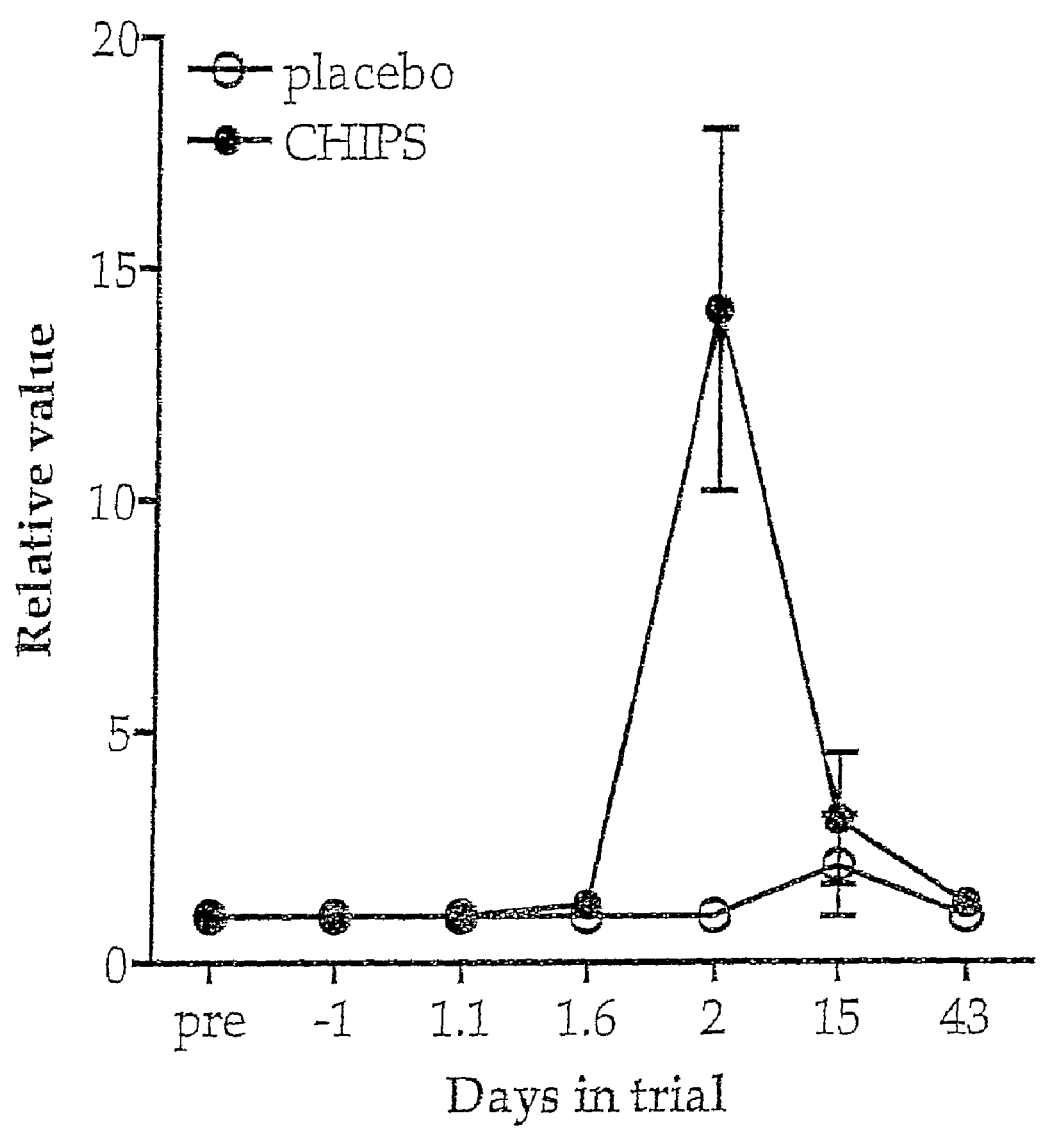

FIG. 7—Level of circulating peripheral white blood cells (a) and serum inflammation marker CRP (b). At various time points after iv injection of CHIPS, WBC counts and CRP measurements were performed. (1.1 and 1.6 indicate 1 day and 1 or 6 hours respectively). Data for WBC are expressed relative to the value at T=0 and data for CRP are expressed as mg L$^{-1}$. Values are mean±SD for placebos (•) and CHIPS receivers (▲).

Figure 8:
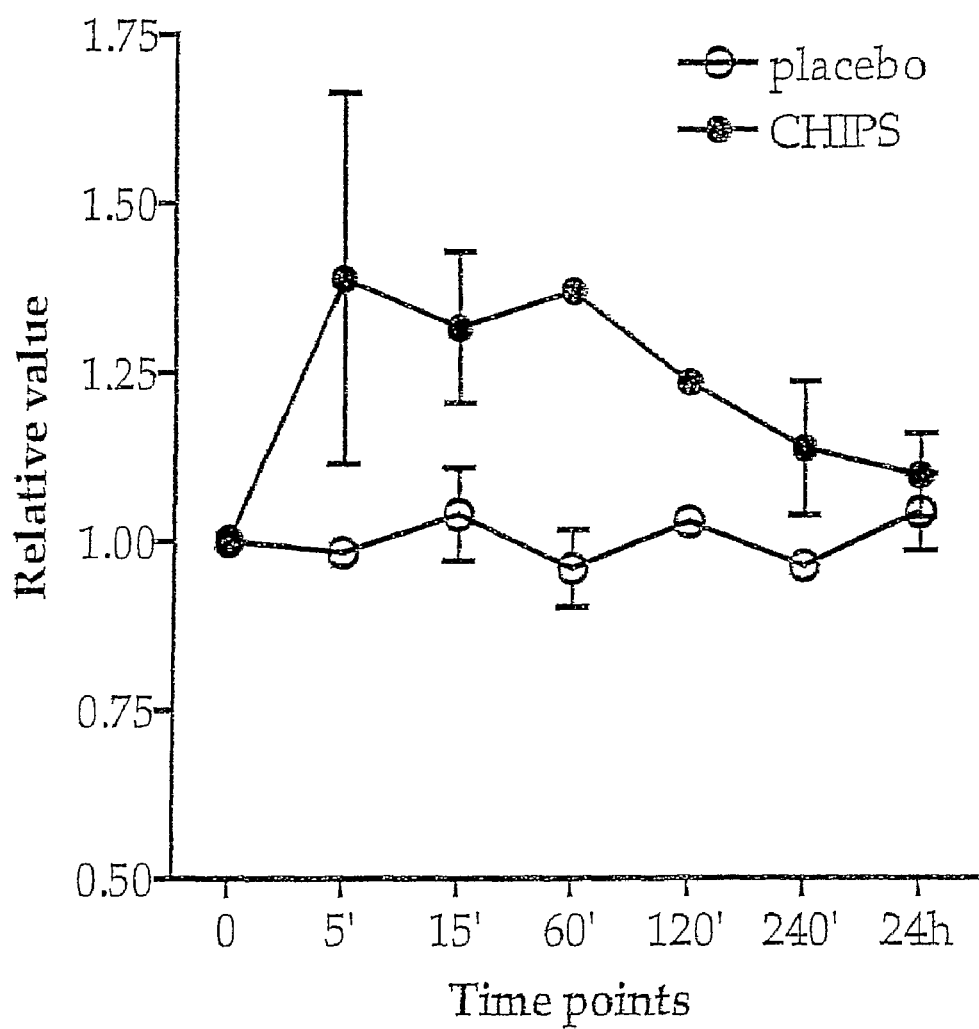
Figure 8:
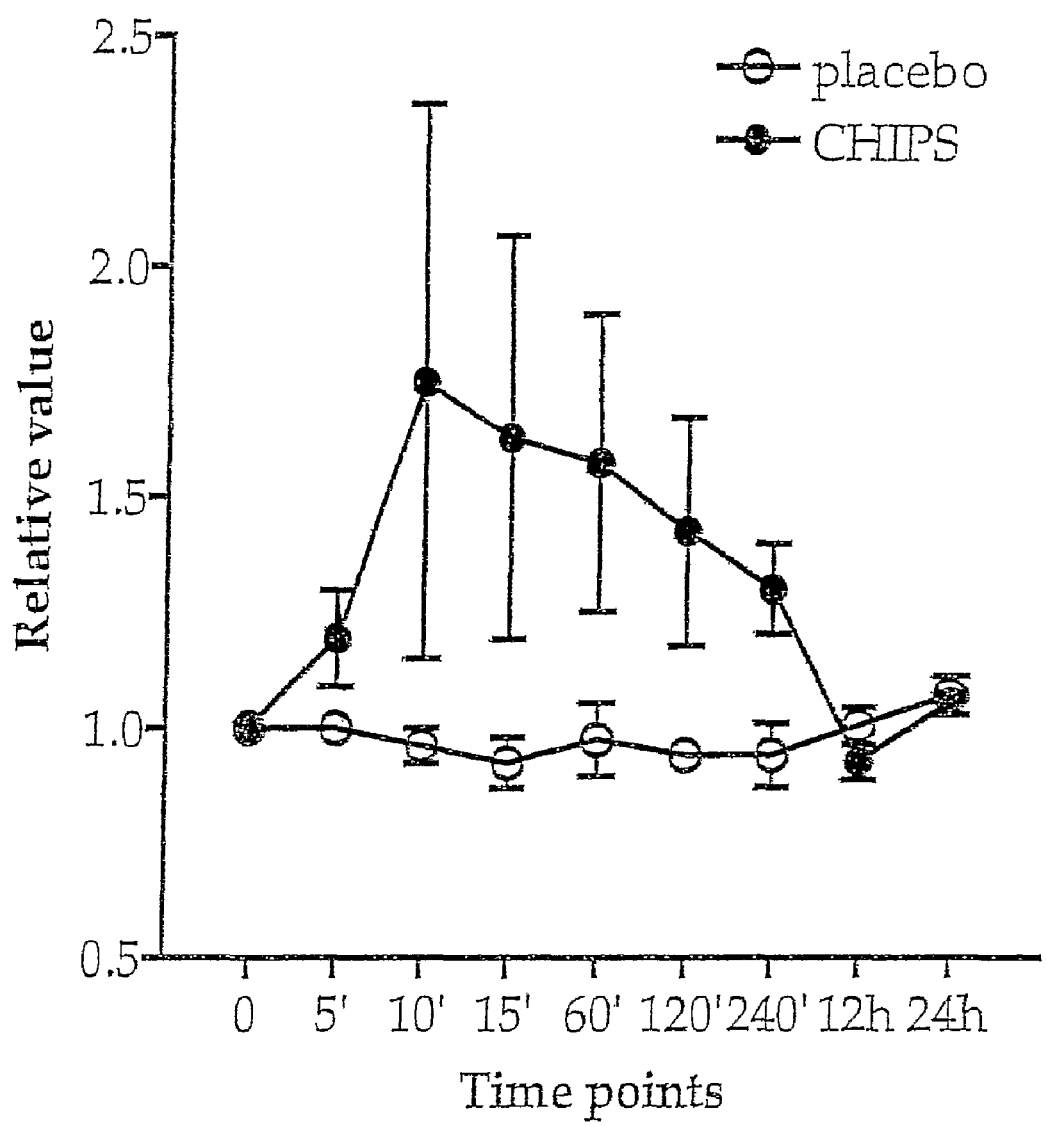
Figure 9A:
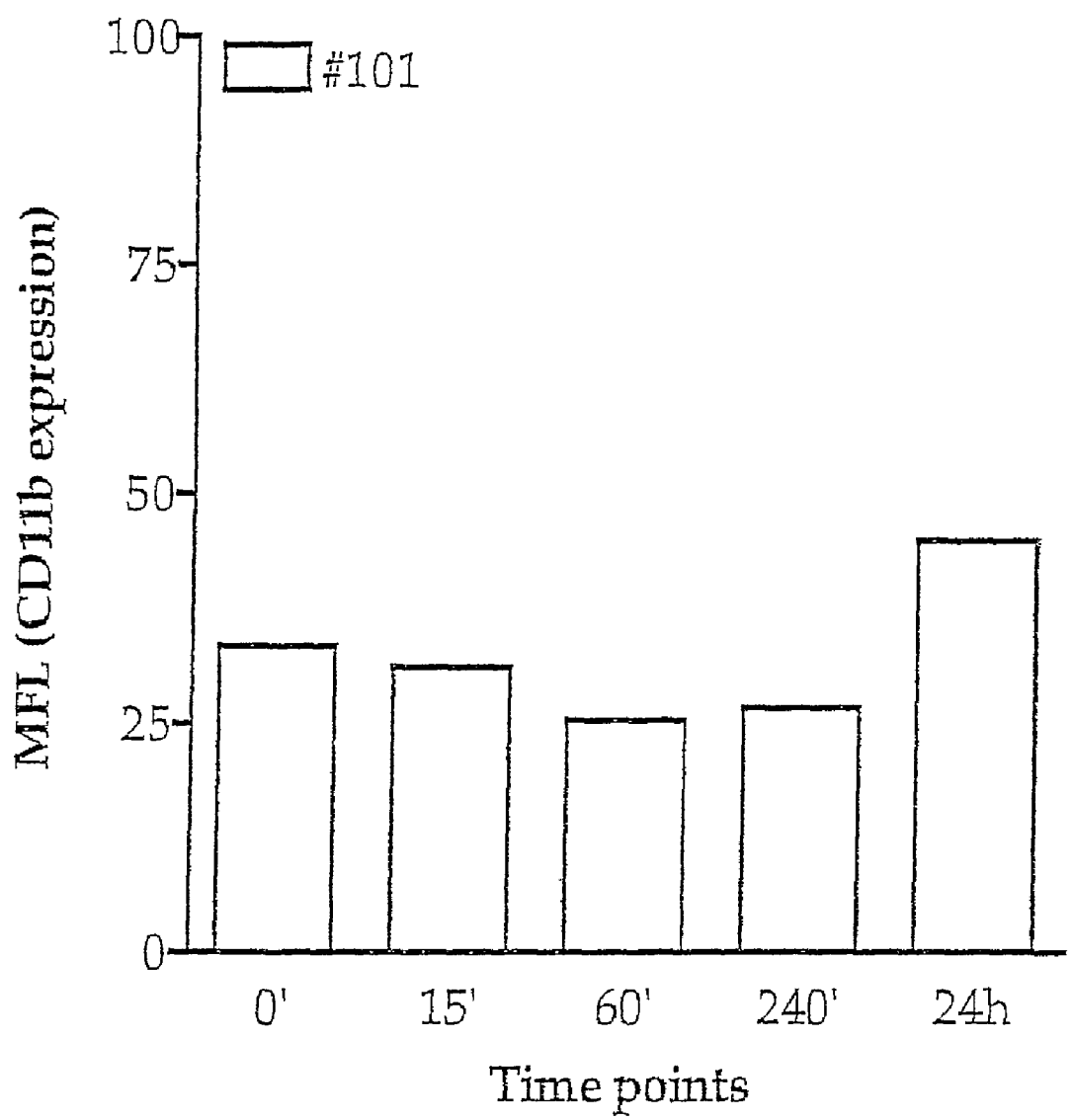
Figure 9A:
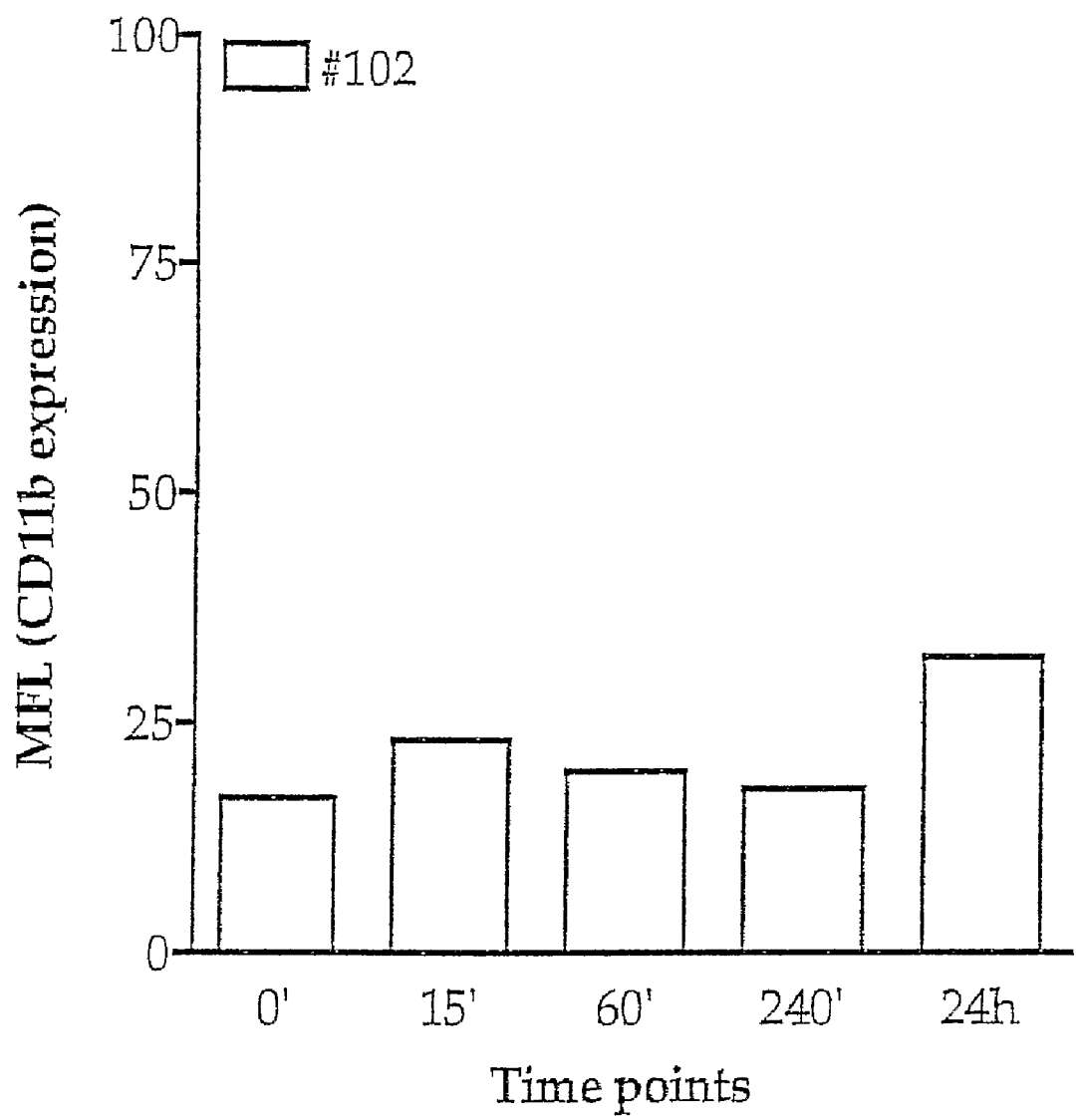
Figure 9A:
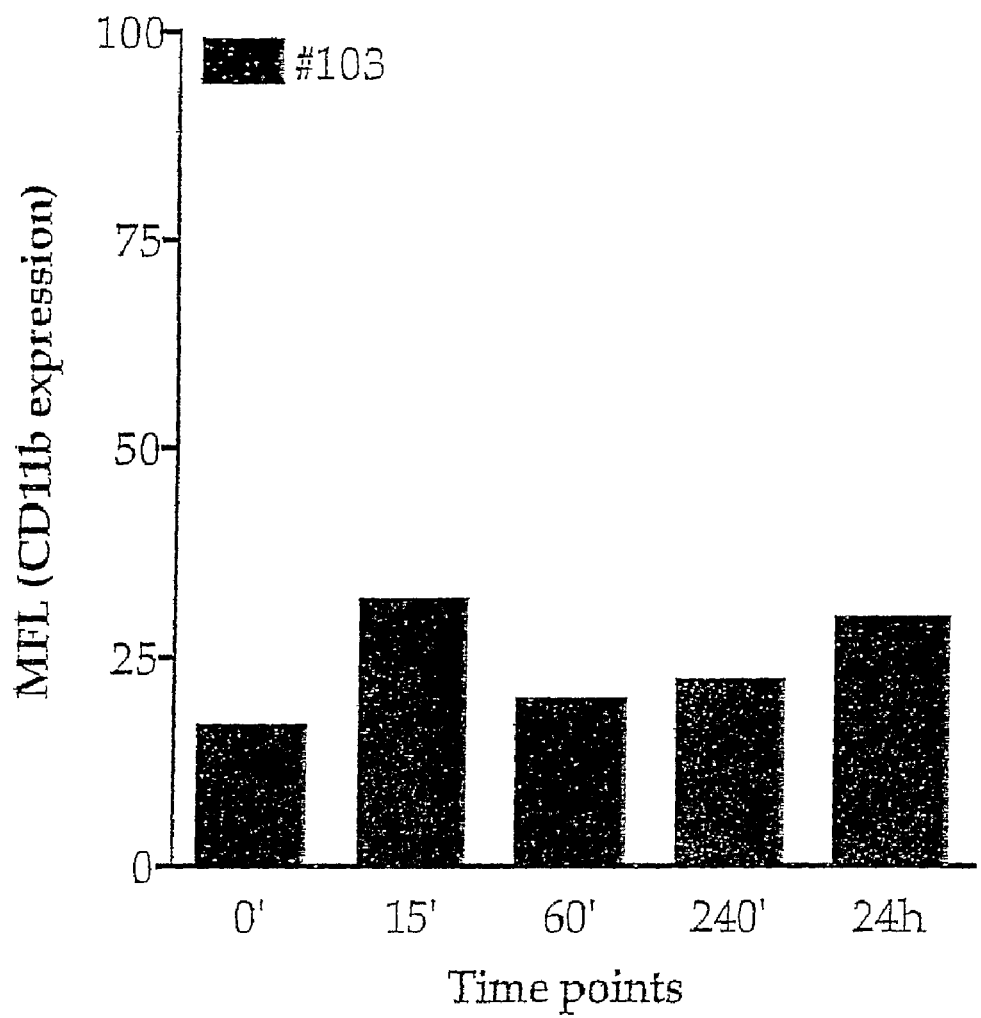
Figure 9A:
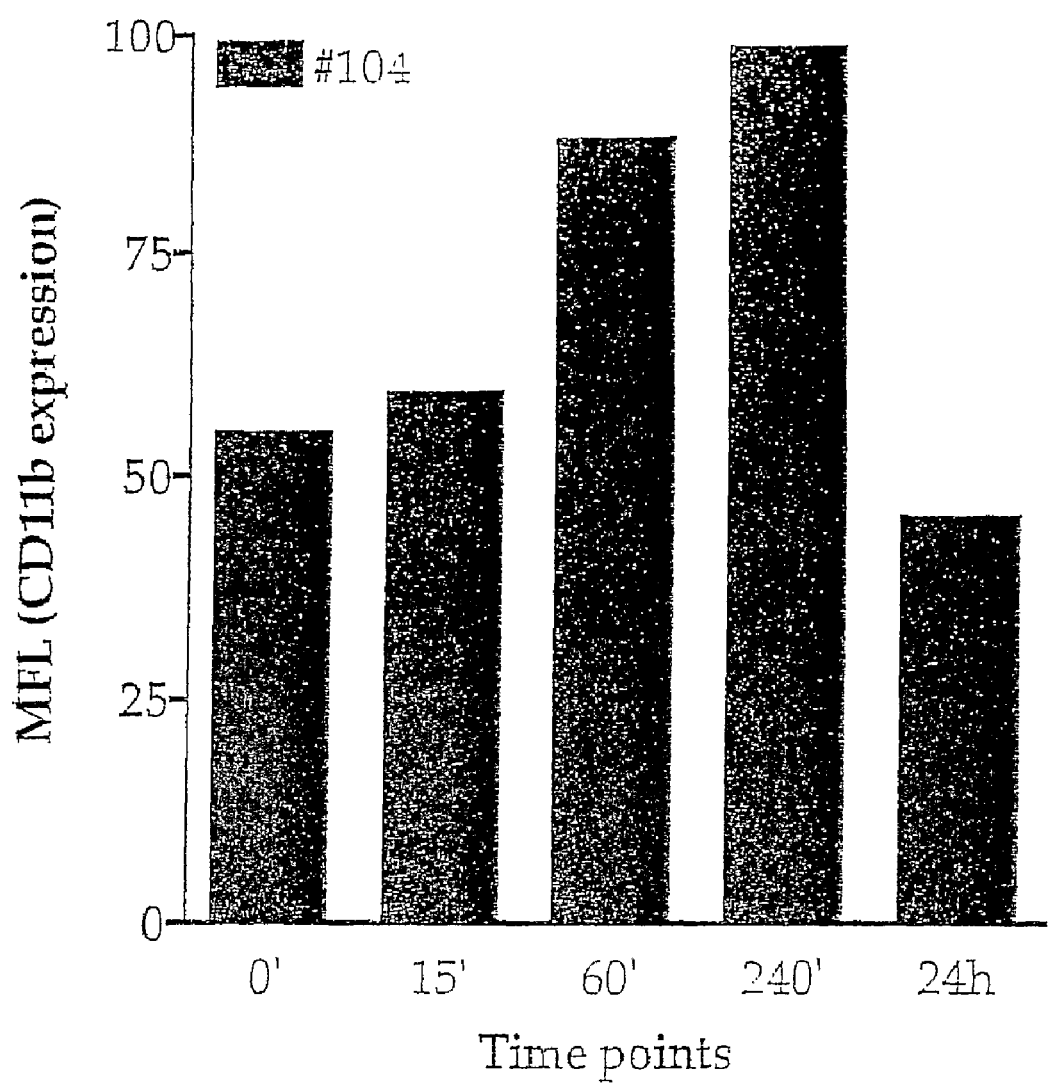
Figure 9A:
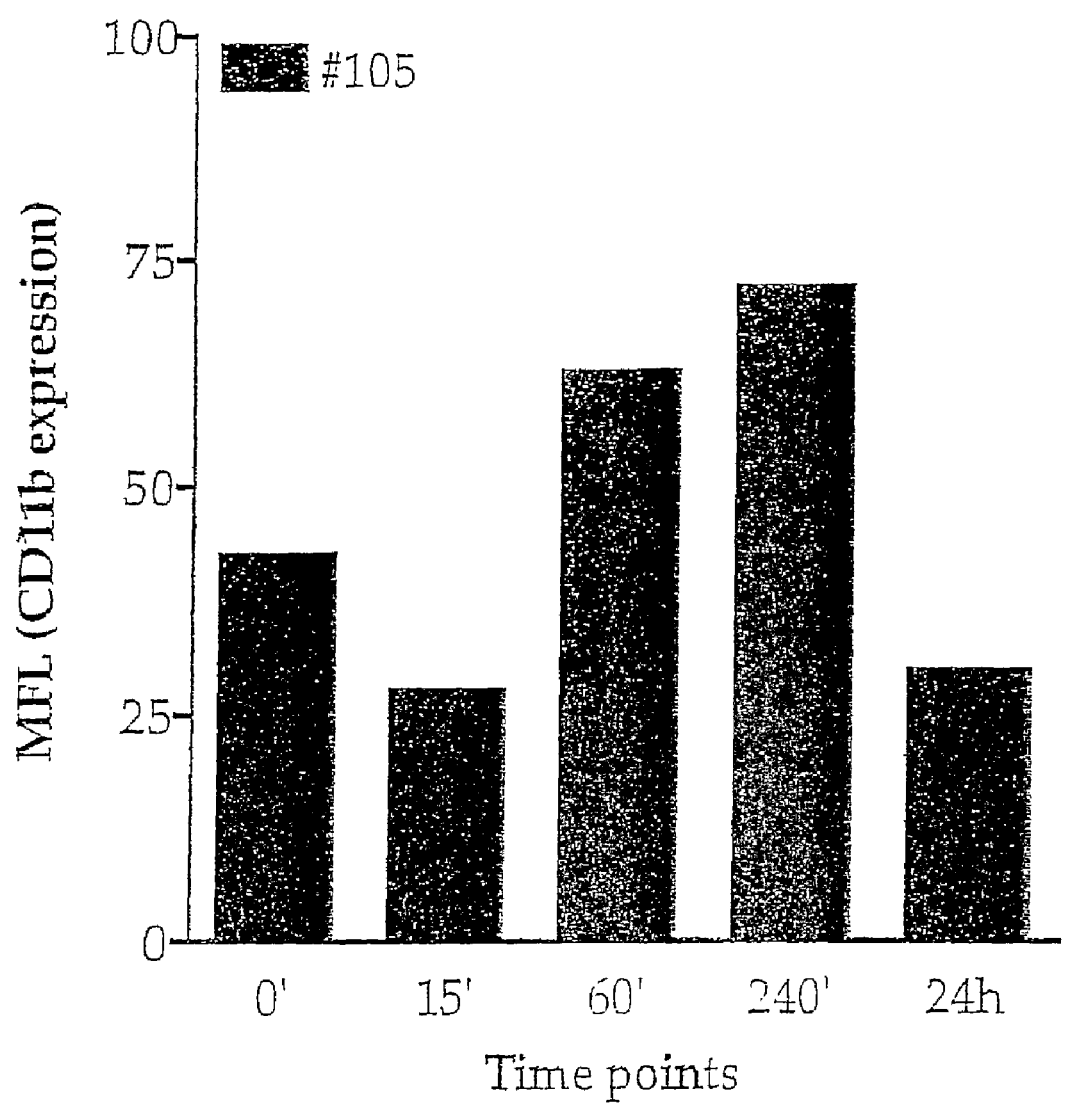
Figure 9A:
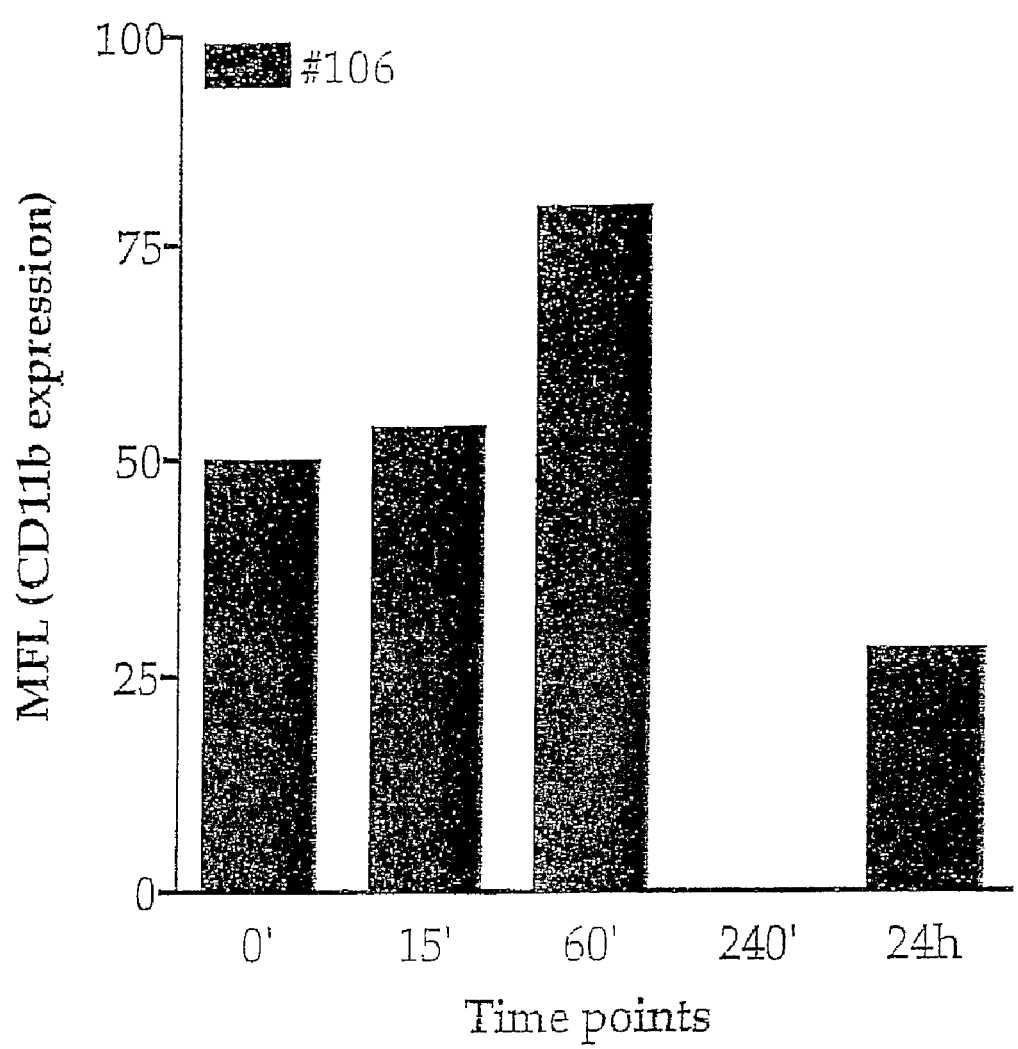
Figure 9B:
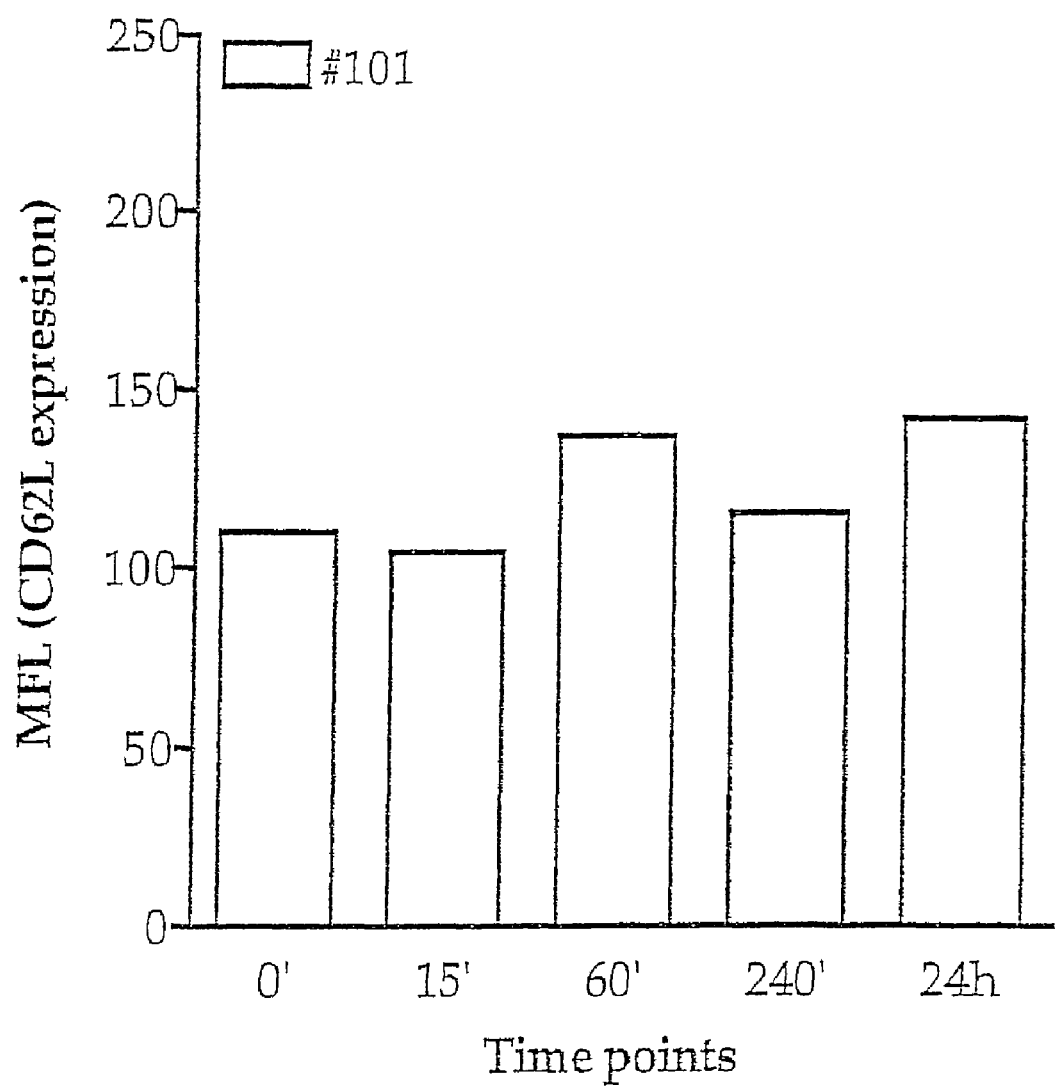
Figure 9B:
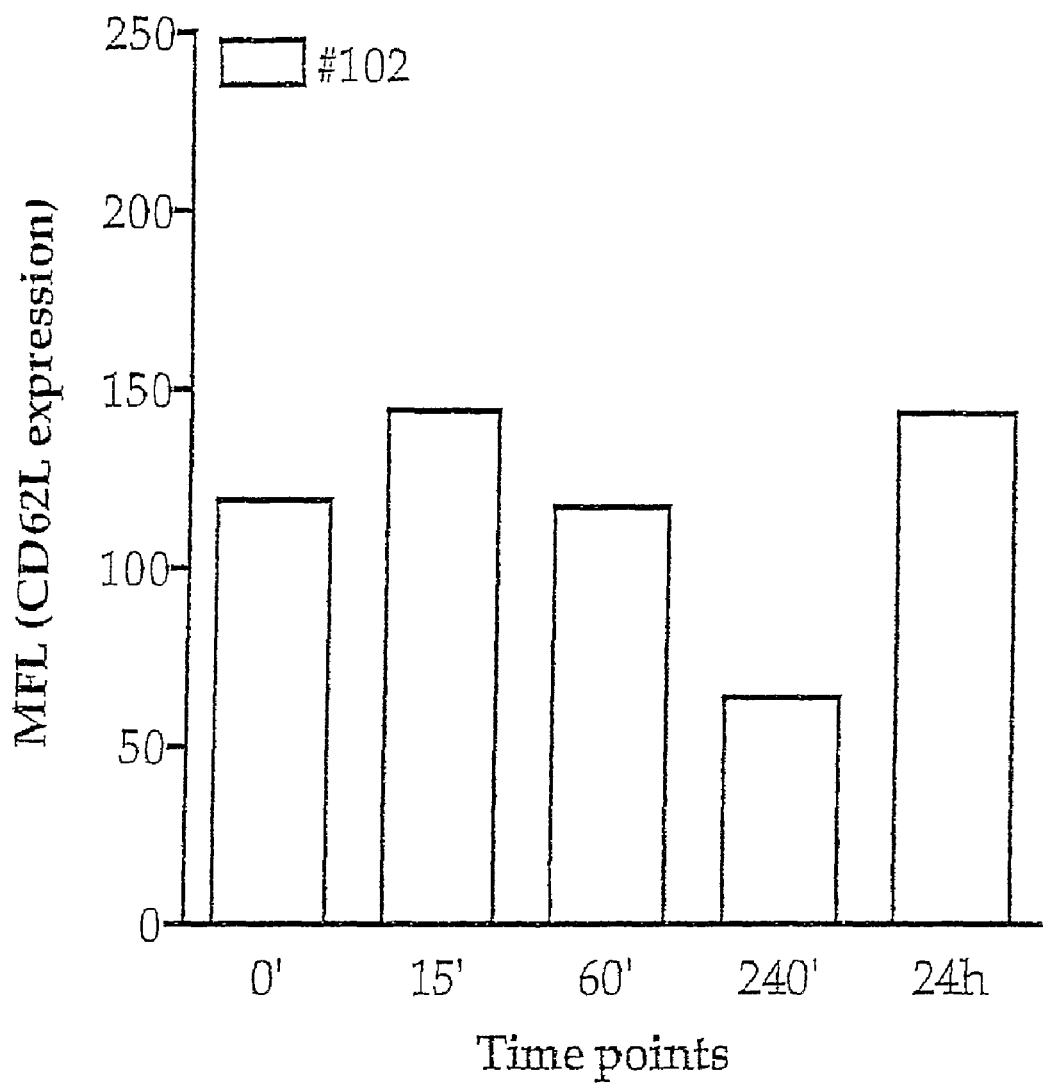
Figure 9B:
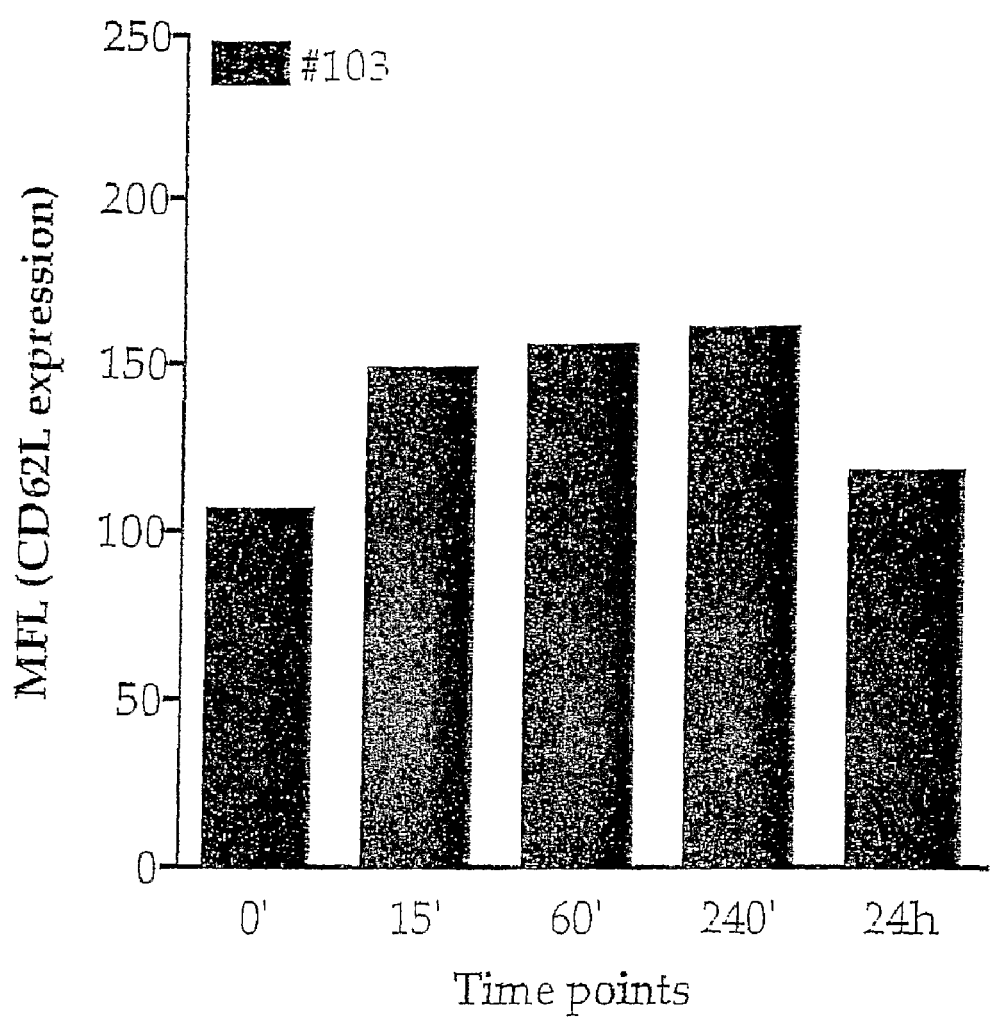
Figure 9B:
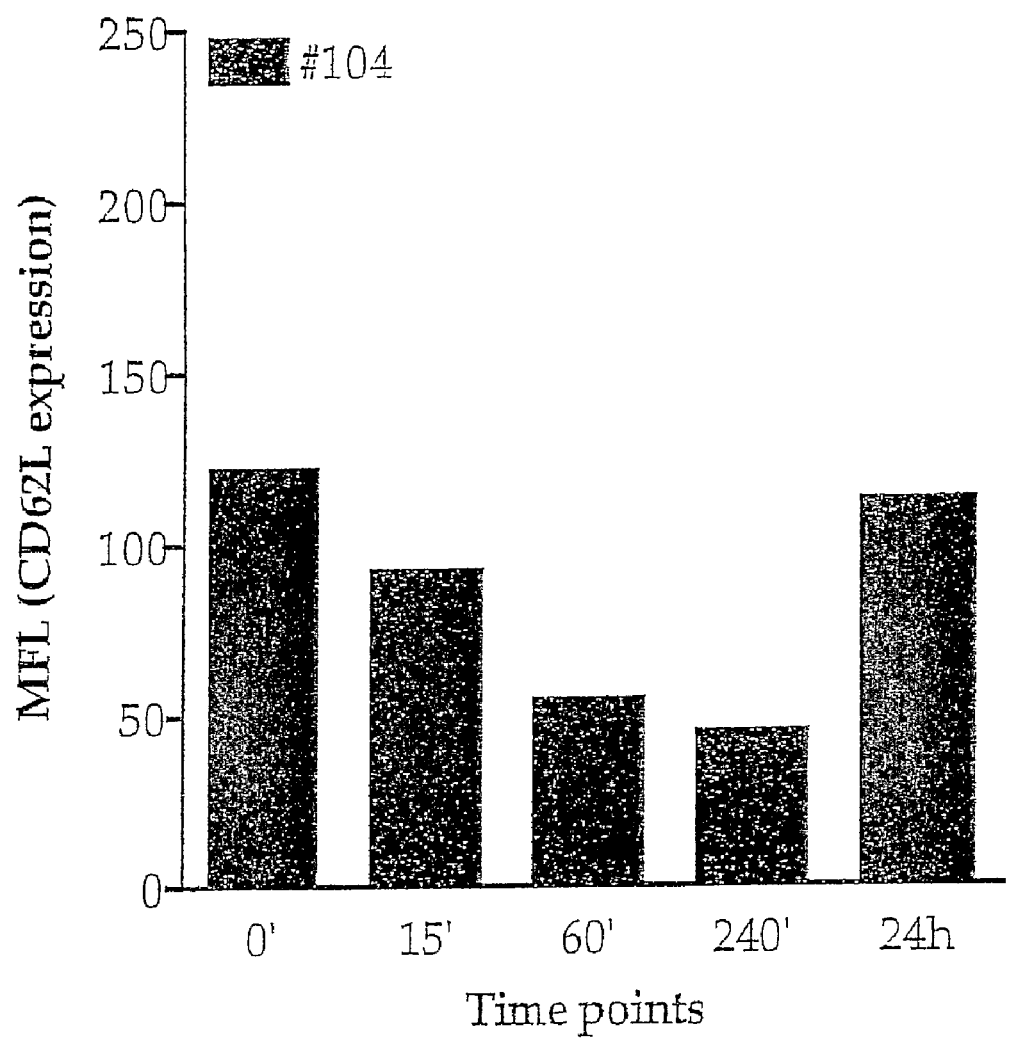
Figure 9B:
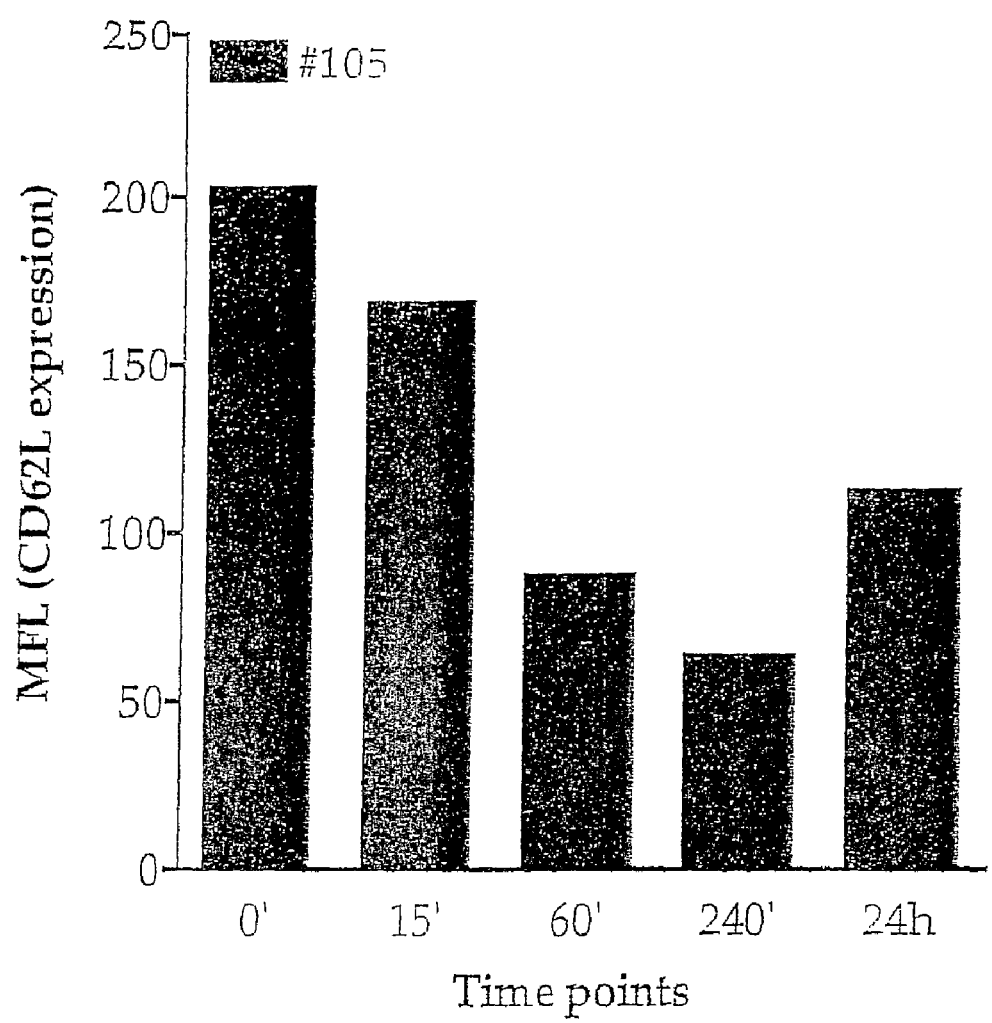
Figure 9B:
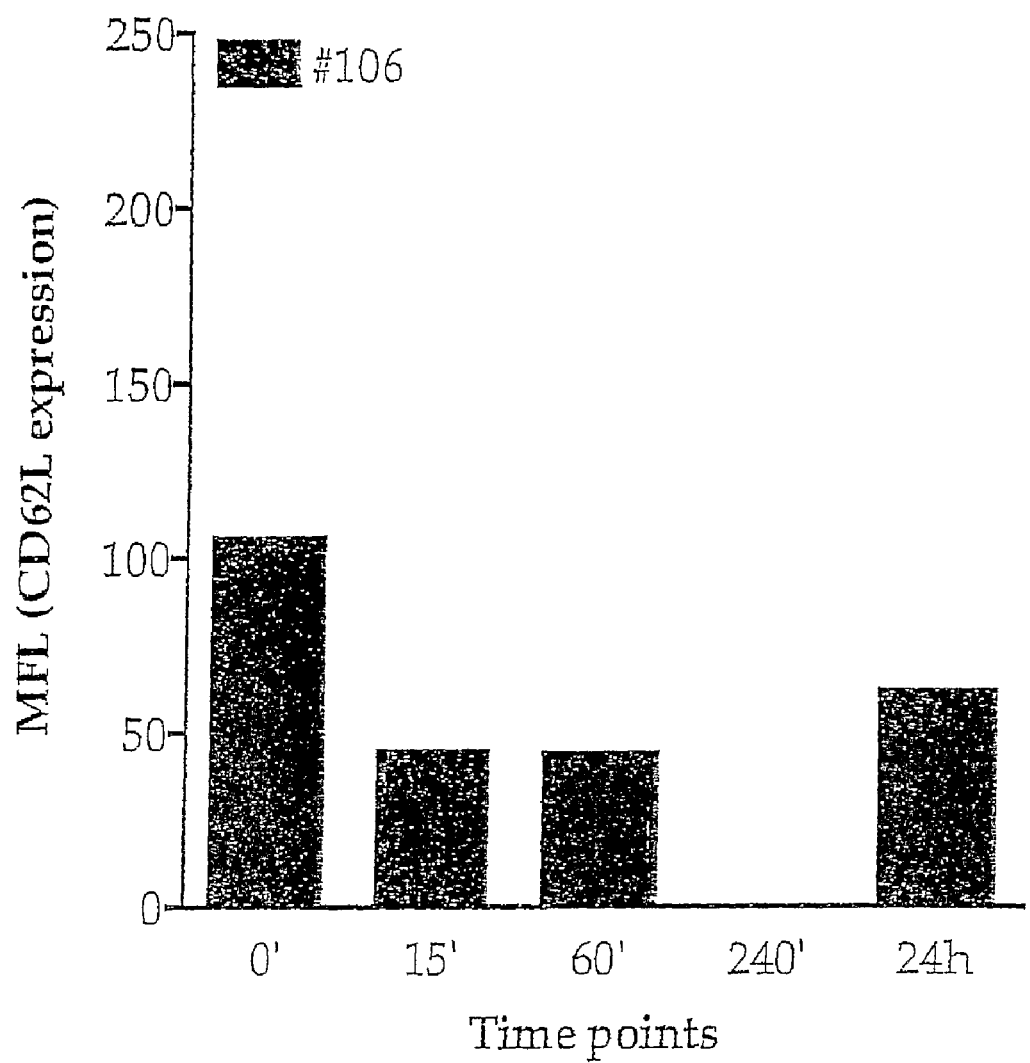

FIG. 8—Adverse effects of CHIPS as measured by levels of Circulating Immune Complexes (CIC; (a)) and mast cell marker tryptase (b). At various time points after iv injection of CHIPS, specific assays were performed for both markers. Data are expressed relative to the value at T=0 and shown as mean±SD for placebos (•) and CHIPS receivers (▲).

FIG. 9—Expression index of CD11b and CD62L on circulating peripheral blood neutrophils at various time points after iv injection of CHIPS. For each subject the expression of CD11b and CD62L was normalised for every time point relative to the initial expression level at T=0. These values were used to calculate the activation index for each subject at every time point (relative value for CD11b/relative value for CD62L).

Figure 10:
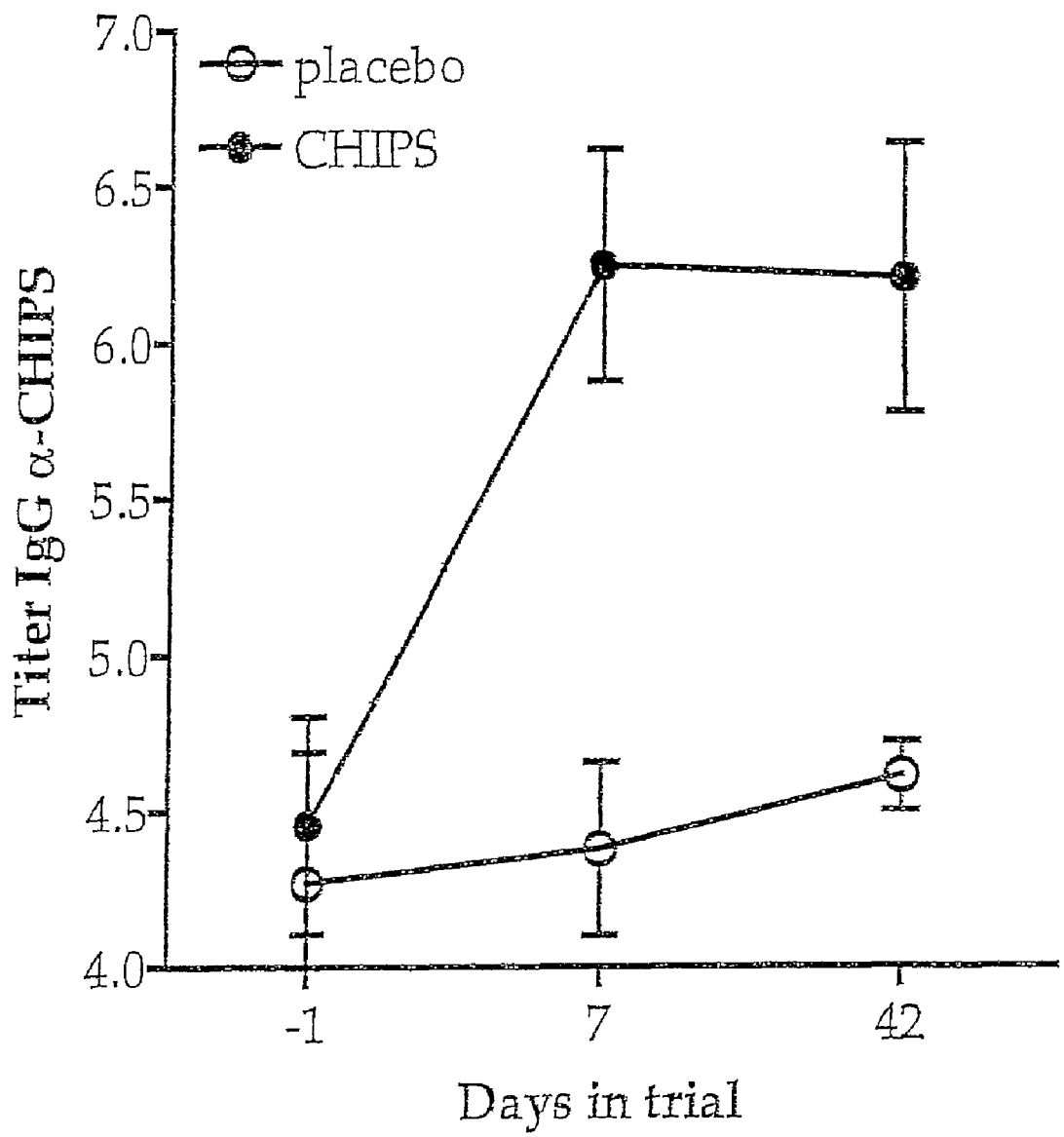

FIG. 10—Immunogenicity of CHIPS in healthy human subjects. Specific IgG titers towards CHIPS were determined in all subjects before trial start and 7 and 42 days after trial closing. Values are mean±SD for placebos (•) and CHIPS receivers (■).

Figure 11:
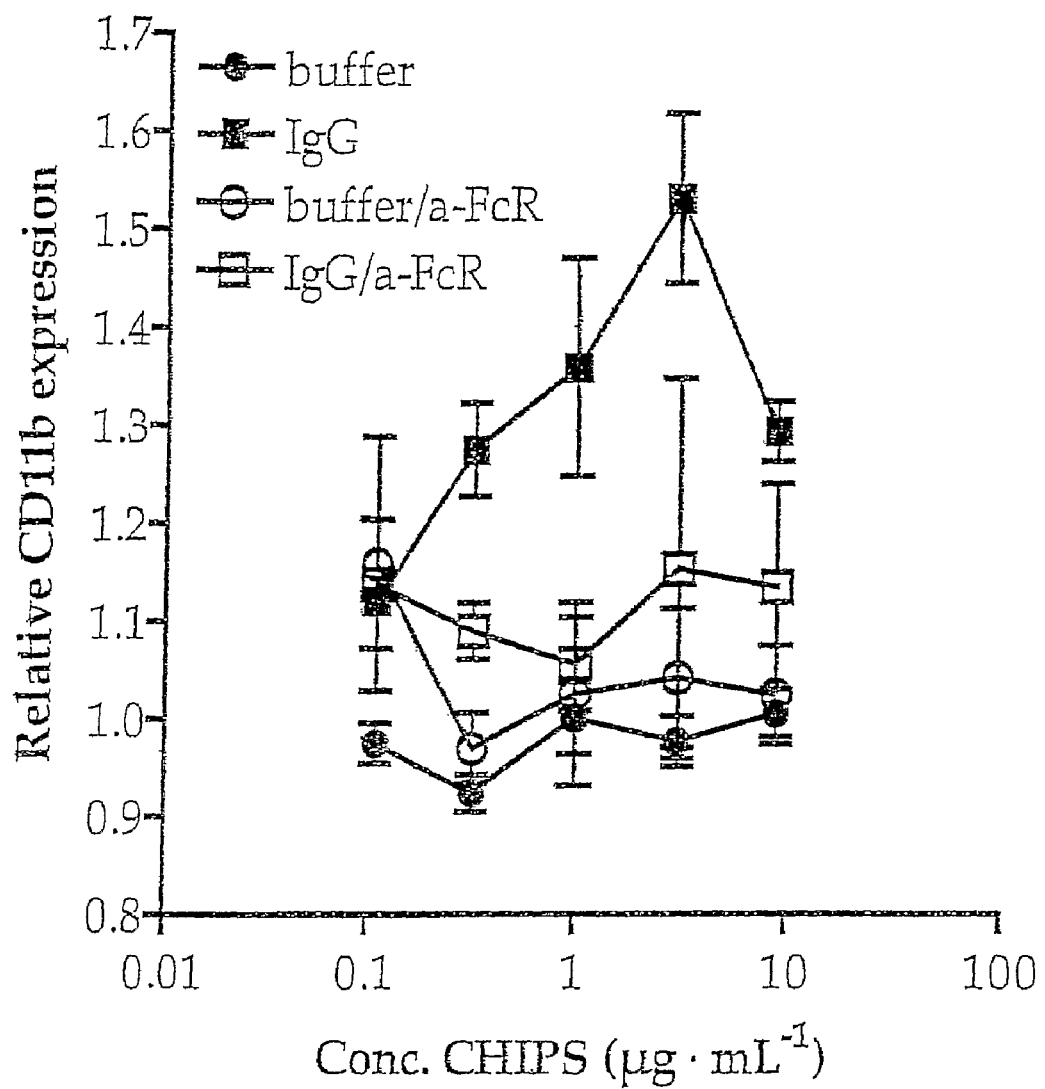

FIG. 11-R*elative* CD11b expression on neutrophils induced by CHIPS-IgG complexes in vitro. Isolated neutrophils from healthy volunteers were challenged with increasing concentration of CHIPS with (■) or without (•) 20 μg·mL$^{-1}$ affinity purified human α-CHIPS IgG. To address the role of FcγR, cells were pretreated with blocking mAb anti-FcRII (IV-3) and F(ab')$_2$ anti-FcRIII (3G8), washed and used to stimulate with CHIPS in buffer (□) or anti-CHIPS IgG (○). After challenge cells were incubated on ice with fluorescent-labelled anti-CD11b mAb to determine the level of cell activation. Data are expressed relative to the CD11b expression of cells in buffer only (without CHIPS or IgG) and shown as mean±SEM (n≧3).

Figure 12:
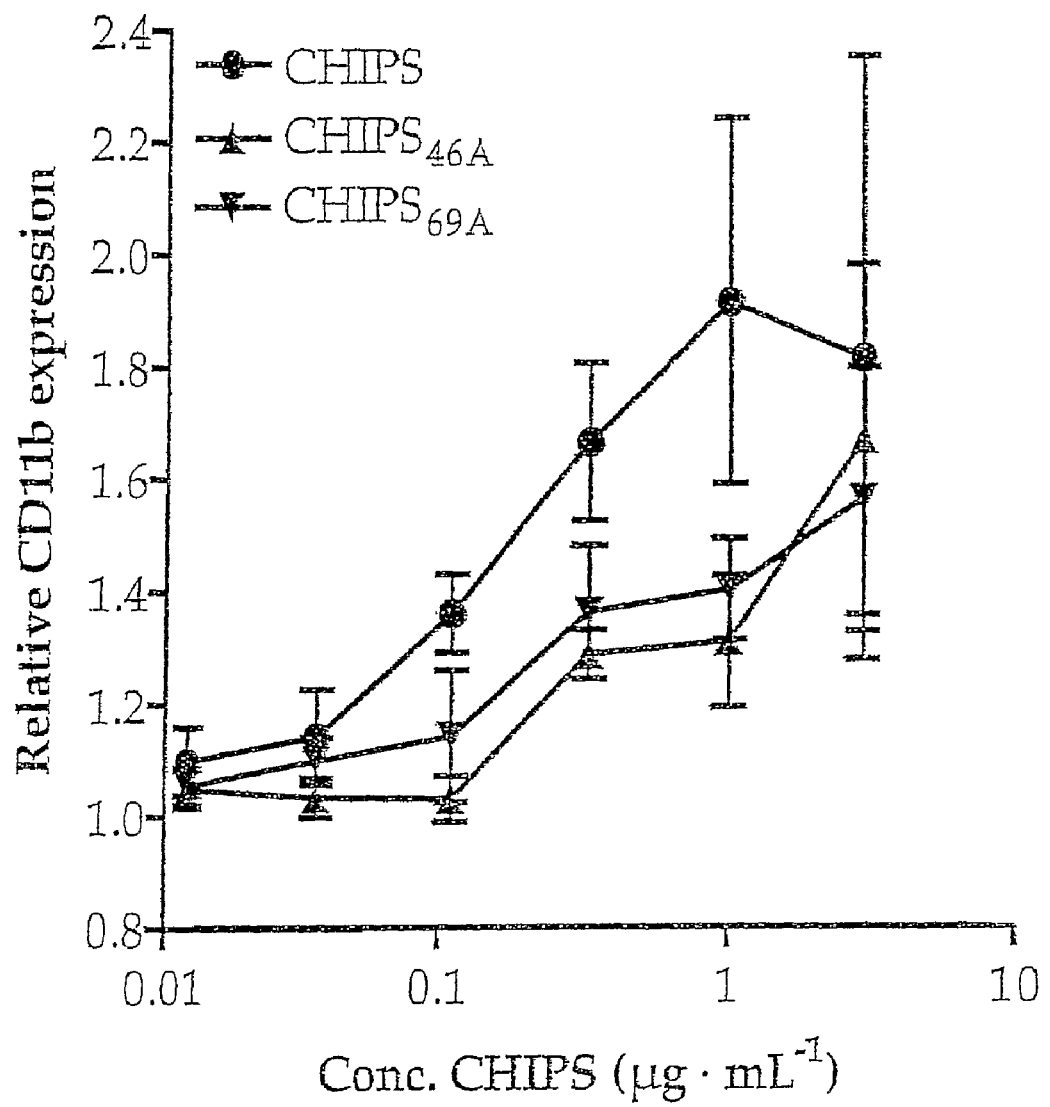

FIG. 12-R*elative* CD11b expression on whole blood neutrophils induced by CHIPS and alanine substitution mutants ex vivo. EDTA blood from healthy volunteers was challenged with increasing concentrations wild-type CHIPS (CHIPS$_{WT}$), alanine substitution mutant for arginine at position 46 (CHIPS$_{R46A}$) and mutant for lysine at position 69 (CHIPS$_{K69A}$). CD11b expression was determined with a specific mAb on ice and data expressed as relative to buffer only cells as means±SEM (n≧3).

Figure 13:
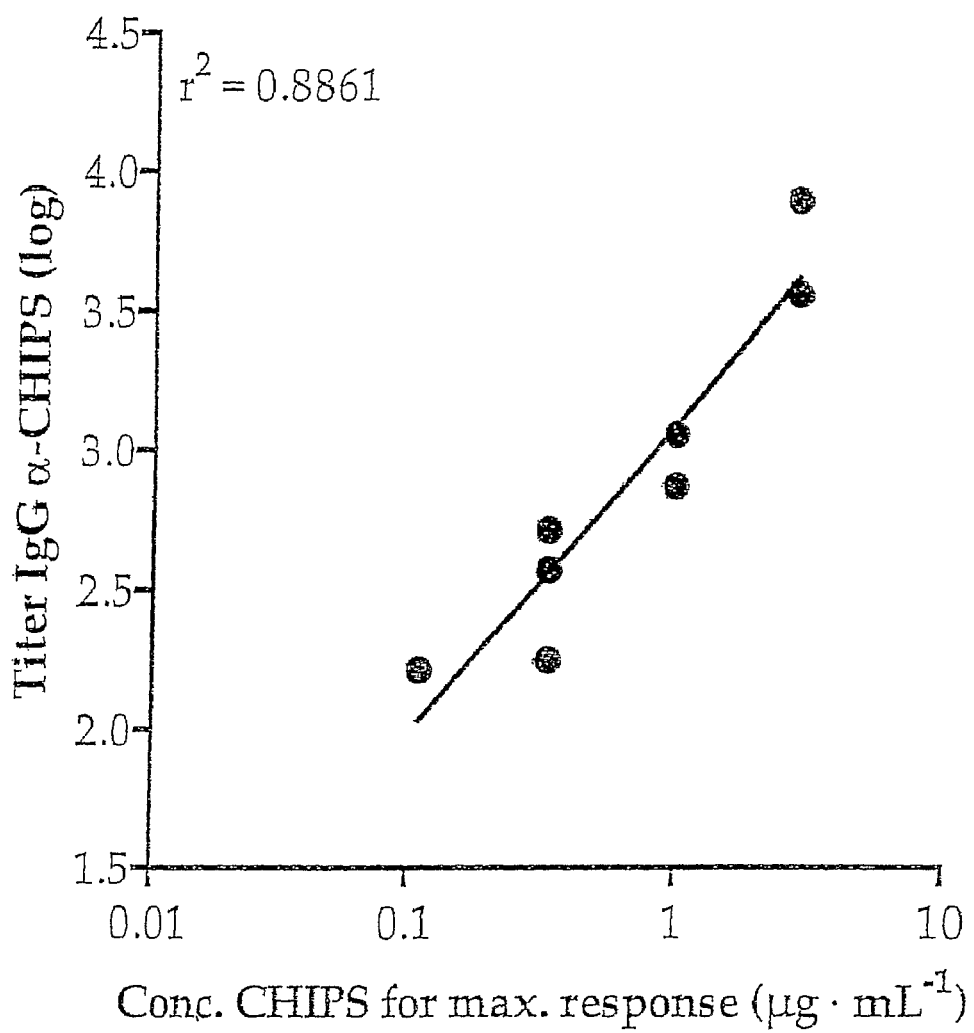

FIG. 13—Correlation between specific anti-CHIPS IgG titre and amount of CHIPS required for maximal stimulation of whole blood neutrophils ex vivo. EDTA blood from healthy volunteers was challenged with increasing concentrations CHIPS and CD11b expression measured as indication for cell activation. IgG anti-CHIPS titers were determined by ELISA and defined as the log serum dilution that gives an absorbance of 0.300. Regression analysis was performed using the formula: y=intercept+slope×ln(x)

Figure 14:
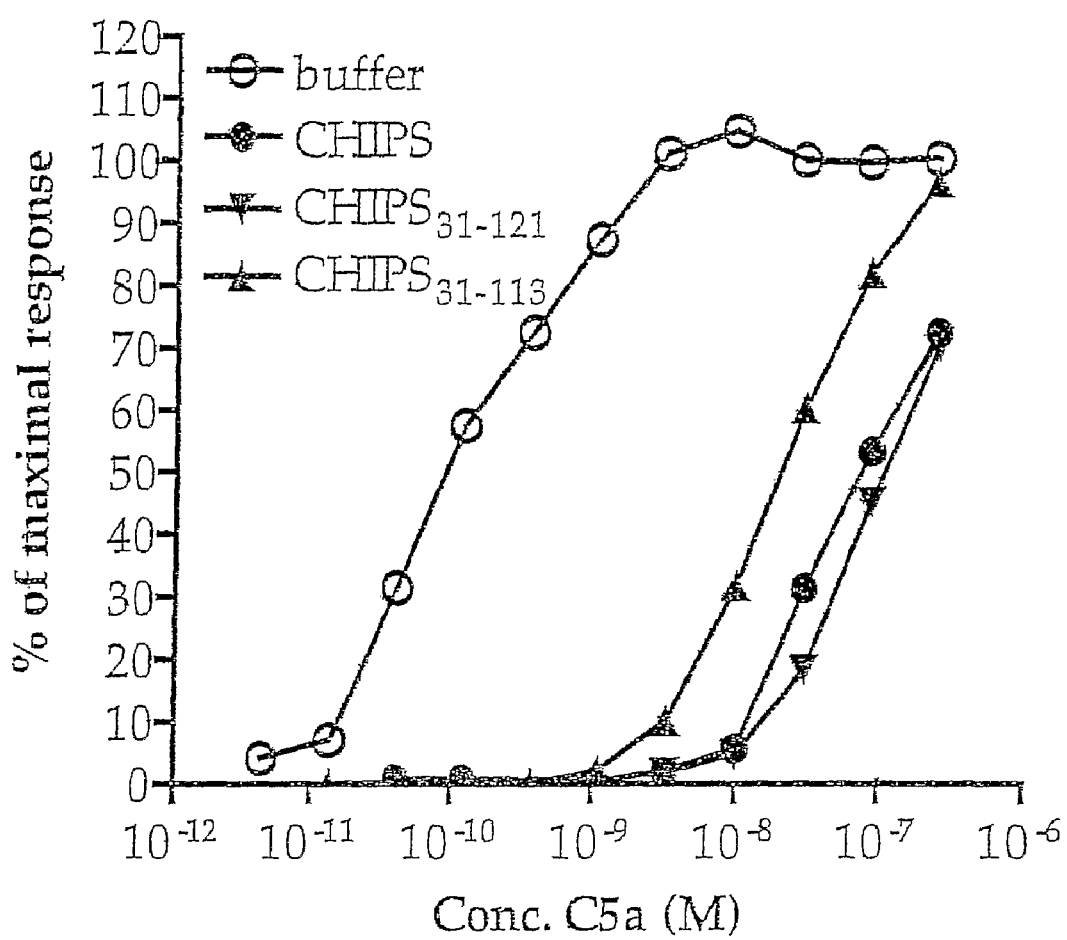

FIG. 14—CHIPS$_{31-113}$ inhibits C5a-induced cell activation. Fluo-3 labelled U937/C5aR cells were incubated with buffer or 1 μg·mL$^{-1}$ CHIPS(CHIPS$_{wt}$) or truncated CHIPS (CHIPS$_{31-421}$ and CHIPS$_{31-113}$). Cells were stimulated with different concentrations C5a and increase in fluorescence representing cell activation was measured in a flowcytometer.

Figure 15:
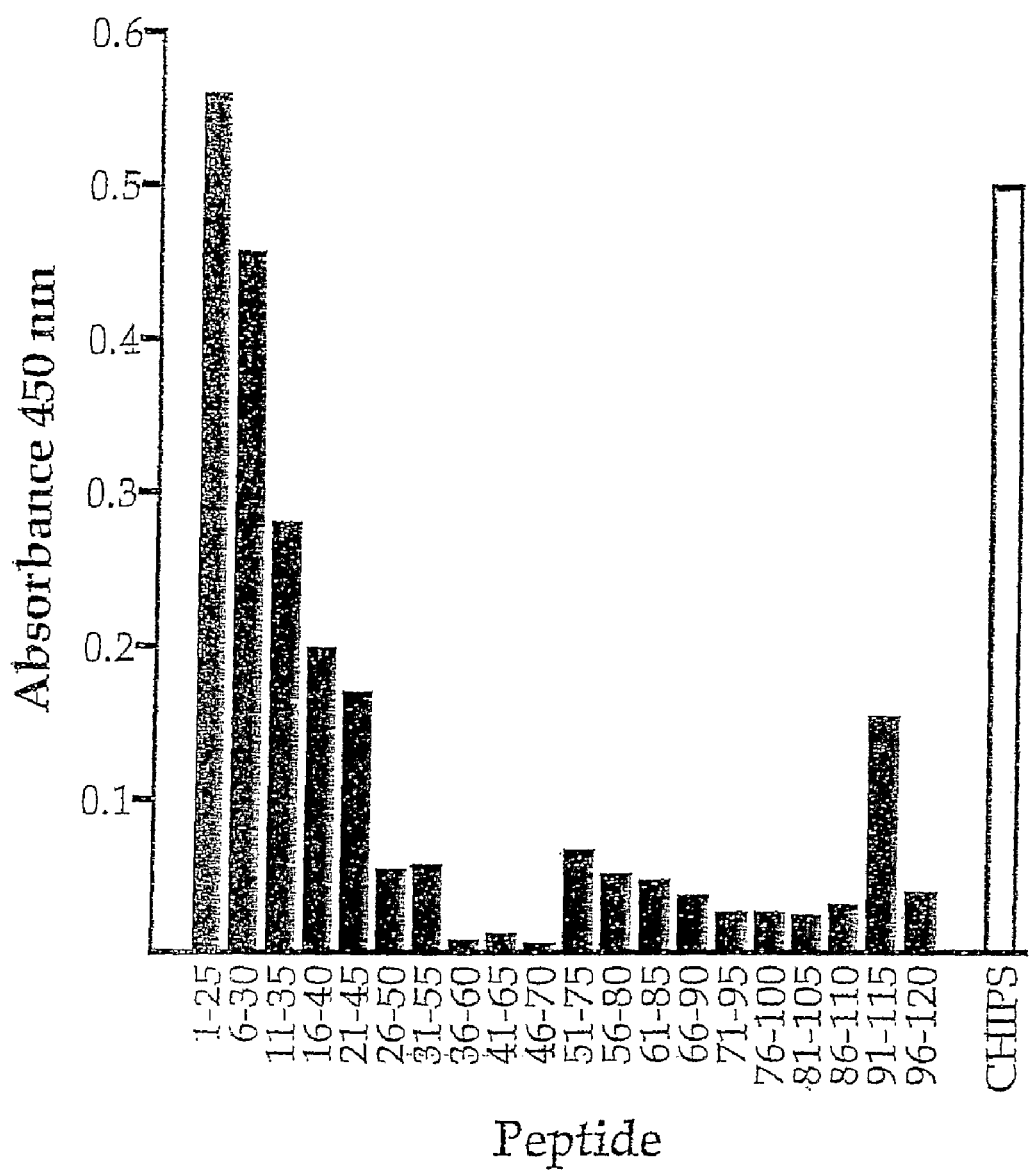

FIG. 15—Affinity purified α-CHIPS antibodies were tested in their ability to bind CHIPS derived peptides. 50 μL CHIPS (1 μg·mL$^{-1}$) or CHIPS derived peptide (10 μM) were coated to 96-well microtitre plates. Plates were blocked with 5% BSA and incubated with affinity purified α-CHIPS antibodies. Bound antibodies were detected with peroxidase conjugated goat-α-human-IgG and TMB as substrate.

Figure 16:
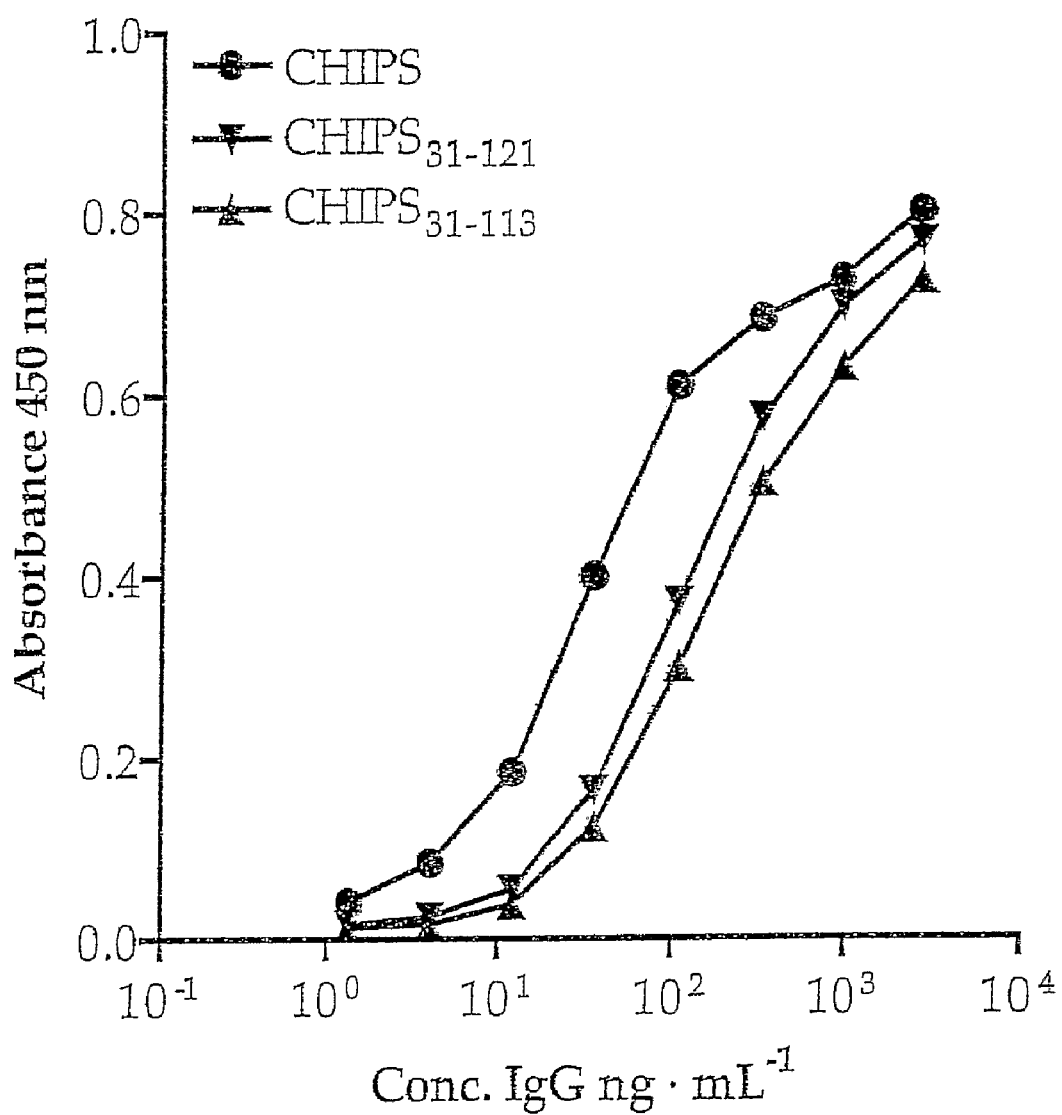
Figure 16:
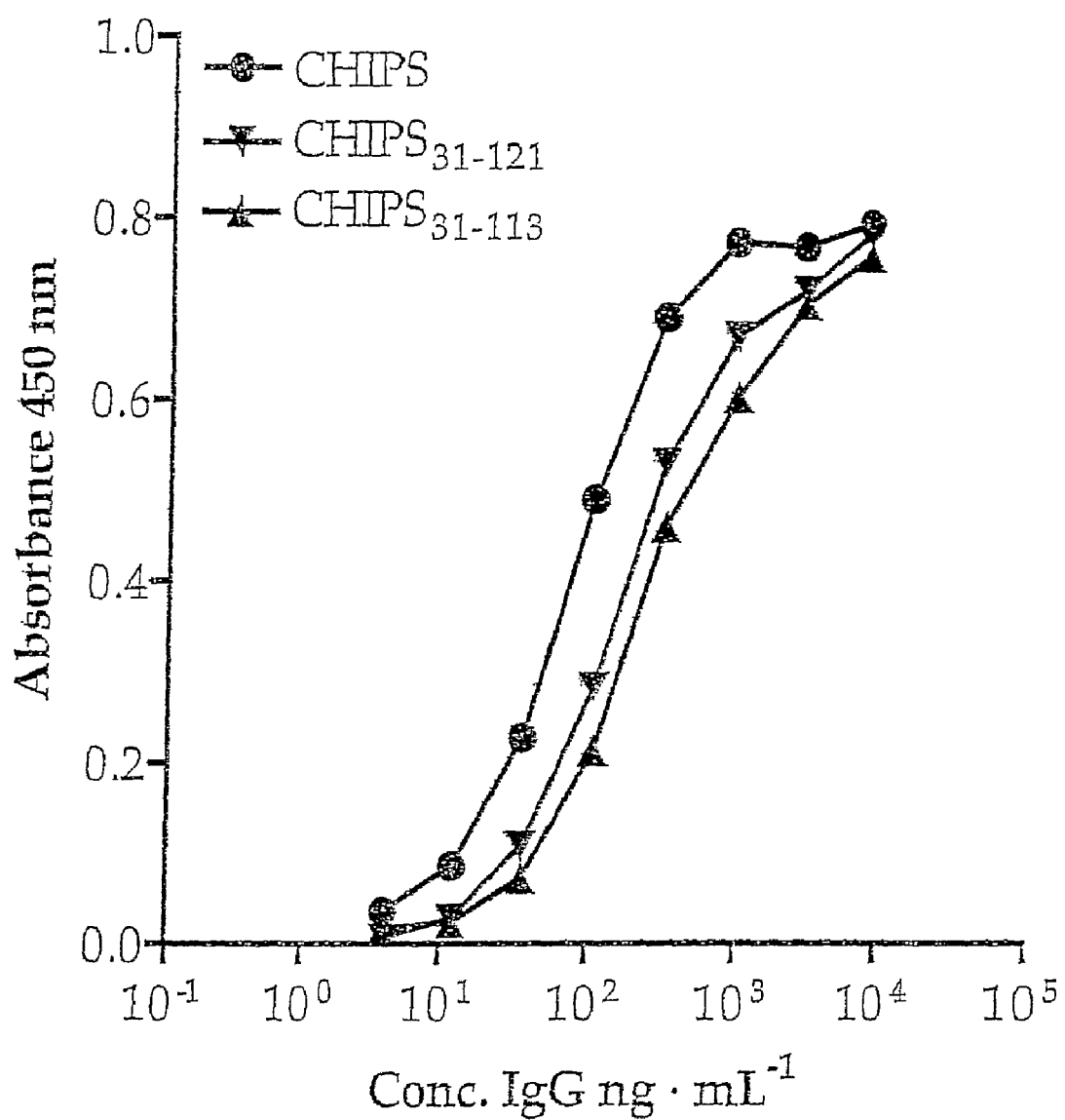
Figure 16:
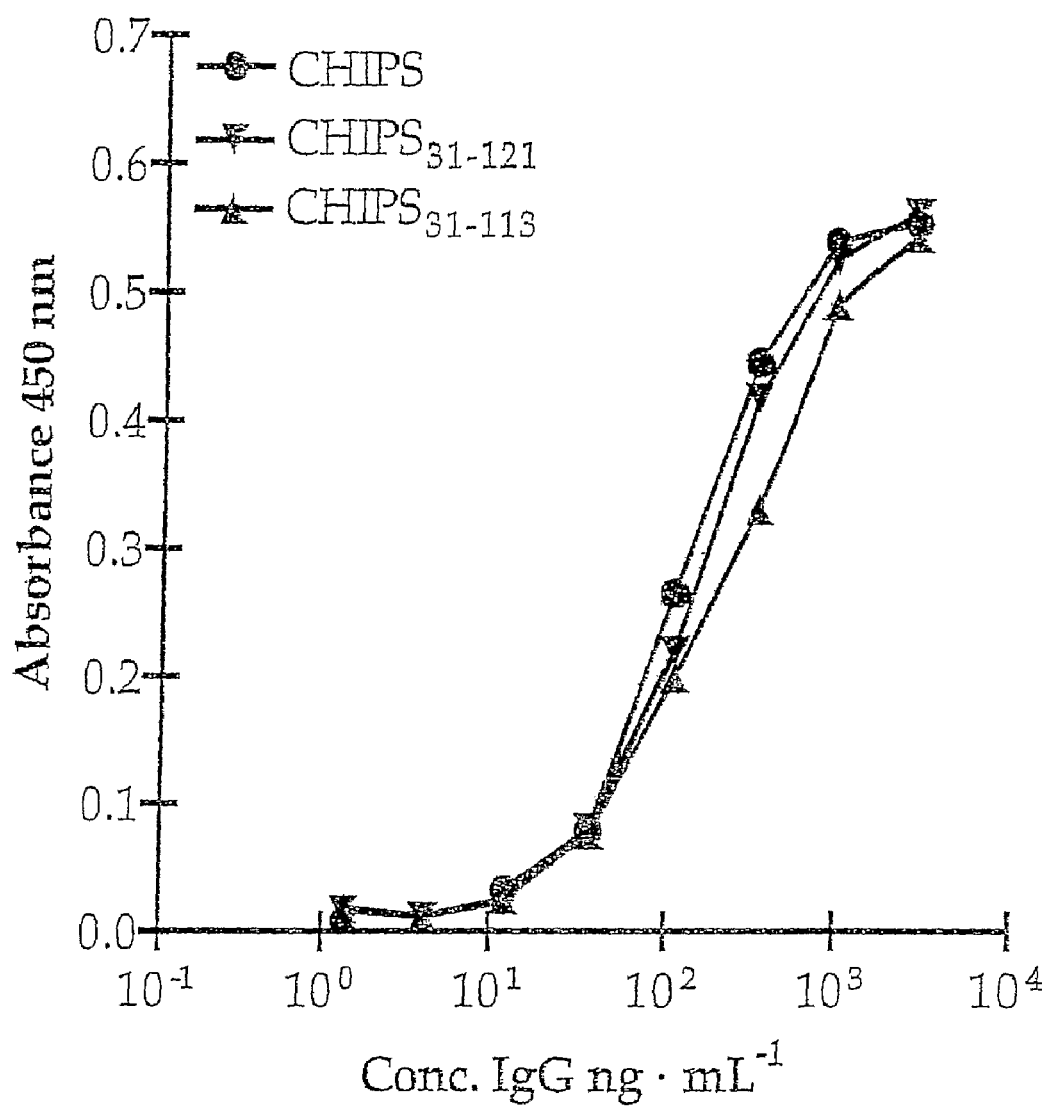

FIG. 16—Different affinity purified α-CHIPS antibodies were tested for their ability to interact with CHIPS or truncated CHIPS variants in ELISA. 1 μg·mL$^{-1}$ CHIPS or truncated CHIPS was coated on a 96-well microtitre plate. The wells were washed and incubated with different concentrations affinity purified antibody. Species-specific peroxidase conjugated goat IgG and TMB were used to detect bound antibodies. A CHIPS specific mouse monoclonal antibody (2G8) was used as a control.

Figure 17:
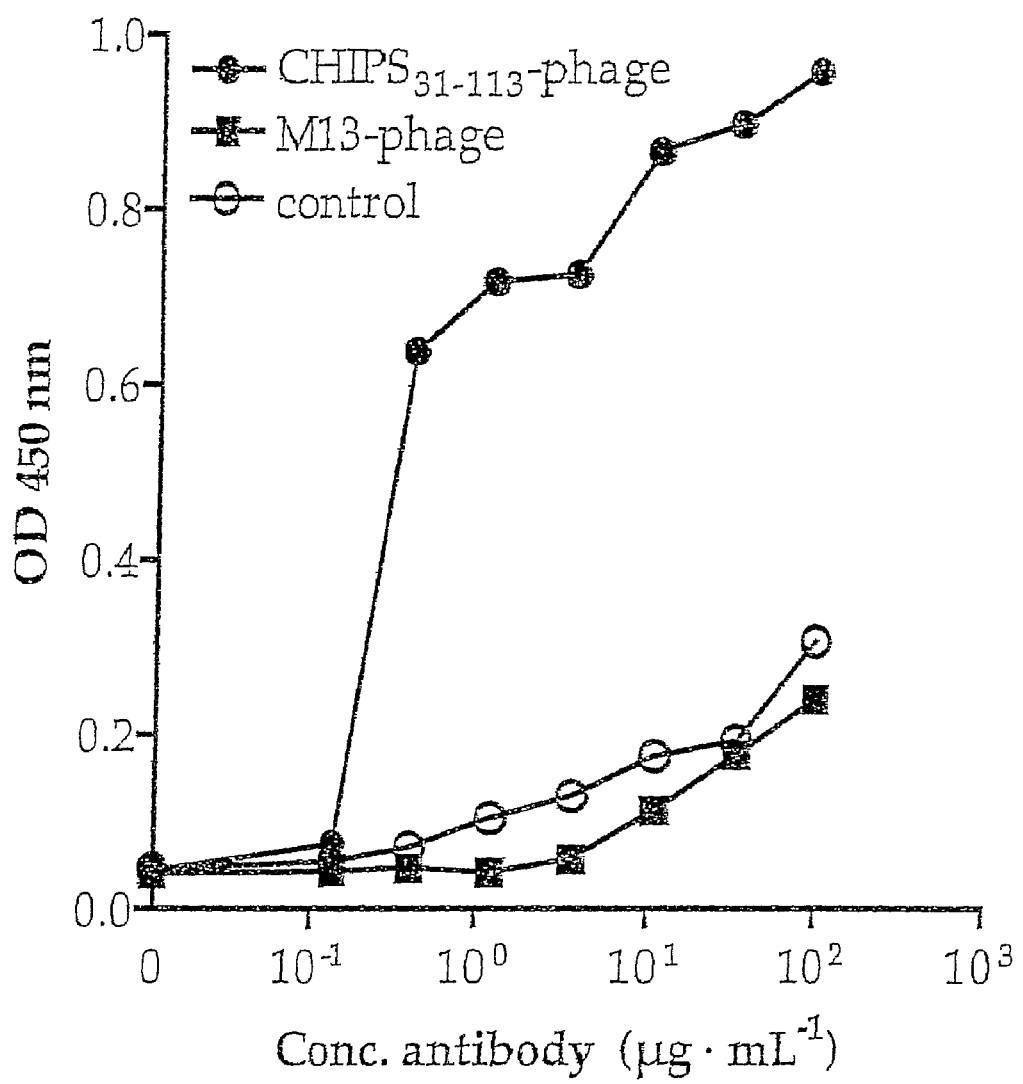
Figure 18A:
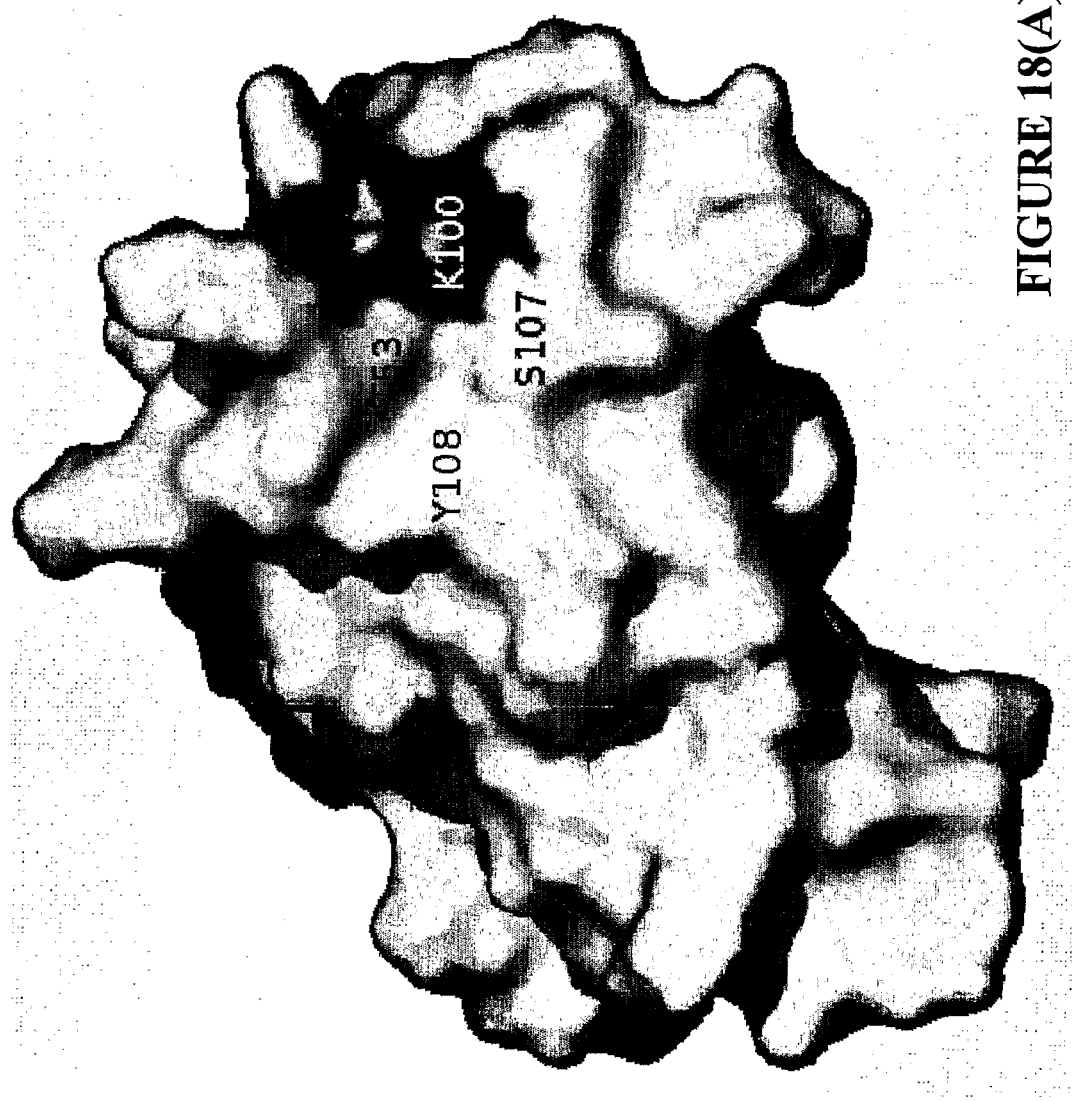
Figure 18B:
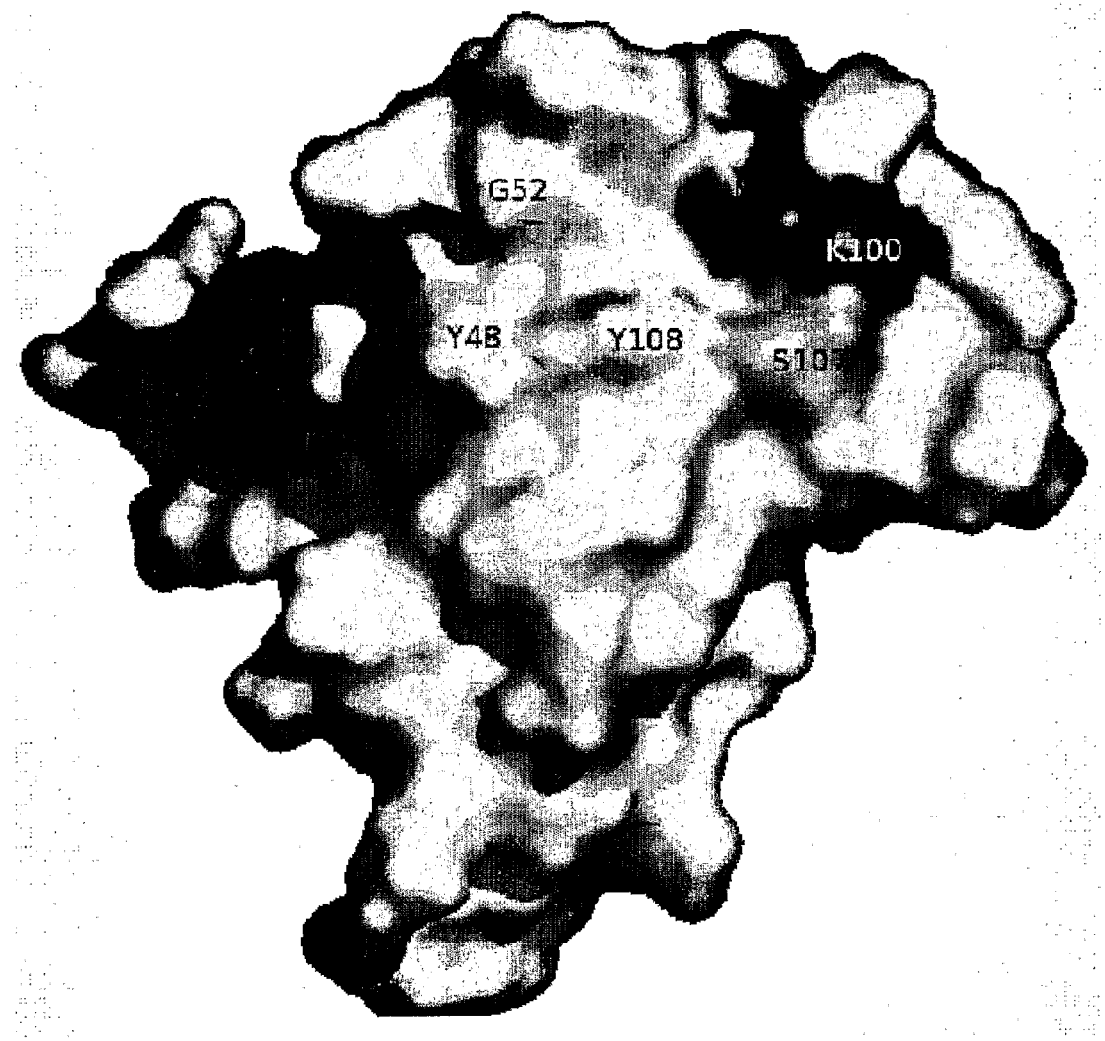
Figure 18C:
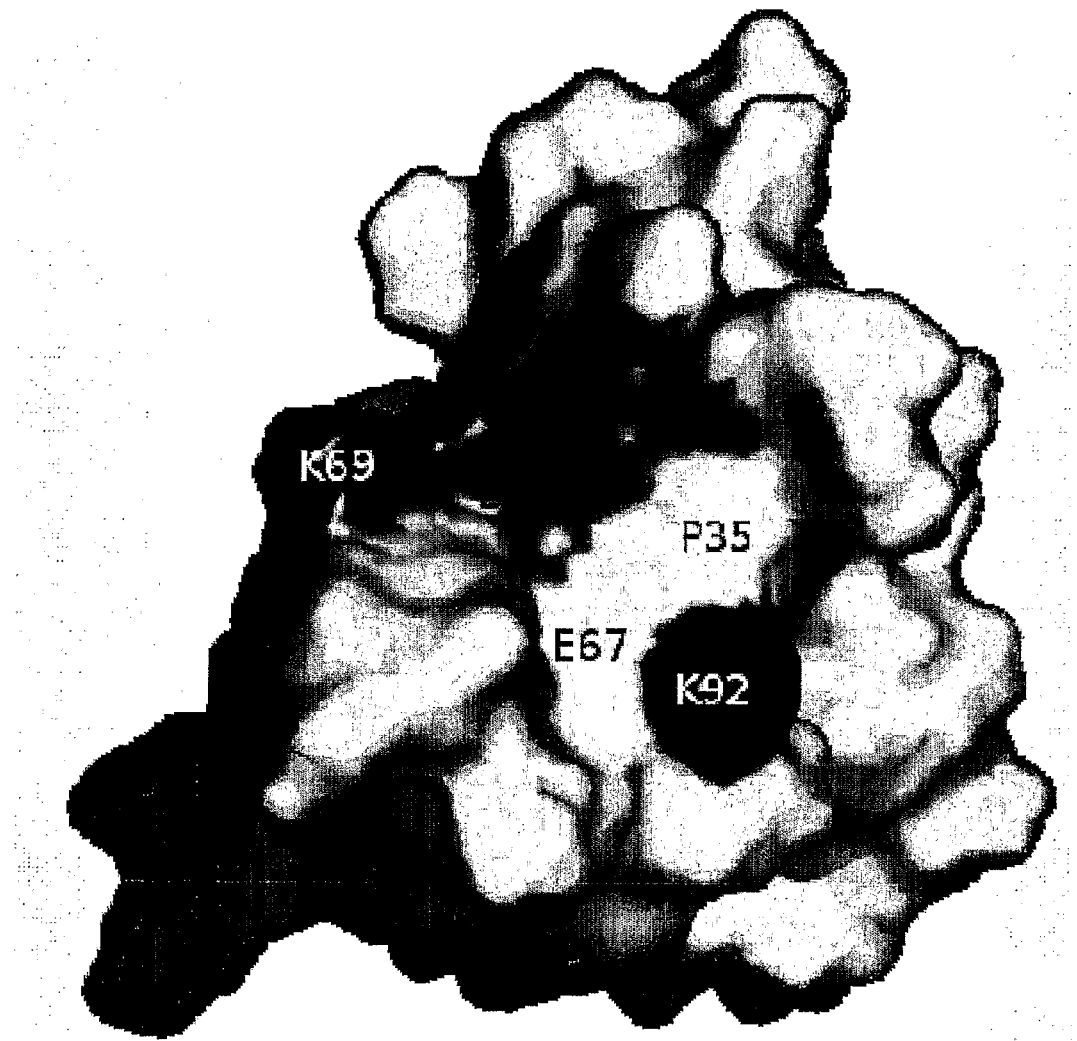
Figure 18D:
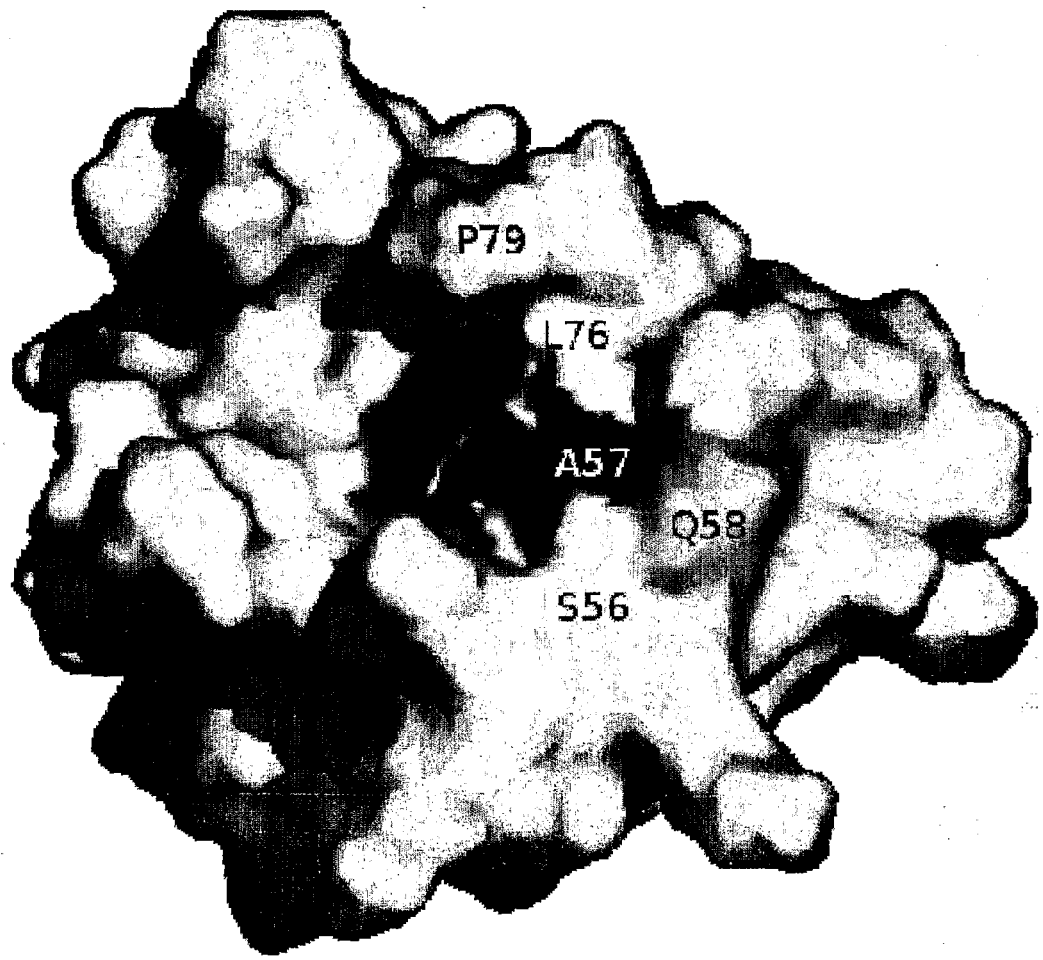

FIG. 17—Anti-phage reactivity of human affinity purified-α-CHIPS$_{31-113}$-IgG. A maxisorb 96-well plate was coated with M13 phages expressing CHIPS, wild type phages or buffer in order to test the reactivity of human affinity purified-α-CHIPS$_{31-113}$-IgG. Data show that the antibody preparation reacts only with the expressed CHIPS protein and not with the wild type phage.

FIG. 18—Conformational epitopes mapped onto the surface of the CHIPS molecule.

Figure 19:
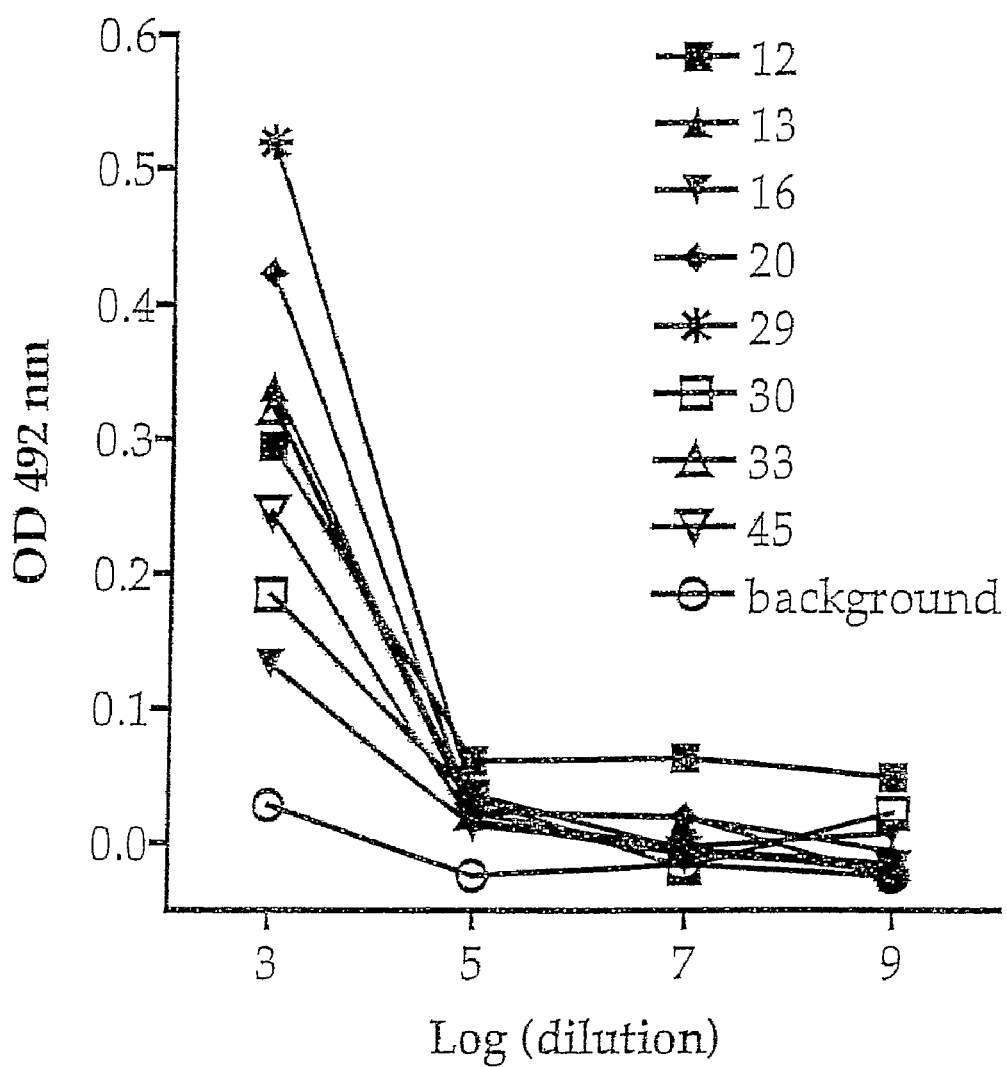
Figure 19:
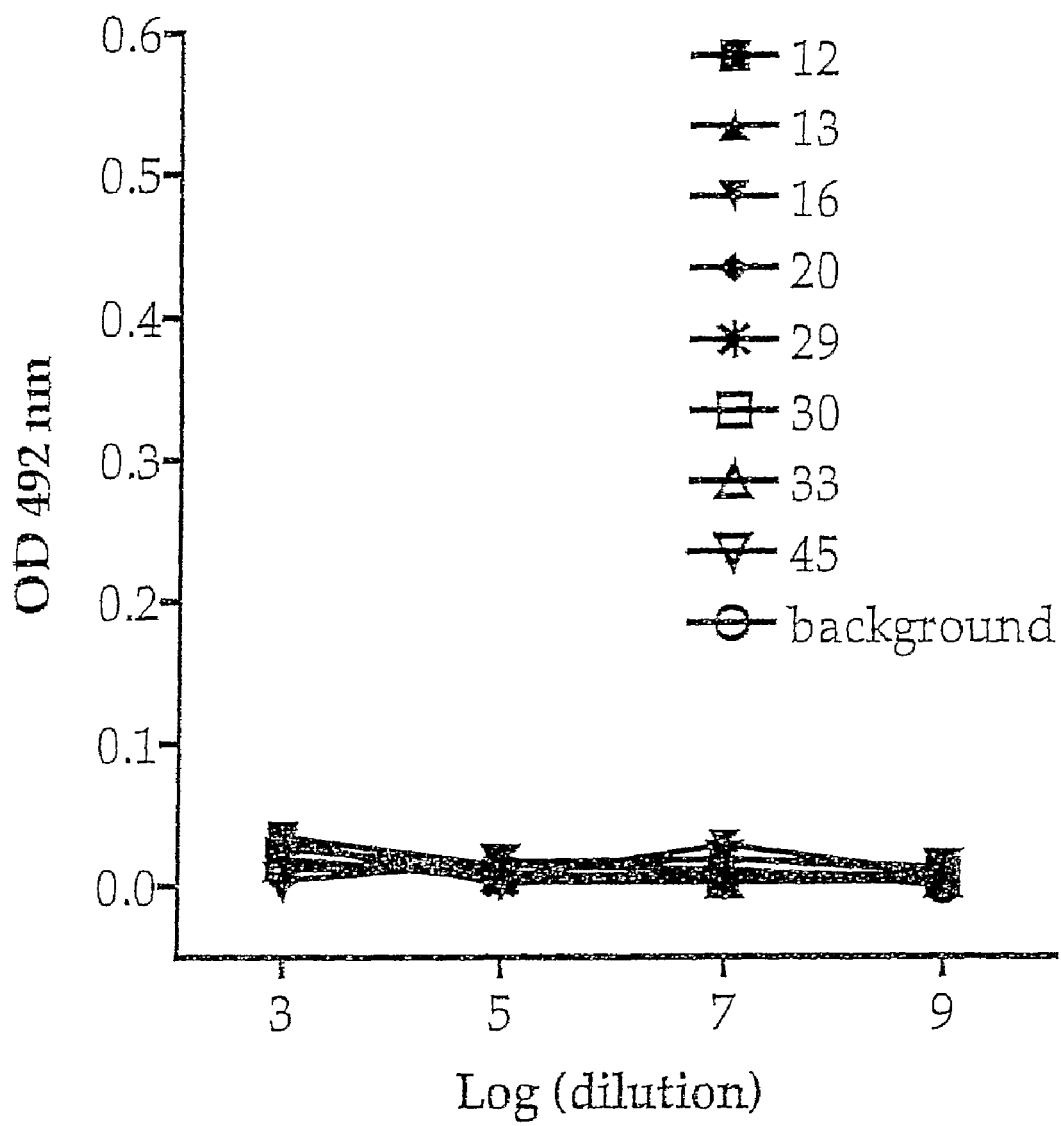

FIG. 19—Characterisation of selected phages. Eight different phages were tested for their ability to bind affinity-purified α-CHIPS$_{31-113}$ IgG. 100 μg·mL$^{-1}$ affinity purified α-CHIPS$_{31-113}$ IgG (a) or BSA (b) was coated onto a 96-well ELISA plate. Different dilutions of the amplified phage stocks were incubated with the coated plates. The bound phages were detected using an α-M13 mAb. Selected phages were able to bind to the affinity purified α-CHIPS$_{31-113}$ IgG but not BSA.

Figure 20:
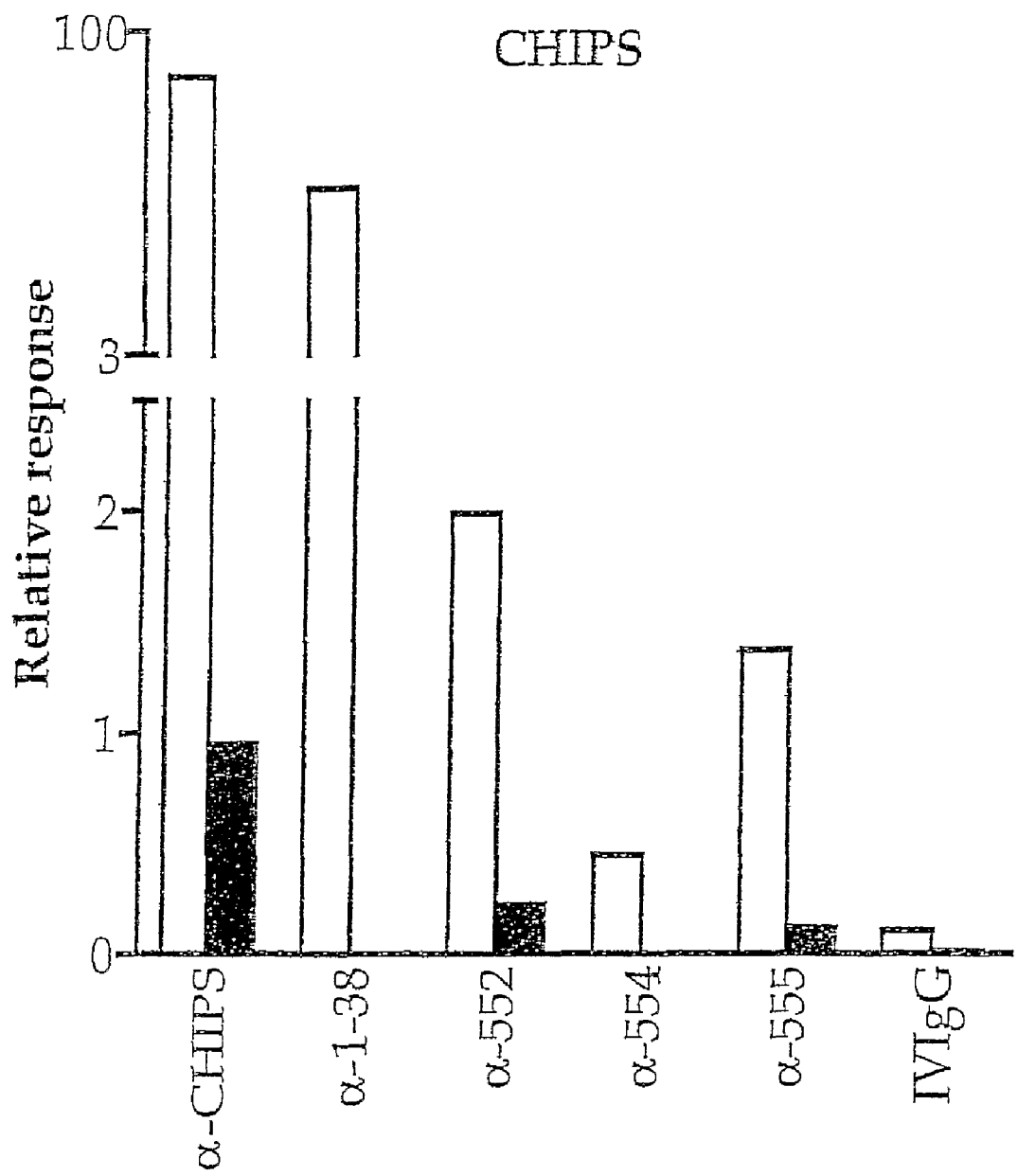
Figure 20:
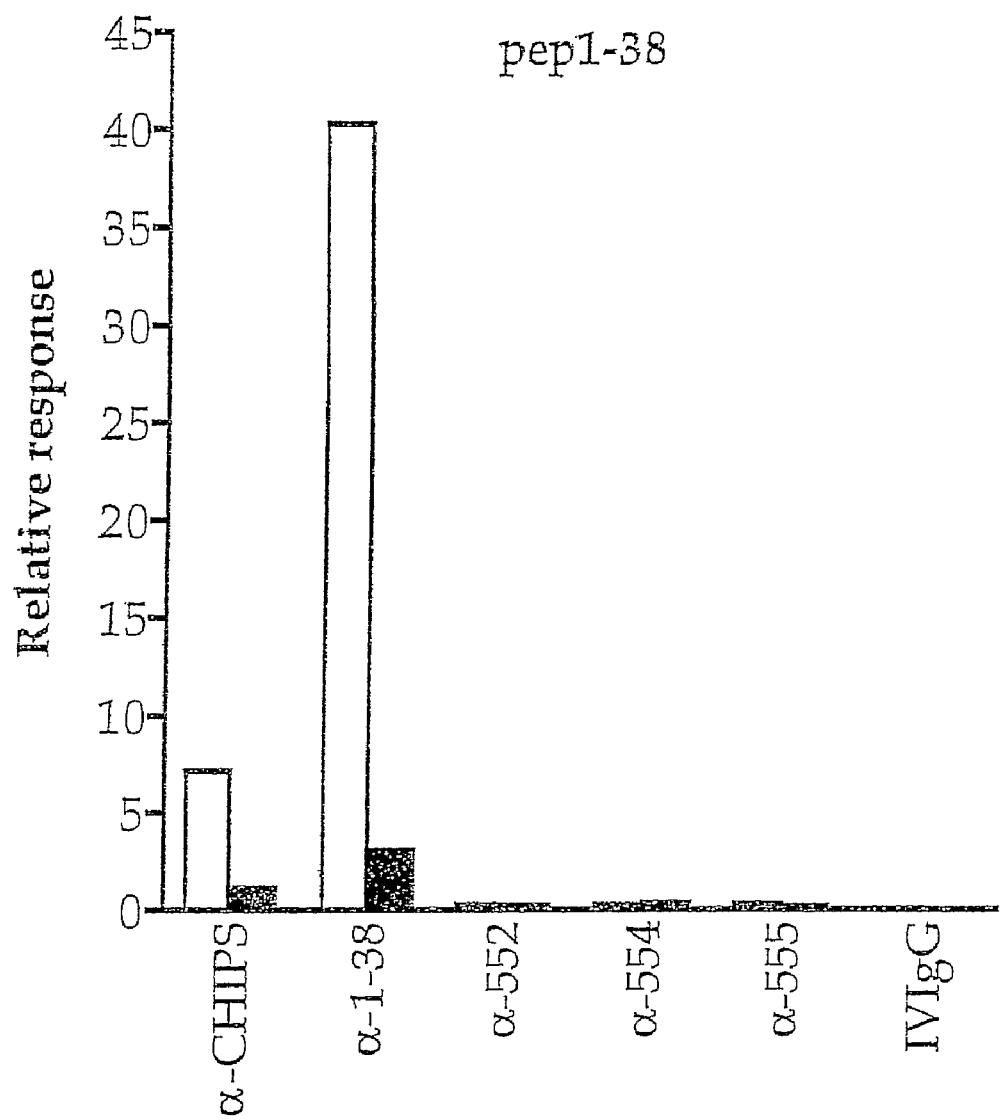
Figure 20:
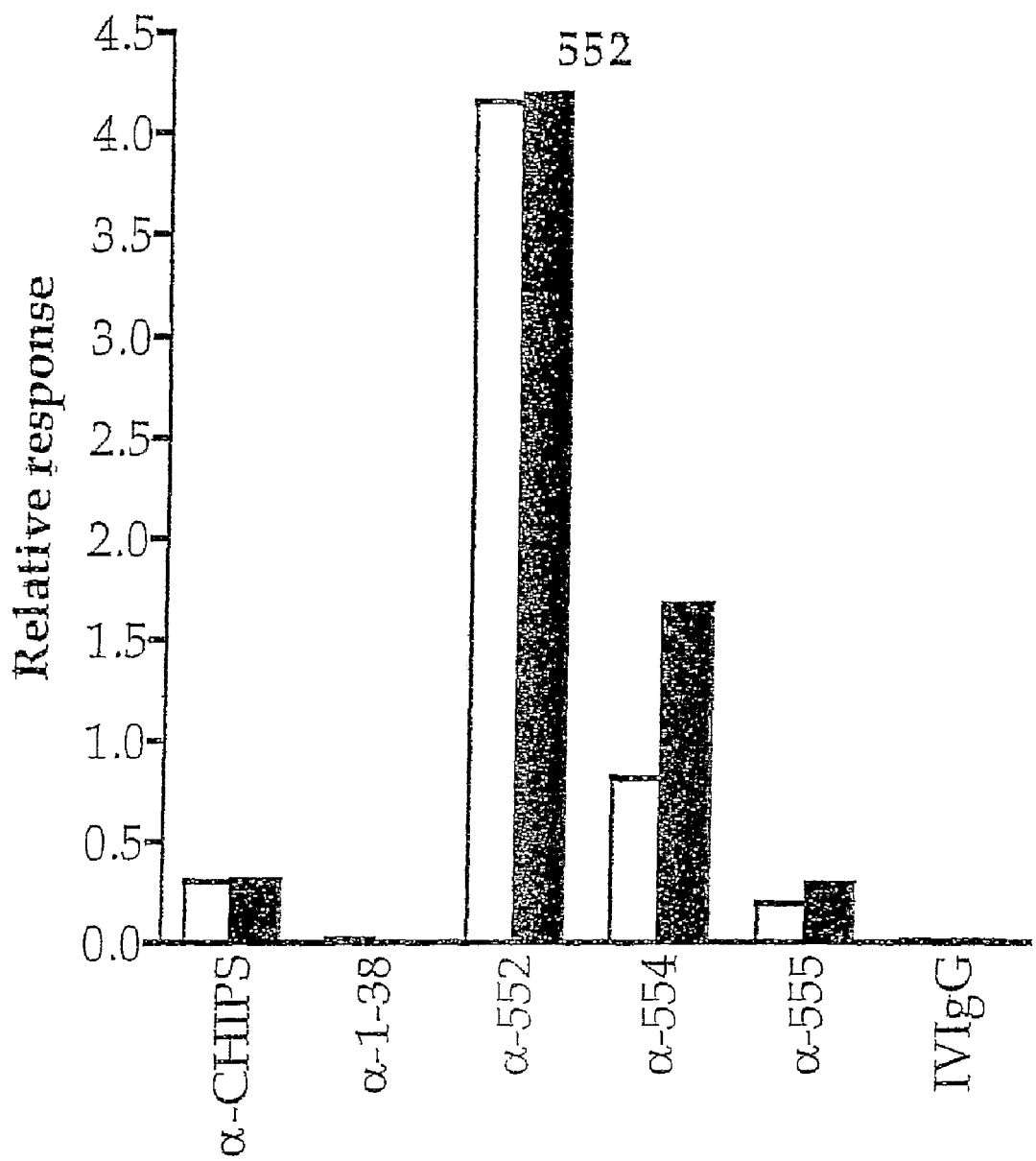
Figure 20:
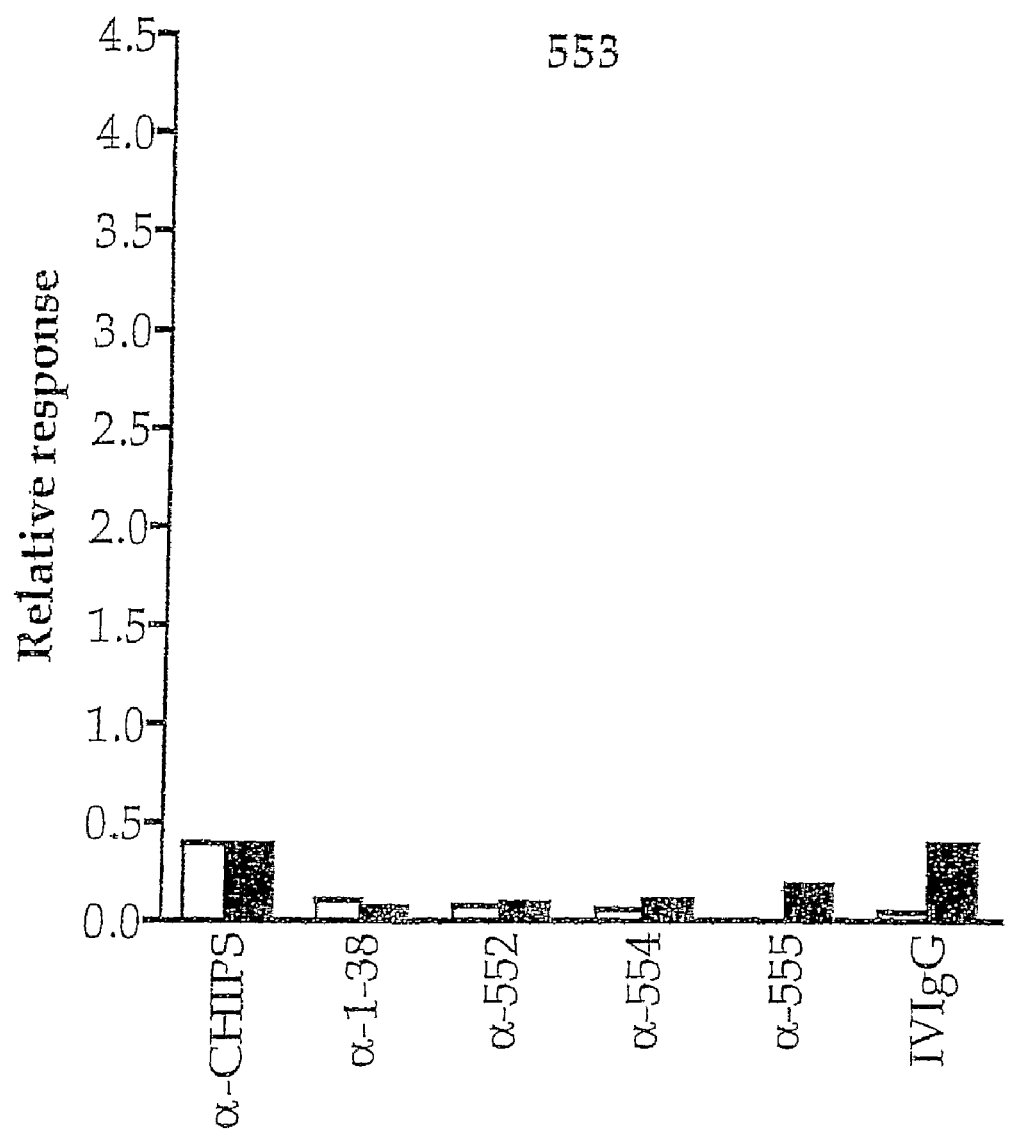
Figure 20:
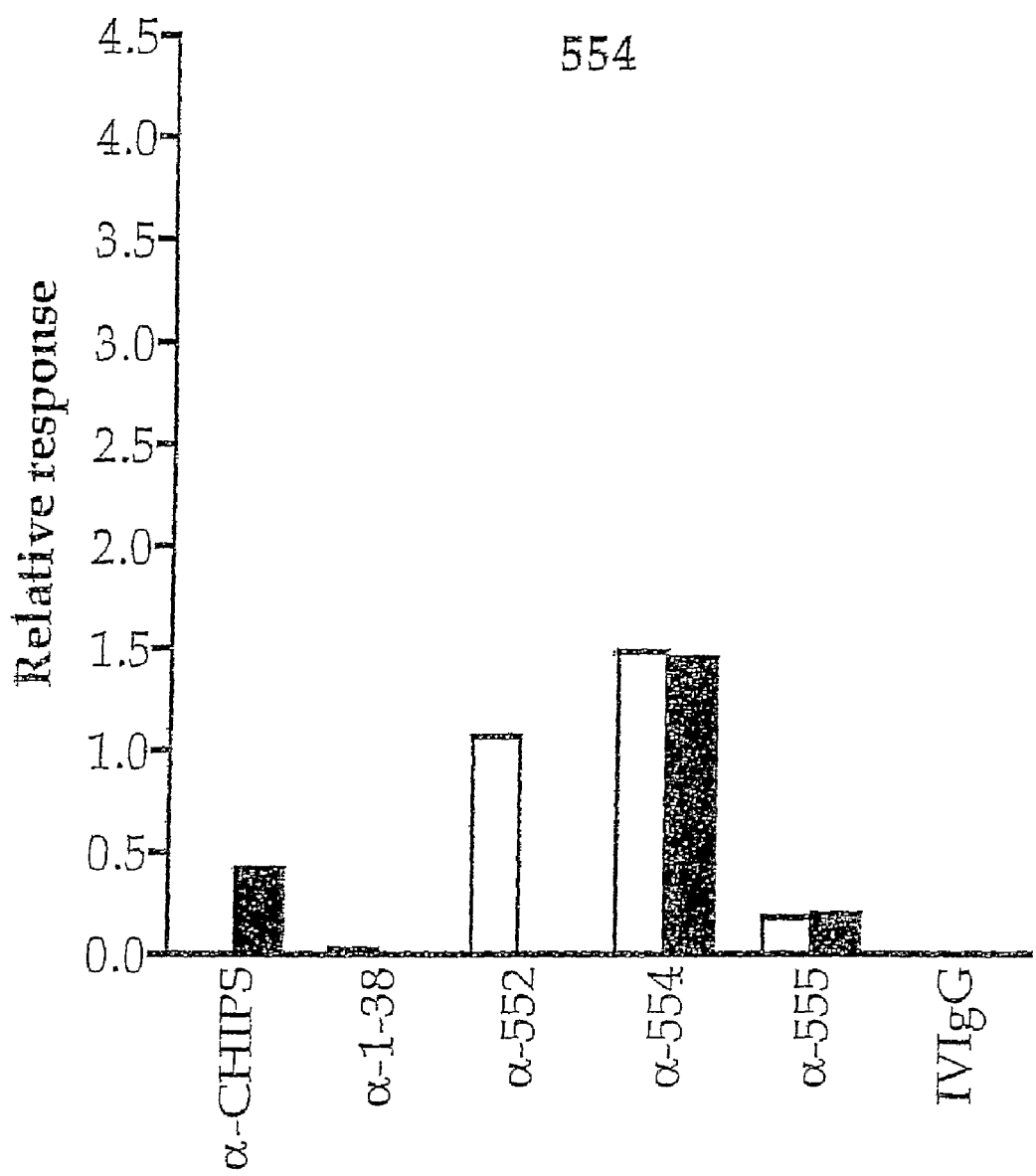
Figure 20:
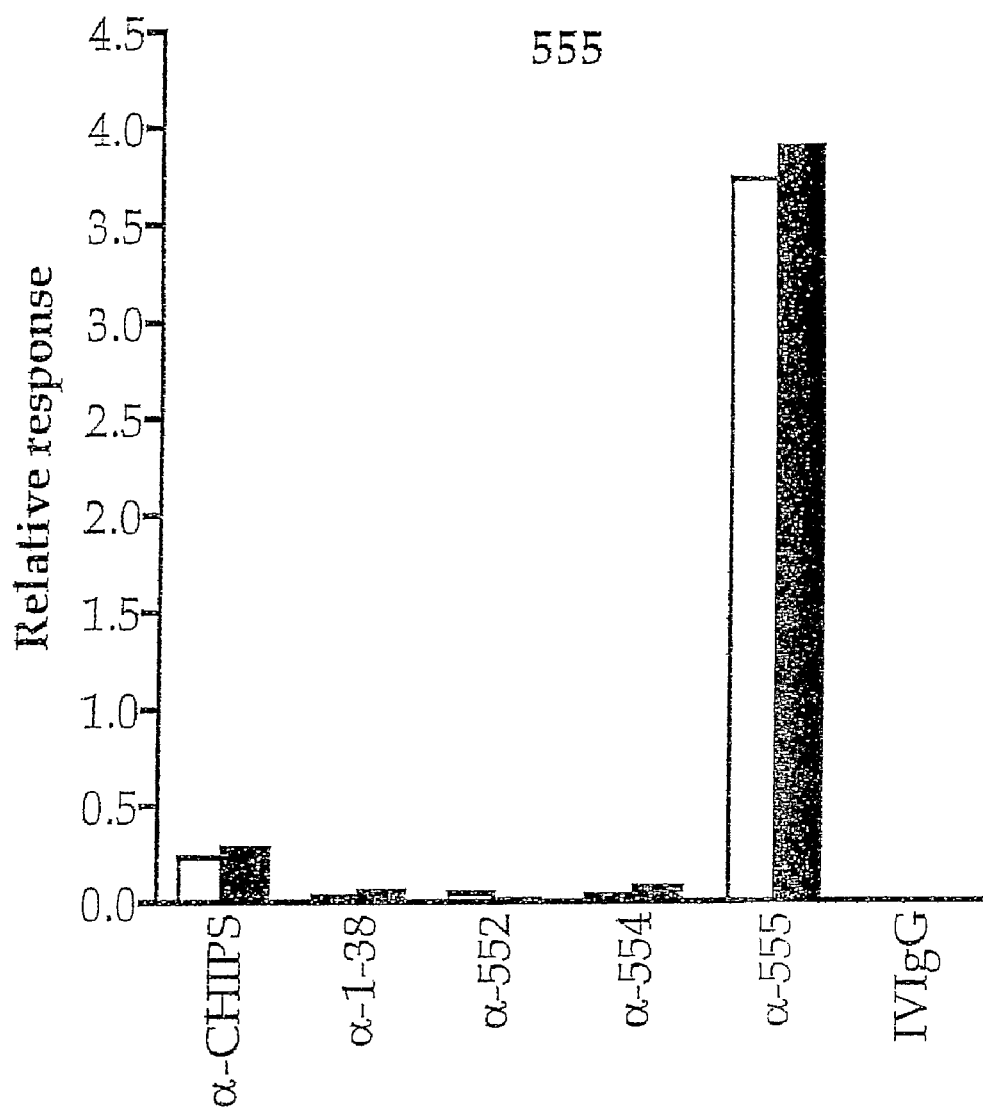

FIG. 20—Binding of affinity purified antibodies and IVIgG to the CHIPS protein and synthetic peptides. 7-mer peptides comprising the mapped epitope sequences and containing an additional GGGC [SEQ ID NO:3] spacer and a synthetic peptide derived from the CHIPS N-terminus (pep1-38) were used for affinity purification of human IgG. The affinity purified α-peptide antibody preparations (10 μg·mL$^{-1}$) were tested in their ability to bind the individual peptides and wild type CHIPS covalently bound to the surface of a CM5 sensor chip. The SPR responses were corrected for the amount and size of the immobilised ligand. The black bars represent binding of the different affinity purified antibodies. The white bars show binding of antibodies that were pre-incubated with 1 mg mL$^{-1}$ CHIPS.

Figure 21:
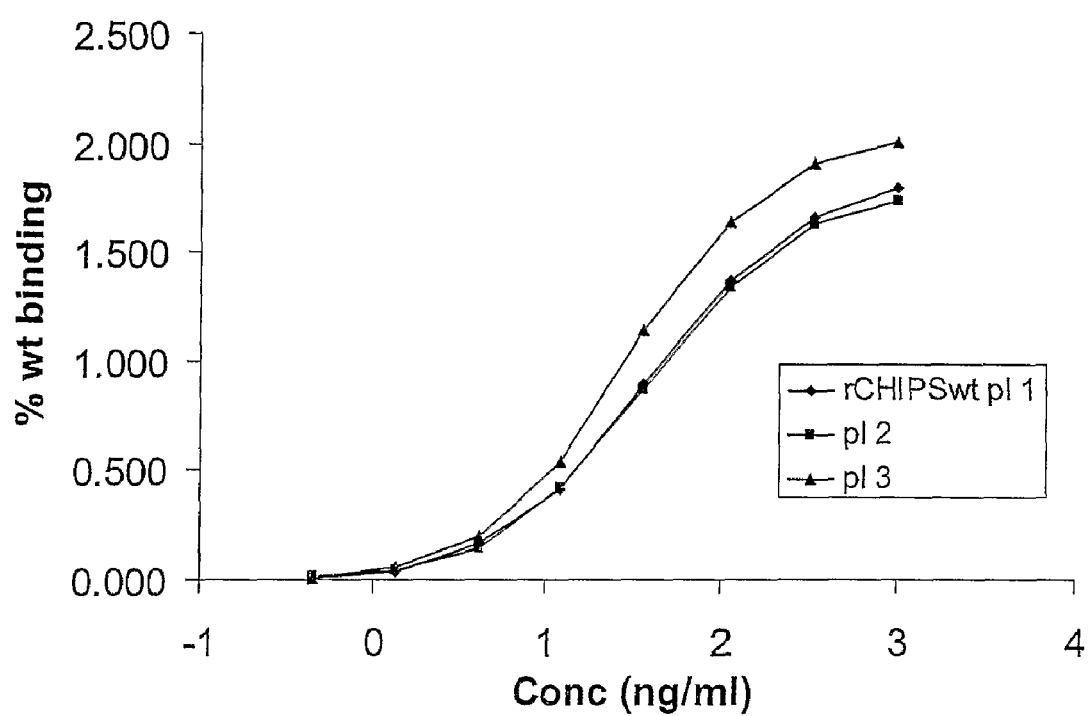

FIG. 21—CHIPS peptide ELISA: Standard curve

Figure 22:
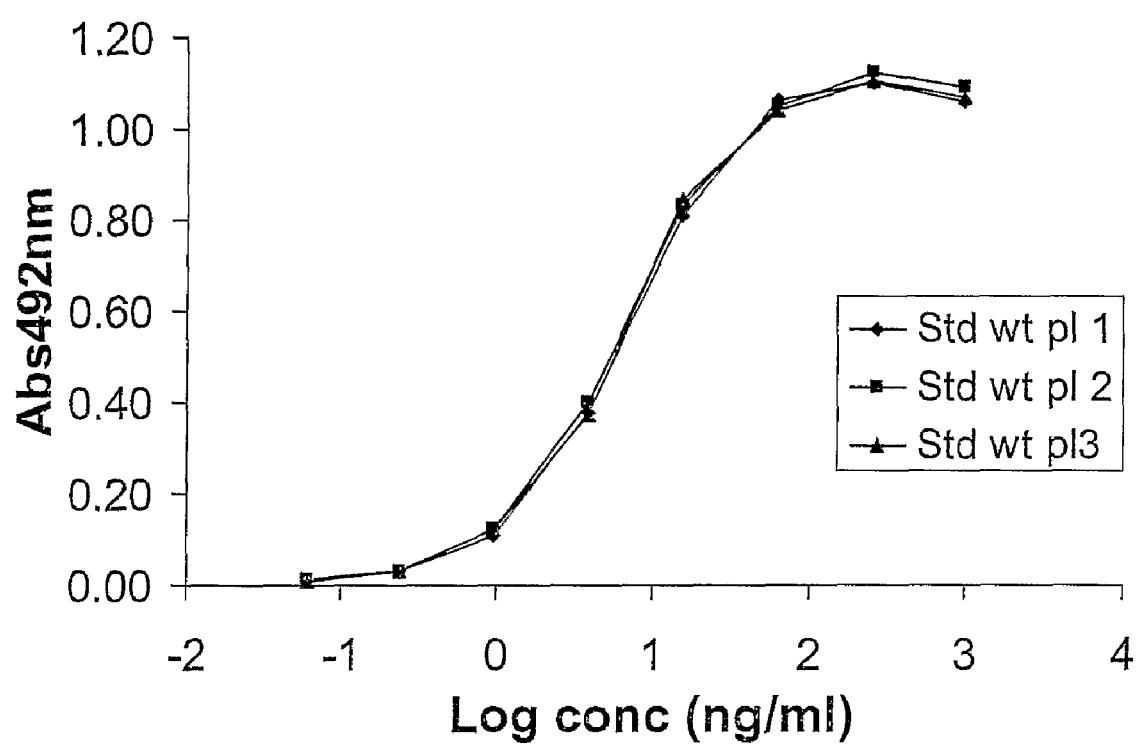

FIG. 22—Anti-CHIPS ELISA: CHIPS$_{wt}$ Standard curve

Figure 23:
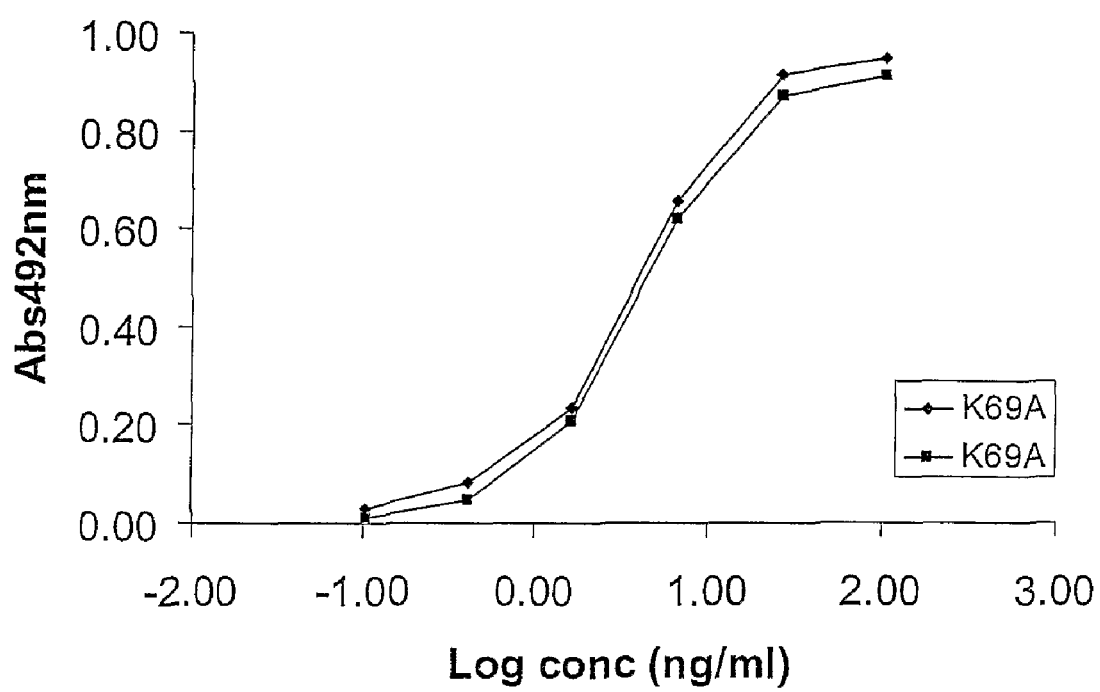

FIG. 23—Anti-CHIPS ELISA: CHIPS$_{K69A}$ absorbance

Figure 24:
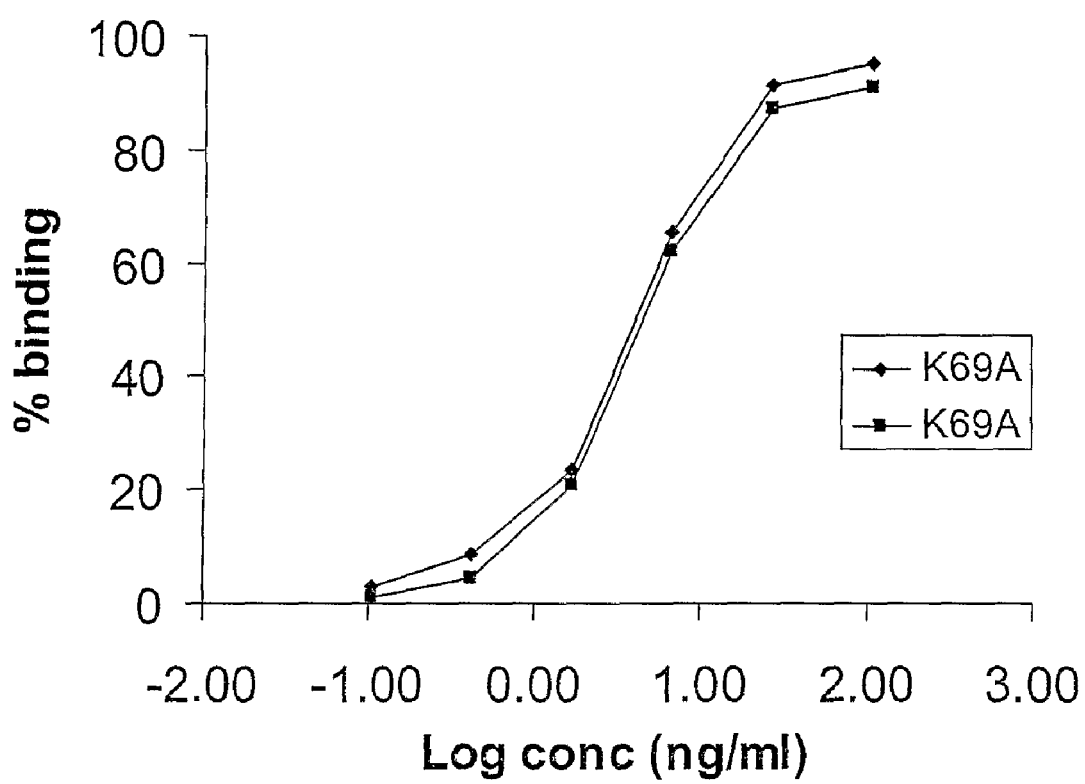

FIG. 24—Anti-CHIPS ELISA: CHIPS$_{K69A}$ binding

Figure 25:
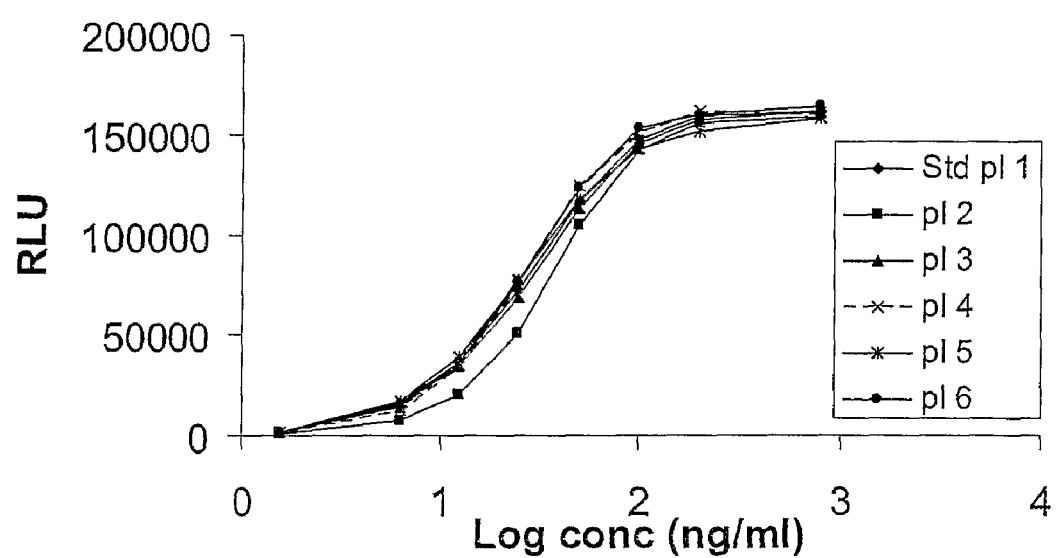

FIG. 25—Expression ELISA: CHIPS$_{wt}$ Standard curve

Figure 26:
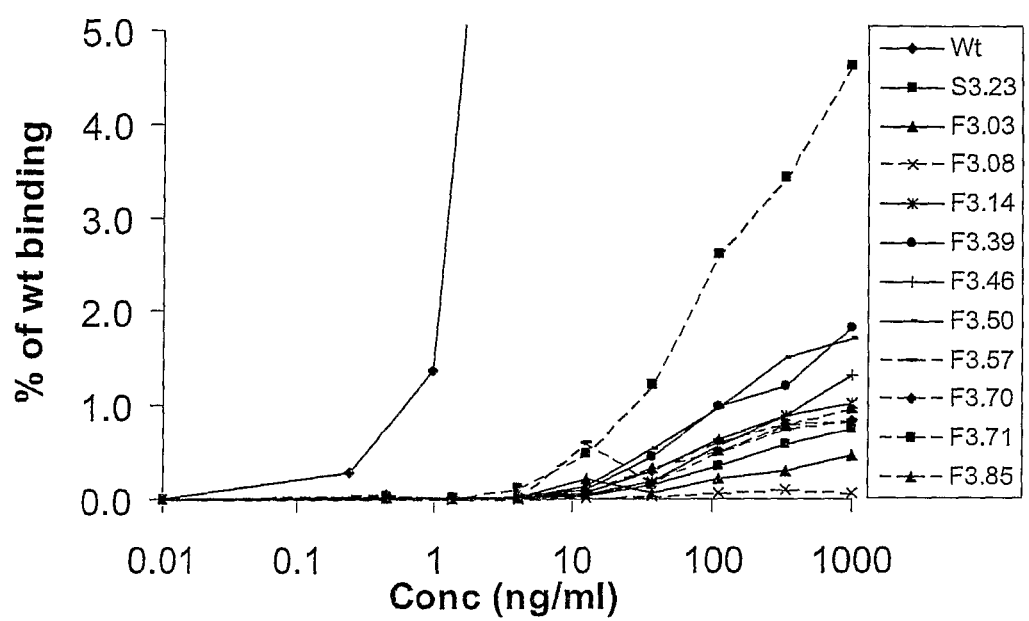

FIG. 26—Binding of exemplary CHIPS mutants to human anti-CHIPS antibodies, as measured by anti-CHIPS ELISA (See Example E for sequence details).

Figure 27:
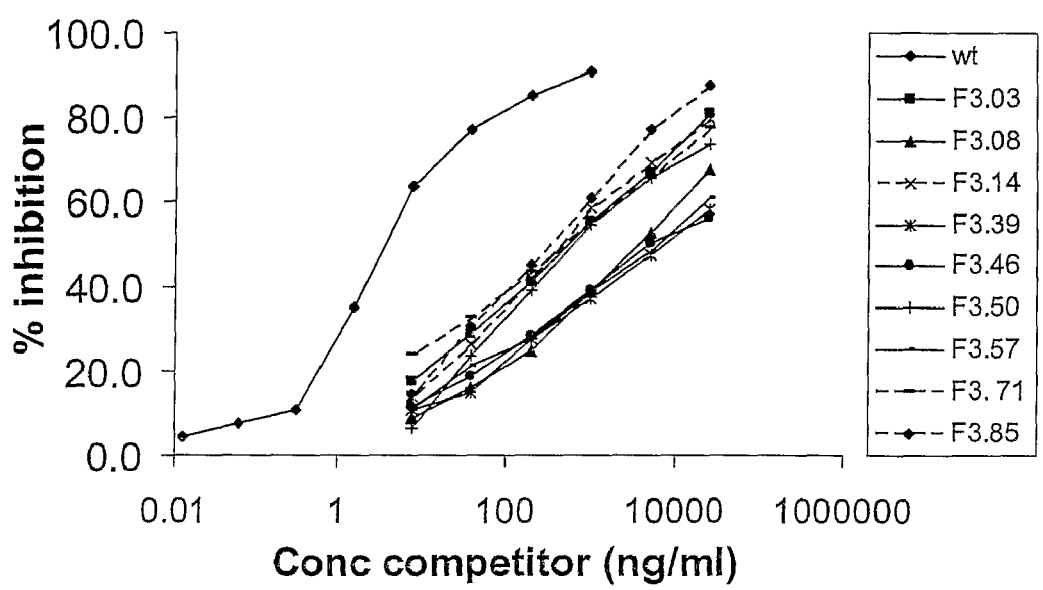

FIG. 27—Binding of exemplary CHIPS mutants to human anti-CHIPS antibodies in competition with the wt CHIPS protein, as measured by inhibition ELISA (See Example E for sequence details).

Figure 28:
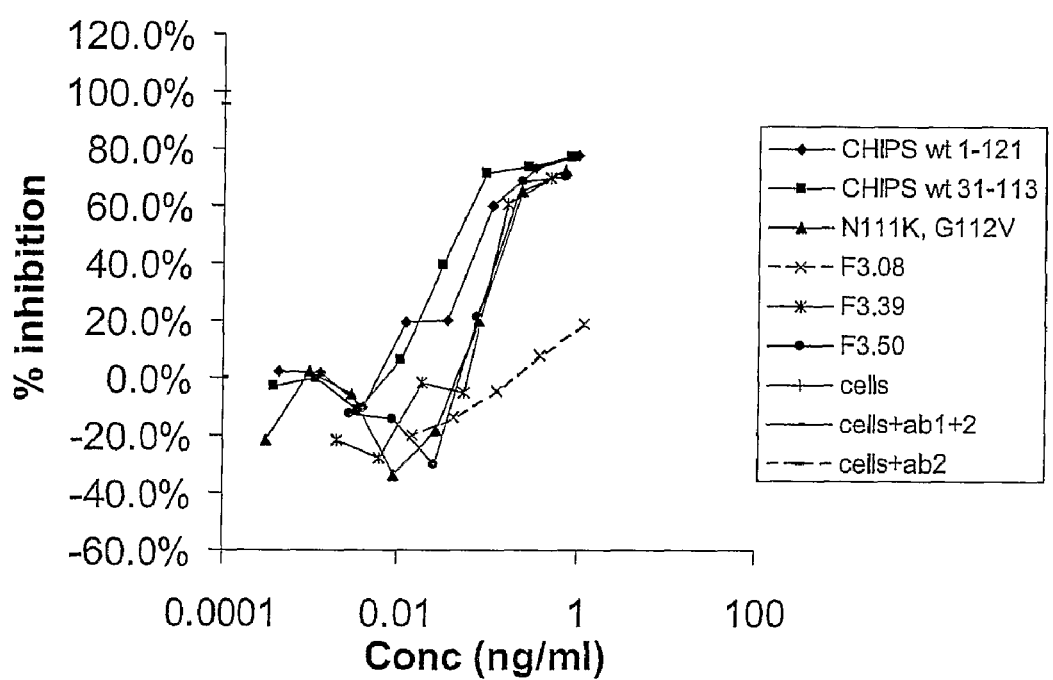
Figure 28:
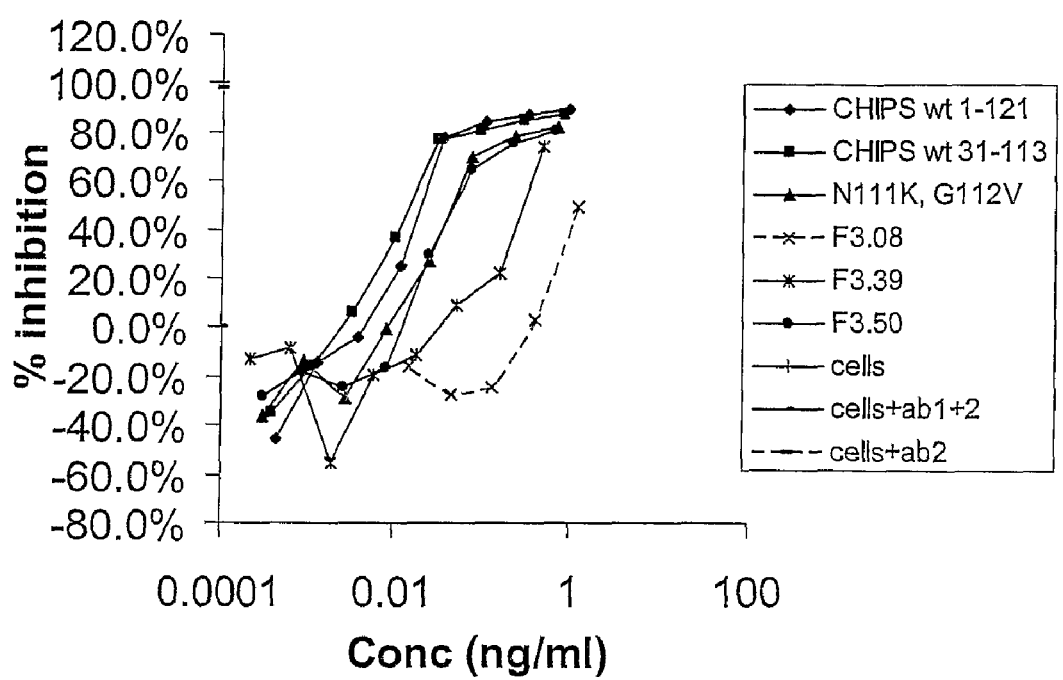

FIG. 28—Inhibition of C5aR in (a) U937 cells and (b) neutrophils by exemplary CHIPS mutants based on amino acids 31 to 113 of SEQ ID NO: 1.

Key: CHIPS wt 1-121=The wildtype CHIPS polypeptide of SEQ ID NO:1
 CHIPS wt 31-113=The polypeptide consisting of amino acids 31 to 113 of SEQ ID NO:1
 N111K, G112V=A mutant version of 'CHIPS wt 31-113' in which amino acids 111 and 112 are mutated as indicated
 F.3.08 31-113=(See Example E for sequence details)
 F.3.39 31-113=(See Example E for sequence details)
 F.3.50 31-113=(See Example E for sequence details)
 Cells=Negative control, without detection Ab (i.e. 100% 'inhibition')
 Cells+ab1+2=Positive control, maximum signal with all C5aR detected (not inhibited by CHIPS)
 Cells+ab2=Control showing no background signal with secondary Ab (i.e. 100% 'inhibition')

EXAMPLES

Example A

CHIPS Activity in Vivo

Materials & Methods
Preclinical Assessment of Chips Toxicity in Animal Models

Different pre-clinical toxicology studies were preformed to investigate the safety of CHIPS. These included; (i) The effects of CHIPS on various cardiovascular and respiratory parameters in one group of three anesthetized beagle dogs. The dogs were administered CHIPS in incremental doses 0.2, 2.0 and 20 mg kg$^{-1}$, infused intravenously over 1 minute at approximately 30 minute intervals. (ii) Behavioral ('Irwin') test in mice: CHIPS was administered as a single intravenous injection to male ICR CD-1 mice (3 per group) at doses of 7.5, 25 and 75 mg kg$^{-1}$ in order to assess effects on general behavior. An additional group received an equivalent volume (10 mL kg$^{-1}$) of vehicle (0.9% w/v sterile saline). (iii) Acute intravenous toxicity study in rat: Intravenous administration of 96.1 mg kg$^{-1}$ CHIPS as a single dose (the maximum practically achievable due to volume considerations) to 5 male and 5 female rats. (iv) Acute intravenous toxicity in mice: Intravenous administration of 96.1 mg kg$^{-1}$ CHIPS as a single dose to 5 male and 5 female mice. (v) Seven-day intravenous bolus preliminary toxicity study in rats (24 males and 24 females, max dose 10 mg kg$^{-1}$). (vi) Seven day intravenous bolus toxicity study in rats (76 males and 76 females, max dose 10 mg kg$^{-1}$). (vii) Seven day intravenous bolus dose range finding study in dogs (2 males and 2 females, max dose 20 mg kg$^{-1}$). (viii) Seven day intravenous bolus toxicity study in the dogs (12 males and 12 females, max dose 20 mg kg$^{-1}$).
Including Human Volunteers Inclusion criteria for healthy volunteers were as follows: (i) Subjects should be men. (ii) Subjects should meet the following body mass index (BMI) range: 18-30 (kg m2) and age range: 18-50 years, both inclusive. (iii) Medical screening was divided in 2 parts. Subjects were pre-screened for anti-CHIPS antibody levels. Only subjects with a low titer were screened for the second part within 3 weeks before dosing and include: medical history, physical examination, measurement of blood pressure, heart rate, respiration and temperature, alcohol breath test, blood and urine tests, electrocardiogram (ECG) and drug screening.

Admission and Follow-Up

Six selected subjects (4 receiving CHIPS and 2 controls) were admitted to the Clinical Pharmacology Unit (Kendle, Utrecht, The Netherlands) on the day before dosing. Baseline measurements, including blood samples for safety, urinalysis, interim medical history, physical examination, vital signs and ECG were done. On the day of dosing wildtype CHIPS (0.1 mg kg$^{-1}$ administered as a single dose of sterile frozen isotonic saline solution containing CHIPS at a concentration of 5 mg mL$^{-1}$) or placebo (0.9% NaCl) was administered by iv infusions over 5 minutes. Subjects were connected to a telemetry system for cardiac monitoring from 30 minutes before dosing until 4 hours after start of dosing. The blood pressure of subjects was measured continuously using a Finapres from 5 minutes before dosing until 30 minutes after start dosing. Vital signs were measured and ECGs were made at certain time points during the admission period. For safety, clinical status and laboratory values (haematology, biochemistry, coagulation and urinalysis) of all subjects were monitored. Adverse events were documented and characterised according to their severity and relationship to CHIPS or placebo. The subjects were discharged at 24 hours after dosing. Two weeks after dosing subjects returned to the Unit for a visit to evaluate vital signs, ECG, blood and urine and anti-CHIPS antibody level. A follow up visit was scheduled 6 weeks after dosing.

Cloning and Expression of CHIPS

CHIPS was cloned and expressed as described in Haas et al. (2004) *J. Immunol.* 173:5704-11. Briefly, the gene, without the signal sequence, was cloned into the pRSET vector directly downstream of the enterokinase cleavage site and before the EcoRI restriction site by overlap extension PCR. Bacteria were lysed with CELLYTIC B Bacterial Cell lysis/Extraction Reagent (Sigma) and lysozyme according to the manufacturer's description. The histidine-tagged protein was purified using a nickel column (HITRAP Chelating HP, 5 mL, Amersham Biosciences) following the manufacturer's instructions and cleaved afterwards with enterokinase (Invitrogen). Samples were checked for purity and presence of protein by means of 15% SDS-PAGE (Polyacrylamide gel electrophoresis, MINI PROTEAN 3 System, Bio-Rad) and Coomassie Brilliant Blue (Merck) staining.

Purification of CHIPS for iv Use

Full length CHIPS was expressed in an *E. coli* strain containing the coding sequence of CHIPS directly downstream a PelB coding sequence in a growth media consisting of Soya peptone and yeast extract in 8 L fermentation media. CHIPS was isolated both from the growth media and the cells by a two-stage cation exchange purification process followed by a desalting step. Bacterial cell pellet was re-suspended in phosphate buffer (30 mM; pH 7.0), containing NaCl (10 mM), DTT (10 mM) and frozen. This was subsequently thawed at 37° C., incubated on ice and sonicated. After centrifugation at 15,000 rpm an amber coloured "cell" supernatant was recovered. The supernatant was diluted four-fold with 30 mM phosphate buffer and passed over a Source S-30 column. Material was eluted with a phosphate buffer salt gradient and fractions containing CHIPS were combined and purified further by using a polishing column with a shallow salt gradient. Fractions containing CHIPS with purity greater than 97% (by HPLC) were combined and passed through a SEPHADEX G 25 desalting column to remove phosphate and excess of sodium chloride. Endotoxin was removed by gently shaking over an AFFI-PREP resin (Biorad) and the preparation was sterilized through ultra filtration. The purity was checked by HPLC-MS on a Microbondapac CN-RP column with a gradient mobile phase consisting of water-TFA to Methanol-TFA. CHIPS generally eluted at about 13 minutes. The product was diluted with sterile saline to the required concentration and stored at −20° C.

Anti CHIPS Antibodies

Rabbits were immunised with recombinant CHIPS using Freund's Complete Adjuvants and boosted with Freund's incomplete adjuvants. Bleedings were checked for reactivity with CHIPS by ELISA as described earlier (see Haas et al., 2004, *J Immunol* 173(9):5704-11). From the final bleeding, IgG was purified by standard Protein-G (Pharmacia) affinity chromatography according to the manufacturer's instructions. Specific mouse monoclonals towards CHIPS were generated as described and IgG purified with Protein-G Sepharose columns (see Haas et al., 2004, *J Immunol* 173(9): 5704-11).

Isolation of Affinity Purified Human-α-CHIPS IgG

CHIPS$_{1-121}$ was coupled to a solid matrix using CNBR-activated Sepharose 4B according to the manufacturer's general instructions (Pharmacia, GE). Approximately 8 mg of purified CHIPS was coupled onto 1 gram Sepharose. A small column (±1 mL) was packed with the material, equilibrated with PBS and slowly perfused with human IgG for intravenous use (IgG-IV; Sanquin, Amsterdam, The Netherlands) diluted in PBS. The column was extensively washed with PBS and subsequently eluted with 0.1 M Glycine HCl buffer at pH 3. Fractions of 0.5 mL were collected into tubes containing 50 µL 1 M Tris/HCl pH8, for neutralization. Fractions with the highest OD$_{280}$ were pooled and dialyzed against PBS. The final preparation was analyzed for IgG content with an ELISA. Therefore plates were coated with sheep anti-human IgG (ICN) at 2 µg·mL$^{-1}$ in PBS, blocked with 5% BSA and incubated with serial dilutions of a standard IgG preparation (reference serum; Boehringer) and unknowns.

Captured IgG was detected with a peroxidase labeled goat anti-human IgG (Southern) and TMB as substrate. The IgG concentration was calculated from the reference curve.

Anti CHIPS ELISA

Microtitre plates (Greiner) were coated with 50 µL CHIPS per well at 1 µg·mL$^{-1}$ in PBS overnight at 4° C. All wash steps were performed thrice with PBS-0.05% Tween-20 and subsequent incubations were done for 1 hour at 37° C. Plates were blocked with PBS-0.05% Tween-20 4% BSA, washed and incubated with sera or antibodies diluted in PBS-0.05% Tween-20 1% BSA. Bound antibodies were detected with species-specific goat anti-IgG conjugated with peroxidase (all from Southern, Birmingham, USA) and TMB as substrate. The reaction was stopped with H$_2$SO$_4$ and the absorbance measured at 450 nm in a BioRad ELISA-reader.

Capture ELISA

Microtitre plates were coated with 50 µL_-CHIPS mAb 2G8 at 3 µg·mL−1 in PBS overnight at 4° C. Plates were blocked with 4% BSA in PBS containing 0.05% Tween-20, washed and incubated with diluted samples and a two-fold dilution range of CHIPS as standard in PBS/Tween containing 1% BSA. Subsequently, plates were incubated with 0.33 µg·mL$^{-1}$ rabbit α-CHIPS IgG and 1:5000 diluted peroxidase-conjugated goat anti-rabbit IgG (Southern). Bound antibodies were quantified with TMB as substrate, the reaction stopped with 1 N H$_2$SO$_4$ and measured at 450 mm on a BioRad ELISA reader.

Isolation of Human PMN

Blood obtained from healthy volunteers was collected into tubes containing sodium heparin (Greiner Bio-One) as anticoagulant. Heparinised blood was diluted 1/1 (v/v) with PBS and layered onto a gradient of 10 mL Ficoll (Amersham Biosciences, Uppsala, Sweden) and 12 mL HISTOPAQUE (density 1.119 g·mL$^{-1}$; Sigma-Aldrich, St. Louis, Mo.). After centrifugation (320×g, for 20 min at 22° C.), the neutrophils were collected from the Histopaque phase and washed with cold RPMI 1640 medium containing 25 mM HEPES buffer, L-glutamine (Invitrogen Life Technologies) and 0.05% HSA (Sanguin). The remaining erythrocytes were lysed for 30 s with ice-cold water, after which concentrated PBS (10×PBS) was added to restore isotonicity. After washing, cells were counted and resuspended in RPMI-1640/0.05% HSA at 107 neutrophils mL−1.

Neutrophil Antigen Expression

Whole blood was collected into K3-EDTA tubes and put on ice. Optimal dilutions of fluorescent-labeled mAb were alliquoted into Falcon tubes and mixed with 50 µL blood for 30 min on ice under gentle agitation. Red blood cells were lysed with FACS-Lysing solution (BD) followed by a buffer wash and cell pellets resuspended into 0.5% paraformaldehyde in PBS with 0.1% azide. Neutrophil surface antigen expression was analyzed in a FACsCalibur based on forward and sideward scatters for gating. Calibration beads (Calibrite; BD) and isotype matched controls were used to set appropriate background values and electronic compensation. The following mAb and probes were used: anti-CD11b (CR3) APC-labeled (clone 44; BD); anti-CD62L (L-selectin) PE-labeled (clone Dreg 56 BD); anti-CD88 (C5aR) FITC-labeled (clone W17/1; Serotec); Fluorescein labeled formyl-Nle-Leu-Phe-Nle-Tyr-Lys ('FITC-fMLP'; Molecular Probes); Rabbit anti-CHIPS IgG (EWI) and FITC-labeled F(ab)'2 Goat anti-Rabbit IgG (Sigma).

Whole Blood Ex Vivo Stimulation

Part of the K3-EDTA blood was kept at room temperature and used for ex vivo neutrophil stimulation. Therefore blood was mixed with 10-fold concentrated stimuli (buffer control, $1 \times 10^{-8}$ MfMLP) and incubated for 30 min at 37° C. with gentle shaking. Tubes were put on ice to stop the reaction and mixed with anti-CD11b plus anti-CD62L mAb. After 30 min on ice samples were treated as described above.

CD11b Expression on CHIPS/IgG Stimulated Neutrophils

Different concentrations CHIPS (final concentration 0-9 µg·mL$^{-1}$) were incubated with affinity purified human-α-CHIPS-IgG (0-40 µg·mL$^{-1}$) for 30 min at 37° C. Thereafter, 50 µL isolated human neutrophils (107 mL$^{-1}$) were added to the CHIPS/α-CHIPS mixture and incubated with gentle shaking for 30 min at 37° C. Cells were put on ice for 10 min after which 3.5 µL flourescent mouse-α-human-CD11b (BD-biosciences, San Diego, Calif.) was added and incubated on ice for 30 min. Cells were washed with RPMI 1640/0.05% HSA and fixed with 200 µL 0.5% paraformaldehyde.

CD11b expression on cells in whole blood was performed using blood collected from human volunteers, selected for different α-CHIPS titers. Since IgG is already present in the whole blood the samples (50 µL) were only incubated with CHIPS (0-9 µmL$^{-1}$) for 30 min at 37° C. The sample was put on ice for 10 min after which 3.5 µL fluorescent labeled mouse-anti human-CD11b was added and incubated on ice for 30 min. The erythrocytes were lysed and cells were fixed by adding 1 mL FACS lysing solution diluted 1:10 with H$_2$O for 4 min. Cells were spun for 10 min at 1200 rpm and pellet was washed with ice cold RPMI 1640/0.05% HSA. Finally cells were resuspended in 175 µL RPMI 1640/0.05% HSA. Receptor expression representing cell activation was measured in a FACSCalibur flowcytometer (BD Biosciences).

Circulating Immune Complexes (GIC)

CIC were determined by 2 different ELISAs from Quidel (San Diego, Calif.): the CIC-C1q enzyme immunoassay is based on the principle that complement fixing IC will bind to immobilised human C1q purified protein; the CIC-Raji Cell Replacement enzyme immunoassay measures IC containing C3 activation fragments by using a mAb that specifically binds the iC3b, C3dg and C3d activation fragments of C3 in a manner which is analogous to the classical Raji cell CR2 binding reaction. The data of both assays were combined and results expressed relative to the value at time point 0.

Serum Tryptase Concentration

Serum derived tryptase (both α and β form) was measured on the UniCAP R-100 using the IMMUNOCAP technology from Pharmacia Diagnostics (Woerden, The Netherlands). The normal geometric mean for healthy controls is 5.6 µg L$^{-1}$ (Pharmacia). Results were expressed relative to the value at time point 0.

The study protocol and any amendments were approved by an independent ethics committee. The study was performed in compliance with the European Community (EC) rules of Good Clinical Practice (GCP) and the 'Declaration of Helsinki' (2000).

Results

CHIPS Shows No Evident Toxicity in Pre-Clinical Toxicology Studies

In none of the toxicology animal studies did administration of CHIPS cause any CHIPS related toxicologically significant changes in clinical observations, body weight, food consumption, haematology, coagulation, blood chemistry parameters, opthalmoscopy, electrocardiograms, macroscopic or microscopic pathology or behavior.

The effects of CHIPS on various cardiovascular and respiratory parameters in anesthetised beagle dogs was examined. In the dogs receiving low dose CHIPS (0.02 and 2 mg kg$^{-1}$) there was no evidence of cardiovascular or respiratory effects when compared to infusion of vehicle (isotonic saline). Following intravenous administration of 20 mg kg$^{-1}$ CHIPS a transient decrease in mean arterial blood pressure (~40%) was recorded approximately 1 minute after start of administration. Mean arterial blood pressure levels returned to pre-dose levels within approximately 5 minutes following the start of dosing. The effect on blood pressure coincided with transient, inconsistent changes in heart rate. One dog was administered a repeat intravenous dose of CHIPS (20 mg kg$^{-1}$) approximately 30 minutes following the first administration of CHIPS. Transient effects on cardiorespiratory parameters similar to those recorded following the first dose were not apparent after the repeat administration of CHIPS. However, the second administration produced a prolonged reduction in mean arterial blood pressure reaching a maximum of 18% at approximately 30 minutes following the second administration. In this animal only, twelve minutes following the repeated administration of CHIPS a generalized skin reaction appeared consistent with some form of mild allergic reaction.

The results of this study suggested that cardiorespiratory effects are unlikely to be observed in the human subjects in the used dose range (0.1 mg kg$^{-1}$). Furthermore, any effects that might occur were expected to be transient and reversible.

Distribution of α-CHIPS Antibody Titers

Since *S. aureus* is a common bacterium and the CHIPS gene is present in the majority of *S. aureus* strains we hypothesised that all individuals possess circulating α-CHIPS antibodies. Therefore we tested the amount of α-CHIPS IgG in serum of healthy volunteers. FIG. 1 shows the distribution of α-CHIPS IgG titers in a set of 168 healthy human volunteers. In the set of measured samples there were no titers below the detection limit of the used ELISA. The studied population is considered representative for the general population. Concluding from this data, over 99% of people in the general population have detectable α-CHIPS IgG serum levels. Also indicated in FIG. 1 are the titers of the subjects included in the trial.

Pharmokinetics of iv Administered CHIPS

Figure 3B:
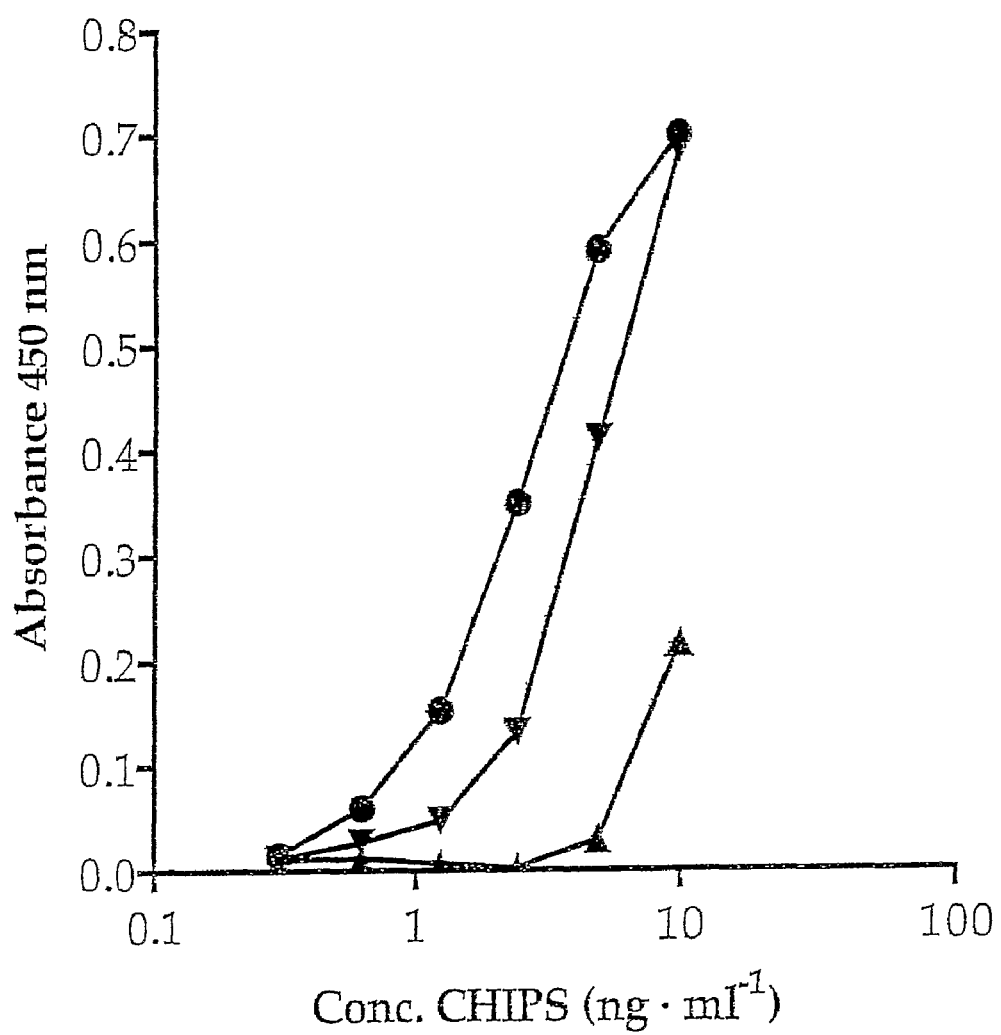

At four different time points after CHIPS administration the CHIPS serum titers were determined by ELISA (FIG. 2). Increase in CHIPS titer was observed only in individuals receiving CHIPS that had a low α-CHIPS antibody titer, (subjects 104 and 105). We determined the effect of human serum on the CHIPS ELISA. CHIPS was spiked into various concentrations pooled human serum and detected by capture ELISA. FIG. 3a shows that serum inhibits the capture ELISA. Depletion of IgG using a protein G-sepharose column eliminates the inhibitory effect (FIG. 3b).

CHIPS Binds the FPR and C5aR In Vivo

CHIPS binds the FPR and C5aR on neutrophils with high affinity and can be detected with α-CHIPS antibodies as described earlier for mouse mAb.158 At various timepoints after CHIPS administration the amount of CHIPS present on the surface of neutrophils was determined using a rabbit-α-CHIPS antibody as shown in FIG. 4. Only in subjects with a low α-CHIPS antibody titer (subjects #104 and #105) CHIPS was detected on the surface of neutrophils. Moreover, within these two subjects the detection of CHIPS negatively correlates to the α-CHIPS antibody titer. Since α-CHIPS antibodies present in serum interfere with the direct detection of CHIPS a negative result of this direct detection can not exclude CHIPS binding the receptor. However, CHIPS bound to the FPR and C5aR interferes with the detection of these receptors by α-FPR and α-C5aR antibodies as described earlier (see Veldkamp et al., 2000, *Infect Immun* 68(10):5908-13). FIG. 5 shows the FPR and C5aR receptor expression determined by FITC-fMLP and α-C5aR antibody binding. Subjects with a low _-CHIPS antibody titer show a decrease in FPR and C5aR expression indicating that CHIPS has occupied the receptors. In the subjects with a high α-CHIPS antibody titer (103 and 106) there is no change in FPR and C5aR expression indicating that α-CHIPS antibodies interfere with CHIPS binding to the receptor.

CHIPS Inhibits fMLP Induced Neutrophil Activation Ex Vivo Dependent of α-CHIPS Antibody Titer Upon cell activation there is a decrease in CD62L expression and an increase in CD11b expression. In order to test the effects of intravenous CHIPS on neutrophil inhibition we measured ex vivo fMLP-induced expression of CD62L and CD11b. Neutrophils were activated ex vivo with fMLP in a whole blood assay. As shown in FIG. 6, intravenous administered CHIPS is able to inhibit fMLP induced activation of neutrophils ex vivo. This inhibition is only observed in subjects with a detectable CHIPS serum concentration (subject 104 and 105).

CHIPS Induced Adverse Effects

Serious side effects were observed directly after administration of CHIPS. Most serious adverse events were observed for subject 106, these included: muscle pain, dyspnea, abdominal pain, vomiting, muscle spasms, chills, sweating, edema orbita and dizziness. The conclusive diagnosis of these symptoms is anaphylactoid reaction. The subject was treated with clemastine, IV fluids, tramadol and prednisolone.

Other adverse events reported include: palpitations, feeling warm, chest pain, flushing, feeling cold, tired legs, postural dizziness, fever, headache, nausea, blurred vision. Apart from the severe back pain for subject 106, subjects 103 and 105 reported mild back pain. Subject 104 reported muscle cramps. Fever up to 38.6° C. was observed for subjects 104 and 105 starting approximately 4 hours post dosing with resolution in the evening of day 1.

There were no changes in blood pressure and no ECG abnormalities. No abnormalities in oxygen saturation were observed except for intermittent low readings for subject 106 (89% oxygen saturation) during the adverse events described above. No adverse events were reported in subjects receiving placebo.

Intravenous CHIPS Induces a Leukocytopenia and Increased CRP Levels

We measured the white blood cell count (WBC) and C-reactive protein concentration (CRP) pre- and post-dosing as shown in FIG. 7. CHIPS induced a transient leuko-cytopenia in the subjects receiving CHIPS that resolved within 2 days. Furthermore there is an increase in CRP concentration starting at day 1 post dose that had returned to normal levels when subjects were screened during follow up at day 15 (FIG. 7b).

Circulating Immune Complexes and Increase Serum Tryptase Indicate an Anaphylactoid Reaction We measured the amount of circulating immune complexes and the serum tryptase concentration. Intravenous administration of CHIPS induces the formation of immune complexes in subjects receiving CHIPS (FIG. 8a). We also observed an increase in tryptase serum concentration that reached a maximum at approximately 10 minutes post dose (FIG. 8b).

CHIPS Induces Cell Activation in Vivo

To study the direct effect of CHIPS on cell activation we determined the CD62L and CD11b receptor expression on neutrophils. Receptor expression was measured immediately after collection of blood samples without any further cell stimulation. Subjects 104, 105 and 106 show a decrease in CD62L and a increase in CD11b expression on neutrophils representing in vivo cell activation (FIG. 9).

α-CHIPS Antibody Titers Increase after CHIPS Administration

The immunogenicity of a protein is characterized by the potency to induce antibodies. We determined the immunogenicity of CHIPS in healthy human subjects. The subjects that received intravenous CHIPS show an increase in α-CHIPS IgG (FIG. 10).

CHIPS Activation of Neutrophils In Vitro is Dependent on Antibody Concentration

We studied the activation of neutrophils by CHIPS-IgG complexes in vitro. Different concentrations CHIPS were preincubated with 20 μg mL$^{-1}$ human affinity purified-α-CHIPS IgG and used to stimulate isolated neutrophils as shown in FIG. 11. Affinity purified-α-CHIPS IgG was not able to activate neutrophils in the absence of CHIPS (data not shown). CHIPS-IgG complexes were able to stimulate neutrophils in a dose dependant way. FIG. 5.11 also shows that there is a optimal CHIPS concentration needed for maximal cell activation. The CHIPS-IgG induced cell activation was completely inhibited by FcR blocking antibodies. Therefore we conclude that the CHIPS-IgG induced cell activation in this assay is Fc-receptor mediated.

CHIPS$_{R46A}$ (arginine at position 46 replaced with alanine) and CHIPS$_{K69A}$ (lysine at position 96 replaced with alanine) are two CHIPS mutants with a single amino acid substitution, described earlier (see Haas et al., 2005, *J Mol Biol* 353(4): 859-872). These CHIPS mutants show a decreased affinity for purified-α-CHIPS IgG as measured by ELISA (data not shown). When used in the whole blood cell activation assay these mutants have a lower cell activating potential compared to wild type CHIPS (FIG. 12). For CHIPS$_{R46A}$ and CHIPS$_{K69A}$ a ten fold higher concentration is needed to give the same cell activation compared to wild type CHIPS. This shows that next to the antibody titer the level of reactivity with the antigen determine the amount of cell activation.

Ex Vivo Activation of Neutrophils by CHIPS is Also Dependent on α-Chips IgG Concentration We measured the effect of CHIPS on neutrophil activation in a whole blood ex vivo assay. Since α-CHIPS antibodies are already present in whole blood we did not preincubate CHIPS with affinity purified-α-CHIPS IgG. Different concentrations CHIPS were added to blood from human volunteers and CD11b expression, representing cell activation was measured. FIG. 13 shows the CHIPS concentration needed for maximal neutrophil stimulation measured by CD11b expression in whole blood from 8 healthy volunteers with different α-CHIPS IgG titers. As shown in the in vitro experiments maximum neutrophil stimulation depends on the CHIPS/α-CHIPS ratio. This is also observed in this ex vivo assay. A higher concentration CHIPS is needed for maximum stimulation of neutrophils when a higher α-CHIPS concentration is present.

Discussion

The Chemotaxis Inhibitory Protein of *S. aureus* is a very potent inhibitor of the human C5a-receptor and formyl-peptide-receptor. Both receptors, but especially the C5aR, have been described as important targets in the treatment of a variety of inflammatory diseases. The potent capacity of CHIPS to inhibit the C5aR and FPR make this protein a candidate therapeutic agent in the treatment of these diseases. Furthermore the fact that the activity towards the C5aR and the FPR are located on distinct regions of the CHIPS molecule allows for specific receptor targeting (see Haas et al., 2004, *J Immunol* 173(9):5704-11). The human specificity of the CHIPS protein, as evident from a 30 fold difference in activity toward human cells compared to mouse cells, hampers the evaluation of in vivo CHIPS activity in an animal model (see de Haas et al., 2004, *J Exp Med* 199(5):687-95).

We studied the activity, pharmokinetics and toxicity of the Chemotaxis Inhibitory Protein of *S. aureus* in a set of six healthy human subjects. Pre-clinical toxicology studies with administration of high concentrations CHIPS (single intravenous doses up to 96.1 mg kg$^{-1}$ in mouse) in different animal models show no remarkable signs of toxicity. Therefore a starting dose of 0.1 mg kg$^{-1}$ administered intravenously over 5 minutes was considered safe.

Since *S. aureus* is a common bacterium and the CHIPS protein is expressed in the majority of *S. aureus* strains we hypothesized that α-CHIPS antibodies are present in all individuals. This was confirmed by screening of α-CHIPS IgG titres in a pool of 168 randomly collected sera from human volunteers. Experiments with mouse monoclonal antibodies showed that these monoclonal antibodies can interfere with CHIPS activity in vitro (see Haas et al., 2004, *J Immunol* 173(9):5704-11). Therefore, it is reasonable to assume that α-CHIPS antibodies present in the healthy subjects receiving the CHIPS protein also interfere with activity.

The administration of CHIPS to human subjects was an unique opportunity to study activity and pharmokinetics in vivo. After intravenous administration of 0.1 mg kg$^{-1}$ CHIPS we measured the CHIPS serum concentration. FIG. 2 shows the CHIPS serum concentration on different time points post dosing. In only two out of four subjects that received the CHIPS protein we measured an increase in CHIPS serum concentration (subject 104 and 105). Interesting was the observation that these two individuals also showed the lowest α-CHIPS IgG titers. This shows that α-CHIPS antibodies interfere with the detection of CHIPS. Consequently, because of this interference the measured CHIPS serum concentration in subjects 104 and 105 is an underestimation. Based on these data we calculated a predicted half life of CHIPS in vivo of at least 1.5 hours.

We observed the same correlation with α-CHIPS IgG titer when detecting the amount of CHIPS present on the neutrophil membrane surface. CHIPS could be detected on the surface of neutrophils from subjects 104 and 105 only. Furthermore, we showed that these CHIPS molecules occupy the FPR and C5aR since there is a downregulation in the detection of both receptors by α-FPR and α-C5aR antibodies in these individuals. Also, only neutrophils from subjects 104 and 105 showed a decreased activation upon stimulation with fMLP. Unfortunately, experiments with C5a stimulation failed due to technical problems. However these experiments clearly show that intravenous administered CHIPS has an inhibitory effect on neutrophil activation ex vivo and that this effect is inhibited by α-CHIPS antibodies.

No relevant adverse effects were observed in pre-clinical animal toxicity studies. The administration of 0.1 mg kg$^{-1}$ CHIPS in human subjects was tolerated by 2 subjects (subjects 103 and 104) moderately tolerated in subject 105 but subject 106 developed serious symptoms directly after the CHIPS infusion, which were diagnosed as an anaphylactoid reaction. We measured the neutrophil CD11b surface expression in all subjects to investigate CHIPS-induced cell-activation. Activation of cells was observed for subjects 104, 105 and 106. Within the group of subjects that received CHIPS there was a increase in C-reactive protein at day 2 post dose compared to controls.

Mast cells, which are leukocytes found in peripheral tissue, play a central role in inflammation and immediate allergic reactions. The release of tryptase from the secretory granules is a characteristic feature of mast cell degranulation. Serum mast cell tryptase concentration is increased in anaphylaxis and in other allergic conditions (see Payne & Kam, 2004, *Anaesthesia* 59(7):695-703). The anaphylactoid reaction, observed after CHIPS administration, was confirmed by an increase in tryptase levels representing mast cell activation. The rise in tryptase levels was preceded by an increase in circulating immune complexes. Immune complexes can activate mast cells by FcγR crosslinking and through activation of complement and the generation of C5a (see Jancar & Crespo, 2005, *Trends Immunol* 26(1):48-55).

In vitro experiments confirmed the cell activating properties of CHIPS in the presence of α-CHIPS antibodies. CHIPS induced neutrophil activation was inhibited by blocking FcγRII and FcγRIII blocking antibodies. This indicates that the CHIPS induced activation of these cells is most likely caused by CHIPS/α-CHIPS immune complexes. When we look for circulating immune complexes in the tested subjects we also find an increase in immune complexes in the subjects receiving intravenous CHIPS. The relation between α-CHIPS antibody titer and CHIPS induced cell activation is also clear from the in vitro and ex vivo experiments. This is in contrast with the observation that subject 103, who has the highest α-CHIPS antibody titer, reports only minor adverse effects. Of course, the studied population was limited to only 4 subjects and a large amount of different factors influence the development and perception of the adverse effects within an individual. Furthermore, in vitro experiments demonstrate that there is an optimal antibody concentration that induces cell activation. It is possible that a very high α-CHIPS antibody titer decreases the development of an anaphylactoid reaction. Earlier studies showed that CHIPS does not bind other cells than those expressing the C5aR and FPR and there is no evidence of direct cell activation by CHIPS. Although antibodies clearly play a role in cell activation the small number of observations and the complexity of in vivo hampers interpretation of these data.

We demonstrated that two CHIPS mutants with a reduced affinity for α-CHIPS IgG (CHIPS$_{R46A}$ and CHIPS$_{K69A}$) show a decreased cell activating potential in vitro. Despite the neutralizing effect of α-CHIPS antibodies we were able to detect significant serum concentrations of the CHIPS protein. Moreover intravenous administered CHIPS was detected on circulating neutrophils, bound to the FPR and C5aR and able to inhibit neutrophil responses upon ex vivo stimulation with fMLP. This indicates that the CHIPS protein is able to find its target, the FPR and C5aR, in vivo.

We showed that the half-life of the CHIPS protein in serum is approximately 1.5 hours. Furthermore, the same half life was also observed for CHIPS bound to its receptors on the cell surface indicating a functional half life in the same order of magnitude. This indicates that the CHIPS protein is not immediately cleared from the blood. It might be possible to increase the half life of the CHIPS protein by introducing point mutations, as has been shown for streptokinase, a protein drug used for thrombolysis in acute myocardial infarction (see Wu et al., 1998, *Appl Environ Microbiol* 64(3):824-829). However, a half-life of 1.5 hours implies that any (immunosuppressive) effect will rapidly disappear when dosing is stopped. This could be an advantage over antibody drugs with a long half-life, like Infliximab, that has been associated with an increase in the incidence of infections (see Listing et al., 2005, *Arthritis Rheum* 52(11):3403-3412; Crum et al., 2005, *Medicine (Baltimore)* 84(5):291-302).

Example B

Identification of Conformational Epitopes for Human IgG on the Chemotaxis Inhibitory Protein of *Staphylococcus aureus* Using a Random Peptide Phage Display Library Materials & Methods
Cloning, Expression and Purification of Recombinant Proteins

CHIPS, $CHIPS_{31-121}$ (CHIPS without the first 30 amino acids) and $CHIPS_{31-113}$ (CHIPS without the first 30 and last 8 amino acids) were created as described earlier (see de Haas et al., 2004, *J Exp Med* 199(5):687-95; Haas et al., 2004, *J Immunol* 173(9):5704-11). The genes were cloned into the pRSET-B vector directly downstream the enterokinase cleavage site and before the EcoRI restriction site by overlap extension PCR (see Ho et al., 1989, *Gene* 77(1):51-59). Initially the CHIPS gene was amplified from chromosomal *S. aureus* DNA. This product was used as template for further cloning. The amplification reactions were performed using PFU TURBO DNA polymerase (Stratagene, Cedar Creek, Tex.). The final PCR product was purified using PCR Purification Kit (Qiaquick, Qiagen), cloned into the EcoRI and XbaI site of the pRSET-B vector and propagated in TOP10F' *E. coli* following manufacturer's instructions (Invitrogen). After verification of the correct sequence by using ABI Prism 377 (Applied Biosystems), the recombinant protein was expressed in Rosetta-Gami *E. coli* (Novagen, MERCK Biosciences) by induction with 1 mM IPTG (Isopropyl β-D-Thiogalactoside, Invitrogen).

Bacteria were lysed with CELLYTIC B Bacterial Cell lysis/Extraction Reagent (Sigma) and lysozyme according to the manufacturer's description. The histidine-tagged protein was purified using a nickel column (HiTrap Chelating HP, 5 mL, Amersham Biosciences) following the manufacturer's instructions and cleaved afterwards with enterokinase (Invitrogen). Samples were checked for purity and presence of protein by means of 15% SDS-PAGE (Polyacrylamide gel electrophoresis, MINI PROTEAN R3 System, Bio-Rad) and Coomassie Brilliant Blue (Merck) staining. Protein concentrations were determined by absorbance at 280 nm.

Cell Culture

U937 cells (human promonocytic cell line) transfected with C5aR (U937/C5aR) were a generous gift from Dr Prossnitz (University of New Mexico, Albuquerque, N. Mex.). Alternatively, such cells may be produced using techniques well known in the art.

Cells were grown in 75 $cm^2$ cell culture flasks with 2 μL vent caps (Corning, Acton, Mass.) placed in a 5% CO2 incubator at 37° C. Cells were maintained in RPMI 1640 medium with L glutamine (Invitrogen Life Technologies) including 1 mM sodium pyruvate (Invitrogen Life Technologies), 2.5 mg $mL^{-1}$ glucose (Sigma-Aldrich), 10% FCS (Invitrogen Life Technologies) and 10 $\mu g \cdot mL^{-1}$ gentamycin (Invitrogen Life Technologies). Cells were diluted 1/10 (v/v) twice a week (see Haas et al., 2004, *J Immunol* 173(9):5704-11).

CHIPS Activity Assays

The activation by chemoattractants initiates a rapid and transient increase in the free intracellular calcium concentration. Calcium mobilization with U937/C5aR cells was measured as previously described (see Haas et al., 2004, *J Immunol* 173(9):5704-11). Briefly, wild type CHIPS and truncated CHIPS variants ($CHIPS_{31-121}$ and $CHIPS_{31-113}$) were tested for their ability to inhibit the C5a-induced calcium mobilisation. Cells ($5\times10^6$ $mL^{-1}$ in RPMI 1640/0.05% HSA) were incubated with $2\times10^{-6}$ M Fluo-3-AM (Molecular Probes, Eugene, Oreg.) at room temperature for 20 min, washed twice, and suspended in RPMI 1640/0.05% HSA ($10^6$ $mL^{-1}$). The cells were preincubated with buffer, or 1 $\mu g \cdot mL^{-1}$ CHIPS or CHIPS variant at room temperature for 30 min. Incubation with buffer served as blank control. Cells were stimulated with an increasing concentration of C5a (Sigma-Aldrich). Increase in fluorescence representing cell activation was measured in a FACSCalibur flowcytometer.

Anti-CHIPS ELISA

Microtitre plates (Greiner) were coated with 50 μL CHIPS per well at 1 $\mu g \cdot mL^{-1}$ in PBS overnight at 4° C. All wash steps were performed thrice with PBS-0.05% Tween-20 and subsequent incubations were done for 1 hour at 37° C. Plates were blocked with PBS-0.05% Tween-20 4% BSA, washed and incubated with antibodies diluted in PBS-0.05% Tween-20 1% BSA. Bound antibodies were detected with species-specific goat anti-IgG conjugated with peroxidase (all from Southern, Birmingham, USA) and TMB as substrate. The reaction was stopped with $H_2SO_4$ and the absorbance measured at 450 nm in a BioRad ELISA-reader. For peptide experiments, plates were coated with ±10 μM25-mer peptides (Department of Pharmaceutical Chemistry, Utrecht, The Netherlands; see Haas et al., 2004, *J Immunol* 173(9):5704-11) in PBS overnight at 4° C. and treated as described for CHIPS.

Affinity Purification of Human-α-CHIPS-IgG

CHIPS or truncated CHIPS variant was coupled to CNBr activated sepharose 4B (Amersham Biosciences, Uppsala, Sweden) and packed onto a Tricon 5/20 column (Amersham Biosciences) according to manufacturer's instructions. Human IgG (60 $mg \cdot mL^{-1}$) (Sanquin, Amsterdam, The Netherlands) was diluted three times in PBS and filtered through a 0.2 μm filter. Affinity purification was performed on an ÄKTAPRIME system using a 50 mL loop (Amersham Biosciences) according to the manufacturer's protocol. Briefly, the column was washed with 10 column volumes PBS followed by running a total of 1 g human-IgG (20 $mg \cdot mL^{-1}$) over the column at a flowrate of 0.5 mL $min^{-1}$. The column was washed with 10 column volumes PBS and bound human-IgG was eluted with 0.1M glycine pH 3.0. 0.5 mL fractions were collected in tubes containing 50 μL 1MTris pH 8.0. Eluted fractions containing protein (as measured by $OD_{280}$) were pooled and buffer was changed to PBS using Amicon Ultra 15 5000 MWCO spin columns. Sodium azide was added to a final concentration of 0.02% and affinity purified-human-α-CHIPS-IgG was stored at 4° C.

Preparation of Phages Expressing the $CHIPS_{31-113}$ Protein

Phage stocks were prepared according to standard protocols, using VSCM13 (Stratagene, La Jolla, Calif., USA) as helper phage. Briefly, The $CHIPS_{31-113}$ gene was cloned into the pFAB75 vector (see Engberg et al., 1996, *Mol Biotechnol* 6(3):287-310) directly upstream the PIII gene and transformed into *E. coli* TOP10F' (Invitrogen, Carlsbad, Calif., USA). Bacteria were cultured until log-phase and infected with helper phage (multiplicity of infection: ~20). The superinfected bacteria were incubated for 30 min at 37° C. without shaking. Bacterial cells were collected by centrifugation and used to inoculate LB medium containing ampicillin (50 $\mu g \cdot mL^{-1}$), kanamycin (10 $\mu g \cdot mL^{-1}$), tetracyclin (10 $\mu g \cdot mL^{-1}$) and isopropyl-α-D-thiogalactoside (IPTG)(1 mM). The culture was incubated for 15 h at 30° C. with vigorous shaking. Supernatant was collected by centrifugation and phages were precipitated by adding 1⁄16 culture volume 25% PEG6000 (Fluka), 3MNaCl. Precipitated phages were resuspended in PBS 1% BSA and filtered sterile through a 0.45 μm filter Anti-Phage Reactivity of Human Affinity Purified-α-$CHIPS_{31-113}$-IgG Two Maxisorb 96 well plates (Nunc, Rochester, N.Y., USA) were incubated overnight at 4° C. with 1 μg·mL−1 mouse-_-M13 monoclonal antibody (Amersham Pharmacia Biotech Inc., Piscataway, N.J., USA) in PBS. Plates were washed three times with PBS-0.05% Tween-20 and blocked with 200 μL PBS-0.05% Tween-20 5% BSA for 1 h at 37° C. Plates were washed with PBS-0.05% Tween-20 and 100 μL PBS, M13 phage or M13 phage expressing the $CHIPS_{31-113}$ protein ($2\times10^{11}$ cfu $mL^{-1}$) was added and incubated for 1 h at 37° C. After washing plates were incubated for 1 h at 37° C. with 100 μL human affinity purified-α-$CHIPS_{31-113}$-IgG, or rabbit-α-CHIPS-IgG at different concentrations.

Next, plates were washed and 100 μL goat-α-human IgG-HRP (Jackson ImmunoResearch, West Grove, Pa., USA) or goat-α-rabbit-IgG-HRP (Southern Biotech, Birmingham, Ala., USA) at optimal concentration was added. Plates were washed three times and substrate (0.67 mg $mL^{-1}$ o-phenylenediamine, 35 mM sodium citrate, 67 mM NaPO3, pH 5 and 0.012% $H_2O_2$) was added. The reaction was stopped with 100 μL 1M $H_2SO_4$ and absorbance was measured at 490 nm.

Random Peptide Phage Library and Phage Selection

Phage libraries were purchased from New England Biolabs (Ipswich, Mass.). The Ph.D.-7 Display Peptide library consists of 7-mer random peptides fused with a linker sequence (Gly-Gly-Gly-Ser) to the N-terminus of the major coat protein pIII of bacteriophage M13. The library consists of ~2.8× $10^9$ electroporated sequences (compared to $20^7=1.28\times10^9$ possible 7-residue sequences), to yield ~70 copies of each sequence in 10 μL phage stock. The randomised segment of the Ph.D.-C7C™ library is flanked by a pair of cysteine residues, which are oxidized during phage assembly to a disulfide linkage, resulting in the displayed peptides being presented to the target as loops. The Ph.D.-7™ and Ph.D.-C7C™ libraries were used to map the epitopes for human IgG on the surface of the CHIPS protein 100 μL protein-G coated magnetic beads (Dynal) were washed three times with 1 mL PBS-0.05% Tween-20. The washed beads were blocked with 1 mL PBS-0.05% Tween-20 5% BSA for 1 h at 22° C. Beads were washed four times and resuspended in 1 mL PBS-0.05% Tween-20. One half of these blocked beads was used for preclearing the phage stock. Therefore, 10 μL Ph.D.-7™ and 10 μL Ph.D.-C7C™ was suspended in 180 μL PBS-0.05% Tween-20 containing the blocked beads and were incubated for 30 min at 22° C. under continuous agitation.

1 μL affinity purified human-α-$CHIPS_{31-113}$-IgG (300 $\mu g \cdot mL^{-1}$, final concentration approximately 10 nM) was added to the precleared phages and incubated at 22° C. for 30 min. The phage/IgG suspension was added to the remaining blocked beads and incubated at 22° C. for 30 min. The beads were washed 10 times with PBS-0.05% Tween-20 to wash away unbound phages. The Tween concentration in wash step was raised stepwise up to 0.5% in consecutive rounds to increase stringency. The bound phages were eluted with 125 μL 0.2 M glycine, pH 2.2, 0.1% BSA for 8 min after which the pH of the eluate was immediately neutralised with 15 μL 1M Tris-HCL, pH 8.

The eluate was amplified and 10 μL of amplified phages was used as input for a next selection round. To further increase the specificity of the phage selection the bound phages in the fourth round were eluted using competition elution with the CHIPS protein. Bound phages were eluted by overnight incubation with 1.8 mg $mL^{-1}$ CHIPS.

Phage Titration and Amplification

Since the library phage are derived from the common cloning vector M13mp19, which carries the lacZa gene, phage plaques appear blue when plated on media containing Xgal and IPTG. Environmental filamentous phage will typically yield white plaques when plated on the same media.

10 mL LB-medium was inoculated with a single colony ER2738 *E. coli* and incubated at 37° C. with vigorous shaking until mid-log phase ($OD_{600}$ ~0.5). Top agar (50% LB-agar, 50% LB-medium) was melted and cooled to approximately 45° C. 3 mL melted top agar was added to 200 μL ER2738 *E. coli* and poured on top of a LB/IPTG/Xgal plate (LB-agar plate containing 0.5 mM IPTG, 80 $\mu g \cdot mL^{-1}$ Xgal). 1 μL phage eluate was used to make ten fold serial dilutions. 10 μL of each dilution in LB-medium was spotted on the prepared culture plates and incubated overnight at 37° C. The next day plaques were counted in order to calculate phage titers.

The remaining phage eluate was added to 20 mL ER2738 *E. coli* culture at early log phase ($OD_{600}$ 0.4-0.5) and incubated with vigorously shaking at 37° C. for 4.5 h. Cultured cells were centrifuged at 10000 rpm for 10 min at 4° C. The supernatant was poured into a new tube and 1⁄6 volume of 25% PEG6000 (Fluka), 3 M NaCl was added and phages were precipitated overnight at 4° C. The precipitated phages were centrifuged for 15 min at 10000 rpm, 4° C. The pellet containing the amplified phages was resuspended in 200 μL PBS and titrated as described above. After the fourth selection round, no phage amplification was performed but phages were directly characterized by DNA sequencing.

Characterisation of Binding Phages

An overnight culture of ER2738 *E. coli* was diluted 1:100 in LB-medium. 48 different plaques from the titration plates were stabbed with a pipette tip and transferred to 1 mL of the diluted culture. The infected culture was incubated for 4.5~0.5 h at 37° C. Cultures were centrifuged for 30 s at 13600 rpm and 500 μl of the supernate was transferred to a fresh microcentrifuge tube. 200 μL PEG6000, 3 M NaCl was added and phages were precipitated for 10 min at 22° C. The sample was centrifuged for 10 min at 13600 rpm. The pellet was resuspended in 100 μL Iodide buffer (4 M NaI, 10 mM EDTA, pH 8) and 250 μL 95% EtOH was added and incubated for 10 min at 22° C. to preferentially precipitate the single stranded phage DNA. Samples were centrifuged for 10 min at 13600 rpm and the pellet was washed with 70% EtOH, dried and send for sequencing using the '-96 PIII sequencing' primer (5'-CCCTCATAGTTAGCGTAACG-3' [SEQ ID NO:2], New England Biolabs).

Epitope Mapping

The amino acid sequences of the selected phages were aligned using Clustal-W (see Aiyar, 2000, *Methods. Mol. Biol.* 132:221-41). Consensus sequences were manually mapped onto the surface of the CHIPS protein using the CHIPS$_{31-121}$ PDB file (PDB access code 1XEE) and the PyMol molecular graphics program (see DeLano, 2002, The PyMol Molecular Graphics System. Delano Scientific, San Carlos).

Binding Specificity of Selected Phages

A phage ELISA was used to test the binding specificity of the selected phages for affinity purified human-α-CHIPS$_{31-113}$- IgG. A 96 well Maxisorb plate was coated overnight with 100 μg·mL$^{-1}$ affinity purified human-α-CHIPS$_{31-113}$IgG in PBS at 4° C. The plate was washed four times with PBS-0.05% Tween-20 and blocked with 300 μL PBS-0.05% Tween-20 5% BSA for 1 h at 37° C. Simultaneously a second Maxisorb plate was blocked with PBS-0.05% Tween-20 5% BSA to serve as control for binding to BSA coated plastic. Plates were washed four times and incubated for 1 h at 37° C. with different dilutions of the purified phage stocks in PBS-0.05% Tween-201% BSA. Plates were washed four times and incubated for 1 h at 37° C. with 50 μL mouse-α-M13-mAb (1 μg·mL-1) (Amersham) in PBS-0.05% Tween-20 1% BSA. Plates were washed and incubated with 50 μL Rabbit-α-mouse IgG-HRP (1:2000 in PBS-0.05% Tween-20 1% BSA) for 1 h at 37° C. After washing 100 μL substrate was added and the reaction was stopped with 150 μL 1MHCl. Absorbance at 492 nm was measured in an ELISA plate reader.

Affinity Purification of hu-α-peptide IgG

Peptides of 7 amino acids, compromising the phage derived sequences, were synthesised with an additional C-terminal spacer of three Glycines and a Cysteine for efficient coupling (Isogen Life Science; IJsselstein, The Netherlands and Bio-Synthesis; Lewisville, Tx). Two control peptides were included, one with the minimal 7-mer sequence (plus GGGC [SEQ ID NO:3] for coupling) recognised by a mAb (clone S5/1) directed against the human C5a-Receptor (Bio-Synthesis), and a 38-mer peptide compromising the N-terminal part of CHIPS (first 37 amino acids plus an additional Cystein; Pepscan Systems; Lelystad, the Netherlands). Peptides were dissolved in H$_2$O and stored at −20° C. For ELISA, peptides were diluted to 25 μg·mL-1 in 0.1 M Tris/HCl at pH 8 and coated for 90 min onto Nunc Covalink NH plates that were treated for 30 min with 10 mM N-succinimidyl 3-(2-pyridyldithio)propionate (SPDP) to introduce free amino groups and washed with H$_2$O. Thereafter the plates were treated according to the same protocol as for the other ELISAs. To couple the peptides to a solid matrix, peptides were first reduced using agarose linked Tris(2-Carboxyethyl) Phosphine (TCEP, Pierce) and subsequently mixed with Sulfo-Link agarose beads (Pierce) in 50 mM Tris/HCl buffer pH 8.3 with 5 mM EDTA and incubated for 2 hours at room temperature. Unreacted groups were blocked with L-cysteine and beads were extensively washed with coupling buffer and PBS. Small 1 ml columns were used for affinity purification of IgG from a human immunoglobulin preparation for iv use (Sanquin) as described for CHIPS. Eluted IgG was mixed with 100 μg·mL$^{-1}$ pure human albumin, dialyzed overnight against PBS and the actual IgG content determined by ELISA.

Analysis of Antibody Binding to Selected Peptides Using Surface Plasmon Resonance Binding of affinity purified antibodies and pooled human IgG to the synthetic peptides and the CHIPS protein was studied on a Biacore 1000 instrument. Peptides containing a C-terminal cysteine residue were coupled to a carboxymethyl dextran sensor chip CM5 using N-ethyl-N' (dimethylaminopropyl) carbodiimide (EDC) and N-hydroxysuccinimide (NHS) chemistry with the Thiol coupling kit (Pharmacia Biacore) to activate the CM5 dextran. After activation, 20 μL of 2-(2-pyrdinyldithio) ethaneamine (PDEA) was injected and subsequently, 35 μL of the cysteine containing peptide, 1 mg·mL$^{-1}$ in 0.1 M NaAc, 1 M NaCl, pH 4 were injected during 7 minutes. Unreacted groups were blocked by injection of 20 μL L-cysteine during 4 minutes. For CHIPS coupling, 20 μL CHIPS (1 mg·mL$^{-1}$) was directly injected onto an EDC/NHS activated sensor chip. Remaining reactive groups on the sensor chip surface were saturated by injection of 50 μL 1 M ethanolamine-HCL pH 8.5 (Pharmacia).

The binding assays were performed at a constant flow rate of 5 μL·min$^{-1}$ at 25° C. Affinity purified antibodies and IV-IgG were diluted in HBS-EP buffer (10 mM HEPES (pH 7.4) containing 150 mM NaCl, 3 mM EDTA and 0.005% surfactant P20). Antibodies were allowed to interact with immobilized peptides for 210 s followed by a two minute dissociation phase. Additionally the antibodies were preincubated with 1 mg mL$^{-1}$ CHIPS protein to study competition. Affinity purified α-peptide antibodies were tested at a concentration of 10 μg·mL$^{-1}$. Residual bound antibody was removed from the sensor chip surface by washing the chip for three minutes with 10 mMglycine-HCl (pH 1.5).

Results

Activity of CHIPS$_{31-113}$

Previously, we described the CHIPS$_{31-121}$ protein that showed a complete preservation of C5aR blocking activity (see Haas et al., 2005, *J Mol Biol* 353(4):859-872). In order to find a smaller active CHIPS variant we deleted part of the C-terminus outside the folded core of the protein (see Haas et al., 2005, *J Mol Biol* 353(4):859-872). FIG. 14 shows the activity of different CHIPS variants compared to wild type CHIPS. All CHIPS variants were able to inhibit C5a induced activation U937/C5aR cells.

Affinity Purified α-Chips Antibodies Recognize Conformational Epitopes

Pooled human IgG was affinity purified using a column packed with immobilised-CHIPS resin. We tested the binding of affinity purified α-CHIPS antibodies to a set of CHIPS derived 25 mer peptides spanning the total CHIPS sequence (see Haas et al., 2004, *J Immunol* 173(9):5704-11). As shown in FIG. 15 only wild type CHIPS and peptides derived from the N-terminus of CHIPS were recognised by the affinity purified α-CHIPS antibodies. This suggests that these α-CHIPS antibodies do not recognise linear epitopes between residue 30 and 113.

To confirm the presence of conformational epitopes in the CHIPS protein we tested the reactivity of two different affinity purified antibody preparations (α-CHIPS$_{1-121}$ and α-CHIPS$_{31-113}$) to wild type CHIPS(CHIPS$_{wt}$), and two truncated CHIPS proteins (CHIPS$_{31-121}$ and CHIPS$_{31-113}$). FIG. 16 shows that all antibodies react with the CHIPS protein. Although affinity purified α-CHIPS$_{1-121}$ contains epitopes directed against the N-terminus (FIG. 15) there is no significant difference in reactivity towards the different CHIPS variants between the preparations. This could indicate an excess of conformational epitopes over linear. A CHIPS specific mouse monoclonal antibody directed against a conformational epitope served as control.

Affinity Purified α-CHIPS IgG Does not React with Wild Type M13 Phage

Human-α-phage IgG, present in the affinity purified α-CHIPS$_{31-113}$ IgG preparation, could potentially interfere with the phage selection experiments. Therefore we tested the binding of affinity purified α-CHIPS$_{31-113}$ IgG to empty M13 phages (M13 phages expressing a wild type pIII surface protein) by ELISA. FIG. 17 shows that affinity purified α-CHIPS$_{31-113}$ IgG does not react with wild type M13 phages but is perfectly recognises M13 phages expressing the CHIPS protein. Affinity purified α-CHIPS IgG up to a concentration of 100 µg·mL$^{-1}$ was used. Even at this high concentration there was no difference in binding to empty phages compared to background. Therefore, we conclude that no significant amount of α-phage antibodies are present in the affinity purified α-CHIPS$_{31-113}$ IgG preparation that could interfere with the selection experiments.

Biopanning and Characterisation of Recombinant Phages

The affinity purified α-CHIPS$_{31-113}$ IgG was used to select phages from two random peptide phage libraries and map the epitopes for human IgG onto the CHIPS protein surface. After four rounds of biopanning 48 recombinant phage clones were randomly selected and characterized by DNA sequencing. The sequences of 47 clones are shown in table 3 (sequencing of clone 27 failed). The sequence 'MNKTWYP' [SEQ ID NO:4] occurred 12 times in this set of 47 sequences and is thereby the most abundant followed by 'MNKTFWF' [SEQ ID NO:5] that was selected 4 times. Interestingly, the sequence 'FNKSYYG' [SEQ ID NO:6] occurred 3 times but these sequences differed in genetic sequence and therefore are not a simple amplification of a single selected phage (data not shown). Although we started out with a mixture of two different libraries (Ph.D.-7™ and Ph.D.-C7C™) the selected sequences were all originating from the Ph.D.-7™ library.

TABLE 3

Table 3: Peptide sequences of 47 recombinant phage clones after 4 rounds of panning.

| Clone | Sequence |
|---|---|
| 01 | M N K T W Y P [SEQ ID NO: 7] |
| 02 | G K L P I A M [SEQ ID NO: 8] |
| 03 | M N K T W Y P [SEQ ID NO: 9] |
| 04 | M N K T F W F [SEQ ID NO: 10] |
| 05 | Y N K S F F M [SEQ ID NO: 11] |
| 06 | A A A P S H H [SEQ ID NO: 12] |
| 07 | Y N K S F F P [SEQ ID NO: 13] |
| 08 | G K L P I P Y [SEQ ID NO: 14] |
| 09 | M N K T F S A [SEQ ID NO: 15] |
| 10 | M N K T W Y P [SEQ ID NO: 16] |
| 11 | G K L P K M T [SEQ ID NO: 17] |
| 12 | M N K S Y T I [SEQ ID NO: 18] |
| 13 | V N K T Y W K [SEQ ID NO: 19] |
| 14 | M N K V Y L P [SEQ ID NO: 20] |
| 15 | G K L P P P I [SEQ ID NO: 21] |
| 16 | A L Q A S R H [SEQ ID NO: 22] |
| 17 | M N K T W Y P [SEQ ID NO: 23] |
| 18 | M N K T W Y P [SEQ ID NO: 24] |
| 19 | F N K S W F P [SEQ ID NO: 25] |
| 20 | M N K T W Y P [SEQ ID NO: 26] |
| 21 | M N K T W Y P [SEQ ID NO: 27] |
| 22 | M N K Y H N P [SEQ ID NO: 28] |
| 23 | M N K T F W F [SEQ ID NO: 29] |
| 24 | G K M M V S E [SEQ ID NO: 30] |
| 25 | M N K S Y H L [SEQ ID NO: 31] |
| 26 | L N K T F Y Y [SEQ ID NO: 32] |
| 28 | M N K T F V P [SEQ ID NO: 33] |
| 29 | M N K T F F S [SEQ ID NO: 34] |
| 30 | G K L P K E S [SEQ ID NO: 35] |
| 31 | M N K T F W F [SEQ ID NO: 36] |
| 32 | M N K T W Y P [SEQ ID NO: 37] |
| 33 | F N K S Y Y G [SEQ ID NO: 38] |
| 34 | Y N K S F F M [SEQ ID NO: 39] |
| 35 | A G A P R H H [SEQ ID NO: 40] |
| 36 | M N K T F W F [SEQ ID NO: 41] |

TABLE 3-continued

Table 3: Peptide sequences of 47 recombinant phage clones after 4 rounds of panning.

| Clone | Sequence |
|---|---|
| 37 | M N K T F V D [SEQ ID NO: 42] |
| 38 | M N K S Y H L [SEQ ID NO: 43] |
| 39 | F N K S Y Y G [SEQ ID NO: 44] |
| 40 | M N K T W Y P [SEQ ID NO: 45] |
| 41 | M N K T W Y P [SEQ ID NO: 46] |
| 42 | M N K T W Y P [SEQ ID NO: 47] |
| 43 | M N K T W Y P [SEQ ID NO: 48] |
| 44 | M N K T F W F [SEQ ID NO: 49] |
| 45 | M P L R A S Q [SEQ ID NO: 51] |
| 46 | G K L P W P K [SEQ ID NO: 52] |
| 47 | F N K S Y Y G [SEQ ID NO: 53] |
| 48 | M N K T F F S [SEQ ID NO: 54] |

The combined Ph.D.-7™ and Ph.D.-C7C™ random peptide phage libraries were selected for binding to affinity purified α-CHIPS$_{31\text{-}113}$ IgG in four consecutive panning rounds. Phages in the last round were selectively eluted using competition with a high CHIPS concentration (1.7 mg mL$^{-1}$). 48 Single phages were amplified and isolated single stranded DNA was sequenced (sequencing of clone 27 failed). Data show the translated sequences representing the expressed random peptides.

The selected peptides could be divided into different groups based on their amino acid sequence as shown in Table 4. Furthermore, based on the sequence similarities within each group, we calculated consensus sequences. Amino acids that occurred most frequently among the aligned sequences within each group were classified as consensus residue. The consensus sequences for each group are shown in Table 4.

The selected sequences were manually mapped onto the surface of the CHIPS protein using the PyMol molecular graphics program and the CHIPS31-121 pdb file (PDB access code 1XEE) as shown in FIG. 18. A fourth epitope was identified from the selected sequences. Although the sequence 'PLRASQ' [SEQ ID NO:55] expressed by phage ø45) appeared only once among the 47 sequenced recombinant phages, this sequence could be perfectly mapped onto the surface of the CHIPS molecule. Additionally the peptide sequence expressed by phage ø16 ('ALQASRH' [SEQ ID NO:56]) shows a very high similarity to this 'epitope'.

8 different recombinant phages, that express a peptide sequence most similar to the predicted epitopes, were further characterized by ELISA (Table 5). FIG. 19a shows that these phages specifically bind to affinity purified α-CHIPS$_{31\text{-}113}$ IgG but not BSA (FIG. 19b). Earlier we showed that the affinity purified α-CHIPS$_{31\text{-}113}$ IgG does not react with empty phages (FIG. 17). Therefore, we conclude that the binding of the selected phages to affinity purified α-CHIPS$_{31\text{-}113}$ IgG is specific for the expressed peptide.

TABLE 4

Table 4: Grouping of the peptide sequences.

| | | | | | | | |
|---|---|---|---|---|---|---|---|
| M | N | K | T | W | Y | P | (12) [SEQ ID NO: 57] |
| M | N | K | T | F | W | F | (4) [SEQ ID NO: 58] |
| M | N | K | T | F | S | A | [SEQ ID NO: 59] |
| M | N | K | V | Y | L | P | [SEQ ID NO: 60] |
| L | N | K | T | F | Y | Y | [SEQ ID NO: 61] |
| M | N | K | T | F | V | D | [SEQ ID NO: 62] |
| V | N | K | T | Y | W | K | [SEQ ID NO: 63] |
| M | N | K | T | W | Y | P | [SEQ ID NO: 64] |
| F | N | K | S | Y | Y | G | (3) [SEQ ID NO: 65] |
| M | N | K | S | Y | H | L | (2) [SEQ ID NO: 66] |
| Y | N | K | S | F | F | M | (2) [SEQ ID NO: 67] |
| Y | N | K | S | F | F | P | [SEQ ID NO: 68] |
| F | N | K | S | W | F | P | [SEQ ID NO: 69] |
| F | N | K | S | Y | Y | G | [SEQ ID NO: 70] |
| G | K | L | P | I | A | M | [SEQ ID NO: 71] |
| G | K | L | P | W | P | K | [SEQ ID NO: 72] |
| G | K | L | P | I | P | Y | [SEQ ID NO: 73] |
| G | K | L | P | P | P | I | [SEQ ID NO: 74] |
| G | K | L | P | K | M | T | [SEQ ID NO: 75] |
| G | K | L | P | K | E | S | [SEQ ID NO: 76] |
| G | K | L | P | x | x | x | [SEQ ID NO: 77] |

Peptide sequences selected from the Ph.D.-7 ™ phage library were divided into different groups based on the amino acid sequence. The numbers in the parenthesis indicate the number of sequences that were found more than once. Three different groups can be distinguished. Also shown are the consensus sequences for each group. Amino acids that occurred most frequently among the aligned sequences within each group were classified as consensus residue.

Synthetic Peptides Mimic the Mapped Epitopes

Based on the results from the phage selections and epitope mapping 4 different peptides were synthesised (insert FIG. 20) All peptides contained a C-terminal cysteine residue that allowed immobilisation by thiol coupling chemistry. Since the N-terminus of the CHIPS protein was found to contain epitopes for human IgG (FIG. 15) a synthetic peptide comprising the N-terminal 37 CHIPS residues and an additional cysteine (pep1-38) was used as a positive control. The peptides were coupled to thiol activated sepharose to create different affinity columns. These columns were used for affinity purification of human IgG. Binding of the affinity purified α-peptide antibodies to the different peptides and the CHIPS molecule was verified by ELISA (data not shown) and studied in a Biacore 1000 instrument (FIG. 20).

The affinity purified α-peptide antibodies show an increase in binding to their specific peptide as compared to IVIgG. Pre-incubating the affinity purified antibodies with 1 mg mL$^{-1}$ CHIPS does not decrease this interaction. α-552 and α-554 antibodies cross react with peptide 552 and 554. This is not surprising since these peptides have a high sequence similarity (insert FIG. 20)

The affinity purified α-peptide antibodies show an increased binding to the CHIPS protein compared to IVIgG. This interaction is disrupted by pre-incubation of the affinity purified α-peptide antibodies with 1 mg mL−1 CHIPS.

TABLE 5

Table 5: Sequences selected for further characterization.

| Clone | Sequence |
|---|---|
| ø 12 | M N K S Y T I [SEQ ID NO: 78] |
| ø 13 | V N K T Y W K [SEQ ID NO: 79] |
| ø 16 | A L Q A S R H [SEQ ID NO: 80] |
| ø 20 | M N K T W Y P [SEQ ID NO: 81] |
| ø 29 | M N K T F F S [SEQ ID NO: 82] |
| ø 30 | G K L P K E S [SEQ ID NO: 83] |
| ø 33 | F N K S Y Y G [SEQ ID NO: 84] |
| ø 45 | M P L R A S Q [SEQ ID NO: 85] |

Based on the mapped epitopes we selected 8 phages expressing different peptides for further characterization by ELISA.

Discussion

Antibody epitopes are often formed by amino acids that are distant from each other in the primary sequence of a protein, but are brought together as a reactive site on the surface of the folded molecule. We show that this is especially true for CHIPS, since affinity purified α-CHIPS antibodies fail to recognize linear parts of the CHIPS protein between residue 31 and 113. Consequently, the utility of truncated molecules in epitope mapping is limited, as even small deletions and substitutions can have considerable impact on the structure of the molecule. The use of random peptide libraries overcomes the limitations of epitope mapping with truncated molecules.

Previous studies show the potential of random peptide phage display libraries in identifying linear epitopes (see Yang et al., 2005, *J Immunol Methods* 304(1-2):15-29) and conformational epitopes of monoclonal antibodies (see Cook et al., 1998, *J Autoimmun* 11(3):205-211; Myers et al., 2000, *J Immunol* 165(7):3830-3838; Shaw et al., 2002, *Biochem J* 363(Pt 1):137-145). These studies show that peptides expressed by phage display are capable of adopting a conformation that mimics the conformational epitope and allows for affinity purification. In this study, epitopes on CHIPS were mapped using a random peptide phage display library. To our knowledge the present study is the first report of mapping conformational epitopes in a polyclonal antibody preparation.

We selected phages for binding to affinity purified α-CHIPS$_{31-113}$ IgG. Schluederberg et al. (1980, *Nature* 283 (5749):792-4) showed that phages indistinguishable from M13 can be isolated from human faeces. Despite the large amount of M13 phages in the environment we showed that our affinity purified antibody preparation did not contain any detectable α-M13 phage antibody levels. However, to increase the specificity of selected phages for binding to α-CHIPS antibodies we used competition elution with a high concentration CHIPS.

After four selection rounds 47 clones were sequenced. Phage selection depends on a large variety of factors. For instance, arginines in the displayed peptide sequence interfere with secretion of pIII; consequently, clones with peptides containing Arg are strongly selected against (see Peters et al., 1994, *J Bacterial* 176(14):4296-4305). Also, the stringency and nature of wash steps can favor certain phages (see Smith & Petrenko, 1997, *Chem Rev* 97(2):391-410). Therefore, although the sequence 'MNKTWMP' [SEQ ID NO:86] was most frequently isolated no further conclusions can be inferred from this observation. The Ph.D.-7™ and Ph.D.-C7C™ libraries both consists of ~2.8×10$^9$ electroporated sequences (compared to 20$^7$=1.28×10$^9$ possible 7-residue sequences) and contain a wide diversity of sequences with no obvious positional biases. From this large library we selected 4 sequences that could be mapped onto the surface of the CHIPS molecule. These similarities cannot be explained by coincidence and therefore we conclude that these sequences represent conformational epitopes.

Further characterisation of 8 phages, each expressing a different peptide sequence most similar to the predicted epitopes, was performed by ELISA. These phages show binding to affinity purified α CHIPS IgG. Earlier we showed that the affinity purified α-CHIPS IgG does not contain any detectable amounts of anti M13 phage antibodies. Therefore, we conclude that this interaction is specific for the expressed peptide.

To confirm that the expressed peptides were able to mimic the conformational epitopes on the CHIPS protein, additional experiments were performed. Using synthetic peptides, similar to the peptides selected from the phage library, we affinity purified antibodies from a pool, of IgG that specifically recognized the CHIPS protein. These affinity purified antibodies interacted with their specific peptide. This interaction did not compete with CHIPS protein. From these observations we conclude that α-peptide antibodies are present in the IV-IgG pool that recognise different conformations of the synthetic peptide. Most of these conformations differ from the CHIPS conformational epitope and therefore do not compete with the CHIPS protein. Since the synthetic peptides contain a spacer (Gly-Gly-Gly-Cys [SEQ ID NO:87]) it is possible that the purified antibody preparations contain α-spacer or α-spacer-peptide antibodies.

Binding studies of the affinity purified a peptide antibodies to the CHIPS protein reveal a subset that specifically recognize the CHIPS protein. The conformation of the epitope recognised by these antibodies on the CHIPS protein surface is constrained and therefore there is no competition with other α-peptide antibodies recognizing different peptide conformations.

Although CHIPS is a small, compact folded protein it is difficult to estimate the total amount of epitopes present. The Ph.D.-7™ and Ph.D.-C7C™ libraries we used are limited in the size of the expressed peptides to seven residues and therefore limits the size of the mimicked epitopes. We mapped four epitopes onto the surface of the CHIPS molecule. Additional selections using libraries that express larger peptides could be used to identify additional epitopes.

We focused on the CHIPS$_{31-113}$ molecule, the part of CHIPS responsible for blocking the C5aR. Interestingly we did not isolate a peptide phages mimicking a linear epitope.

This is in accordance with the results of the pepscan ELISA in which we observed no interaction between the affinity purified α-CHIPS antibodies and CHIPS derived peptides.

For the affinity purification of α-CHIPS IgG we started with a pool of IgG obtained from a large group of donors. It is most likely that different individuals recognise a subset of epitopes. Using the described selection technique in future research can give more insight in the distribution of epitope recognition between different individuals.

Example C

Exemplary Variant CHIPS Polypeptides I

Chips Peptide ELISA: Single Point Measurement of Library
    Goal: To determine peptide binding capacity of CHIPS mutants in crude cell lysate.
    Summary: A tandem sandwich ELISA was optimised with Streptavidin as coating, followed by a biotinylated C5aR peptide to which CHIPS binding was detected by a monoclonal antibody, mAb 2H7, followed by a secondary HRP conjugated polyclonal antibody and substrate. A standard curve with purified recombinant CHIPS$_{wt}$ was prepared for each ELISA plate. Absorbance at 492 nm was measured and plotted against concentration of standard and analysed in a 4-parameter curve fitting model, from which the peptide binding of the mutants was calculated and correlated to the expressed concentration as specific activity.
Materials and Methods
10×PBS (BioWhittaker #BE17-517Q, lot 4MB0102)
PBS Tween 20 (0.05%) (Medicago #09-8410-100, lot 113303)
BSA (Merck #1.12018.0100, lot K54593318527)
CELLYTIC B (Sigma #B-3553, lot 114K65156)
SIGMAFAST OPD (Sigma #P9186, lot 055K8204)
F96 Maxisorp (Nunc #442404, lot 079027)
96-well U-shape PP plate
Streptavidin 1 mg/ml (Sigma, Lot 120K1249)
CD88-N-term peptide: ABCF-1, 6.3 mg/ml (lot 050805KaB)
mAb 2H7 monoclonal antibody, 1 mg/ml (Utrecht, lot 2004-12)
Rabbit anti Mouse Ig-HRP (Dako #P0260, lot 00006983)
rCHIPS$_{wt}$, 1.8 mg/ml (Utrecht, lot 2004-12-02)
CHIPS controls (lysate): CHIPSwt, K69A, 2mut.
CHIPS Library:
Equipment:
ELISA washer ELx405 (BioTek Instruments)
Shaker platform Titramax 1000 (Heidolph Instruments)
FLUOstar Optima (BMG)Software
Excel
GraphPad Sigma
Buffers:
Coating buffer: 1×PBS: Add 100 ml 10×PBS to 900 ml of deionised water.
Washing buffer: PBS+0.05% Tween 20 (PBST): Add 1 tablet to 1000 ml of deionised water.
Assay buffer A: PBST+1% BSA(w/v)+1% Cellytic(v/v)
Assay buffer B: PBST+1% BSA(w/v)
Blocking solution: PBST+4% BSA(w/v)
Protocol (3 Plates)
1. Coating: Prepare Streptavidin, 5.0 μg/ml in coating buffer (PBS). Pipett 100 μl/well in a 96-well Maxisorp plate. Incubate over night at 4° C.
2. Blocking: Add blocking solution 200 μl/well. Incubate 1 hour (h) at room temperature (RT) at a shaker platform at 600 rpm (S).
3. Biotinylated peptide: CD88-N-term peptide ABCF-1: 0.3 μg/ml in Assay buffer B (PBST+1% BSA). Dilute stock 1:10=0.63 mg/ml.
   32 ml buffer+15.2 μl peptide (0.63 mg/ml).
   Add 100 μl/well. Incubate 1 h at RT. S.
4. rCHIPS$_{wt}$ standard curve: In 15 ml test tubes: Prepare a threefold serial dilution in Assay buffer A, 1000-0.42 ng/ml.
   Dilution of rCHIPSwt (stock 1.8 mg/ml) 1:100 in Assay buffer A: 5 μL
   CHIPS+495 μL, buffer=18 μg/ml
   1000 ng/ml: 85 μl CHIPS+1445 μl buffer
   333 ng/ml: 5000 CHIPS (1000 ng/ml)+1000 μl buffert
   ↓
   Tot 8 conc.
   Controls and library: Prepare a threefold serial dilution 1:300, 1:900 and 1:2700 (in robot or manually) in 96-well U-shape PP-plates.
   1:5 dilution: 150 μl lysate+600 μl Assay buffer B (PBST+1% BSA)
   1:100 dilution: 25 μl (1:5 dil)+475 μl Assay buffer A (PBST+1% BSA+1% CL)
   1:300 dilution: 150 μl (1:100 dil)+300 μl Assay buffer A
   ↓
   1:900 and 1:2700.
   Pipette 100 μl/well in duplicate for standard curve and controls and single point for library. Blank: Pipette 100 μl Assay buffer A to four wells.
   Incubate 1 h RT. S.
5. Detection antibody: Mab 2H7, 1 μg/ml in Assay buffer B (PBS+1% BSA)
   32 μl ab+32 ml buffer
   Pipette 100 μl/well. Incubate 1 h at RT. S.
6. Secondary antibody: Rabbit anti Mouse Ig-HRP. Prepare a 1:2 000 dilution in Assay buffer B.
   16 μl ab+32 ml buffer.
   Add 100 μl/well. Incubate 1 h at RT.S.
7. Extended wash: Add washing buffer 200 ml/well. Incubate 5 min. at RT. S.
8. Substrate: SIGMAFAST OPD. (According to instruction.)
   Solve 2 buffer- and 2 substrate tablets in 40 ml deionised water. Add 100 μl/well. Incubate in dark at RT. S. Approx 3-6 min
   Stop reaction by adding 1M HCl, 150 μl/well.
   Measure Abs 492 nm.
***Between all steps: Wash×3 with PBST in EL405. #3×96 Greiner****
Plate Layout (see Table 6)

TABLE 6

|   | 1 | 2 | 3 | 4 | 5 | 6 | 7 | 8 | 9 | 10 | 11 | 12 |
|---|---|---|---|---|---|---|---|---|---|----|----|----|
| A | Std wt 1000 ng/ml |  | → wt1 | → | 1D1 | 1F9 | 2H5 | 2G9 | 3B5 | 5H1 | 6B2 | 7A2 |
| B | 333.0 |  | wt2 |  | 1G1 | 1B12 | 2A6 | 2B11 | 3D5 | 5C2 | 6B4 | 7B2 |
| C | 111.0 |  | K69A 1 |  | 1D3 | 2C1 | 2G6 | 3H1 | 3E6 | 5E2 | 6G4 | 7H2 |
| D | 37.0 |  | K69A 2 |  | 1E3 | 2D1 | 2D7 | 3D2 | 4A1 | 5F2 | 6E5 | 7A3 |
| E | 12.3 |  | 2mut1 |  | 1E4 | 2G2 | 2G7 | 3F2 | 4A2 | 5A6 | 6G5 | 7B3 |

TABLE 6-continued

|   | 1 | 2 | 3 | 4 | 5 | 6 | 7 | 8 | 9 | 10 | 11 | 12 |
|---|---|---|---|---|---|---|---|---|---|----|----|----|
| F | 4.1 |   | 2mut2 |       | 1B6 | 2A4 | 2G8 | 3C4 | 4D2 | 5D6 | 6D6 | 7G3 |
| G | 1.4 |   | Blank | Blank | 1B7 | 2H4 | 2C9 | 3D4 | 4E5 | 6E1 | 7C1 | 7B4 |
| H | 0.5 |   | Blank | Blank | 1F8 | 2D5 | 2D9 | 3F4 | 4C6 | 6A2 | 7E1 | 7E4 |

Calculations

Standard curves were analysed using BMG reader software, Excel and/or Sigma GraphPad (see FIG. 21).

Excel: Calculate Mean of standard curve, controls and Blank. Calculate CV (%) of Blank Perform a blank subtraction for all data points.

In GraphPad: Standard curve: plot Absorbance against Log concentration of standard. Perform curve fit in model: Sigmoidal curve fit with variable Report EC50 value and R2-value. Analyse peptide binding in controls and library. (Abs 492 as Y, unknown as X gives binding as Log conc. Recalculate: 10^(log conc)=conc.

Calculate specific activity (%): 100*(Conc peptide binding/Conc(expression))

(See Table 7).

TABLE 7

| Conc expr (µg/ml) | Conc sample (ng/ml) | Clone | Abs 492 nm | Pep. bind. Log (ng/ml) | Pep. bind. (ng/ml) | Spec. activity pep/expr (%) |
|---|---|---|---|---|---|---|
| 38.98 | 129.9 | wt | 1.477 | 2.190 | 154.8 | 119 |
| 35.57 | 118.6 | wt | 1.409 | 2.099 | 125.6 | 106 |
| 32.6 | 108.7 | K69A | 1.410 | 2.100 | 126.0 | 116 |
| 32.1 | 107.0 | K69A | 1.393 | 2.079 | 120.0 | 112 |
| 13.3 | 44.2 | 2mut | 0.538 | 1.225 | 16.8 | 38 |
| 12.2 | 40.7 | 2mut | 0.527 | 1.213 | 16.3 | 40 |

CHIPS1004 Anti-CHIPS ELISA. Single Point Measurement of Library in 1:1000 Dilution in Secondary Screening Goal: To be able, in a single point measurement, to select clones with decreased binding to human polyclonal anti-CHIPS.

Summary: Mutated clones, based on K69A, selected from primary screening (phage display) were tested for Human anti-CHIPS binding in a tandem sandwich ELISA. The ELISA was optimised with a monoclonal antibody binding to the first 30 amino acids (N-terminal) of CHIPS as coating antibody and polyclonal human anti CHIPS IgG as detection antibody. A HRP conjugated polyclonal antibody was used as second antibody followed by HRP-substrate. A standard curve with purified recombinant $CHIPS_{wt}$ was prepared for each ELISA plate as inter plate control and a serial dilution of K69A lysate was used for calculation and comparison of the library. Absorbance 492 nm was measured and plotted against concentration and analysed in a Sigmoidal curve fit with variable slop model. Expected binding (abs) was calculated for the mutants as if K69A. Deviation from expected value: measured-expected was calculated and reported.

Material and Method:
10×PBS (BioWhittaker #BE17-517Q, lot 4MB0102)
PBS Tween 20 (0.05%) (Medicago #09-8410-100, lot 113303)
Skim milk powder (Semper, lot 041203)
CELLYTIC B (Sigma #B-3553, lot 114K65156)
SIGMAFAST OPD (Sigma #P9186, lot 055K8204)
F96 Maxisorp (Nunc #442404, lot 079027)
96-well U-shape PP plate (Nunc #267245, lot 075860)
mAb 2H7 monoclonal antibody, 1 mg/ml (Utrecht, lot 2004-12)
Human anti-CHIPS (31-113) IgG (HaCHIPS), 2.54 mg/ml (Alligator Bioscience, 050223KaB)
Goat anti human IgG (Fcγ)—HRP (Jackson Immunotech Research #, lot 64067) rCHIPSwt, 1.8 mg/ml (Utrecht, lot 2004-12-02)
CHIPS Mutants:
Equipment:
ELISA washer ELx405 (BioTek Instruments)
Shaker platform Titramax 1000 (Heidolph Instruments)
Multiscan Ascent (Labsystems)
GraphPad Sigma
Excel
Buffers:
Coating buffer: 1×PBS: Add 100 mL 10×PBS to 900 mL of deionised water.
Washing buffert: PBS+0.05% Tween 20 (PBST): Add 1 tablet to 1000 mL of deionised water.
Assay buffer A: PBST+1% Skim milk powder (MP) (w/v)+1% Cellytic(v/v)
Assay buffer B: PBST+1% MP(w/v)
Blocking solution: PBST+3% MP(w/v)
Dilution buffer: 1.25×PBS (Add 12.5 ml 10×PBS to 87.5 ml deionised water. Protocol (3 plates)
1. Coating: Prepare monoclonal antibody mAb 2H7, 3.0 µg/ml in coating buffer (PBS).
   Pipette 100 µl/well in a 96-well Maxisorp plate.
   Incubate over night at 4° C.
2. Blocking: Add blocking solution 2000/well. Incubate 1 hour (h) at room temperature (RT) at a shaker platform at 600 rpm (S).
3. Sample: rCHIPSwt standard curve 1000-0.06 ng/ml. In eppendorf tubes:
   Prepare a four fold serial dilution in Assay buffer A (PBST+1% MP+1% Callytic).
   Dilution of rCHIPSwt (stock 1.8 mg/ml) 1:100 in Assay buffer A:
   5 µL CHIPS+495 µL buffer=18 µg/ml
   Serial dilution:
   1000 ng/ml: 33 µl CHIPSwt (18 µg/ml)+651 µl buffer
   250 ng/ml: 150 µl CHIPS (1000 ng/ml)+450 µl buffer
   ↓
   In total 8 concentrations
   Control K69A (lysate): Prepare a four fold serial dilution 1:100-1:102 400 from two clones.
   In 96-well U-shape PP plate: 1:5 dilution in 1.25×PBS: 60 µl lysate+240 µl 1.25×PBS
   In eppendorf tubes:
   1:100 30 ml lysate+570 µl Assay buffer B
   1:400 150 µl (1:100 dil)+450 µl Assay buffer A
   ↓
   In total 6 concentrations
   Control wt, 2mut (lysate) and library: Prepare a 1:1000 dilution in Assay buffer A in a 96-well U-shape PP plate.
   1: 5 dilution in 1.25×PBS: 60 µl lysate+240 µl 1.25×PBS
   1:100 dilution in Assay buffer A (PBST+1% MP+1% cellytic)

Control wt and 2 mut (lysate): 75 µl (1:5 dil)+1425 µl buffer
Library: 15 µl (1:5 dil)+285 µl buffer
To ELISA plate (according to plate layout):
rCHIPSwt std curve and control K69A: Pipette 100 ml/well.
Control wt and 2mut (lysate) and library: Pipette 90 µl Assay buffer A+10 µl sample (1:100 dil).
Blank: Pipette Assay buffer A, 100 µl/well to three Wells. Incubate 1 h at RT. S.
4. Detection antibody: Human antiCHIPS (31-113) 0.1 µg/ml in Assay buffer B.
   1:10 Dilution of stock: 5 µl+295 µl Assay buffer B=254 µg/ml
   13.4 µl HaCHIP (254 µg/ml)+34 ml Assay buffer B
   Pipette 100 µl/well. Incubate 1 h at RT. S.
5. Secondary antibody: Goat anti HumanIgG-HRP diluted 1:12000 in Assay buffer B.
   3 µl ab+35 ml Assay buffer B
   Add 100 µl/well. Incubate 1 h at RT. S.
6. Extended wash: Add 200 µl washing buffer. Incubate 5 min at RT.S.
7. Substrate: SIGMAFAST OPD. (According to instruction.) Solve 2 buffer- and 2 substrate tablets in 40 ml deionised water. Add 100 µl/well. Incubate in dark at RT. S. Approx 3-6 min
   Stop reaction by adding 1M HCl, 150 µl/well.
   Measure Abs 492 nm.
***Between all steps: Wash ×3 with PBST in EL405. #3×96 Greiner****
Plate Layout (see Table 8)

TABLE 8

|   | 1 | 2 | 3 | 4 | 5 | 6 | 7 | 8 | 9 | 10 | 11 | 12 |
|---|---|---|---|---|---|---|---|---|---|---|---|---|
| A | Std wt 1000 ng/ml | K69A1 x100 | K69A2 x100 | wt4 | 1:A1 | 1:A2 | 1:A3 | 1:A4 | 1:A5 | 1:A6 | 1:A7 | 1:A8 |
| B | 250 | x400 | x400 | wt5 | 1:B1 | 1:B2 | 1:B3 | 1:B4 | 1:B5 | 1:B6 | 1:B7 | 1:B8 |
| C | 62.5 | x1600 | x1600 | wt6 | 1:C1 | 1:C2 | 1:C3 | 1:C4 | 1:C5 | 1:C6 | 1:C7 | 1:C8 |
| D | 15.625 | x6400 | x6400 | 2mut3 | 1:D1 | 1:D2 | 1:D3 | 1:D4 | 1:D5 | 1:D6 | 1:D7 | 1:D8 |
| E | 3.90625 | x25600 | x25600 | 2mut4 | 1:E1 | 1:E2 | 1:E3 | 1:E4 | 1:E5 | 1:E6 | 1:E7 | 1:E8 |
| F | 0.976562 | x102400 | x102400 | Blank | 1:F1 | 1:F2 | 1:F3 | 1:F4 | 1:F5 | 1:F6 | 1:F7 | 1:F8 |
| G | 0.244140 | Blank | Blank | Blank | 1:G1 | 1:G2 | 1:G3 | 1:G4 | 1:G5 | 1:G6 | 1:G7 | 1:G8 |
| H | 0.061035 | Blank | Blank | Blank | 1:H1 | 1:H2 | 1:H3 | 1:H4 | 1:H5 | 1:H6 | 1:H7 | 1:H8 |

Calculations:
CHIPS$_{wt}$ Standard curve was analysed using Excel and Sigma GraphPad.
Calculate mean and CV (%) of Blank (Excel)
Perform a blank subtraction for all data points (Excel)
CHIPS$_{wt}$ Standard curve: plot Abs 492 nm against Log concentration of standard.
Perform curve fit in model "Sigmoidal curve fit with variable slope" (GraphPad). Report EC50 value and R2-value.
Perform the same calculations for K69A lysate (2 samples). Measure EC50 R2 and Top value (Abs).
Recalculate the values as % Binding for K69A using the Top value as 100% binding. (Excel)
Calculate % Binding for the clones=measured binding (Excel)
K69A standard curve: plot % Binding against log conc of K69A Perform a curve fit in model "Sigmoidal curve fit with variable slope" (GraphPad).
Use the curve fit model for calculation of Human anti CHIPS binding for the clones using the concentrations measured in the expression ELISA=calculated binding.
Calculate the deviation between measured binding and calculated binding of the clones.

If the introduced mutations don't affect the binding to Human antiCHIPS, the measured binding for mutants should be equal to measured binding of K69A. If the introduced mutations do affect the binding, there will be a discrepancy between measured and calculated binding. A weak binder will show lower inhibition capacity than K69A and the deviation will be negative.

Deviation (discrepancy)=measured−calculated.

Results are shown in FIGS. 22 to 24 and Table 9.

TABLE 9

| Clone | Conc (ng/ml) | Log (conc) | Abs 492 nm | Determined anti-CHIPS binding % | Calc. anti-CHIPS binding % | Deviation (determined vs. calculated) |
|---|---|---|---|---|---|---|
| wt4 | 19.58 | 1.29 | 0.677 | 67.9 | 85.51 | −17.61 |
| wt5 | 18.27 | 1.26 | 0.709 | 71.1 | 84.68 | −13.61 |
| wt6 | 14.62 | 1.16 | 0.624 | 62.5 | 81.39 | −18.87 |
| 2mut3 | 3.52 | 0.55 | 0.024 | 2.5 | 43.37 | −40.91 |
| 2mut4 | 3.62 | 0.56 | 0.025 | 2.5 | 44.12 | −41.61 |

CHIPS 1004 Expression ELISA. Single Point Measurement of Library in 1:100 and 1:500 Dilution
Goal: To determine concentration of CHIPS mutants in crude cell lysate after expression in pRSET vector.
Summary: A tandem sandwich ELISA was optimised with two monoclonal antibodies binding to the first 30 amino acids (N-terminal) of CHIPS as coating- and detection antibodies. A HRP conjugated polyclonal antibody was used as second antibody followed by HRP-luminescence substrate. A standard curve with purified recombinant CHIPSwt was prepared for each ELISA plate. Relative Light Units (RLU) was measured and plotted against concentration of standard and analysed in a 4-parameter curve fitting model, from which the concentrations of the mutants was calculated.
Material and Method:
10×PBS (BioWhittaker #BE17-517Q, lot 4MB0102)
PBS Tween 20 (0.05%) (Medicago #09-8410-100, lot 113303)
BSA (Merck #1.12018.0100, lot K54593318527)
CELLYTIC B (Sigma #B-3553, lot 114K65156)
SuperSignal ELISA Pico Chemiluminescent Substrate (Pierce #37069, lot FK97655)
96-well flat-bottom high binding white LIA-plate (Greiner #655074, lot 04410129)
96-well U-shape PP plate
mAb 2H7 monoclonal antibody, 1 mg/ml (Utrecht, lot 2004-12)
Rabbit anti CHIPS-N-Pep IgG, 6 mg/ml (Utrecht, lot 2000-12-06)
Goat anti rabbit IgG (H+L)-HRP (Southern Biotechnologies #40-50-05, lot C4103-S194D)

rCHIPSwt, 1.8 mg/ml (Utrecht, lot 2004-12-02)
CHIPS Mutants:
Equipment:
 ELISA washer ELx405 (BioTek Instruments)
 Shaker platform Titramax 1000 (Heidolph Instruments)
 FLUOstar Optima (BMG)Software
 Excel
 GraphPad Sigma
Buffers:
 Coating buffer: 1×PBS: Add 100 mL 10×PBS to 900 mL of deionised water.
 Washing buffert: PBS+0.05% Tween 20 (PBST): Add 1 tablet to 1000 mL of deionised water.
 Assay buffer A: PBST+1% BSA(w/v)+1% Cellytic(v/v)
 Assay buffer B: PBST+1% BSA(w/v)
 Blocking solution: PBST+4% BSA(w/v)
Protocol (6 plates)
1. Coating: Prepare monoclonal antibody mAb 2H7, 3.0 µg/ml in coating buffer (PBS). Pipette 100 µl/well in a 96-well white high binding F-bottom LIA-plate. Incubate over night at 4° C.
2. Blocking: Add blocking solution 200 µl/well. Incubate 1 hour (h) at room temperature (RT) at a shaker platform at 600 rpm (S).
3. Sample: rCHIPSwt standard curve 800-1.6 ng/ml. In 15 ml test tubes: Prepare a twofold serial dilution (in Assay buffer A) in 10 steps of which 8 concentrations were used for the standard curve (see Table 10). Dilution of rCHIPSwt (stock 1.8 mg/ml) 1:100 in Assay buffer A: 5 µL CHIPS+495 µl, buffer=18 µg/ml CHIPS mutants (lysate): Prepare 1:100 dilution in Assay buffer B (PBS+1% BSA) in a 96-well U-shape PP plate.
 For 1:100 dilution: Add 100 µl/well in the ELISA plate
 For 1:500 dilution: Add 200/well+800 Assay buffer A (PBS+1% BSA+1% Cellytic)/well. Single points.
 Blank: Add 100 µl Assay buffer A to at least 2 wells.
 Incubate 2 h at RT, S.
4. Detection antibody: Rabbit anti CHIPS-N-pep, 3 µg/ml in Assay buffer B (PBS+1% BSA)
 31 µl ab+62 ml buffer
 Pipette 100 ml/well. Incubate 1 h at RT: S.
5. Secondary antibody: Goat anti rabbit IgG (H+L)-HRP. Prepare a 1:20 000 dilution in Assay buffer B.
 3.1 µl ab+62 ml buffer.
 Add 100 µl/well. Incubate 1 h at RT.S.
6. Extended wash: Add washing buffer 200 ml/well. Incubate 5 min. at RT. S.
7. Substrate: SuperSignal pico: Mix equal volumes of solution A and B (in dark). Add 100 µ/well. Shake for 1 min at 600 rpm (in dark). Measure the luminescence. Gain set to 80% of the highest concentration at the standard curve. (about 3000).
***Between all steps: Wash ×3 with PBST in EL405. #3×96 Greiner****
Plate layout (see Table 11)

TABLE 11

|   | 1 | 2 | 3 | 4 | 5 | 6 | 7 | 8 | 9 | 10 | 11 | 12 |
|---|---|---|---|---|---|---|---|---|---|---|---|---|
| A | Std wt 800 ng/ml | → | wt4 | → | 1:A1 | 1:A2 | 1:A3 | 1:A4 | 1:A5 | 1:A6 | 1:A7 | 1:A8 |
| B | 200 | | wt5 | | 1:B1 | 1:B2 | 1:B3 | 1:B4 | 1:B5 | 1:B6 | 1:B7 | 1:B8 |
| C | 100 | | wt6 | | 1:C1 | 1:C2 | 1:C3 | 1:C4 | 1:C5 | 1:C6 | 1:C7 | 1:C8 |
| D | 50 | | K69A 3 | | 1:D1 | 1:D2 | 1:D3 | 1:D4 | 1:D5 | 1:D6 | 1:D7 | 1:D8 |
| E | 25 | | K69A 4 | | 1:E1 | 1:E2 | 1:E3 | 1:E4 | 1:E5 | 1:E6 | 1:E7 | 1:E8 |
| F | 12.5 | | 2mut3 | | 1:F1 | 1:F2 | 1:F3 | 1:F4 | 1:F5 | 1:F6 | 1:F7 | 1:F8 |
| G | 6.25 | | 2mut4 | | 1:G1 | 1:G2 | 1:G3 | 1:G4 | 1:G5 | 1:G6 | 1:G7 | 1:G8 |
| H | 1.26 | | Blank | | 1:H1 | 1:H2 | 1:H3 | 1:H4 | 1:H5 | 1:H6 | 1:H7 | 1:H8 |

TABLE 10

| Standard curve | Conc ng/ml | fr dilution | Assay buffer A (PBS, 1% BSA, 1% cellytic) |
|---|---|---|---|
| 1 | 800 | 133.3 | 2867 µl |
|   | 400 | 1500 | 1500 µl |
| 2 | 200 | 1500 | 1500 µl |
| 3 | 100 | 1500 | 1500 µl |
| 4 | 50 | 1500 | 1500 µl |
| 5 | 25 | 1500 | 1500 µl |
| 6 | 12.5 | 1500 | 1500 µl |
| 7 | 6.25 | 1500 | 1500 µl |
|   | 3.13 | 1500 | 1500 µl |
| 8 | 1.56 | 1500 | 1500 µl |

Add 100 µL/well in duplicate according to the protocol.
Controls (lysate): Prepare 1:100 dilution in Assay buffer B (PBS+1% BSA)
 For 1:100 dilution: Add 100 µl/well in duplicate
 For 1:500 dilution: Add 20 µl+80 µl Assay buffer A/well in duplicate Calculations:
Standard curve were analysed using BMG reader software, Excel and/or Sigma GraphPad (see FIG. 25)
Calculate CV (%) of Blank
Perform a blank subtraction for all data points.
Standard curve: plot mean of RLU against Log concentration of standard.
Perform curve fit in model "4 parameter fit" (software) or "Sigmoidal curve fit with variable slope" (GraphPad). Report EC50 value and R2-value.
Use the curve fit models for calculation of concentration of samples.

A summary of the results from exemplary clones analysed in anti-CHIPS ab ELISA and in the peptide ELISA is shown in Table 12.

TABLE 12

| name clone | EC50 ng/ml anti-chips | Max signal ab ELISA | (%) "specific activity" | amino acid changes |
|---|---|---|---|---|
| 2D5 | 13.6 | 0.4567 | 132 | K40E, K69A, N111K, G112V |
| 3H1 | 13.3 | 1.227 | 109 | G112V |
| 2C9 | 10.7 | 1.212 | 115 | K54R, K69R, K100R, K105R |

TABLE 12-continued

| name clone | EC50 ng/ml anti-chips | Max signal ab ELISA | (%) "specific activity" | amino acid changes |
|---|---|---|---|---|
| 7E4 | 10.2 | 1.387 | 65 | K40N, K92R |
| 6E1 | 9.8 | 1.41 | 76 | S104Y |
| 7B3 | 9 | 1.329 | 140 | N111I |
| 3C4 | 8.4 | 1.263 | 94 | K69A, G112V |
| 4E5 | 7.5 | 1.322 | 76 | K69T |
| 1F8 | 7.4 | 1.38 | 93 | Y48H, D83G, L90P |
| 5H1 | 7.1 | 1.453 | 88 | K50N |
| 2H5 | 6.4 | 1.39 | 113 | K69A, K100R, K101R |
| std pl3 | 6.3 | 1.554 | | |
| K69A pl3 | 5.0 | 1.503 | 116 | K69A |
| wt pl3 | 6.8 | 1.555 | 106 | |

Example D

Exemplary Variant CHIPS Polypeptides II

Materials & Methods

The properties of further exemplary variant CHIPS polypeptides were studied.

Expression ELISA, specific binding studies and anti-CHIPS ELISA were performed as described above.

Results

The results are shown in Table 13

TABLE 13

| Mutations | expr ELISA Konc (µg/ml) lysat | pept-ELISA mplemen bindn (%) | antCHIPS-ELISA 060130 | | | |
|---|---|---|---|---|---|---|
| | | | EC50 (ng/ml) | EC50 (ng/ml) min | EC50 (ng/ml) max | TOP (% of std) |
| K69A | 17.0 | 15 | 3.9 | 2.959 | 5.185 | 108 |
| wt | 27.9 | 21 | 6.3 | 5.411 | 7.309 | 106 |
| N31A | 46.3 | 16 | 8.9 | 7.975 | 9.988 | 106 |
| N31A | 29.3 | 23 | 7.9 | 7.469 | 8.251 | 111 |
| S32A | 44.5 | 15 | 8.0 | 7.680 | 8.293 | 114 |
| S32A | 47.0 | 15 | 8.3 | 7.293 | 9.553 | 112 |
| G33A | 48.1 | 13 | 7.3 | 6.339 | 8.341 | 117 |
| G33A | 50.2 | 13 | 7.5 | 5.993 | 9.338 | 118 |
| L34A | 62.0 | 13 | 7.8 | 6.775 | 9.060 | 111 |
| L34A | 76.5 | 12 | 7.7 | 5.995 | 9.761 | 113 |
| P35A | 47.5 | 54 | 8.9 | 8.210 | 9.637 | 110 |
| P35A | 28.3 | 68 | 8.1 | 6.634 | 9.844 | 111 |
| Y48A | 46.7 | 86 | 6.3 | 5.138 | 7.678 | 116 |
| Y48A | 61.5 | 70 | 7.0 | 5.182 | 9.465 | 113 |
| G52A | 123.5 | 19 | 9.6 | 6.488 | 14.26 | 106 |
| G52A | 119.3 | 20 | 7.4 | 6.922 | 7.863 | 104 |
| T53A | 38.7 | 7 | 8.2 | 7.057 | 9.471 | 105 |
| T53A | 45.3 | 7 | 8.0 | 7.075 | 8.999 | 105 |
| N55A | 26.3 | 8 | 8.2 | 7.654 | 8.767 | 99 |
| N55A | 25.8 | 9 | 8.3 | 7.104 | 9.800 | 99 |
| S56A | 49.5 | 18 | 6.5 | 5.721 | 7.318 | 104 |
| S56A | 53.7 | 16 | 7.3 | 6.127 | 8.655 | 106 |
| Q58A | 28.3 | 2 | 8.0 | 7.611 | 8.451 | 108 |
| Q58A | 50.0 | 3 | 7.1 | 5.734 | 8.672 | 110 |
| E67A | 42.6 | 52 | 6.0 | 4.422 | 8.153 | 109 |
| E67A | 57.2 | 39 | 6.1 | 5.548 | 6.627 | 107 |
| L76A | 20.5 | 1 | 164 | 1.634 | 16434 | 22 |
| L76A | 15.8 | 2 | 1266 | 1.082 | 1.4820e+011 | 49 |
| P79A | 18.7 | 28 | 9.5 | 9.114 | 10.00 | 96 |
| P79A | 19.8 | 25 | 9.5 | 9.245 | 9.761 | 95 |
| L90A | 94.2 | 25 | 8.5 | 7.870 | 9.095 | 110 |
| L90A | 98.4 | 24 | 7.5 | 5.855 | 9.547 | 110 |
| S107A | 42.8 | 11 | 9.5 | 8.413 | 10.63 | 102 |
| S107A | 45.2 | 11 | 9.6 | 9.411 | 9.768 | 105 |
| Y108A | 72.2 | 1 | 13.1 | 10.13 | 16.91 | 92 |
| Y108A | 64.2 | 1 | 13.8 | 10.63 | 17.83 | 95 |
| K40E K69A | 49.8 | 201 | 11.2 | 7.022 | 17.71 | 60 |
| N111K G112V | 51.3 | 214 | 9.4 | 6.398 | 13.71 | 60 |

Example E

Exemplary Variant CHIPS Polypeptides III

Materials & Methods

Random Mutagenesis

To create diverse libraries of CHIPS variants, different methods of random mutagenesis were used. GeneMorph II (Stratagene) was performed as recommended by the manufacturer. Briefly, 1 ng or 10 pg of DNA (the CHIPS gene harbouring mutations K61A, K69A or K100A) was added to the PCR reaction consisting of 250 ng of each primer (Fw: 5'-TCGCGGCC CAGCCGGCCATGGCCTT-TACTTTTGAACCG-3' [SEQ ID NO:88] and Rev: 5'-GCCT-GCGG CCGCAGATCTACCATTAATTA CATAAG-3') [SEQ ID NO:89], 0.8 mM dNTP, 1× Mutazyme buffer, 2.5 U Mutazyme DNA polymerase in a total volume of 50 µl. The PCR program consisted of a denaturing step at 95° C. for 2 min, 40 cycles of 95° C. for 1 min, 60° C. for 1 min and 72° C. for 1 min and finally elongation at 72° C. for 10 minutes. To achieve one library with a high frequency of mutations, and one with lower mutation frequency, the 1 ng library was subjected to one more round of Genemorph II mutagenesis. This time, the amount of DNA in the PCR reaction was 10 ng.

Error-prone PCR was performed as described previously (Leung et al, 1989, *Technique* 1: 11-15). One library with high mutation frequency and one with low mutation frequency were created. Briefly, 10 ng DNA was added to a PCR reaction consisting of 20 µM of each primer (described above), 0.8 mM dNTP (New England Biolabs, MA, USA), 1× AMPLITAQ reaction buffer, 3.2 mM extra dGTP or dTTP respectively, 7.5 mM $MgCl_2$, 0.64 mM $MnCl_2$, 2.5 U AMPLI-TAQ Thermostable DNA polymerase (Applied Biosystems, CA, USA) in a total volume of 50 µl. The PCR program consisted of a denaturing step at 94° C. for 5 min, 20 cycles of 94° C. for 30 s, 55° C. for 30 s and 72° C. for 40 s and finally elongation at 72° C. for 10 minutes. The PCR products were sub cloned into the PGEM-T vector (Promega) according to the manufacturer's recommendations and the sequences were verified and base exchanges evaluated.

Generation of Variant CHIPS Libraries using FIND® Technology

In one particular embodiment, the variants were generated using the FIND® (Fragment Induced Diversity) technology of Alligator Bioscience AB, as described in International Patent Applications Nos. WO 2002/48351, WO 03/097834 and PCT/GB2006/004294, which are incorporated herein by reference.

Phage Display

Libraries of variant CHIPS polypeptides were cloned into the phagemid pFAB75 (Engberg) SfiI and NotI sites and transformed into *E. coli* TOP 10 F' (Invitrogen, Carlsbad, Calif., USA) for expression on phage particles. Phage stocks were prepared according to standard protocols, using VSCM13 (Stratagene, La Jolla, Calif., USA) as helper phage. An exponentially growing culture was infected with helper phages (multiplicity of infection: ~20) and incubated without shaking at 37° C. for 30 minutes. The superinfected *E. coli* were spun down and used to inoculate LB supplemented with ampicillin (50 µg/ml), kanamycin (10 µg/ml), tetracycline (10 µg/ml) and isopropyl-β-D-thiogalactoside (IPTG) (1 mM). The culture was grown at 30° C. with shaking for approximately 15 hours, before it was pelleted by centrifugation and subjected to polyethylene glycol/NaCl precipitation. The phages were redissolved in PBS containing 1% bovine serum albumin (BSA) (Sigma-Aldrich, St. Louis, Mo., USA) and filtered through a 0.45 µm filter.

Positive Selection for C5aR Peptide Affinity

Selections were performed on a biotinylated C5aR peptide consisting of amino acids 7-28 (AnaSpec, USA) and Streptavidin coated magnetic Dynabeads (Dynal, Norway). Separations were made on a magnetic stand for 2 minutes. Prior to the selections, the streptavidin beads (50 µl) were washed three times in 1 ml selection buffer (PBS containing 3% BSA and 0.05% Tween-20). 500 µl phage stock (containing ~$10^{11}$ phage particles) were pre-incubated with washed beads for 30 min at room temperature on rotation in order to remove any potential streptavidin binders. Peptide was added to the pre-cleared phages at a final concentration of $10^{-7}$ M and the mixture was incubated for 1 hour on rotation at room temperature. At the same time, 500 streptavidin beads were blocked in selection buffer for 1 hour on rotation at room temperature. The peptide/phage mix was added to the beads and further incubated for 15 minutes on rotation at room temperature. The beads were then washed five times in 1 ml selection buffer, followed by three times in 1 ml PBS. To elute peptide binders, 450 µl 0.1M Glycine 0.1% BSA, pH 2.2 was added to the washed beads. After 10 min incubation at room temperature, 50 µl µM Tris pH 9.0 was added to neutralize the eluate. A few microliters of the eluted phages was saved and used for titration of the output phages, while the rest was used to infect exponentially growing *E. coli* TOP10 F' (Invitrogen, Carlsbad, Calif., USA) for preparation of new phage stocks. The selection protocol was then repeated once as described above.

Negative Selection for Human Anti-CHIPS IgG Affinity

Directly after the second round of positive selection, CHIPS phage stocks were subjected to a round of negative selection for human anti-$CHIPS_{31-113}$ IgG affinity. Magnetic beads coated with human anti-$CHIPS_{31-113}$ IgG were washed three times in 1 ml selection buffer and then blocked in 1 ml selection buffer for 1 hour on rotation at room temperature. The eluate from the positive selection was added to the beads and they were incubated for 15 minutes at room temperature. After separation on a magnet, the supernatant was saved as eluate 1. Four rounds of elutions were made; 100 µl PBS was added to the beads followed by 5 minutes incubation at room temperature. After separation on the magnet, the PBS was saved as eluate 2. This was repeated two times (eluates 3 and 4). Eluate 1 and a pool of eluates 2-4 were used to infect exponentially growing *E. coli* TOP 10 F'(Invitrogen, Carlsbad, Calif., USA) and the phagemids were then purified from the *E. coli*.

Cloning and Expression of Libraries in *E. coli*

After phage selections, a selected pool of CHIPS variants were cleaved out from the pFAB75 vector and cloned into the pRSET vector (Invitrogen) BbsI and BglII sites for expression in *E. coli* lysates. Libraries were transformed into *E. coli* BL21 star DE3 pLysS (Invitrogen), plated on 20 cm Qtray plates with LB agar supplemented with 50 µg/ml ampicillin and 34/ml chloramphenicol and incubated at 37° C. overnight. The following day, *E. coli* colonies were picked and inoculated in 96 well Greiner round bottom plates containing 150 µl LB supplemented with 50 µg/ml ampicillin and 34 µg/ml chloramphenicol using a Qpix robot. The cultures were incubated at 37° C. with 78% humidity and shaking at 700 rpm in a Multitron plate shaker overnight. Day cultures were prepared from the overnight cultures by inoculating 5 µl overnight culture in 145 µl LB/ampicillin/chloramphenicol at 37° C. as above. To induce protein expression, 0.5 mM IPTG (Isopropyl β-D-Thiogalactoside) was added to the cultures after three hours, and the cultures were then cultivated for another three hours. Protein was expressed in *E. coli* lysates which were prepared by freeze-thawing the *E. coli* pellet in 90 p. 1 buffer consisting of PBS-0.05% Tween-20, Complete EDTA-free protease inhibitor (Roche), 25 U/ml Benzonase (Sigma) and 1 KU/ml rLysozyme (Novagen). The lysates were incubated for 10 min at room temperature with shaking. A 20 µl fraction of the lysates was diluted 10 times in PBS-0.05% Tween-20 with 1% BSA. The diluted and undiluted lysates were all kept at −20° C. until analyzed in ELISA.

Anti-CHIPS ELISA

In order to measure binding of CHIPS variants to affinity purified human anti-CHIPS$_{31-113}$, Maxisorb 96 or 384 well plates (Nunc, Rochester, N.Y., USA) were coated overnight at 4° C. with 1 µg/ml mouse anti-CHIPS N-terminal mAb 2H7 (Haas JI, 2004) in PBS. Plates were washed three times with washing buffer (PBS containing 0.05% Tween 20) and blocked in blocking buffer (PBS-0.05% Tween-20 with 3% milk powder) for 1 hour at room temperature. Plates were washed as described above, followed by addition of lysates from CHIPS clones (diluted as described above) and incubation for 1 hour at room temperature. Plates were washed and then further incubated with 0.1 µg/ml affinity purified human anti-CHIPS$_{31-113}$ polyclonal IgG in dilution buffer (PBS-0.05% Tween-20 with 1% milk powder) for 1 hour at room temperature. Plates were washed again and incubated for 1 hour at room temperature with goat-anti-human IgG HRP (Jackson ImmunoResearch, West Grove, Pa., USA) diluted 1/10000 in dilution buffer. Plates were washed another three times and SuperSignal ELISA Pico Chemiluminescent Substrate (Pierce) was added and luminescence was measured.

Expression ELISA

In order to measure the expression level of CHIPS variants in *E. coli* lysates, ELISA was performed as described above, except 3 µg/ml in Ab 2H7 was used for coating and blocking buffer consisted of PBS-0.05% Tween-20 with 4% BSA and dilution buffer of PBS-0.05% Tween-20 with 1% BSA. Furthermore, 3 µg/ml of a polyclonal rabbit anti-CHIPS N-terminal IgG and goat anti-rabbit IgG-HRP (Southern Biotech) diluted 1/20000 were used for detection.

Inhibition ELISA

In order to measure the binding of CHIPS variants to affinity purified human anti-CHIPS$_{31-113}$ in competition with the wt CHIPS protein, an inhibition ELISA was performed. The washing steps, blocking and dilutions were made as in the expression ELISA. 50 ng/ml purified wt CHIPS was used for coating. Then, 5-fold dilution series (0.16-2500 ng/ml) of the CHIPS variants were mixed in a Nunc polypropylene plate with 60 ng/ml affinity purified human anti-CHIPS$_{31-113}$ polyclonal IgG and incubated for 2 hours at room temperature. Then, 100 µl of the mixture was added to the ELISA plates and further incubated for 2 hours at room temperature. Detection was performed with goat-anti-human IgG HRP diluted 1/12000. OPD substrate was used as described above.

Peptide ELISA

In order to measure the binding of CHIPS variants towards the C5aR 7-28 peptide described above, ELISA was performed as described for the expression ELISA, except 5 µg/ml Streptavidin (Sigma) was used for coating. Furthermore, the C5aR peptide was added to a final concentration of 0.3 µg/ml after washing and blocking the plates. CHIPS lysates were added in a xxx dilution. Detection was performed with 1 µg/ml mAb 2H7 and Rabbit anti-mouse IgG-HRP (Dako) diluted 1/2000. OPD substrate (1 tablet O-phenylenediamine in 35 ml; 34.7 mM Na-Citrate, 66.7 mM NaPO$_4$, 0.01% H$_2$O$_2$) was added for detection. The reaction was stopped by addition of 1 M HCl and the absorbance was recorded at 492 nm.

See also above-described expression ELISA.

Combination ELISA

The combination ELISA is a combination of the anti-CHIPS ELISA and the peptide ELISA. This ELISA was performed as described for the peptide ELISA with the following modifications. PBS-0.05% Tween-20 with 2% BSA was used for blocking and 0.1 µg/ml affinity purified human anti-CHIPS$_{31-113}$ polyclonal IgG/goat-anti-human IgG HRP diluted 1/6000 were used for detection. SuperSignal ELISA Pico Chemiluminescent Substrate (Pierce) was used as HRP substrate and luminescence was measured.

Selection Strategy

The binding of mutants were always compared to the achieved binding of wt CHIPS to anti-CHIPS abs or the peptide (% binding were calculated). The best mutants from the primary screening were selected based on the following criteria:
1. At least 80% binding to the peptide
2. Less than 70% binding to the anti-CHIPS abs in the combination ELISA. 3% of wt binding in double ELISA/% binding in peptide ELISA should be 0.05-0.6

The selected clones were analysed in a secondary screening with expression ELISA and anti-CHIPS ELISA as described above.

Preferred clones (exhibiting less than 40% binding to the anti-CHIPS abs) were further analysed in anti-CHIPS ELISA and inhibition ELISA. The best 42 clones based on above criteria was expressed and analysed for binding in cellular in vitro/vivo experiments. To express high concentrations of the CHIPS variants, a cell free expression system, Expressway Cell-Free *E. coli* Expression Kit (Invitrogen), was used. The expression was performed as described by the manufacturer. Briefly, 0.5 μg plasmid DNA was mixed in a microtiter plate with *E. coli* extract, reaction buffer, amino acids and T7 enzyme mix and incubated with shaking at 30° C. for 30 min. A feeding buffer with amino acids was added to the samples and they were further incubated at 30° C. for 5.5 hours. Plates were centrifuged and the supernatant containing the protein was kept at −20° C. until analyzed in an assay for binding to C5aR on U937/C5aR cells and for a binding assay for C5aR and SQL binding on neutrophils (naturally expressing C5aR and fMPL). These assays were run twice with in vitro expressed material and analysed separately ranking the clones for C5aR binding. The 10 best performing clones were selected for further analysis.

Binding to U937/C5aR Cells $7.5\times10^4$ U937/C5aR cells in 25 μl RPMI/HAS was incubated with 25 μl CHIPS lysates on ice for 30 min. Cells were washed once with RPMI/HAS resuspended and incubated with 50 μl 5 μg/ml 2H7 Ab on ice for 30 min. Washed once resuspended and incubated with 50 μl 1/50 diluted goat-anti-mouse-RPE Ab on ice for 30 min. Washed once with RPMI/HAS and resuspended in 250 μl 0.5% Paraformaldehyde/RPMI/HAS and vortexed. Kept dark at 4° C. Analysed by FACS, measure mean CHIPS Activity Bioassay Dual fMLP-F/a-C5aR-PE (Microtitreplate)

Procedure to test multiple samples of CHIPS (dilutions) for bioactivity with human neutrophils, both for MLP and C5a simultaneously. CHIPS containing samples will prevent the binding of FITC-fMLP and anti-C5aR mAb to the cells. A second incubation step stains the mAb with PE and samples are analyzed by flow cytometry.

The 10 clones showing best ranked binding in the above cell-based assays were selected (see 'Results' below).

Results

Exemplary variant CHIPS polypeptides generated using the FIND® technology are disclosed in Table 14 below (corresponding to the ten clones showing best ranked binding in the above cell-based assays).

TABLE 14

| | Amino acid mutations* | | | | | | | | | | | |
|---|---|---|---|---|---|---|---|---|---|---|---|---|
| Clone | K40 | D42 | K50 | K69 | N77 | D83 | L90 | K92 | K100 | K105 | N111 | G112 |
| F3.03 | | | N | R | Y | | | R | | | K | V |
| F3.08 | E | V | | | Y | | | | R | R | K | V |
| F3.14 | | | N | | Y | | | R | | | K | V |
| F3.39 | E | V | | | Y | | | | | | K | V |
| F3.46 | E | V | | | Y | | | R | | | K | V |
| F3.50 | | | N | | Y | | | | | | K | V |
| F3.57 | E | V | N | | Y | | | R | | | K | V |
| F3.70 | N | | N | | Y | | | R | | | I | |
| F3.71 | N | | | | Y | G | P | | | | K | V |
| F3.85 | | | N | | Y | | | R | R | | I | |

*The 'parental' polypeptide sequence, in which the above mutations are made, corresponds to amino acids 1 to 112 of SEQ ID NO: 1, together with two additional amino acids at the C-terminus (an 'R' at amino acid position 113 and an S at amino acid position 114).

Thus, Clone F3.03 consists of the following amino acid sequence:

SEQ ID NO: 90
FTFEPFPTNEEIESNKKMLEKEKAYKESFKNSGLPTTLGKLDERLRN

YL*N*KGTKNSAQFEKMVILTEN*R*GYYTVYL*Y*TPLAEDRKNVELLG*R*MY

KTYFFKKGESKSSYVI *KVRS*

One additional mutant CHIPS polypeptide was used in certain experiments, designated 'S3.23', which corresponds to amino acids 1 to 112 of SEQ ID NO: 1, together with amino acids RS at positions 113 and 114, with the following mutations:

K40N, D42V, N77Y, D83G, L90P, N111K and G112V.

Additional binding data on the above selected in vitro expressed clones are shown in Table 15.

process showing decreased binding of anti-CHIPS antibodies to the CHIPS mutants as compared to wild type.

In a series of further experiments, exemplary mutants from those identified above were modified to delete the thirty eleven amino acids from the N-terminus and the final one amino acid from the C-terminus. Thus, the modified mutants corresponded to amino acids 31 to 113 of SEQ ID NO: 1 in which the mutations identified in Table 14 are incorporated.

The inhibition of C5aR by the modified 31-113 mutants is shown in FIG. 28. Expression and purification of the F3.08, F3.39 and F3.50 mutants and subsequent analysis of their binding to C5aR, either expressed as a stably transfected protein in U937 cells or naturally on neutrophils, confirmed the screening data demonstrating retained binding properties.

Example F

Surface Accessibility and Closeness of CHIPS Amino Acids

Materials & Methods

RSA values were determined as described in Amitai et al., 2004, *J. Mol. Biol.* 344:1135-1146, using the NACCESS program (see also Hubbard, 1996, NACCESS, 2.1.1 edit.,

TABLE 15

| Clone | Peptide ELISA % of wt 1-112 | antiChips Top (%) | Inh ELISA IC50 (nM) | Biacore IC50 (nM) | Dual bind PMN (%) | Binding U937cells C5aR (0.3 μg/ml) % of wt 1-112 |
|---|---|---|---|---|---|---|
| F3.03 | 113 | 4.8 | 43 | | 82 | 65 |
| F3.08 | 115 | 2.6 | 276 | 226 | 84 | 87 |
| F3.14 | 113 | 6.6 | 41 | | | |
| F3.39 | 129 | 12 | 561 | 115 | | |
| F3.46 | 132 | 9.3 | 524 | 112 | | |
| F3.50 | 122 | 13 | 67 | | | |
| F3.57 | 126 | 7.5 | 428 | 138 | | |
| F3.71 | 123 | 19 | 34 | | 95 | 97 |
| F3.85 | 106 | 10 | 24 | | | |
| wt 1-112-RS | 100 | 100 | 0.40 | 14.50 | 100 | 100 |
| wt 1-121 | | | | | 112 | 28 |

Results of the anti-CHIPS ELISA studies and inhibition ELISA studies are shown in detail in FIGS. 26 and 27, respectively. These findings confirm the data from the screening Biomolecular Structure and Modelling Unit, University College, London, UK).

In brief, the NACCESS program calculates the atomic accessible surface defined by rolling a probe of given size around a van der Waals surface. This program is an implementation of the method of Lee & Richards (1971) J. Mol. Biol 55, 379-400. The program is dimensioned for up to 20000 atoms, and allows the variation of the probe size and atomic radii by the user. The program outputs 3 files:

(1) An atomic accessibility file (.asa file) containing the calculated accessible surface for each atom in a PDB file, as well as the assigned van der Waal radii.

(2) A residue accessibility (.rsa) file containing summed atomic accessible surface areas over each protein or nucleic acid residue, as well as the relative accessibility of each residue calculated as the % accessibility compared to the accessibility of that residue type in an extended ALA-x-ALA tripeptide (for amino acids). See Hubbard, Campbell & Thornton (1991) J. Mol. Biol. 220, 507-530.

(3) A log file (.log) containing information concerning the calculation.

Relative Surface Accessibility (RSA)

The Relative Surface Accessibility (RSA) of amino acids within the wildtype CHIPS protein is shown in Table 15. An RSA >30% is taken as indicative of an exposed residue.

TABLE 15

| Residue | Amino Acid | Closeness Value | Relative Surface Accessibility |
|---|---|---|---|
| 31 | ASN | −0.606 | 95.1 |
| 32 | SER | −1.591 | 81.4 |
| 33 | GLY | −1.14 | 47.1 |
| 34 | LEU | −1.066 | 75.6 |
| 35 | PRO | −0.429 | 56.9 |
| 36 | THR | −0.043 | 23.2 |
| 37 | THR | 0.141 | 24.6 |
| 38 | LEU | 1.085 | 4.5 |
| 39 | GLY | −0.36 | 22.1 |
| 40 | LYS | −0.093 | 62.1 |
| 41 | LEU | 1.484 | 13.9 |
| 42 | ASP | 1.371 | 7.9 |
| 43 | GLU | −0.217 | 57.5 |
| 44 | ARG | 0.25 | 45.2 |
| 45 | LEU | 2.139 | 0.0 |
| 46 | ARG | 1.12 | 17.8 |
| 47 | ASN | 0.141 | 52.1 |
| 48 | TYR | 1.262 | 33.9 |
| 49 | LEU | 1.262 | 1.7 |
| 50 | LYS | −0.313 | 63.0 |
| 51 | LYS | −0.628 | 77.4 |
| 52 | GLY | −0.217 | 68.9 |
| 53 | THR | −0.474 | 23.2 |
| 54 | LYS | −1.56 | 95.7 |
| 55 | ASN | −1.432 | 69.1 |
| 56 | SER | −0.289 | 15.9 |
| 57 | ALA | −1.432 | 99.2 |
| 58 | GLN | −1.366 | 45.3 |
| 59 | PHE | 0.278 | 8.0 |
| 60 | GLU | −0.313 | 16.1 |
| 61 | LYS | 0.818 | 21.6 |
| 62 | MET | 1.923 | 0.0 |
| 63 | VAL | 1.408 | 8.5 |
| 64 | ILE | 2.095 | 0.0 |
| 65 | LEU | 1.017 | 13.5 |
| 66 | THR | 0.916 | 0.0 |
| 67 | GLU | −0.606 | 16.2 |
| 68 | ASN | −0.835 | 47.0 |
| 69 | LYS | −0.541 | 61.6 |
| 70 | GLY | 0.363 | 1.1 |
| 71 | TYR | 0.599 | 70.2 |
| 72 | TYR | 1.484 | 13.7 |
| 73 | THR | 0.95 | 37.6 |
| 74 | VAL | 1.678 | 2.8 |
| 75 | TYR | 0.391 | 47.6 |
| 76 | LEU | 0.786 | 15.4 |
| 77 | ASN | −0.649 | 81.6 |
| 78 | THR | −0.496 | 51.1 |
| 79 | PRO | −0.313 | 87.7 |

TABLE 15-continued

| Residue | Amino Acid | Closeness Value | Relative Surface Accessibility |
|---|---|---|---|
| 80 | LEU | 0.195 | 10.3 |
| 81 | ALA | −1.122 | 42.8 |
| 82 | GLU | −1.01 | 65.9 |
| 83 | ASP | −1.298 | 80.9 |
| 84 | ARG | −0.043 | 53.3 |
| 85 | LYS | −0.712 | 43.1 |
| 86 | ASN | −0.649 | 83.0 |
| 87 | VAL | −0.168 | 49.1 |
| 88 | GLU | 0.114 | 69.6 |
| 89 | LEU | 0.851 | 2.7 |
| 90 | LEU | 0.141 | 59.2 |
| 91 | GLY | 0.168 | 9.6 |
| 92 | LYS | 0.25 | 28.0 |
| 93 | MET | 1.639 | 9.8 |
| 94 | TYR | 1.017 | 23.4 |
| 95 | LYS | 0.983 | 34.8 |
| 96 | THR | 1.226 | 0.0 |
| 97 | TYR | 1.334 | 21.4 |
| 98 | PHE | 1.408 | 0.0 |
| 99 | PHE | 0.786 | 13.6 |
| 100 | LYS | −0.383 | 29.0 |
| 101 | LYS | −1.211 | 70.4 |
| 102 | GLY | −1.606 | 98.9 |
| 103 | GLU | −0.606 | 37.4 |
| 104 | SER | −1.211 | 91.0 |
| 105 | LYS | −0.691 | 67.0 |
| 106 | SER | −0.119 | 35.9 |
| 107 | SER | −0.541 | 51.9 |
| 108 | TYR | 0.818 | 27.0 |
| 109 | VAL | −0.043 | 54.3 |
| 110 | ILE | 1.371 | 15.1 |
| 111 | ASN | 0.168 | 75.1 |
| 112 | GLY | −0.289 | 22.7 |
| 113 | PRO | −0.383 | 56.9 |
| 114 | GLY | −0.068 | 1.8 |
| 115 | LYS | −0.691 | 84.2 |
| 116 | THR | −0.289 | 12.2 |
| 117 | ASN | −0.336 | 34.3 |
| 118 | GLU | −1.383 | 64.2 |
| 119 | TYR | −1.544 | 71.9 |
| 120 | ALA | −1.513 | 66.3 |
| 121 | TYR | −2.512 | 123.1 |

Predicted Functional Residues

Predicted functional amino acid residues within the wildtype CHIPS protein are indicated in Table 16.

(Note: Residues at the protein core have higher closeness value than those at the protein surface. However, active site residues, although residing on the protein surface, have even higher closeness value than core residues)

Thresholds:

Closeness Z Score>=1

3<=Relative Surface Area<=200

TABLE 16

| Residue | Amino Acid | Closeness Value | Relative Surface Accessibility |
|---|---|---|---|
| 38 | LEU | 1.085 | 4.5 |
| 41 | LEU | 1.484 | 13.9 |
| 42 | ASP | 1.371 | 7.9 |
| 46 | ARG | 1.12 | 17.8 |
| 48 | TYR | 1.262 | 33.9 |
| 63 | VAL | 1.408 | 8.5 |
| 65 | LEU | 1.017 | 13.5 |
| 72 | TYR | 1.484 | 13.7 |
| 93 | MET | 1.639 | 9.8 |
| 94 | TYR | 1.017 | 23.4 |
| 97 | TYR | 1.334 | 21.4 |
| 110 | ILE | 1.371 | 15.1 |

The invention claimed is:

1. A polypeptide having a biological activity of the Chemotaxis Inhibitory Protein of *Staphylococcus aureus* ('CHIPS'), the polypeptide comprising a variant of the amino acid sequence of SEQ ID NO:1., wherein the following amino acids are modified: K40, D42, N77, K100, K105, N111 and G112.

2. The polypeptide according to claim 1 wherein the polypeptide comprises amino acids 1 to 112 of SEQ ID NO: 1.

3. The polypeptide according to claim 1 wherein the polypeptide comprises one or more of the following amino acid mutations relative to SEQ ID NO: 1:
K100R, N111I, N111K or G112V.

4. The polypeptide according claim 1 wherein the polypeptide is less immunogenic in humans than the wildtype CHIPS protein.

5. The polypeptide according to claim 1 wherein the biological activity of the polypeptide is greater than the biological activity wildtype CHIPS protein.

6. The polypeptide according to claim 1 wherein the polypeptide is capable of inhibiting C5a-induced activation of neutrophils and inhibiting fMLP-induced activation of neutrophils.

7. The polypeptide according to claim 1 wherein C5a-induced activation of neutrophils and/or fMLP-induced activation of neutrophils is inhibited by at least 10%.

8. The polypeptide according to claim 1 wherein the polypeptide is between 80 and 500 amino acids in length.

9. The polypeptide according to claim 1 wherein the polypeptide is between 110 and 120 amino acids in length.

10. The polypeptide according to claim 9 wherein the polypeptide is 112 amino acids in length.

11. The polypeptide according to claim 1 wherein the polypeptide comprises a fragment of the amino acid sequence of SEQ ID NO:1.

12. The polypeptide according to claim 11 wherein the polypeptide comprises amino acids 31 to 113 of the amino acid sequence of SEQ ID NO:1.

13. The polypeptide according to claim 1 wherein the polypeptide comprises one or more additional amino acids, inserted at either the N- or C-termini of the amino acid sequence of SEQ ID NO:1.

14. The polypeptide according to claim 13 wherein the polypeptide comprises at least 2 additional amino acids.

15. The polypeptide according to claim 14 wherein the polypeptide comprises 6 additional amino acids.

16. The polypeptide according to claim 13 wherein the additional amino acids are located at the C-terminus of the amino acid sequence of SEQ ID NO:1.

17. The polypeptide according to claim 13, wherein the amino acid consists of amino acids 1 to 112 of SEQ ID NO:1 comprising the following modifications:
K40E, N111K and G112V.

18. The polypeptide according to claim 1 wherein the polypeptide comprises one or more of the following amino acid mutations relative to the wildtype sequence:
K40E, K40N, D42V, N77Y, K100R, K105R, N111K, N111I or G112V.

19. The polypeptide according to claim 1 wherein the polypeptide is a polypeptide comprising amino acids 1 to 112 of SEQ ID NO:1 comprising the following modifications:
K40E, D42V, N77Y, K100R, K105R, N111K and G112V.

20. The polypeptide according to claim 19 wherein the polypeptide further comprises amino acids R and S at positions 113 and 114, respectively.

21. The polypeptide according to claim 1 wherein the polypeptide is a polypeptide comprising amino acids 31 to 113 of SEQ ID NO:1 comprising the following modifications:

K40E, D42V, N77Y, K100R, K105R, N111K and G112V.

22. A pharmacological composition comprising a polypeptide according to claim 1.

23. The polypeptide according to claim 1 wherein the polypeptide consists of amino acids 1 to 112 of SEQ ID NO:1 comprising amino acid substitution relative to SEQ ID NO:1 at the following amino acids:

K40, D42, N77, K100, K105, N111 and G112.

24. The polypeptide according to claim 1 wherein the polypeptide consists of a fragment of the amino acid sequence of SEQ ID NO:1, wherein the fragment is selected from the group consisting of amino acids 1 to 114, amino acids 31 to 112, or amino acids 31 to 121 of SEQ ID NO: 1.

25. The polypeptide according to claim 11 wherein the polypeptide consists of amino acids 31 to 113 of the amino acid sequence of SEQ ID NO: 1.

26. The polypeptide according to claim 1 wherein the polypeptide consists of one or more additional amino acids, inserted at either the N- or C-termini of the amino acid sequence of SEQ ID NO:1.

27. The polypeptide according to claim 26 wherein the polypeptide consists of at least 2 additional amino acids.

28. The polypeptide according to claim 27 wherein the polypeptide consists of 6 additional amino acids.

29. The polypeptide according to claim 1 wherein the polypeptide is a polypeptide consisting of amino acids 1 to 112 of SEQ ID NO:1 comprising the following modifications:

K40E, D42V, N77Y, K100R, K105R, N111K and G112V.

30. The polypeptide according to claim 1 wherein the polypeptide is a polypeptide consisting of amino acids 31 to 113 of SEQ ID NO:1 comprising the following modifications:

K40E, D42V, N77Y, K100R, K105R, N111K and G112V.

31. The polypeptide according to claim 1 wherein C5a-induced activation of neutrophils and/or fMLP-induced activation of neutrophils is inhibited by at least 50%.

32. The polypeptide according to claim 1 wherein the polypeptide is between 80 and 130 amino acids in length.

33. The polypeptide according to claim 1 wherein the polypeptide comprises a fragment of the amino acid sequence of SEQ ID NO:1, wherein the fragment is selected from the group consisting of amino acids 1 to 114, amino acids 31 to 112, amino acids 31 to 113 or amino acids 31 to 121 of SEQ ID NO:1.

34. The polypeptide according to claim 1 wherein the polypeptide consists of a fragment of the amino acid sequence of SEQ ID NO:1, wherein the fragment is selected from the group consisting of amino acids 1 to 114, amino acids 31 to 112, amino acids 31 to 113 or amino acids 31 to 121 of SEQ ID NO:1.

* * * * *

SEQUENCE LISTING

<160> NUMBER OF SEQ ID NOS: 90

<210> SEQ ID NO 1
<211> LENGTH: 121
<212> TYPE: PRT
<213> ORGANISM: Staphylococcus auras
<220> FEATURE:
<223> OTHER INFORMATION: Chemotaxis Inhibitory Protein

<400> SEQUENCE: 1

Phe Thr Phe Glu Pro Phe Pro Thr Asn Glu Glu Ile Glu Ser Asn Lys
1               5                   10                  15

Lys Met Leu Glu Lys Glu Lys Ala Tyr Lys Glu Ser Phe Lys Asn Ser
            20                  25                  30

Gly Leu Pro Thr Thr Leu Gly Lys Leu Asp Glu Arg Leu Arg Asn Tyr
        35                  40                  45

Leu Lys Lys Gly Thr Lys Asn Ser Ala Gln Phe Glu Lys Met Val Ile
    50                  55                  60

Leu Thr Glu Asn Lys Gly Tyr Tyr Thr Val Tyr Leu Asn Thr Pro Leu
65                  70                  75                  80

Ala Glu Asp Arg Lys Asn Val Glu Leu Leu Gly Lys Met Tyr Lys Thr
                85                  90                  95

Tyr Phe Phe Lys Lys Gly Glu Ser Lys Ser Ser Tyr Val Ile Asn Gly
            100                 105                 110

Pro Gly Lys Thr Asn Glu Tyr Ala Tyr
        115                 120

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct
<220> FEATURE:
<223> OTHER INFORMATION: 96 PIII sequencing PCR primer

<400> SEQUENCE: 2
ccctcatagt tagcgtaacg                                              20

<210> SEQ ID NO 3
<211> LENGTH: 4
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Coupling sequence

<400> SEQUENCE: 3

Gly Gly Gly Cys
1

<210> SEQ ID NO 4
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: random phage library peptide

<400> SEQUENCE: 4

Met Asn Lys Thr Trp Tyr Pro

```
<210> SEQ ID NO 5
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: random phage library peptide

<400> SEQUENCE: 5

Met Asn Lys Thr Phe Trp Phe
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: random phage library peptide

<400> SEQUENCE: 6

Phe Asn Lys Ser Tyr Tyr Gly
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 01

<400> SEQUENCE: 7

Met Asn Lys Thr Trp Tyr Pro
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 02

<400> SEQUENCE: 8

Gly Lys Leu Pro Ile Ala Met
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 03

<400> SEQUENCE: 9

Met Asn Lys Thr Trp Tyr Pro
1               5

<210> SEQ ID NO 10
<211> LENGTH: 7
```

```
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 04

<400> SEQUENCE: 10

Met Asn Lys Thr Phe Trp Phe
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 05

<400> SEQUENCE: 11

Tyr Asn Lys Ser Phe Phe Met
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 06

<400> SEQUENCE: 12

Ala Ala Ala Pro Ser His His
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 07

<400> SEQUENCE: 13

Tyr Asn Lys Ser Phe Phe Pro
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: CLONE 08

<400> SEQUENCE: 14

Gly Lys Leu Pro Ile Pro Tyr
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic Construct
<220> FEATURE:
```

<223> OTHER INFORMATION: Clone 09

<400> SEQUENCE: 15

Met Asn Lys Thr Phe Ser Ala
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 10

<400> SEQUENCE: 16

Met Asn Lys Thr Trp Tyr Pro
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 11

<400> SEQUENCE: 17

Gly Lys Leu Pro Lys Met Thr
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 12

<400> SEQUENCE: 18

Met Asn Lys Ser Tyr Thr Ile
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 13

<400> SEQUENCE: 19

Val Asn Lys Thr Tyr Trp Lys
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 14

<400> SEQUENCE: 20

Met Asn Lys Val Tyr Leu Pro

```
<210> SEQ ID NO 21
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 15

<400> SEQUENCE: 21

Gly Lys Leu Pro Pro Pro Ile
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 16

<400> SEQUENCE: 22

Ala Leu Gln Ala Ser Arg His
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 17

<400> SEQUENCE: 23

Met Asn Lys Thr Trp Tyr Pro
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 18

<400> SEQUENCE: 24

Met Asn Lys Thr Trp Tyr Pro
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 19

<400> SEQUENCE: 25

Phe Asn Lys Ser Trp Phe Pro
1               5

<210> SEQ ID NO 26
<211> LENGTH: 7
```

```
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 20

<400> SEQUENCE: 26

Met Asn Lys Thr Trp Tyr Pro
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 21

<400> SEQUENCE: 27

Met Asn Lys Thr Trp Tyr Pro
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 22

<400> SEQUENCE: 28

Met Asn Lys Tyr His Asn Pro
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 23

<400> SEQUENCE: 29

Met Asn Lys Thr Phe Trp Phe
1               5

<210> SEQ ID NO 30
<211> LENGTH: 7
<212> TYPE: PRT
<213> ORGANISM: Artificial Sequence
       <220.
<223> OTHER INFORMATION: Synthetic Construct
<220> FEATURE:
<223> OTHER INFORMATION: Clone 24

<400> SEQUENCE: 30

Gly Lys Met Met Val Ser Glu
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic Construct
<220> FEATURE:
```

<223> OTHER INFORMATION: Clone 25

<400> SEQUENCE: 31

Met Asn Lys Ser Tyr His Leu
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 26

<400> SEQUENCE: 32

Leu Asn Lys Thr Phe Tyr Tyr
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 28

<400> SEQUENCE: 33

Met Asn Lys Thr Phe Val Pro
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 29

<400> SEQUENCE: 34

Met Asn Lys Thr Phe Phe Ser
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 30

<400> SEQUENCE: 35

Gly Lys Leu Pro Lys Glu Ser
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 31

<400> SEQUENCE: 36

Met Asn Lys Thr Phe Trp Phe

```
<210> SEQ ID NO 37
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 32

<400> SEQUENCE: 37

Met Asn Lys Thr Trp Tyr Pro
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 33

<400> SEQUENCE: 38

Phe Asn Lys Ser Tyr Tyr Gly
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 34

<400> SEQUENCE: 39

Tyr Asn Lys Ser Phe Phe Met
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 35

<400> SEQUENCE: 40

Ala Gly Ala Pro Arg His His
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 36

<400> SEQUENCE: 41

Met Asn Lys Thr Phe Trp Phe
1               5

<210> SEQ ID NO 42
<211> LENGTH: 7
```

```
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 37

<400> SEQUENCE: 42

Met Asn Lys Thr Phe Val Asp
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 38

<400> SEQUENCE: 43

Met Asn Lys Ser Tyr His Leu
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 39

<400> SEQUENCE: 44

Phe Asn Lys Ser Tyr Tyr Gly
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 40

<400> SEQUENCE: 45

Met Asn Lys Thr Trp Tyr Pro
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 41

<400> SEQUENCE: 46

Met Asn Lys Thr Trp Tyr Pro
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic Construct
<220> FEATURE:
```

<223> OTHER INFORMATION: Clone 42

<400> SEQUENCE: 47

Met Asn Lys Thr Trp Tyr Pro
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 43

<400> SEQUENCE: 48

Met Asn Lys Thr Trp Tyr Pro
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 44

<400> SEQUENCE: 49

Met Asn Lys Thr Phe Trp Phe
1               5

<210> SEQ ID NO 50
<211> LENGTH: 0
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Unknown

<400> SEQUENCE: 50

000

<210> SEQ ID NO 51
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 45

<400> SEQUENCE: 51

Met Pro Leu Arg Ala Ser Gln
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 46

<400> SEQUENCE: 52

Gly Lys Leu Pro Trp Pro Lys
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 47

<400> SEQUENCE: 53

Phe Asn Lys Ser Tyr Tyr Gly
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone 48

<400> SEQUENCE: 54

Met Asn Lys Thr Phe Phe Ser
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Phage phi 45 peptide

<400> SEQUENCE: 55

Pro Leu Arg Ala Ser Gln
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Phage phi 16 peptide

<400> SEQUENCE: 56

Ala Leu Gln Ala Ser Arg His
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Ph.D.-7TM phage library peptide 1

<400> SEQUENCE: 57

Met Asn Lys Thr Trp Tyr Pro
1               5

<210> SEQ ID NO 58
<211> LENGTH: 7
<212> TYPE: PRT

```
<213> ORGANISM: Artificial Sequence
<220> FEATURE:
<223> OTHER INFORMATION: Synthetic Construct
<220> FEATURE:
<223> OTHER INFORMATION: Ph.D.-7TM phage library peptide 2

<400> SEQUENCE: 58

Met Asn Lys Thr Phe Trp Phe
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Ph.D.-7TM phage library peptide 3

<400> SEQUENCE: 59

Met Asn Lys Thr Phe Ser Ala
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Ph.D.-7TM phage library peptide 4

<400> SEQUENCE: 60

Met Asn Lys Val Tyr Leu Pro
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Ph.D.-7TM phage library peptide 5

<400> SEQUENCE: 61

Leu Asn Lys Thr Phe Tyr Tyr
1               5

<210> SEQ ID NO 62
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Ph.D.-7TM phage library peptide 6

<400> SEQUENCE: 62

Met Asn Lys Thr Phe Val Asp
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Ph.D.-7TM phage library peptide 7
```

```
<400> SEQUENCE: 63

Val Asn Lys Thr Tyr Trp Lys
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Ph.D.-7TM phage library peptide 8

<400> SEQUENCE: 64

Met Asn Lys Thr Trp Tyr Pro
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Ph.D.-7TM phage library peptide 9

<400> SEQUENCE: 65

Phe Asn Lys Ser Tyr Tyr Gly
1               5

<210> SEQ ID NO 66
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Ph.D.-7TM phage library peptide 10

<400> SEQUENCE: 66

Met Asn Lys Ser Tyr His Leu
1               5

<210> SEQ ID NO 67
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Ph.D.-7TM phage library peptide 11

<400> SEQUENCE: 67

Tyr Asn Lys Ser Phe Phe Met
1               5

<210> SEQ ID NO 68
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Ph.D.-7TM phage library peptide 12

<400> SEQUENCE: 68

Tyr Asn Lys Ser Phe Phe Pro
1               5
```

```
<210> SEQ ID NO 69
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Ph.D.-7TM phage library peptide 13

<400> SEQUENCE: 69

Phe Asn Lys Ser Trp Phe Pro
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Ph.D.-7TM phage library peptide 14

<400> SEQUENCE: 70

Phe Asn Lys Ser Tyr Tyr Gly
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Ph.D.-7TM phage library peptide 15

<400> SEQUENCE: 71

Gly Lys Leu Pro Ile Ala Met
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Ph.D.-7TM phage library peptide 16

<400> SEQUENCE: 72

Gly Lys Leu Pro Trp Pro Lys
1               5

<210> SEQ ID NO 73
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Ph.D.-7TM phage library peptide 17

<400> SEQUENCE: 73

Gly Lys Leu Pro Ile Pro Tyr
1               5

<210> SEQ ID NO 74
<211> LENGTH: 7
<212> TYPE: PRT
```

<210> SEQ ID NO 75
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Ph.D.-7TM phage library peptide 18

<400> SEQUENCE: 74

Gly Lys Leu Pro Pro Pro Ile
1               5

<210> SEQ ID NO 75
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Ph.D.-7TM phage library peptide 19

<400> SEQUENCE: 75

Gly Lys Leu Pro Lys Met Thr
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Ph.D.-7TM phage library peptide 20

<400> SEQUENCE: 76

Gly Lys Leu Pro Lys Glu Ser
1               5

<210> SEQ ID NO 77
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Ph.D.-7TM phage library peptide consensus
<220> FEATURE:
<221> NAME/KEY: VARIATION
<222> LOCATION: 5
<223> OTHER INFORMATION: Xaa = Ile, Trp, Pro or Lys
<220> FEATURE:
<221> NAME/KEY: VARIATION
<222> LOCATION: 6
<223> OTHER INFORMATION: Xaa = Ala, Pro, Met or Glu
<220> FEATURE:
<221> NAME/KEY: VARIATION
<222> LOCATION: 7
<223> OTHER INFORMATION: Xaa = Met, Lys, Tyr, Ile, Thr or Ser

<400> SEQUENCE: 77

Gly Lys Leu Pro Ile Ala Met
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone phi 12

<400> SEQUENCE: 78

```
Met Asn Lys Ser Tyr Thr Ile
1               5

<210> SEQ ID NO 79
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone phi 13

<400> SEQUENCE: 79

Val Asn Lys Thr Tyr Trp Lys
1               5

<210> SEQ ID NO 80
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone phi 16

<400> SEQUENCE: 80

Ala Leu Gln Ala Ser Arg His
1               5

<210> SEQ ID NO 81
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone phi 20

<400> SEQUENCE: 81

Met Asn Lys Thr Trp Tyr Pro
1               5

<210> SEQ ID NO 82
<211> LENGTH: 7
<212> TYPE: PRT
<213> ORGANISM: Artificial Sequence
<220> FEATURE:
<223> OTHER INFORMATION: Clone phi 29

<400> SEQUENCE: 82

Met Asn Lys Thr Phe Phe Ser
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone phi 30

<400> SEQUENCE: 83

Gly Lys Leu Pro Lys Glu Ser
1               5

<210> SEQ ID NO 84
<211> LENGTH: 7
<212> TYPE: PRT
```

```
<213> ORGANISM: Artificial Sequence
<220> FEATURE:
<223> OTHER INFORMATION: Synthetic Construct
<220> FEATURE:
<223> OTHER INFORMATION: Clone phi 33

<400> SEQUENCE: 84

Phe Asn Lys Ser Tyr Tyr Gly
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone phi 45

<400> SEQUENCE: 85

Met Pro Leu Arg Ala Ser Gln
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Modal phage library isolate

<400> SEQUENCE: 86

Met Asn Lys Thr Trp Met Pro
1               5

<210> SEQ ID NO 87
<211> LENGTH: 4
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Peptide spacer

<400> SEQUENCE: 87

Gly Gly Gly Cys
1

<210> SEQ ID NO 88
<211> LENGTH: 38
<212> TYPE: DNA
<213> ORGANISM: Artificial Sequence
<220> FEATURE:
<223> OTHER INFORMATION: Synthetic Construct
<220> FEATURE:
<223> OTHER INFORMATION: CHIPS forward PCR primer

<400> SEQUENCE: 88
tcgcggccca gccggccatg gcctttactt ttgaaccg                          38

<210> SEQ ID NO 89
<211> LENGTH: 35
<212> TYPE: DNA
<213> ORGANISM: Artificial Sequence
<220> FEATURE:
<223> OTHER INFORMATION: Synthetic Construct
<220> FEATURE:
<223> OTHER INFORMATION: CHIPS reverse PCR primer
```

```
<400> SEQUENCE: 89
gcctgcggcc gcagatctac cattaattac ataag                                      35

<210> SEQ ID NO 90
<211> LENGTH: 114
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Clone F3.03

<400> SEQUENCE: 90

Phe Thr Phe Glu Pro Phe Pro Thr Asn Glu Glu Ile Glu Ser Asn Lys
1               5                   10                  15

Lys Met Leu Glu Lys Glu Lys Ala Tyr Lys Glu Ser Phe Lys Asn Ser
            20                  25                  30

Gly Leu Pro Thr Thr Leu Gly Lys Leu Asp Glu Arg Leu Arg Asn Tyr
        35                  40                  45

Leu Asn Lys Gly Thr Lys Asn Ser Ala Gln Phe Glu Lys Met Val Ile
    50                  55                  60

Leu Thr Glu Asn Arg Gly Tyr Tyr Thr Val Tyr Leu Tyr Thr Pro Leu
65                  70                  75                  80

Ala Glu Asp Arg Lys Asn Val Glu Leu Leu Gly Arg Met Tyr Lys Thr
                85                  90                  95

Tyr Phe Phe Lys Lys Gly Glu Ser Lys Ser Ser Tyr Val Ile Lys Val
            100                 105                 110

Arg Ser
```